(12) United States Patent
Hallahan et al.

(10) Patent No.: US 8,129,356 B2
(45) Date of Patent: Mar. 6, 2012

(54) BMX MEDIATED SIGNAL TRANSDUCTION IN IRRADIATED VASCULAR ENDOTHELIUM

(75) Inventors: Dennis E. Hallahan, Nashville, TN (US); Christopher D. Willey, Birmingham, AL (US)

(73) Assignee: Vanderbilt University, Nashville, TN (US)

( * ) Notice: Subject to any disclaimer, the term of this patent is extended or adjusted under 35 U.S.C. 154(b) by 54 days.

(21) Appl. No.: 12/243,640

(22) Filed: Oct. 1, 2008

(65) Prior Publication Data

US 2009/0136487 A1 May 28, 2009

Related U.S. Application Data

(60) Provisional application No. 60/997,124, filed on Oct. 1, 2007.

(51) Int. Cl.
*A61K 31/70* (2006.01)
*C07H 21/04* (2006.01)

(52) U.S. Cl. ........................................ 514/44; 536/24.5

(58) Field of Classification Search .................. None
See application file for complete search history.

(56) References Cited

U.S. PATENT DOCUMENTS

| 5,595,979 | A | * | 1/1997 | Snyder ............................ 514/49 |
| 6,074,640 | A | * | 6/2000 | Curiel et al. ............... 424/130.1 |
| 6,160,010 | A | * | 12/2000 | Uckun et al. .................. 514/521 |
| 6,214,986 | B1 | * | 4/2001 | Bennett et al. ............... 536/24.5 |
| 6,258,824 | B1 | * | 7/2001 | Yang ............................. 514/312 |
| 7,345,027 | B2 | * | 3/2008 | Tolentino et al. ........... 514/44 A |
| 2002/0142982 | A1 | * | 10/2002 | Hla et al. ........................ 514/44 |
| 2003/0181377 | A1 | * | 9/2003 | Hallahan et al. ................ 514/12 |
| 2005/0009876 | A1 | * | 1/2005 | Bhagwat et al. .............. 514/338 |
| 2007/0292352 | A1 | * | 12/2007 | Marnett et al. ................ 424/9.6 |

OTHER PUBLICATIONS

Dai et al. Cancer Research 2006, vol. 66, pp. 8058-8064.*

* cited by examiner

*Primary Examiner* — Tracy Vivlemore
(74) *Attorney, Agent, or Firm* — Jenkins, Wilson, Taylor & Hunt, PA

(57) ABSTRACT

Provided are methods for modulating the proliferation of cells and tissues. In some embodiments, the methods include administering to a subject an effective amount of a modulator of a biological activity of a bone marrow X kinase (Bmx) gene product. Also provided are methods for increasing the radiosensitivity of a target cell or tissue, methods for suppressing tumor growth, methods for inhibiting tumor blood vessel growth, and compositions that include modulators of a biological activity of a bone marrow X kinase (Bmx) gene product.

37 Claims, 20 Drawing Sheets

```
         *:::************..:**********.*****.******..****..*****..:*****..***.******.******.*********.******:;**.
Human2   MDTKSILEELLLKRSQQKKMSPNNYKERLFVLTKTNLSYYEYDKMKRGSRKGSIEIKKIRCVEKVNLEEQTPVERQYPFQIVYKDGLLYVYASNEESRS  100
Human1   MDTKSILEELLLKRSQQKKMSPNNYKERLFVLTKTNLSYYEYDKMKRGSRKGSIEIKKIRCVEKVNLEEQTPVERQYPFQIVYKDGLLYVYASNEESRS  100
Macaca1  MDTKSILEELLLKRSQQKKMSPNNYKERLFVLTKTNLSYYEYDKMKRGSRKGSIEIKKIRCVEKVNLEEQTPVERQYPFQIVYKDGLLYVYASNEESRS  100
Macaca2  MDTKSILEELLLKRSQQKKMSPNNYKERLFVLTKTNLSYYEYDKMKRGSRKGSIEIKKIRCVEKVNLEEQTPVERQYPFQIVYKDGLLYVYASNEESRS  100
Macaca3  MDTKSILEELLLKRSQQKKMSPNNYKERLFVLTKTNLSYYEYDKMKRGSRKGSIEIKKIRCVEKVNLEEQTPVERQYPFQIVYKDGLLYVYASNEESRS  100
Bovine   MDTKSILEELLLKRSQQKKMSPNNYKERLFVLTKTNLSYYEYDKMKRGSRKGSIEIKKIRCVEKVNLEEQTPVERQYPFQIVYKDGLLYVYASNEESRS  100
Canis    MDTKSILEELLLKRSQQKKMSPSNYKERLFVLTKTNLSYYEYDKMKRGSRKGSIEIKKIRCVEKVNLEEQTPVERQYPFQIVYKDGLLYVYASNEESRS  100
Equus    MDTKSILEELLLKRSQQKKMSPNNYKERLFVLTKTNLSYYEYDKMKRGSKKGSIEIKKIRCVEKVNEEQTPAERQYPFQIVYKDGLLYVYASNEKSRS  100
Mouse    MESKSILEELLLKKSQQKKMSPNNYKERLFVLTKT SLSYYEYDKMKRGSRKGSIEIKKIRCVEKVNLEEQTPVERQYPFQIVYKDGLLYVYASNEESRC  100
Rat      MDSKSILEELLLKKSQQKKMSPINYKERLFVLTKTSLSYYEYDKMKRGSRKGSIEVKKIRCVEKVNLEEQTPVERQYPFQIVYKDGLLYVYASNEESRC  100
         1........10........20........30........40........50........60........70........80........90........100

********************:****:*::******:****..****..**.****..*.*.****:.**.****..***...**..*..              *
Human2   QWLKALQKEIRGNPHLLIKYHSGFFVDGKFLCCQQSCKAAPGCTLWEAYANLHTAVNEEKHRVPTFPDRVLKIPRAVPVLKMDAPSSSTTLAQYDNESKK  200
Human1   QWLKALQKEIRGNPHLLIKYHSGFFVDGKFLCCQQSCKAAPGCTLWEAYANLHTAVNEEKHRVPTFPDRVLKIPRAVPVLKMDAPSSSTTLAQYDNESKK  200
Macaca1  QWLKALQKEIRGNPHLLIKYHSGFFVDGKFLCCQQSCKAAPGCTLWEAYANLHTAVNEEKHRVPTFPDRVLKIPRAVPVLKMDAPSSSTTLAQYDNESKK  200
Macaca2  QWLKALQKEIRGNPHLLIKYHSGFFVDGKFLCCQQSCKAAPGCTLWEAYANLHTAVNEEKYRVPTFPDRVLKIPRAVPVLKMDAPSSSTTLAQYDNESMK  200
Macaca3  QWLKALQKEIRGNPHLLIKYHSGFFVDGKFLCCQQSCKAAPGCTLWEAYANLHIAVNEEKYRVPTFPDRVLKIPRAVPVLKMDAPSSSTTLAQYDNESMK  200
Bovine   QWLKALQKEIRGNPHLLIKYHSGFFVDGKFLCCQQSCKAAPGCTLWEAYADLHTAPKEEKHGVPIFPDRVLKIPRAVPILKVDEPSSSTTLAQYDSDSKK  200
Canis    QWLKALQKEIRGNPHLLIKYHSGFFVDGKFLCCQQSCKAAPGCTLWEAYADLHITTHEEKHRVPIFPDRVLKIPRAVPILKIPRAVPIFKMNEPSSSTTVAPYDSDSKK  200
Equus    QWLKALQKEIRGNPHLLIKYHSGFFVDGKFLCCQQSCKAAPGCTLWEAYADLHIATNEEKHRAPTFPDRVLKIPRAVPVFKMDEPSSSTTLAQYDSDSKK  200
Mouse    QWLKALQKEIRGNPHLLIKYHSGFFVDGKFLCCQQSCKAAPGCTLWEAYADLHIAISDEKHRAPTFPERLLKIPRAVPVLKMDASSSGAILPQYDSYSKK  200
Rat      QWLKALQKEIRGNPHLLIKYHSGFFVDGKFLCCQQSCKAAPGCTLWEAYADLHIAISDEKHRAPTFPERILKIPRAVPILKMDASSSAIPPQYDSHLKK  200
         .......110........120........130........140........150........160........170........180........190........200
```

Figure 8

```
Human2    NYGSQPPSSSTSLAQYDSNSKKIYGSQPNFNMQYIPREDFPDWWQVRKLKSSSSEDVASSNQKER-NVNHTTSKISWEFPESSSSEEEENLDDYDWFAG 299
Human1    NYGSQPPSSSTSLAQYDSNSKKIYGSQPNFNMQYIPREDFPDWWQVRKLKSSSSEDVASSNQKER-NVNHTTSKISWEFPESSSSEEEENLDDYDWFAG 299
Macaca1   NYGFQPPSSSTTVAQYDSNSKKIYGSQPNFNMQYIPKEDYPDWGQERKLKSSSSEDVASSNQKER-NVNHTTKISWGFPESSSSEEEANLDDYDWFAG 299
Macaca2   NYGFQPPSSSTTVAQYDSNSKKIYGSQPNFNMQYIPKEDYPDWGQERKLKSSSSEDVASSNQKER-NVNHTTKISWGFPESSSSEEEANLDDYDWFAG 299
Macaca3   NYGFQPPSSSTTVAQYDSNSKKIYGSQPNFNMQYIPKEDYPDWGQERKLKSSSSEDVASSNQKER-NVNHTTKISWGFPESSSSEEEANLDDYDWFAG 299
Bovine    NYG---------------------SQSNINMKYISKEDFPDWWQVRKLRSASSSEDLACSNQRERNVVNHNTSKMSWGSPESSSEEEENLDDYDWFAG 278
Canis     NYG---------------------SQLNANMQHFPREDCPDWWQLTKCVFCRSSDDFAGSNQRERTGVNHSTSKMSWGFPESSSEEEENLEDYDWFAG 278
Equus     DYG---------------------SQSNVKMRYIPKEDFPDWWQVRKLKSSVNSEDFACSNQRERDVVNHSTSKMSWGFPESSSEEEENLDDYDWFAG 278
Mouse     SCG---------------------SQPTSNIRYIPREDCPDWWQVRKLK---SEEDIACSNQLERNIASHSTSKMSWGFPESSSEEEENLHAYDWFAG 275
Rat       SYD---------------------SQPTVNIRYIPREDCPDWWQIRKPK---SEEDIARSNQLERNIVSHSPSKMSWGFPESSSEEEENLDAYDWFAG 275
          .........210.........220.........230.........240.........250.........260.........270.........280.........290.........300
```

Figure 8 (cont'd)

BMX MEDIATED SIGNAL TRANSDUCTION IN IRRADIATED VASCULAR ENDOTHELIUM

CROSS REFERENCE TO RELATED APPLICATION

The presently disclosed subject matter claims the benefit of U.S. Provisional Patent Application Ser. No. 60/997,124, filed Oct. 1, 2007; the disclosure of which is incorporated herein by reference in its entirety

GOVERNMENT INTEREST

The presently disclosed subject matter was made with U.S. Government support under Grant No. 2R01-CA89674-04 awarded by the National Institutes of Health/National Cancer Institute. Thus, the U.S. Government has certain rights in the presently disclosed subject matter.

TECHNICAL FIELD

The presently disclosed subject matter relates to methods and compositions for modulating cellular and/or tissue proliferation. In some embodiments, the compositions comprise a modulator of a Bmx gene product biological activity. In some embodiments, the methods comprise administering a composition comprising a modulator of a Bmx gene product biological activity to a subject in order to modulate cellular or tissue proliferation.

BACKGROUND

Ionizing radiation is useful in the treatment of cancer and for ablation of pathologic tissues because of the cytotoxic effects which result from persistent DNA double strand breaks or activation of program cell death (Haimovitz-Friedman et al., 1994; Garcia-Barros et al., 2003; Brown & Attardi, 2005). Radiation causes rapidly proliferating cells, such as tumor and cancer cells, to undergo cell death by apoptosis, both in vivo and in vitro (Antonakopoulos et al., 1994; Li et al., 1994; Mesner et al., 1997).

Current radiation therapy is frequently unsuccessful at completely eradicating cancer cells from a patient, however. This is true for at least two reasons. One reason cancer can recur is that it is often not possible to deliver a sufficiently high dose of local radiation to kill tumor cells without concurrently creating an unacceptably high risk of damage to the surrounding normal tissue. Another reason is that tumors show widely varying susceptibilities to radiation-induced cell death. Ionizing radiation activates pro-survival response through phosphoinositide 3-kinase/Akt (PI3K/Akt) and mitogen-activated protein kinase (MAPK) signal transduction pathways (Dent et al., 2003; Tan & Hallahan, 2003; Tan et al., 2006; Yacoub et al., 2006). PI3K catalyzes the addition of a phosphate group to the inositol ring of phosphoinositides normally present in the plasma membrane of cells (Wymann & Pirola, 1998). The products of these reactions, including phosphatidyl-4,5-bisphosphate and phosphatidyl-3,4,5-trisphosphate, are potent second messengers of several RTK signals (Cantley, 2002). In vitro studies have indicated that PI3K and Akt are involved in growth factor-mediated survival of various cell types (Datta et al., 1999), including neuronal cells (Yao & Cooper, 1995; Dudek et al., 1997; Weiner & Chun, 1999), fibroblasts (Kauffmann-Zeh et al., 1997; Fang et al., 2000), and certain cells of hematopoietic origin (Katoh et al., 1995; Kelley et al., 1999; Somervaille et al., 2001).

Another obstacle to designing effective radiotherapy is that there is a poor correlation between cellular responses to ionizing radiation in vitro and in vivo. For example, glioblastoma multiforme (GBM) is insensitive to radiation treatment, and has a universally fatal clinical outcome in both children and adults (Walker et al., 1980; Wallner et al., 1989; Packer, 1999). In vitro studies, however, show that human GBM cell lines exhibit radiosensitivity that is similar to that seen in cell lines derived from more curable human tumors (Allam et al., 1993; Taghian et al., 1993). In accord with the clinical data, the use of in vivo animal models has shown that GBM tumors in vivo are much more radioresistant than the cell lines used to produce them are in vitro (Baumann et al., 1992; Allam et al., 1993; Taghian et al., 1993; Advani et al., 1998; Staba et al., 1998). Thus, the inability to predict the radiosensitivity of a tumor in vivo based upon in vitro experimentation continues to be a significant obstruction to the successful design of radiotherapy treatments of human cancers.

Tumor cells could show enhanced radiosensitivity in vitro compared to in vivo due to the absence of an angiogenic support network in vitro, the presence of which appears to contribute to a tumor's radioresistance in vivo. The response of tumor microvasculature to radiation is dependent upon the dose and time interval after treatment (Kallman et al., 1972; Song et al., 1972; Hilmas & Gillette, 1975; Johnson, 1976; Yamaura et al., 1976; Ting et al., 1991). Tumor blood flow decreases when high doses of radiation in the range of 20 Grays (Gy) to 45 Gy are used (Song et al., 1972). In contrast, blood flow increases when relatively low radiation doses, for example below 500 rads, are administered (Kallman et al., 1972; Hilmas & Gillette, 1975; Johnson, 1976; Yamaura et al., 1976; Gorski et al., 1999). In irradiated mouse sarcomas, for example, blood flow increased during the 3 to 7 days immediately following irradiation (Kallman et al., 1972). Thus, the microvasculature might serve to protect tumor cells from radiation-induced cell death.

Thus, there exists an ongoing and long-felt need in the art for effective therapies for enhancing the efficacy of radiotherapy, particularly in the context of tumors that are resistant to radiotherapy. To address this need, the presently disclosed subject matter provides inter alia methods for increasing the radiosensitivity of a cell or tissue. Such methods can be useful for enhancing the efficacy of anti-proliferative treatments such as, but not limited to chemotherapy and radiotherapy, among other applications.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides methods for modulating proliferation of a cell or of a tissue in a subject. In some embodiments, the methods comprise administering to the subject an effective amount of a modulator of a biological activity of a bone marrow X kinase (Bmx) gene product. In some embodiments, the cell is a tumor cell or a vascular endothelial cell. In some embodiments, the subject is a mammal. In some embodiments, the Bmx gene product is encoded by a naturally occurring nucleic acid sequence that is at least 95% identical to nucleotides 174-2198 of SEQ ID NO: 1 or is encoded by a naturally occurring nucleic acid sequence that is at least 95% identical to nucleotides 112-2136 of SEQ ID NO: 3. In some embodiments, the modulator is an inhibitor of a biological activity of a Bmx gene product. In some embodiments, the inhibitor is selected from the group consisting of (2Z)-2-Cyano-N-(2,5-dibromophenyl)-3-hydroxy-2-butenamide, an antibody that specifically binds to the Bmx gene product to inhibit a biological activity of the Bmx gene product, and a nucleic acid that inhibits a biological activity of the Bmx gene product by RNA interference. In some embodiments, the nucleic acid that inhibits a biological activity of the Bmx gene product by RNA interference comprises a short interfering RNA (siRNA) or a short hairpin RNA (shRNA) that targets a Bmx gene product encoded by a nucleic acid sequence comprising nucleotides 174-2198 of SEQ ID NO: 1 or nucleotides 112-2136 of SEQ ID NO: 3. In some embodiments, the siRNA or the shRNA is encoded by a recombinant virus and the administering comprises administering an effective amount of the recombinant virus to the subject to modulate proliferation of a cell or of a tissue in the subject.

The presently disclosed subject matter also provides methods for increasing the radiosensitivity of a target cell or tissue. In some embodiments, the methods comprise contacting the target cell or tissue with an effective amount of a modulator of a biological activity of a bone marrow X kinase (Bmx) gene product. In some embodiments, the modulator of a biological activity of a Bmx gene product comprises a bone marrow X kinase (Bmx) antagonist, a vector encoding a bone marrow X kinase (Bmx) antagonist, or a combination thereof. In some embodiments, the target cell or tissue comprises an endothelial cell or endothelial tissue. In some embodiments, the endothelial tissue is vascular endothelium. In some embodiments, the target cell or tissue is a tumor cell or a tumor. In some embodiments, the tumor comprises a radiation resistant tumor. In some embodiments, the target cell or tissue comprises vasculature supplying blood flow to a tumor. In some embodiments, the subject is a mammal. In some embodiments, the administering a bone marrow X kinase (Bmx) antagonist comprises administering a minimally therapeutic dose of a Bmx antagonist. In some embodiments, the administering comprises administering a composition comprising a bone marrow X kinase (Bmx) antagonist, a vector encoding a bone marrow X kinase (Bmx) antagonist, or a combination thereof and a pharmaceutically acceptable carrier. In some embodiments, the bone marrow X kinase (Bmx) antagonist is selected from the group consisting of (2Z)-2-Cyano-N-(2,5-dibromophenyl)-3-hydroxy-2-butenamide, an antibody that specifically binds to the Bmx gene product to inhibit a biological activity of the Bmx gene product, and a nucleic acid that inhibits a biological activity of the Bmx gene product by RNA interference. In some embodiments, the bone marrow X kinase (Bmx) antagonist comprises a small interfering RNA (siRNA) targeted to a Bmx gene product.

The presently disclosed subject matter also provides methods for suppressing tumor growth in a subject. In some embodiments, the methods comprise administering to the subject an effective amount of a modulator of a biological activity of a bone marrow X kinase (Bmx) gene product and treating the tumor with ionizing radiation, whereby tumor growth is suppressed. In some embodiments, the subject is a mammal. In some embodiments, the administering comprises administering a minimally therapeutic dose of the modulator. In some embodiments, the administering comprises administering a composition comprising a bone marrow X kinase (Bmx) antagonist, a vector encoding a bone marrow X kinase (Bmx) antagonist, or a combination thereof and a pharmaceutically acceptable carrier. In some embodiments, the modulator is selected from the group consisting of (2Z)-2-Cyano-N-(2,5-dibromophenyl)-3-hydroxy-2-butenamide, an antibody that specifically binds to the Bmx gene product to inhibit a biological activity of the Bmx gene product, and a nucleic acid that inhibits a biological activity of the Bmx gene product by RNA interference. In some embodiments, the modulator comprises a small interfering RNA (siRNA) targeted to a Bmx gene product. In some embodiments, the tumor comprises a radiation resistant tumor. In some embodiments, the treating the tumor with ionizing radiation comprises treating the tumor with a subtherapeutic dose of ionizing radiation.

The presently disclosed subject matter also provides methods for inhibiting tumor blood vessel growth. In some embodiments, the methods comprise administering to the subject an effective amount of a modulator of a biological activity of a bone marrow X kinase (Bmx) gene product and treating the tumor with ionizing radiation, whereby tumor blood vessel growth is inhibited. In some embodiments, the administering comprises administering a minimally therapeutic dose of the modulator. In some embodiments, the modulator comprises a composition comprising a bone marrow X kinase (Bmx) antagonist, a vector encoding a bone marrow X kinase (Bmx) antagonist, or a combination thereof and a pharmaceutically acceptable carrier. In some embodiments, the modulator is selected from the group consisting of (2Z)-2-Cyano-N-(2,5-dibromophenyl)-3-hydroxy-2-butenamide, an antibody that specifically binds to the Bmx gene product to inhibit a biological activity of the Bmx gene product, and a nucleic acid that inhibits a biological activity of the Bmx gene product by RNA interference. In some embodiments, the modulator comprises a small interfering RNA (siRNA) targeted to a Bmx gene product. In some embodiments, the subject is a mammal. In some embodiments, the tumor comprises a radiation resistant tumor. In some embodiments, the treating the tumor with ionizing radiation comprises treating the tumor with a subtherapeutic dose of ionizing radiation. In some embodiments, the methods further comprise reducing the vascular length density of the tumor blood vessels.

The presently disclosed subject matter also provides methods for inhibiting a condition associated with undesirable angiogenesis in a subject. In some embodiments, the methods comprise administering to the subject an effective amount of a bone marrow X kinase (Bmx) antagonist. In some embodiments, the condition associated with undesirable angiogenesis is selected from the group consisting of a cancer, a tumor, macular degeneration, and endometriosis. In some embodiments, the Bmx antagonist is selected from the group consisting of (2Z)-2-Cyano-N-(2,5-dibromophenyl)-3-hydroxy-2-butenamide, an antibody that specifically binds to the Bmx gene product to inhibit a biological activity of the Bmx gene product, and a nucleic acid that inhibits a biological activity of the Bmx gene product by RNA interference. In some embodiments, the nucleic acid that inhibits a biological activity of the Bmx gene product by RNA interference comprises a small interfering RNA (siRNA) targeted to a Bmx gene product. In some embodiments, the subject is a mammal.

The presently disclosed subject matter also provides expression constructs encoding a short interfering RNA (siRNA) or a short hairpin RNA (shRNA) that modulates expression of a Bmx gene product. In some embodiments, the Bmx gene product is encoded by a naturally occurring nucleic acid sequence that is at least 95% identical to nucleotides 174-2198 of SEQ ID NO: 1 or nucleotides 112-2136 of SEQ ID NO: 3, is a naturally occurring non-human ortholog thereof, or a naturally occurring splice variant or allelic variant of any of these. In some embodiments, the naturally occurring non-human ortholog thereof comprises an amino acid sequence that is at least 95% identical to an amino acid sequence as set forth in any of even numbered SEQ ID NOs: 2-20 or is encoded by a naturally occurring nucleic acid sequence that is at least 95% identical to an open reading frame of any of odd numbered SEQ ID NOs: 1-19.

Thus, it is an object of the presently disclosed subject matter to provide methods for modulating proliferation of a cell or of a tissue in a subject.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

FIG. 1A is a Western blot with an antibody directed against phosphotyrosine of total lysates from cells after incubation at 37° C. for the indicated times in minutes. Western blots are shown of phosphor-tyrosine 40 (PY40) Bmx, indicative of activation, as well as total Bmx and actin for normalization.

FIG. 1B depicts the results of in vitro kinase assays (IVK) in which Bmx was immunoprecipitated (IP:Bmx) from the lysates as in FIG. 1A and eluted under non-denaturing conditions. Following elution, kinase assay buffer was added for 20 minutes. Samples were separated by SDS-PAGE. Western blot analysis using anti-phosphotyrosine (IB:PY) antibody was used to detect autophosphorylation.

FIG. 2A depicts Western blot analysis using an anti-Bmx antibody to detect total Bmx levels from total protein lysates of the transfected cells that had been separated by SDS-PAGE and transferred to a solid support.

FIG. 2B is a bar graph showing the results of MTT-based survival assays. Cells infected with either Bmx or control shRNA were incubated for 48 hours prior to plating of 10,000 cells/well in 96-well dishes. Cells were treated with either 0 or 2 Gy and incubated for 24 hours. Cells were then treated with WST-1 reagent and incubated for 2 hours prior to dye quantification at 450 nm ($OD_{450}$). Normalized mean absorbance values with standard errors are shown. Shaded bars—negative control; stippled bars—Bmx shRNA.

FIG. 3A shows the results of in vitro kinase assays (IVK) for LFM-A13. Bmx was immunoprecipitated (IP:Bmx) from lysates of HUVEC pre-treated with either 30 μM LFM-A13 or DMSO vehicle control for 45 minutes prior to 3 Gy irradiation. IP:Bmx samples were then eluted in non-denaturing conditions and subjected to kinase assay. Samples were then loaded for SDS-PAGE and anti-phosphotyrosine (IB:PY) Western blotting.

FIG. 3B is a graph showing the results of clonogenic assays of HUVEC cells with 1 hour pre-incubation with 30 μM LFM-A13 or DMSO vehicle control. Cells were counted and plated and subjected to the indicated doses of radiation and colonies formed over 10 days. Surviving colonies were plotted as a function of cells plated and normalized by the plating efficiency for each condition. Standard error (SE) bars are shown.

FIG. 3C shows the results of analysis of apoptosis in cells treated with 30 μM LFM-A13 or DMSO vehicle alone (negative control). LFM-A13 or DMSO vehicle was added to plated cells with or without 3 Gy radiation (IR). After 24 hours, cells were trypsinized and collected for flow cytometry using Annexin V/Propidium iodide staining. The first five (5) panels are a series of FACS scatter plots showing the percent of cells undergoing early (Q4) and late (Q2) apoptosis compared to viable cells (Q3) and dead cells (Q1). The sixth panel is a plot of the quantification of early+late apoptosis as mean and standard error. *: $p<0.001$ vs. LFM-A13 or 3 Gy alone.

FIG. 3D depicts apoptosis in cells preincubated with 30 μM LFM-A13 or DMSO vehicle control treated with either 3 or 6 Gy of irradiation and incubated at 37° C. for 24 hours prior to fixing and staining with DAPI. The left panel is a fluorescence micrograph of such cells, and the right panel is a bar graph of the percent of cells demonstrating apoptotic morphology shown as mean and standard error. *: $p<0.05$ vs. control. **: $p=0.001$ vs. LFM-A13 alone.

FIG. 4A shows the results of endothelial cell closure assays in which 80% confluent HUVEC were subjected to a gap formation using a 200 μl pipette tip. Cells were then treated with 30 μM LFM-A13 or DMSO vehicle control for one hour followed by 3 Gy. 12 and 24 hours later, cells were fixed with 70% ethanol and stained with methylene blue. Shown are representative photographs.

FIG. 4B is a bar graph of the mean and standard error of relative cell density in the original gap area (n=4). *: $p<0.05$ vs. control. **: $p<0.01$ vs. LFM-A13 alone.

FIG. 4C depicts a micrograph of HUVEC placed onto MATRIGEL™ plugs and treated with either 30 μM LFM-A13 or DMSO vehicle control followed by 3 Gy irradiation.

FIG. 4D is a bar graph of the mean number of tubules of the cells shown in FIG. 4C with standard error bars. The cells depicted in FIG. 4C were fixed and tubules were quantitated by NIH ImageJ software. *: $p<0.05$ vs. control. **: $p<0.005$ vs. LFM-A13 or 3 Gy alone.

FIG. 5A are representative photographs and FIG. 5B is a bar graph of the mean vascular length density and standard error (n=3) for each treatment group. *: $p<0.0014$ vs. LFM-A13 or 3 Gy alone. Lewis lung carcinoma cells were implanted into the hind limb of mice. Once tumors formed, the mice were treated with five consecutive daily treatments of 50 mg/kg LFM-A13 (+LFM-A13) or DMSO control (-LFM-A13) and/or 3 Gy fractions (XRT). Tumors were harvested and stained for anti-CD34.

FIG. 5C is a set of photomicrographs of immunohistochemistry, and FIG. 5D is a bar graph of the mean level of CD34 staining and standard error calculated for each treatment condition. **: p=0.043 vs. IR. *: p=0.0001 vs. LFM-A13 or vehicle control.

FIG. 8 is an alignment of amino acid sequences of Bmx gene products from various species listed in Table 1. Each amino acid sequence was truncated at the N-terminus (if necessary) so that amino acid position number 1 of the human BMX corresponded to the first amino acid of each Bmx gene product. Above each set of ten amino acid sequences are symbols denoting the degree of conservation among the sequences. *—all sequences include the same amino acid. :—high degree of conservation. .—moderate conservation. [no symbol]—lower or no conservation.

BRIEF DESCRIPTION OF THE SEQUENCE LISTING

Figure 1A:
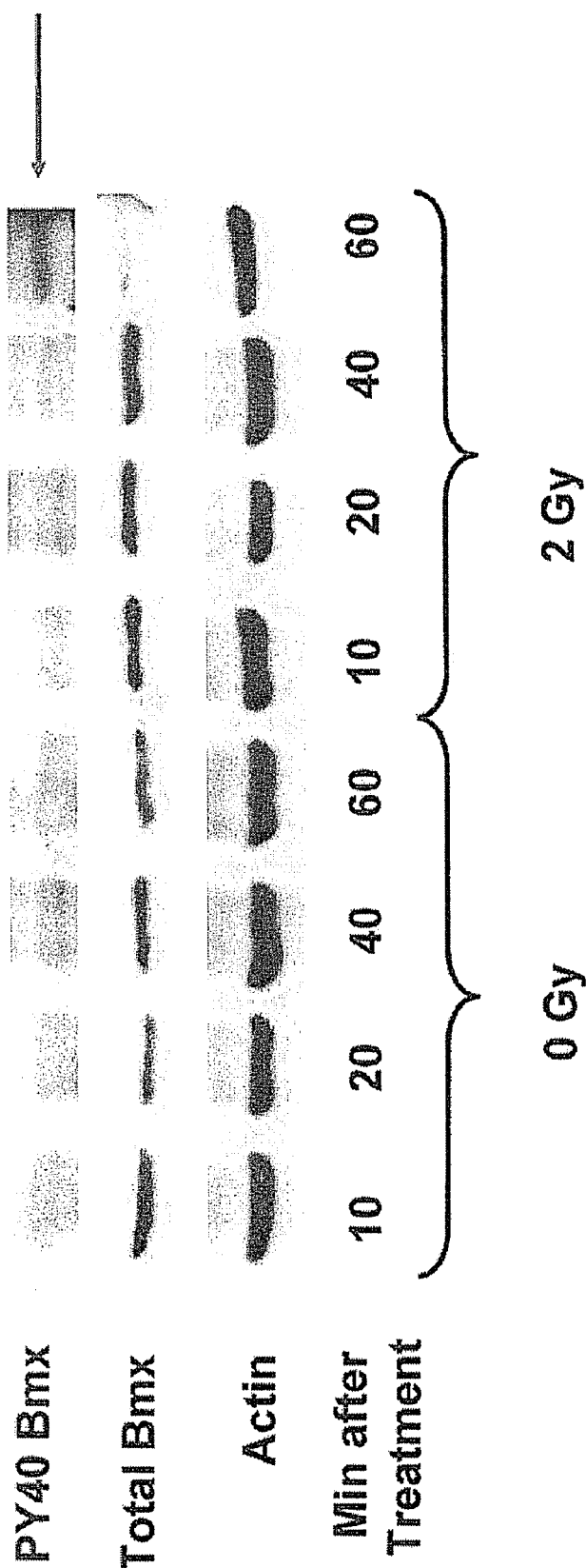
FIGS. 1A and 1B present the results of experiments showing that Bmx is activated by radiation in endothelial cells. Human umbilical vein endothelial cells (HUVEC) were either sham irradiated or radiated with 2 Gy.

SEQ ID NOs: 1 and 2 are a nucleotide and amino acid sequences, respectively, for a human Bmx gene product, transcript variant 1 (GENBANK® Accession Nos. NM_203281 and NP_975010, respectively).

SEQ ID NOs: 3 and 4 are a nucleotide and amino acid sequences, respectively, for a human Bmx gene product, transcript variant 2 (GENBANK® Accession Nos. NM_001721 and NP_001712, respectively).

SEQ ID NOs: 5 and 6 are a nucleotide and amino acid sequences, respectively, for a Macaca mulatta Bmx gene product, transcript variant 1 (GENBANK® Accession Nos. XM_001101349 and XP_001101349, respectively).

SEQ ID NOs: 7 and 8 are a nucleotide and amino acid sequences, respectively, for a Macaca mulatta Bmx gene product, transcript variant 2 (GENBANK® Accession Nos. XM_001101166 and XP_001101166, respectively).

SEQ ID NOs: 9 and 10 are a nucleotide and amino acid sequences, respectively, for a Macaca mulatta Bmx gene product, transcript variant 3 (GENBANK® Accession Nos. XM_001101250 and XP_001101250, respectively).

SEQ ID NOs: 11 and 12 are a nucleotide and amino acid sequences, respectively, for a murine Bmx gene product (GENBANK® Accession Nos. NM_009759 and NP_033889, respectively).

SEQ ID NOs: 13 and 14 are a nucleotide and amino acid sequences, respectively, for a rat Bmx gene product (GENBANK® Accession Nos. NM_001109016 and NP_001102486, respectively).

SEQ ID NOs: 15 and 16 are a nucleotide and amino acid sequences, respectively, for a bovine Bmx gene product (GENBANK® Accession Nos. XM_610012 and XP_610012, respectively).

SEQ ID NOs: 17 and 18 are a nucleotide and amino acid sequences, respectively, for a canine Bmx gene product (GENBANK® Accession Nos. XM_548870 and XP_548870, respectively).

SEQ ID NOs: 19 and 20 are a nucleotide and amino acid sequences, respectively, for an Equus caballus Bmx gene product (GENBANK®Accession Nos. XM_001490091 and XP_001490141, respectively).

DETAILED DESCRIPTION

I. General Considerations

The microvasculature is a major component of cancer and supports tumor growth. Several groups have studied the inherent resistance of tumor vascular endothelium to cytotoxic effects of ionizing radiation (IR). IR activates signal transduction through the phosphatidyl inositol-3 kinase (PI3K)/Akt pathway, which enhances endothelial cell viability (Valerie et al., 2007; Sonveaux et al., 2007; Zingg et al., 2004). It has previously been shown that IR induced Akt activation is eliminated by over-expression of mutant p85 component of PI3K (Tan & Hallahan, 2003). Mutant p85 functions as a dominant negative by preventing activation of p110 catalytic subunit of PI3K. This inhibition prevents the production of phosphatidylinositol phosphates (PIPs) that activate Akt resulting in enhanced radiation effect. Therefore, inhibition of the PI3K signal transduction pathway can abrogate the endothelial cell survival signaling mediated by Akt.

Although the PI3K/Akt pathway is a major contributor to radiation resistance seen in tumor microvasculature, other pathways activated shortly after IR are also being investigated. Indeed, the activation of Akt has been shown to be critically dependent on binding of Akt's pleckstrin homology (PH) domain to specific PIPs, PIP3 in particular, that allows the co-localization of Akt with upstream activators (Chan et al., 1999). Bone marrow X kinase (Bmx), also known as epithelial and endothelial tyrosine kinase (Etk), contains a PH domain as well as Src homology-2 (SH2) and -3 (SH3) domains capable of interacting with several types of second messengers and adaptor proteins that are known to be present in human umbilical vein endothelial cells (HUVEC; Qiu & Kung, 2000; Chen et al., 2001; Smith et al., 2001; Pan et al., 2002; Vargas et al., 2002; Yang et al., 2002; Nore et al., 2003). Bmx is the ubiquitously expressed member of the Tec family of non-receptor tyrosine kinases with high expression in lung, prostate, and the heart (Qiu & Kung, 2000; Smith et al., 2001). In addition, salivary epithelium, granulomonocytic cells, endothelial cells and epithelial cells express this protein in relatively high amounts (Kaukonen et al., 1996; Mano, 1999; Wen et al.; 1999; Qiu & Kung, 2000; Smith et al., 2001). Bmx appears to act both upstream and downstream of PI3K (Qiu et al., 1998; Ekman et al., 2000; Qiu & Kung, 2000; Chen et al., 2001; Smith et al., 2001; Chau et al., 2002; Zhang et al., 2003; Chau et al., 2005). Bmx also interacts with G-proteins (Qiu &

Kung, 2000; Lee et al., 2001; Kim et al., 2002; Cote et al., 2005), integrins/NRTK's (Chen et al., 2001: Abassi et al., 2003), tumor necrosis factor receptors (Pan et al., 2002), as well as various protein tyrosine phosphatases (Jui et al., 2000) and lipid phosphatases (Tomlinson et al., 2004).

Disclosed herein are investigations into Bmx signaling within the vascular endothelium. As set forth in more detail herein below, Bmx was activated rapidly in response to clinically relevant doses of ionizing radiation. Bmx inhibition enhanced the efficacy of radiotherapy in endothelial cells, tumor vascular endothelium in lung cancer tumors in mice. Retroviral shRNA knockdown of Bmx protein enhanced HUVEC radiosensitization. Furthermore, pretreatment of HUVEC with a pharmacological inhibitor of Bmx, LFM-A13, produced significant radiosensitization of endothelial cells as measured by clonogenic survival analysis and apoptosis as well as functional assays including cell migration and tubule formation. In vivo, LFM-A13, when combined with radiation resulted in significant tumor microvascular destruction as well as enhanced tumor growth delay. Bmx therefore represents a molecular target for the development of novel radiosensitizing agents.

II. Definitions

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art. While the following terms are believed to be well understood by one of ordinary skill in the art, the following definitions are set forth to facilitate explanation of the presently disclosed subject matter.

Following long-standing patent law convention, the terms "a", "an", and "the" mean "one or more" when used in this application, including the claims. Thus, the phrase "a cell" refers to one or more cells, and can thus also refer to a tissue or an organ.

The term "about", as used herein when referring to a measurable value such as an amount of weight, time, dose (e.g., radiation dose), etc. is meant to encompass in some embodiments variations of ±20% or ±10%, in some embodiments ±5%, in some embodiments ±1%, in some embodiments ±01%, and in some embodiments ±0.01% from the specified amount, as such variations are appropriate to perform the disclosed methods.

The terms "nucleic acid molecule" and "nucleic acid" each refer to deoxyribonucleotides or ribonucleotides and polymers thereof in single-stranded, double-stranded, or triplexed form. Unless specifically limited, the term encompasses nucleic acids containing known analogues of natural nucleotides that have similar properties as the reference natural nucleic acid. The terms "nucleic acid molecule" and "nucleic acid" can also be used in place of "gene", "cDNA", or "mRNA". Nucleic acids of the presently claimed subject matter can be cloned, synthesized, recombinantly altered, mutagenized, or combinations thereof. Standard recombinant DNA and molecular cloning techniques used to isolate nucleic acids are known in the art. Site-specific mutagenesis to create base pair changes, deletions, or small insertions is also known in the art as exemplified by publications. See e.g., Sambrook & Russell, 2001; Silhavy et al., 1984; Glover & Hames, 1995; and Ausubel, 1995. Nucleic acids can be derived from any source, including any organism.

The term "substantially identical", as used herein to describe a degree of similarity between nucleotide sequences, refers to two or more sequences that have in some embodiments at least about least 60%, in another embodiment at least about 70%, in another embodiment at least about 80%, in another embodiment about 90% to about 99%, in another embodiment about 95% to about 99%, and in some embodiments about 99% nucleotide identity, when compared and aligned for maximum correspondence, as measured using a sequence comparison algorithm or by visual inspection. In some embodiments, the substantial identity exists in nucleotide sequences of at least about 100 residues, in some embodiments in nucleotide sequences of at least about 150 residues, and in some embodiments in nucleotide sequences comprising a full length coding sequence.

In some embodiments, substantially identical sequences can comprise polymorphic sequences. The term "polymorphic" refers to the occurrence of two or more genetically determined alternative sequences or alleles in a population. An allelic difference can be as small as one base pair. In some embodiments, substantially identical sequences can comprise mutagenized sequences, including sequences comprising silent mutations. A mutation can comprise a single base change.

Another indication that two nucleotide sequences are substantially identical is that the two molecules specifically or substantially hybridize to each other under stringent conditions. In the context of nucleic acid hybridization, two nucleic acid sequences being compared can be designated a "probe" and a "target". A "probe" is a reference nucleic acid molecule, and a "target" is a test nucleic acid molecule, often found within a heterogeneous population of nucleic acid molecules. A "target sequence" is synonymous with a "test sequence".

In some embodiments, a nucleotide sequence employed for hybridization studies or assays includes probe sequences that are complementary to or mimic at least an about 14 to 40 nucleotide sequence of a nucleic acid molecule of the presently claimed subject matter. In some embodiments, probes comprise 14 to 20 nucleotides, or even longer where desired, such as 30, 40, 50, 60, 100, 200, 300, or 500 nucleotides or up to the full length of any one of the sequences of the presently claimed subject matter. Such probes can be readily prepared by, for example, chemical synthesis of the fragment, by application of nucleic acid amplification technology, or by introducing selected sequences into recombinant vectors for recombinant production.

The phrase "hybridizing specifically to" refers to the binding, duplexing, or hybridizing of a molecule only to a particular nucleotide sequence under stringent hybridization and wash conditions when that sequence is present in a complex nucleic acid mixture (e.g., total cellular DNA or RNA).

The phrase "hybridizing substantially to" refers to complementary hybridization between a probe nucleic acid molecule and a target nucleic acid molecule and embraces minor mismatches that can be accommodated by reducing the stringency of the hybridization media to achieve the desired hybridization.

"Stringent hybridization conditions" and "stringent hybridization wash conditions" in the context of nucleic acid hybridization experiments such as Southern and Northern blot analysis are both sequence- and environment-dependent. Longer sequences hybridize specifically at higher temperatures. An extensive guide to the hybridization of nucleic acids is found in Tijssen, 1993. Generally, highly stringent hybridization and wash conditions are selected to be about 5° C. lower than the thermal melting point ($T_m$) for the specific sequence at a defined ionic strength and pH. Typically, under "stringent conditions" a probe will hybridize specifically to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.1×SSC at 65° C. An example of stringent wash conditions is 15 minutes in 0.2×SSC buffer at 65° C. See Sambrook & Russell, 2001 for a description of SSC buffer. Often, a high stringency wash is preceded by a low stringency wash to remove background probe signal. An example of medium stringency wash conditions for a duplex of more than about 100 nucleotides is 15 minutes in 1×SSC at 45° C. An example of low stringency wash for a duplex of more than about 100 nucleotides is 15 minutes in 4× to 6×SSC at 40° C. For short probes (e.g., about 10 to 50 nucleotides), stringent conditions typically involve salt concentrations of less than about 1M Na$^+$ ion, typically about 0.01 to 1M Na$^+$ ion concentration (or other salts) at pH 7.0-8.3, and the temperature is typically at least about 30° C. Stringent conditions can also be achieved with the addition of destabilizing agents such as formamide. In general, a signal to noise ratio of 2-fold (or higher) than that observed for an unrelated probe in the particular hybridization assay indicates detection of a specific hybridization.

The following are additional examples of hybridization and wash conditions that can be used to identify nucleotide sequences that are substantially identical to reference nucleotide sequences of the presently claimed subject matter: a probe nucleotide sequence in one example hybridizes to a target nucleotide sequence in 7% sodium dodecyl sulfate (SDS), 0.5M NaPO$_4$, 1 mM EDTA at 50° C. followed by washing in 2×SSC, 0.1% SDS at 50° C.; in another example, a probe and target sequence hybridize in 7% sodium dodecyl sulfate (SDS), 0.5M NaPO$_4$, 1 mM EDTA at 50° C. followed by washing in 1×SSC, 0.1% SDS at 50° C.; in another example, a probe and target sequence hybridize in 7% sodium dodecyl sulfate (SDS), 0.5M NaPO$_4$, 1 mM EDTA at 50° C. followed by washing in 0.5×SSC, 0.1% SDS at 50° C.; in another example, a probe and target sequence hybridize in 7% sodium dodecyl sulfate (SDS), 0.5M NaPO$_4$, 1 mM EDTA at 50° C. followed by washing in 0.1×SSC, 0.1% SDS at 50° C.; in another example, a probe and target sequence hybridize in 7% sodium dodecyl sulfate (SDS), 0.5M NaPO$_4$, 1 mM EDTA at 50° C. followed by washing in 0.1×SSC, 0.1% SDS at 65° C.

A further indication that two nucleic acid sequences are substantially identical is that the proteins encoded by the nucleic acids are substantially identical, share an overall three-dimensional structure, or are biologically functional equivalents. Nucleic acid molecules that do not hybridize to each other under stringent conditions are still substantially identical if the corresponding proteins are substantially identical. This can occur, for example, when two nucleotide sequences are significantly degenerate as permitted by the genetic code.

The term "conservatively substituted variants" refers to nucleic acid sequences having degenerate codon substitutions wherein the third position of one or more selected (or all) codons is substituted with mixed-base and/or deoxyinosine residues (Ohtsuka et al., 1985; Batzer et al., 1991; Rossolini et al., 1994).

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art. See e.g., Kyte & Doolittle, 1982. It is known that certain amino acids can be substituted for other amino acids having a similar hydropathic index or score and still retain a similar biological activity. In making changes based upon the hydropathic index, one example involves the substitution of amino acids whose hydropathic indices are within ±2 of the original value, another example involves those that are within ±1 of the original value, and yet another example involves those within ±0.5 of the original value.

It is also understood in the art that the substitution of like amino acids can be made effectively based on hydrophilicity. U.S. Pat. No. 4,554,101 describes that the greatest local average hydrophilicity of a protein, as governed by the hydrophilicity of its adjacent amino acids, correlates with its immunogenicity and antigenicity, e.g., with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, one example involves the substitution of amino acids whose hydrophilicity values are within ±2 of the original value, another example involves those that are within ±1 of the original value, and still another example involves those within ±0.5 of the original value.

The term "subsequence" refers to a sequence of nucleic acids that comprises a part of a longer nucleic acid sequence. An exemplary subsequence is a probe, described herein above, or a primer. The term "primer" as used herein refers to a contiguous sequence comprising in some embodiments about 8 or more deoxyribonucleotides or ribonucleotides, in some embodiments 10-20 nucleotides, and in some embodiments 20-30 nucleotides of a selected nucleic acid molecule. The primers of the presently claimed subject matter encompass oligonucleotides of sufficient length and appropriate sequence so as to provide initiation of polymerization on a nucleic acid molecule of the presently claimed subject matter. In the context of an siRNA (discussed in more detail herein-below), an exemplary subsequence is a sequence that comprises part of a duplexed region of an siRNA, one strand of which is complementary to the sequence of an mRNA.

III. Radiosensitivity

In some embodiments, a method for increasing the radiosensitivity of a target tissue in a subject via administration of a modulator of a biological activity of a bone marrow X kinase (Bmx) gene product is provided. The method comprises administering a Bmx antagonist to the subject, whereby the radiosensitivity of a target tissue is increased. The presently described subject matter also provides a method for suppressing tumor growth in a subject. The method comprises: (a) administering a modulator of a biological activity of a bone marrow X kinase (Bmx) gene product to a subject bearing a tumor to increase the radiosensitivity of the tumor; and (b) treating the tumor with ionizing radiation, whereby tumor growth is suppressed. The presently claimed subject matter also provides a method for inhibiting tumor blood vessel growth. The method comprises (a) administering modulator of a biological activity of a bone marrow X kinase (Bmx) gene product to a subject bearing a tumor to increase the radiosensitivity of tumor blood vessels; and (b) treating the tumor with ionizing radiation, whereby tumor blood vessel growth is inhibited.

The term "radiosensitivity" as used herein to describe a target tissue refers to a quality of susceptibility to treatment using ionizing radiation. This susceptibility can result from direct effects of the radiation on the cells of the target tissue themselves. For example, radiation can cause the cells of the target tissue to undergo apoptosis as a result of either DNA damage or another cell autonomous mechanism. Alternatively, radiosensitivity can result from indirect effects, such as effects on the microenvironment of the cells of the target tissue, for example, on the blood vessels supplying nutrients and oxygen to the target tissue. Thus, radiotherapy can be used to suppress the growth of a radiosensitive target tissue.

Radiosensitivity can be quantified by determining a minimal amount of ionizing radiation that can be used to delay target tissue growth. Thus, the term "radiosensitivity" refers to a quantitative range of radiation susceptibility.

The term "target tissue" refers to any cell or group of cells present in a subject. This term includes single cells and populations of cells. The term includes but is not limited to cell populations comprising glands and organs such as skin, liver, heart, kidney, brain, pancreas, lung, stomach, and reproductive organs. It also includes but is not limited to mixed cell populations such as bone marrow. Further, it includes but is not limited to such abnormal cells as neoplastic or tumor cells, whether individually or as a part of solid or metastatic tumors. The term "target tissue" as used herein additionally refers to an intended site for accumulation of a modulator of a biological activity of a bone marrow X kinase (Bmx) gene product following administration to a subject. For example, the methods of the presently claimed subject matter employ a target tissue comprising a tumor and/or the vasculature providing oxygen to a tumor.

The term "suppressing tumor growth" refers to an increase in a duration of time required for a tumor to grow a specified amount. For example, treatment can extend the time required for a tumor to increase in volume to 2-fold, 3-fold, 4-fold, 5-fold, or longer relative to an initial day of measurement (day 0) or the time required to grow to a volume of 1 cm$^3$.

The terms "radiation resistant tumor" and "radioresistant tumor" each generally refer to a tumor that is substantially unresponsive to radiotherapy when compared to other tumors. Representative radiation resistant tumor models include but are not limited to glioblastoma multiforme and melanoma.

The term "increase" as used herein to refer to a change in radiosensitivity of a tumor refers to change that renders a tumor more susceptible to destruction by ionizing radiation. Alternatively stated, an increase in radiosensitivity refers to a decrease in the minimal amount of ionizing radiation that effectively suppresses tumor growth. An increase in radiosensitivity can also comprise suppressed tumor growth or inhibited tumor blood vessel growth when a modulator of a biological activity of a bone marrow X kinase (Bmx) gene product is administered with radiation as compared to a same dose of radiation alone. An increase in radiosensitivity refers to an increase of in some embodiments at least about 2-fold, in some embodiments at least about 5-fold, and in some embodiments at least 10-fold. In some embodiments of the presently claimed subject matter, an increase in radiosensitivity comprises a transformation of a radioresistant tumor to a radiosensitive tumor.

The methods of the presently claimed subject matter are useful for increasing the radiosensitivity of a target tissue, for suppressing tumor growth, and/or for inhibiting blood vessel growth in any subject. Thus, the term "subject" as used herein includes any vertebrate species, for example, warm-blooded vertebrates such as mammals and birds. More particularly, the methods of the presently claimed subject matter are provided for the treatment of tumors in mammals such as humans, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants and livestock (such as cattle, oxen, sheep, giraffes, deer, goats, bison, and camels), and horses. Also provided is the treatment of birds, including those kinds of birds that are endangered or kept in zoos, as well as fowl, and more particularly domesticated fowl or poultry, such as turkeys, chickens, ducks, geese, guinea fowl, and the like, as they are also of economic importance to humans.

The term "tumor" as used herein encompasses both primary and metastasized solid tumors and carcinomas of any tissue in a subject, including but not limited to breast; colon; rectum; lung; oropharynx; hypopharynx; esophagus; stomach; pancreas; liver; gallbladder; bile ducts; small intestine; urinary tract including kidney, bladder and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas and meningiomas). The term "tumor" also encompasses solid tumors arising from hematopoietic malignancies such as leukemias, including chloromas, plasmacytomas, plaques and tumors of mycosis fungoides and cutaneous T-cell lymphoma/leukemia, and lymphomas including both Hodgkin's and non-Hodgkin's lymphomas. The term "tumor" also encompasses radioresistant tumors, including radioresistant variants of the any of the tumor listed above.

IV. Modulators of Bmx Gene Product Biological Activities

Any suitable modulator of a biological activity of a Bmx gene product can be used in accordance with the methods of the presently claimed subject matter. In some embodiments, the antagonist has a capacity to increase the radiosensitivity of a target tissue. In some embodiments, a modulator of a biological activity of a Bmx gene product also shows anti-angiogenic activity, angiostatic activity, or both.

The phrase "a modulator of a biological activity of a Bmx gene product" as used herein can refer to a molecule or other chemical entity having a capacity for specifically binding to a Bmx gene product to thereby enhance or suppress a biological activity of the Bmx gene product. Modulators of biological activities of Bmx gene products include but are not limited to small molecule inhibitors, neutralizing antibodies, and nucleic acid-based antagonists (e.g., siRNAs directed against a Bmx gene products).

The term "Bmx" refers to a bone marrow X kinase (Gene Symbol BMX), which is a nonreceptor tyrosine kinase gene of the BTK/ITK/TEC/TXK family. Bmx nucleotide and amino acid sequences from several species have been determined, a non-limiting subset of which are set forth in Table 1. An alignment of the amino acid sequences presented in even-numbered SEQ ID NOs: 2-20 that has been maximized for overlap beginning at amino acid position 1 of SEQ ID NO: 2 is presented in FIG. 8.

TABLE 1

Bmx GENBANK ® Sequences

| Organism | Nucleic Acid Accession No. | Amino Acid Accession No. |
| --- | --- | --- |
| Homo sapiens | NM_203281; SEQ ID NO: 1 NM_001721; SEQ ID NO: 3 | NP_975010; SEQ ID NO: 2 NP_001712; SEQ ID NO: 4 |
| Macaca mulatta | XM_001101349; SEQ ID NO: 5 XM_001101166; SEQ ID NO: 7 XM_001101250; SEQ ID NO: 9 | XP_001101349; SEQ ID NO: 6 XP_001101166; SEQ ID NO: 8 XP_001101250; SEQ ID NO: 10 |
| Mus musculus | NM_009759; SEQ ID NO: 11 | NP_033889; SEQ ID NO: 12 |
| Rattus norvegicus | NM_001109016; SEQ ID NO: 13 | NP_001102486; SEQ ID NO: 14 |
| Bos taurus | XM_610012; SEQ ID NO: 15 | XP_610012; SEQ ID NO: 16 |
| Canis familiaris | XM_548870; SEQ ID NO: 17 | XP_548870; SEQ ID NO: 18 |
| Equus caballus | XM_001490091; SEQ ID NO: 19 | XP_001490141; SEQ ID NO: 20 |

The phrase "open reading frame" (ORF) refers to a sequence of nucleotides that are translated into a polypeptide. An open reading frame generally begins with an initiator codon (ATG/AUG) and terminates with the translation termination codon (e.g., TAG/UAG, TAA/UAA, or TGA/UGA) also referred to as a "stop codon". Table 2 summarizes the nucleotides that correspond to the open reading frames of the Bmx gene products listed in Table 1.

TABLE 2

Bmx Gene Product Open Reading Frames

| Organism | SEQ ID NO: | ORF Nucleotides |
| --- | --- | --- |
| Homo sapiens | SEQ ID NO: 1 | 174-2201 |
| | SEQ ID NO: 3 | 112-2139 |
| Macaca mulatta | SEQ ID NO: 5 | 162-2201 |
| | SEQ ID NO: 7 | 187-2229 |
| | SEQ ID NO: 9 | 143-2170 |
| Mus musculus | SEQ ID NO: 11 | 156-2111 |
| Rattus norvegicus | SEQ ID NO: 13 | 139-2106 |
| Bos taurus | SEQ ID NO: 15 | 1-1965 |
| Canis familiaris | SEQ ID NO: 17 | 1-2628 |
| Equus caballus | SEQ ID NO: 19 | 1-1965 |

The term "binding" refers to an affinity between two molecules, for example, an inhibitor and a target molecule. As used herein, the phrases "specific binding" and "selective binding" refer to a preferential binding of one molecule for another in a mixture of molecules. The binding of an inhibitor to a target molecule generally can be considered specific or selective if the binding affinity is about $1 \times 10^4$ $M^{-1}$ to about $1 \times 10^6$ $M^{-1}$ or greater.

IV.A. Small Molecules

The term "small molecule" as used herein refers to a compound, for example an organic compound, with a molecular weight of in some embodiments less than about 1,000 daltons, in some embodiments less than about 750 daltons, in some embodiments less than about 600 daltons, and in some embodiments less than about 500 daltons. A small molecule also has a computed log octanol—water partition coefficient in the range of about −4 to about +14 in some embodiments, and in the range of about −2 to about +7.5 in some embodiments.

A representative, non-limiting example of a modulator of a biological activity of a Bmx gene product is LFM-A13, which has the chemical names (2Z)-2-cyano-N-(2,5-dibromophenyl)-3-hydroxy-2-butenamide and α-cyano-β-hydroxy-β-methyl-N-(2,5-dibromophenyl)propenamide. Its molecular formula is $C_{11}H_8Br_2N_2O_2$, and it has a molecular weight of 360.00. It is available from Sigma-Aldrich Chemical Co. of St. Louis, Mo., United States of America.

IV.B. Anti-Bmx Antibodies

The presently claimed subject matter further provides a modulator of a biological activity of a Bmx gene product that comprises an antibody that specifically binds a Bmx gene product. Optionally, a modulator of a biological activity of a Bmx gene product can further comprise a carrier for sustained bioavailability of the antibody at a tumor. The disclosure herein provides that a prolonged or sustained release of modulator of a biological activity of a Bmx gene product is optionally employed to enhance the therapeutic effect of combined Bmx modulation and radiation.

The term "antibody" indicates an immunoglobulin protein, or functional portion thereof, including a polyclonal antibody, a monoclonal antibody, a chimeric antibody, a hybrid antibody, a single chain antibody (e.g., a single chain antibody represented in a phage library), a mutagenized antibody, a humanized antibody, and antibody fragments that comprise an antigen binding site (e.g., Fab and Fv antibody fragments). In some embodiments, an antibody of the presently claimed subject matter is a monoclonal antibody.

Techniques for preparing and characterizing antibodies are known in the art. See e.g., Harlow & Lane, 1988 and U.S. Pat. Nos. 4,196,265; 4,946,778; 5,091,513; 5,132,405; 5,260,203; 5,677,427; 5,892,019; 5,985,279; 6,054,561. Single chain antibodies can be identified by screening a phage antibody library, for example as described by U.S. Pat. Nos. 6,174,708; 6,057,098; 5,922,254; 5,840,479; 5,780,225; 5,702,892; and 5,667,988.

An antibody of the presently claimed subject matter can further be mutagenized or otherwise modified to improve antigen binding and/or antibody stability. For example, to prevent undesirable disulfide bond formation, a nucleotide sequence encoding the variable domain of an antibody or antibody fragment can be modified to eliminate at least one of each pair of codons that encode cysteines for disulfide bond formation. Recombinant expression of the modified nucleotide sequence, for example in a prokaryotic expression system, results in an antibody having improved stability. See U.S. Pat. No. 5,854,027.

IV.C. Aptamers

In some embodiments, a biological activity of a Bmx gene product comprises an aptamer that specifically binds to a Bmx polypeptide. As used herein, "aptamer" refers in general to either an oligonucleotide of a single defined sequence or a mixture of said oligonucleotides, wherein the mixture retains the properties of binding specifically to the target molecule. Thus, as used herein "aptamer" denotes both singular and plural sequences of oligonucleotides, as defined hereinabove. The term "aptamer" is meant to refer to a single- or double-stranded nucleic acid which is capable of binding to a protein or other molecule, and thereby disturbing the protein's or other molecule's function.

In general, aptamers comprise in some embodiments about 10 to about 100 nucleotides, in some embodiments about 15 to about 40 nucleotides, in some embodiments about 20 to about 40 nucleotides, in that oligonucleotides of a length that falls within these ranges are readily prepared by conventional techniques. Optionally, aptamers can further comprise in some embodiments a minimum of approximately 6 nucleotides, in some embodiments 10 nucleotides, and in some embodiments 14 or 15 nucleotides, that are necessary to effect specific binding. The only apparent limitations on the binding specificity of the target/oligonucleotide couples of the presently disclosed subject matter concern sufficient sequence to be distinctive in the binding oligonucleotide and sufficient binding capacity of the target substance to obtain the necessary interaction. Aptamers of binding regions containing sequences shorter than 10, e.g., 6-mers, are feasible if the appropriate interaction can be obtained in the context of the environment in which the target is placed. Thus, if there is little interference by other materials, less specificity and less strength of binding can be required.

Aptamers and how to isolate aptamers that bind to specific targets are disclosed in U.S. Patent Application Publication No. 20030175703 and U.S. Pat. Nos. 5,270,163; 5,567,588; 5,683,867; 6,706,482; 6,855,496; and 7,176,295, the disclosure of each of which is hereby incorporated by reference in its entirety.

IV.D. RNAi-Based Bmx Modulators

In some embodiments, the presently disclosed subject matter takes advantage of the ability of short, double stranded RNA molecules to cause the down regulation of cellular genes, a process referred to as RNA interference (RNAi). As used herein, "RNA interference" and "RNAi" refer to a process of sequence-specific post-transcriptional gene silencing mediated by a small interfering RNA (siRNA). See generally Fire et al., 1998; U.S. Pat. No. 6,506,559. The process of post-transcriptional gene silencing is thought to be an evolutionarily conserved cellular defense mechanism that has evolved to prevent the expression of foreign genes (Fire, 1999).

The presence of dsRNA in cells triggers various responses, one of which is RNAi. RNAi appears to be different from the interferon response to dsRNA, which results from dsRNA-mediated activation of an RNA-dependent protein kinase (PKR) and 2',5'-oligoadenylate synthetase, resulting in non-specific cleavage of mRNA by ribonuclease L.

The presence of long dsRNAs in cells stimulates the activity of the enzyme Dicer, a ribonuclease III. Dicer catalyzes the degradation of dsRNA into short stretches of dsRNA referred to as small interfering RNAs (siRNA; Zamore et al., 2000). The small interfering RNAs that result from Dicer-mediated degradation are typically about 21-23 nucleotides in length and contain about 19 base pair duplexes. After degradation, the siRNA is incorporated into an endonuclease complex referred to as an RNA-induced silencing complex (RISC). The RISC is capable of mediating cleavage of single stranded RNA present within the cell that is complementary to the antisense strand of the siRNA duplex. According to Elbashir et al., cleavage of the target RNA occurs near the middle of the region of the single stranded RNA that is complementary to the antisense strand of the siRNA duplex (Elbashir et al., 2001b).

RNAi has been described in several cell type and organisms. Fire et al., 1998 described RNAi in *C. elegans*. Wianny & Zernicka-Goetz, 1999 disclose RNAi mediated by dsRNA in mouse embryos. Hammond et al., 2000 were able to induce RNAi in *Drosophila* cells by transfecting dsRNA into these cells. Elbashir et al. 2001a discloses the presence of RNAi in cultured mammalian cells including human embryonic kidney and HeLa cells by the introduction of duplexes of synthetic 21 nucleotide RNAs.

Experiments using *Drosophila* embryonic lysates revealed certain aspects of siRNA length, structure, chemical composition, and sequence that are involved in RNAi activity. See Elbashir et al., 2001c. In the disclosed assay, 21 nucleotide siRNA duplexes were most active when they contain 3'-overhangs of two nucleotides. Also, the position of the cleavage site in the target RNA was shown to be defined by the 5'-end of the siRNA guide sequence rather than the 3'-end (Elbashir et al., 2001b).

Other studies have indicated that a 5'-phosphate on the target-complementary strand of a siRNA duplex is required for siRNA activity and that ATP is utilized to maintain the 5-phosphate moiety on the siRNA (Nykanen et al., 2001). Other modifications that might be tolerated when introduced into an siRNA molecule include modifications of the sugar-phosphate backbone or the substitution of the nucleoside with at least one of a nitrogen or sulfur heteroatom (PCT International Publication Nos. WO 00/44914 and WO 01/68836) and certain nucleotide modifications that might inhibit the activation of double stranded RNA-dependent protein kinase (PKR), specifically 2'-amino or 2'-O-methyl nucleotides, and nucleotides containing a 2'-O or 4'-C methylene bridge (Canadian Patent Application No. 2,359,180).

Other references disclosing the use of dsRNA and RNAi include PCT International Publication Nos. WO 01/75164 (in vitro RNAi system using cells from *Drosophila* and the use of specific siRNA molecules for certain functional genomic and certain therapeutic applications); WO 01/36646 (methods for inhibiting the expression of particular genes in mammalian cells using dsRNA molecules); WO 99/32619 (methods for introducing dsRNA molecules into cells for use in inhibiting gene expression); WO 01/92513 (methods for mediating gene suppression by using factors that enhance RNAi); WO 02/44321 (synthetic siRNA constructs); WO 00/63364 and WO 01/04313 (methods and compositions for inhibiting the function of polynucleotide sequences); and WO 02/055692 and WO 02/055693 (methods for inhibiting gene expression using RNAi).

In some embodiments, the modulator of a biological activity of a Bmx gene product comprises an siRNA construct targeted to or against a Bmx gene product (e.g., a subsequence of an RNA molecule transcribed from a Bmx gene).

As used herein, the phrase "target RNA" refers to an RNA molecule (for example, an mRNA molecule encoding a Bmx gene product) that is a target for downregulation. Similarly, the phrase "target site" refers to a sequence within a target RNA that is "targeted" for cleavage mediated by an siRNA construct that contains sequences within its antisense strand that are complementary to the target site. Also similarly, the phrase "target cell" refers to a cell that expresses a target RNA and into which an siRNA is intended to be introduced. A target cell is in some embodiments a cell in a subject. For example, a target cell can comprise a tumor cell and/or a cell in tumor vasculature that expresses a Bmx gene. Non-limiting examples of sequences encoding target RNA molecules of the presently disclosed subject matter are presented in Table 1.

As used herein, the phrase "detectable level of cleavage" refers to a degree of cleavage of target RNA (and formation of cleaved product RNAs) that is sufficient to allow detection of cleavage products above the background of RNAs produced by random degradation of the target RNA. Production of siRNA-mediated cleavage products from at least 1-5% of the target RNA is sufficient to allow detection above background for most detection methods.

The terms "small interfering RNA", "short interfering RNA", and "siRNA" are used interchangeably and refer to any nucleic acid molecule capable of mediating RNA interference (RNAi) or gene silencing. See e.g., Bass, 2001; Elbashir et al., 2001a; and PCT International Publication Nos. WO 00/44895, WO 01/36646, WO 99/32619, WO 00/01846, WO 01/29058, WO 99/07409, and WO 00/44914. In some embodiments, the siRNA comprises a double stranded polynucleotide molecule comprising complementary sense and antisense regions, wherein the antisense region comprises a sequence complementary to a region of a target nucleic acid molecule (for example, an mRNA encoding a Bmx polypeptide). In some embodiments, the siRNA comprises a single stranded polynucleotide having self-complementary sense and antisense regions, wherein the antisense region comprises a sequence complementary to a region of a target nucleic acid molecule. In some embodiments, the siRNA comprises a single stranded polynucleotide having one or more loop structures and a stem comprising self complementary sense and antisense regions, wherein the antisense region comprises a sequence complementary to a region of a target nucleic acid molecule, and wherein the polynucleotide can be processed either in vivo or in vitro to generate an active siRNA capable of mediating RNAi. An siRNA that forms such a stem-and-loop structure (i.e., a "hairpin") is also referred to herein as a "short hairpin RNA (shRNA)". As used herein, siRNA molecules need not be limited to those molecules containing only RNA, but further encompass chemically modified nucleotides and non-nucleotides.

Figure 7:
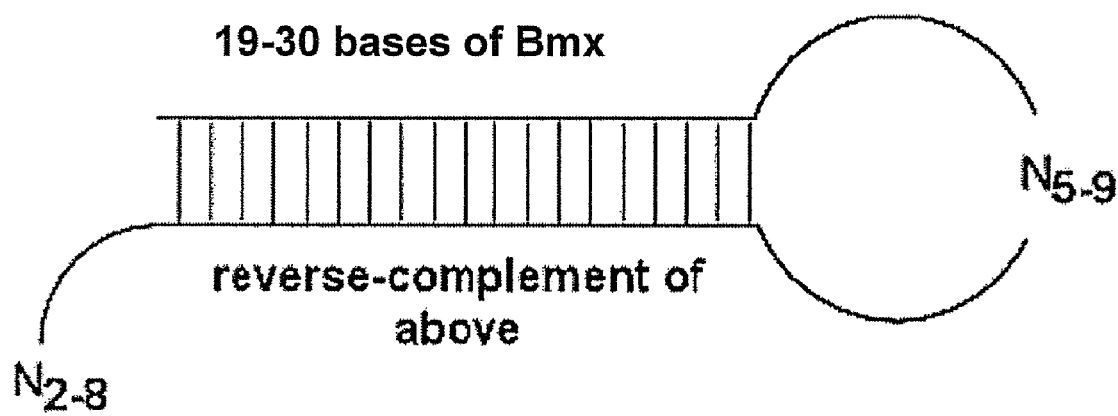
FIG. 7 is a depiction of an exemplary structure for an siRNA targeted to a Bmx gene product.

The siRNA molecules of the presently disclosed subject matter include, but are not limited to an siRNA molecule of the general structure depicted in FIG. 7. For the double-stranded molecule shown in FIG. 7, N can be any nucleotide, provided that in the loop structure identified as $N_{5-9}$, all 5-9 nucleotides remain in a single-stranded conformation. Similarly, $N_{2-8}$ can be any sequence of 2-8 nucleotides or modified nucleotides, provided that the nucleotides remain in a single-stranded conformation in the siRNA molecule. The duplex represented in FIG. 7 as "19-30 bases of Bmx" can be formed using any contiguous 19-30 base sequence of one of the Bmx gene products disclosed herein (for example, in Table 1). In constructing an siRNA molecule of the presently disclosed subject matter, this 19-30 base sequence is followed (in a 5' to 3' direction) by 5-9 random nucleotides ($N_{5-9}$ above), the reverse-complement of the 19-30 base sequence, and finally 2-8 random nucleotides ($N_{2-8}$ above).

The term "gene expression" generally refers to the cellular processes by which a biologically active polypeptide is produced from a DNA sequence and exhibits a biological activity in a cell. As such, gene expression involves the processes of transcription and translation, but also involves post-transcriptional and post-translational processes that can influence a biological activity of a gene or gene product. These processes include, but are not limited to RNA syntheses, processing, and transport, as well as polypeptide synthesis, transport, and post-translational modification of polypeptides. Additionally, processes that affect protein-protein interactions within the cell can also affect gene expression as defined herein.

As used herein, the term "modulate" can refer to a change in the expression level of a gene, or a level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the term "modulate" can mean "inhibit" or "suppress", but the use of the word "modulate" is not limited to this definition.

As used herein, the terms "inhibit", "suppress", "down regulate", and grammatical variants thereof are used interchangeably and refer to an activity whereby gene expression or a level of an RNA encoding one or more gene products is reduced below that observed in the absence of a nucleic acid molecule of the presently disclosed subject matter. In some embodiments, inhibition with an siRNA molecule results in a decrease in the steady state level of a target RNA. In some embodiments, inhibition with a siRNA molecule results in an expression level of a target gene that is below that level observed in the presence of an inactive or attenuated molecule that is unable to mediate an RNAi response. In some embodiments, inhibition of gene expression with an siRNA molecule of the presently disclosed subject matter is greater in the presence of the siRNA molecule than in its absence. In some embodiments, inhibition of gene expression is associated with an enhanced rate of degradation of the mRNA encoded by the gene (for example, by RNAi mediated by an siRNA).

As used herein, the terms "gene" and "target gene" refer to a nucleic acid that encodes an RNA such as, but not limited to a nucleic acid sequence that encodes a Bmx polypeptide. The term "gene" also refers broadly to any segment of DNA associated with a biological function. As such, the term "gene" encompasses sequences including but not limited to a coding sequence, a promoter region, a transcriptional regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence. In some embodiments, a gene is a Bmx gene. Representative Bmx genes correspond to the sequences set forth in Table 1, although this list is not intended to be exhaustive.

As is understood in the art, a gene can comprise a coding strand and a non-coding strand. As used herein, the terms "coding strand" and "sense strand" are used interchangeably, and refer to a nucleic acid sequence that has the same sequence of nucleotides as an mRNA from which the gene product is translated. As is also understood in the art, when the coding strand and/or sense strand is used to refer to a DNA molecule, the coding/sense strand includes thymidine residues instead of the uridine residues found in the corresponding mRNA. Additionally, when used to refer to a DNA molecule, the coding/sense strand can also include additional elements not found in the mRNA including, but not limited to promoters, enhancers, and introns. Similarly, the terms "template strand" and "antisense strand" are used interchangeably and refer to a nucleic acid sequence that is complementary to the coding/sense strand.

The term "complementary sequences", as used herein, indicates two nucleotide sequences that comprise antiparallel nucleotide sequences capable of pairing with one another upon formation of hydrogen bonds between base pairs. As used herein, the term "complementary sequences" means nucleotide sequences which are substantially complementary, as can be assessed by the same nucleotide comparison set forth above, or is defined as being capable of hybridizing to the nucleic acid segment in question under relatively stringent conditions such as those described herein.

Thus, the terms "complementarity" and "complementary" refer to a nucleic acid that can form one or more hydrogen bonds with another nucleic acid sequence by either traditional Watson-Crick or other non-traditional types of interactions. In reference to the nucleic molecules of the presently disclosed subject matter, the binding free energy for a nucleic acid molecule with its complementary sequence is sufficient to allow the relevant function of the nucleic acid to proceed (e.g., RNAi activity. For example, the degree of complementarity between the sense and antisense strands of the siRNA construct can be the same or different from the degree of complementarity between the antisense strand of the siRNA and the target nucleic acid sequence. Complementarity to the target sequence of less than 100% in the antisense strand of the siRNA duplex, including point mutations, is not well tolerated when these changes are located between the 3'-end and the middle of the antisense siRNA, whereas mutations near the 5'-end of the antisense siRNA strand can exhibit a small degree of RNAi activity (Elbashir et al., 2001c). Determination of binding free energies for nucleic acid molecules is well known in the art. See e.g., Freier et al., 1986; Turner et al., 1987.

As used herein, the phrase "percent complementarity" refers to the percentage of contiguous residues in a nucleic acid molecule that can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). The terms "100% complementary", "fully complementary", and "perfectly complementary" indicate that all of the contiguous residues of a nucleic acid sequence can hydrogen bond with the same number of contiguous residues in a second nucleic acid sequence.

The siRNA molecules of the presently disclosed subject matter can be added directly to a cell, or can be complexed with cationic lipids, packaged within liposomes, or otherwise delivered to target cells or tissues. The nucleic acid or nucleic acid complexes can be locally administered to relevant tissues ex vivo, or in vivo through injection, infusion pump or stent, with or without their incorporation into biopolymers. The siRNA molecule of the presently disclosed subject matter can be encoded by a recombinant vector (for example, a viral vector).

As used herein, the term "RNA" refers to a molecule comprising at least one ribonucleotide residue. By "ribonucleotide" is meant a nucleotide with a hydroxyl group at the 2' position of a β-D-ribofuranose moiety. The terms encompass double stranded RNA, single stranded RNA, RNAs with both double stranded and single stranded regions, isolated RNA such as partially purified RNA, essentially pure RNA, synthetic RNA, recombinantly produced RNA, as well as altered RNA, or analog RNA, that differs from naturally occurring RNA by the addition, deletion, substitution, and/or alteration of one or more nucleotides. Such alterations can include addition of non-nucleotide material, such as to the end(s) of the siRNA or internally, for example at one or more nucleotides of the RNA. Nucleotides in the RNA molecules of the presently disclosed subject matter can also comprise non-standard nucleotides, such as non-naturally occurring nucleotides or chemically synthesized nucleotides or deoxynucleotides. These altered RNAs can be referred to as analogs or analogs of a naturally occurring RNA.

As used herein, the phrase "double stranded RNA" refers to an RNA molecule at least a part of which is in Watson-Crick base pairing forming a duplex. As such, the term is to be understood to encompass an RNA molecule that is either fully or only partially double stranded. Exemplary double stranded RNAs include, but are not limited to molecules comprising at least two distinct RNA strands that are either partially or fully duplexed by intermolecular hybridization. Additionally, the term is intended to include a single RNA molecule that by intramolecular hybridization can form a double stranded region (for example, a hairpin). Thus, as used herein the phrases "intermolecular hybridization" and "intramolecular hybridization" refer to double stranded molecules for which the nucleotides involved in the duplex formation are present on different molecules or the same molecule, respectively.

As used herein, the phrase "double stranded region" refers to any region of a nucleic acid molecule that is in a double stranded conformation via hydrogen bonding between the nucleotides including, but not limited to hydrogen bonding between cytosine and guanosine, adenosine and thymidine, adenosine and uracil, and any other nucleic acid duplex as would be understood by one of ordinary skill in the art. The length of the double stranded region can vary from about 15 consecutive basepairs to several thousand basepairs. In some embodiments, the double stranded region is at least 15 basepairs, in some embodiments between 15 and 50 basepairs, and in some embodiments between 15 and 30 basepairs. In some embodiments, the length of the double stranded region is selected from the group consisting of 19, 20, 21, 22, 23, 24, 25, 26, 27, 28, 29, and 30 basepairs. In some embodiments, the double stranded region comprises a first strand comprising a ribonucleotide sequence that corresponds to a coding strand of the Bmx gene and a second strand comprising a ribonucleotide sequence that is complementary to the first strand, and wherein the first strand and the second strand hybridize to each other to form the double-stranded molecule. As used herein, the terms "corresponds to", "corresponding to", and grammatical variants thereof refer to a nucleotide sequence that is 100% identical to at least 19 contiguous nucleotides of a nucleic acid sequence of a Bmx gene. Thus, a first nucleic acid sequence that "corresponds to" a coding strand of a Bmx gene is a nucleic acid sequence that is 100% identical to at least 19 contiguous nucleotides of a Bmx gene, including, but note limited to 5' untranslated sequences, exon sequences, intron sequences, and 3' untranslated sequences.

In a representative embodiment, the length of the double stranded region is 19 basepairs. As describe hereinabove, the formation of the double stranded region results from the hybridization of complementary RNA strands (for example, a sense strand and an antisense strand), either via an intermolecular hybridization (i.e., involving 2 or more distinct RNA molecules) or via an intramolecular hybridization, the latter of which can occur when a single RNA molecule contains self-complementary regions that are capable of hybridizing to each other on the same RNA molecule. These self-complementary regions are typically separated by a short stretch of nucleotides (for example, about 5-10 nucleotides) such that the intramolecular hybridization event forms what is referred to in the art as a "hairpin".

The nucleic acid molecules of the presently disclosed subject matter individually, or in combination or in conjunction with other drugs, can be used to treat diseases or conditions discussed herein. For example, to treat a particular disease or condition, the siRNA molecules can be administered to a subject or can be administered to other appropriate cells evident to those skilled in the art, individually or in combination with one or more drugs under conditions suitable for the treatment.

An exemplary nucleotide sequence employed in the methods disclosed herein comprises sequences that are complementary to each other, the complementary regions being capable of forming a duplex of in some embodiments at least about 15 to 50 basepairs. One strand of the duplex comprises a nucleic acid sequence of at least 15 contiguous bases having a nucleic acid sequence of a nucleic acid molecule of the presently disclosed subject matter (for example, those nucleic acid sequences that correspond to the GENBANK® Accession Nos. set forth in Table 1). In some embodiments, one strand of the duplex comprises a nucleic acid sequence comprising 15 to 18 nucleotides, or even longer where desired, such as 19, 20, 21, 22, 23, 24, 25, 26, 27, 28, 29, or 30 nucleotides or up to the full length of any of those nucleic acid sequences that correspond to the GENBANK® Accession Nos. set forth in Table 1, or any other Bmx transcription product. Such fragments can be readily prepared by, for example, directly synthesizing the fragment by chemical synthesis, by application of nucleic acid amplification technology, or by introducing selected sequences into recombinant vectors for recombinant production. The phrase "hybridizing specifically to" refers to the binding, duplexing, or hybridizing of a molecule only to a particular nucleotide sequence under stringent conditions when that sequence is present in a complex nucleic acid mixture (e.g., total cellular DNA or RNA).

The term "elongated sequence" refers to an addition of nucleotides (or other analogous molecules) incorporated into the nucleic acid. For example, a polymerase (e.g., a DNA polymerase) can add sequences at the 3' terminus of the nucleic acid molecule. In addition, the nucleotide sequence can be combined with other DNA sequences, such as promoters, promoter regions, enhancers, polyadenylation signals, intronic sequences, additional restriction enzyme sites, multiple cloning sites, and other coding segments.

The phrases "operatively linked" and "operably linked", as used herein, refer to a functional combination between a promoter region and a nucleotide sequence such that the transcription of the nucleotide sequence is controlled and regulated by the promoter region. Similarly, a nucleotide sequence is said to be under the "transcriptional control" of a promoter to which it is operably linked. Techniques for operatively linking a promoter region to a nucleotide sequence are known in the art. The phrases are also intended to refer to functional combinations between promoter regions and/or nucleotide sequences and/or other nucleotide sequence features that interact with the promoter regions and/or the nucleotide sequences to affect transcription of the nucleotide sequences and/or the nature of the transcript produced. Exemplary nucleotide sequence features that can also be operably linked to promoters and/or nucleotide sequences include, but are not limited to enhancers, suppressors, transcription termination signals, polyadenylation signals, etc.

The term "heterologous", as used herein to refer to a promoter or any other nucleic acid, refers to a sequence that originates from a source foreign to an intended host cell or, if from the same source, is modified from its original form. Thus, a heterologous nucleic acid in a host cell includes a gene that is endogenous to the particular host cell but has been modified, for example by mutagenesis or by isolation from native cis-regulatory sequences.

The terms "heterologous gene", "heterologous DNA sequence", "heterologous nucleotide sequence", "exogenous nucleic acid molecule", or "exogenous DNA segment", as used herein, each refer to a sequence that originates from a source foreign to an intended host cell or, if from the same source, is modified from its original form. Thus, a heterologous gene in a host cell includes a gene that is endogenous to the particular host cell but has been modified, for example by mutagenesis or by isolation from native transcriptional regulatory sequences. The terms also include non-naturally occurring multiple copies of a naturally occurring nucleotide sequence. Thus, the terms refer to a DNA segment that is foreign or heterologous to the cell, or homologous to the cell but in a position within the host cell nucleic acid wherein the element is not ordinarily found.

The term "recombinant" generally refers to an isolated nucleic acid that is replicable in a non-native environment. Thus, a recombinant nucleic acid can comprise a non-replicable nucleic acid in combination with additional nucleic acids, for example vector nucleic acids, which enable its replication in a host cell.

The term "vector" is used herein to refer to a nucleic acid molecule having nucleotide sequences that enable its replication in a host cell. A vector can also include nucleotide sequences to permit ligation of nucleotide sequences within the vector, wherein such nucleotide sequences are also replicated in a host cell. Representative vectors include plasmids, cosmids, and viral vectors. A vector can also mediate recombinant production of a soluble peptide or polypeptide of the presently disclosed subject matter.

The terms "expression vector" and "expression construct" as used herein refer to a DNA sequence capable of directing expression of a particular nucleotide sequence in an appropriate host cell, comprising a promoter operatively linked to the nucleotide sequence of interest which is operably linked to termination signals. It also typically comprises sequences required for proper translation of the nucleotide sequence. The construct comprising the nucleotide sequence of interest can be chimeric. The construct can also be one that is naturally occurring but has been obtained in a recombinant form useful for heterologous expression.

The term "construct", as used herein to describe an expression construct, refers to a vector further comprising a nucleotide sequence operably inserted with the vector, such that the nucleotide sequence is expressed.

The terms "recombinantly expressed" or "recombinantly produced" are used interchangeably to generally refer to the process by which a polypeptide encoded by a recombinant nucleic acid is produced.

The term "heterologous expression system" refers to a host cell comprising a heterologous nucleic acid and the polypeptide encoded by the heterologous nucleic acid. For example, a heterologous expression system can comprise a host cell transfected with a construct comprising a recombinant nucleic acid, or a cell line produced by introduction of heterologous nucleic acids into a host cell genome.

The term "promoter" or "promoter region" each refers to a nucleotide sequence within a gene that is positioned 5' to a coding sequence of a same gene and functions to direct transcription of the coding sequence. The promoter region comprises a transcriptional start site, and can additionally include one or more transcriptional regulatory elements. In some embodiments, a method of the presently disclosed subject matter employs a hypoxia inducible promoter.

A "minimal promoter" is a nucleotide sequence that has the minimal elements required to enable basal level transcription to occur. As such, minimal promoters are not complete promoters but rather are subsequences of promoters that are capable of directing a basal level of transcription of a reporter construct in an experimental system. Minimal promoters include but are not limited to the CMV minimal promoter, the HSV-tk minimal promoter, the simian virus 40 (SV40) minimal promoter, the human β-actin minimal promoter, the human EF2 minimal promoter, the adenovirus E1B minimal promoter, and the heat shock protein (hsp) 70 minimal promoter. Minimal promoters are often augmented with one or more transcriptional regulatory elements to influence the transcription of an operably linked gene. For example, cell-type-specific or tissue-specific transcriptional regulatory elements can be added to minimal promoters to create recombinant promoters that direct transcription of an operably linked nucleotide sequence in a cell-type-specific or tissue-specific manner Different promoters have different combinations of transcriptional regulatory elements. Whether or not a gene is expressed in a cell is dependent on a combination of the particular transcriptional regulatory elements that make up the gene's promoter and the different transcription factors that are present within the nucleus of the cell. As such, promoters are often classified as "constitutive", "tissue-specific", "cell-type-specific", or "inducible", depending on their functional activities in vivo or in vitro. For example, a constitutive promoter is one that is capable of directing transcription of a gene in a variety of cell types. Exemplary constitutive promoters include the promoters for the following genes which encode certain constitutive or "housekeeping" functions: hypoxanthine phosphoribosyl transferase (HPRT), dihydrofolate reductase (DHFR; (Scharfmann et al., 1991), adenosine deaminase, phosphoglycerate kinase (PGK), pyruvate kinase, phosphoglycerate mutase, the β-actin promoter (see e.g., Williams et al., 1993), and other constitutive promoters known to those of skill in the art. "Tissue-specific" or "cell-type-specific" promoters, on the other hand, direct transcription in some tissues and cell types but are inactive in others. Exemplary tissue-specific promoters include the PSA promoter (Yu et al., 1999; Lee et al., 2000), the probasin promoter (Greenberg et al., 1994; Yu et al., 1999), and the MUC1 promoter (Kurihara et al., 2000) as discussed above, as well as other tissue-specific and cell-type specific promoters known to those of skill in the art.

When used in the context of a promoter, the term "linked" as used herein refers to a physical proximity of promoter elements such that they function together to direct transcription of an operably linked nucleotide sequence The term "transcriptional regulatory sequence" or "transcriptional regulatory element", as used herein, each refers to a nucleotide sequence within the promoter region that enables responsiveness to a regulatory transcription factor. Responsiveness can encompass a decrease or an increase in transcriptional output and is mediated by binding of the transcription factor to the DNA molecule comprising the transcriptional regulatory element.

The term "transcription factor" generally refers to a protein that modulates gene expression by interaction with the transcriptional regulatory element and cellular components for transcription, including RNA Polymerase, Transcription Associated Factors (TAFs), chromatin-remodeling proteins, and any other relevant protein that impacts gene transcription.

In some embodiments, a promoter that is operably linked to a nucleotide sequence encoding a modulator of Bmx is a promoter that is expressed in a cell that expresses Bmx. An exemplary promoter would be a Bmx promoter itself, in some embodiments the promoter of the Bmx gene from the same species in which the compositions and methods of the presently disclosed subject matter are to be deployed. For example, human Bmx gene products correspond to GENBANK® Accession Nos. NM_203281 (SEQ ID NO: 1) and NM_001721 (SEQ ID NO: 3). These sequences are present on human chromosome X, and the genomic sequence that corresponds to the first nucleotide of NM_203281 is found on the plus strand GENBANK® Accession No. NT_011757.15 at position 13,300,583. One of ordinary skill in the art could thus, with routine experimentation, isolate a fragment of human chromosome X in the vicinity of position 13,300,583 of GENBANK® Accession No. NT_011757.15 that corresponds to the Bmx promoter. Once isolated, the promoter fragment can be operably linked to a nucleotide sequence encoding a modulator of Bmx, thereby increasing the likelihood that the modulator of Bmx and Bmx would be co-expressed in a cell type of interest.

Alternatively or in addition, a promoter that includes one or more hypoxia response elements (HREs) can be operably linked to a nucleotide sequence encoding a modulator of Bmx in order to express the modulator of Bmx in hypoxic cells (e.g., in hypoxic regions of a tumor). A representative promoter that contains HRE sequences is the vascular endothelial growth factor (VEGF) promoter. Other HRE-containing promoters are disclosed in U.S. Pat. No. 7,067,649. Additionally, Semenza & Wang, 1992; Blanchard et al., 1992; Firth et al., 1995; and Ebert & Bunn, 1998 teach sequences of HREs, which can be concatamerized and included with one or more minimal promoter elements to produce a synthetic hypoxia-responsive promoter.

The presently disclosed subject matter includes in some embodiments vectors encoding Bmx modulators (e.g., siRNAs targeted to Bmx, antibodies or fragments or derivatives thereof that bind to Bmx, etc.). The term "vector", as used herein refers to a DNA molecule having sequences that enable the transfer of those sequences to a compatible host cell. A vector also includes nucleotide sequences to permit ligation of nucleotide sequences within the vector, wherein such nucleotide sequences are also replicated in a compatible host cell. A vector can also mediate recombinant production of a therapeutic polypeptide, as described further herein below. In some embodiments, a vector is an adenovirus vector or an adeno-associated virus vector.

Nucleic acids of the presently disclosed subject matter can be cloned, synthesized, recombinantly altered, mutagenized, or combinations thereof. Standard recombinant DNA and molecular cloning techniques used to isolate nucleic acids are known in the art. Exemplary, non-limiting methods are described by Silhavy et al., 1984; Ausubel et al., 1992; Ausubel, 1995; Glover & Hames, 1995; and Sambrook &

Russell, 2001). Site-specific mutagenesis to create base pair changes, deletions, or small insertions is also known in the art as exemplified by publications (see e.g., Adelman et al., 1983; Sambrook & Russell, 2001).

In some embodiments, the presently disclosed subject matter provides an siRNA molecule that has been synthesized outside of a target cell prior to introduction of the siRNA into the target cell. In this embodiment, the synthesis can be performed either mechanically (i.e., using an RNA synthesis machine) or using recombinant techniques.

Mechanical synthesis of nucleic acids greater than 100 nucleotides in length is difficult using automated methods, and the cost of such molecules tends to be prohibitive. As used herein, small nucleic acid motifs ("small" referring to nucleic acid motifs in some embodiments no more than 100 nucleotides in length, in some embodiments no more than 80 nucleotides in length, and in some embodiments no more than 50 nucleotides in length; e.g., individual siRNA oligonucleotide sequences or siRNA sequences synthesized in tandem) can be used for exogenous delivery. The simple structure of these molecules increases the ability of the nucleic acid to invade targeted regions of protein and/or RNA structure. Exemplary molecules of the presently disclosed subject matter are chemically synthesized, and others can similarly be synthesized.

Oligonucleotides (e.g., certain modified oligonucleotides or portions of oligonucleotides lacking ribonucleotides) are synthesized using protocols known in the art. See e.g., Caruthers et al., 1992; PCT International Publication No. WO 99/54459; Wincott et al., 1995; Wincott & Usman, 1997; Brennan et al., 1998; and U.S. Pat. No. 6,001,311, each of which is incorporated herein by reference. The synthesis of oligonucleotides makes use of common nucleic acid protecting and coupling groups, such as dimethoxytrityl at the 5'-end and phosphoramidites at the 3'-end. In a non-limiting example, small-scale syntheses can be conducted on a Applied Biosystems 3400 DNA Synthesizer (Applied Biosystems Inc., Foster City, Calif., United States of America) using a 0.2 µmol scale protocol with a 2.5 minute coupling step for 2'-O-methylated nucleotides and a 45 second coupling step for 2'-deoxy nucleotides or 2'-deoxy-2'-fluoro nucleotides. Alternatively, syntheses at the 0.2 µmol scale can be performed on a 96-well plate synthesizer. A 33-fold excess (60 µL of 0.11 M; 6.6 µmol) of 2'-O-methyl phosphoramidite and a 105-fold excess of S-ethyl tetrazole (60 µL of 0.25 M; 15 µmol) can be used in each coupling cycle of 2'-O-methyl residues relative to polymer-bound 5'-hydroxyl. A 22-fold excess (40 µL of 0.11 M; 4.4 µmol) of deoxy phosphoramidite and a 70-fold excess of S-ethyl tetrazole (40 µL of 0.25 M; 10 µmol) can be used in each coupling cycle of deoxy residues relative to polymer-bound 5'-hydroxyl. Average coupling yields on the Applied Biosystems 3400 DNA Synthesizer, determined by colorimetric quantitation of the trityl fractions, are typically 97.5-99%. Other oligonucleotide synthesis reagents for the Applied Biosystems 3400 DNA Synthesizer include the following: detritylation solution is 3% TCA in methylene chloride (Applied Biosystems, Inc.); capping is performed with 16% N-methyl imidazole in THF (Applied Biosystems, Inc.) and 10% acetic anhydride/10% 2,6-lutidine in THF (Applied Biosystems, Inc.); and oxidation solution is 16.9 mM $I_2$, 49 mM pyridine, 9% water in tetrahydrofuran (THF; PerSeptive Biosystmes, Hamburg, Germany). Synthesis Grade acetonitrile (Honeywell BURDICK & JACKSON™, Morritown, N.J., United States of America) is used directly from the reagent bottle. S-Ethyltetrazole solution (0.25 M in acetonitrile) is made up from the solid obtained from American International Chemical, Inc. Alternately, for the introduction of phosphorothioate internucleotide linkages, Beaucage reagent ($^3$H-1,2-benzodithiol-3-one 1,1-dioxide, 0.05 M in acetonitrile) is used.

Deprotection of the DNA-based oligonucleotides is performed as follows: the polymer-bound trityl-on oligoribonucleotide is transferred to a 4 mL glass screw top vial and suspended in a solution of 40% aqueous methylamine (1 mL) at 65° C. for 10 minutes. After cooling to −20° C., the supernatant is removed from the polymer support. The support is washed three times with 1.0 mL of EtOH:MeCN:$H_2O$ (3:1:1), vortexed, and the supernatant is added to the first supernatant. The combined supernatants, containing the oligoribonucleotide, are dried to a white powder.

In some embodiments, the method of synthesis used for RNA including certain siRNA molecules of the presently disclosed subject matter follows the procedure as described in Usman et al., 1987; Scaringe et al., 1990; Wincott et al., 1995; Wincott & Usman, 1997; and makes use of common nucleic acid protecting and coupling groups, such as dimethoxytrityl at the 5'-end, and phosphoramidites at the 3'-end. In a non-limiting example, small-scale syntheses are conducted on an Applied Biosystems 3400 DNA Synthesizer using a 0.2 µmol scale protocol with a 7.5 minute coupling step for alkylsilyl protected nucleotides and a 2.5 minute coupling step for 2'-O-methylated nucleotides. Alternatively, syntheses at the 0.2 µmol scale can be done on a 96-well plate synthesizer. A 33-fold excess (60 µL of 0.11 M; 6.6 µmol) of 2'-O-methyl phosphoramidite and a 75-fold excess of S-ethyl tetrazole (60 µL of 0.25 M; 15 µmol) can be used in each coupling cycle of 2'-O-methyl residues relative to polymer-bound 5'-hydroxyl. A 66-fold excess (120 µL of 0.11 M; 113.2 µmol) of alkylsilyl (ribo) protected phosphoramidite and a 150-fold excess of S-ethyl tetrazole (120 µL of 0.25 M; 30 µmol) can be used in each coupling cycle of ribo residues relative to polymer-bound 5'-hydroxyl. Average coupling yields on the Applied Biosystems 3400 DNA Synthesizer, determined by colorimetric quantitation of the trityl fractions, are typically 97.5-99%. Other oligonucleotide synthesis reagents for the Applied Biosystems 3400 DNA Synthesizer include the following: detritylation solution is 3% TCA in methylene chloride (Applied Biosystems, Inc.); capping is performed with 16% N-methyl imidazole in THF (Applied Biosystems, Inc.) and 10% acetic anhydride/10% 2,6-lutidine in THF (Applied Biosystems, Inc.); oxidation solution is 16.9 mM $I_2$, 49 mM pyridine, 9% water in tetrahydrofuran (THF; PerSeptive Biosystmes, Hamburg, Germany). Synthesis Grade acetonitrile (Honeywell BURDICK & JACKSON™, Morritown, N.J., United States of America) is used directly from the reagent bottle. S-Ethyltetrazole solution (0.25 M in acetonitrile) is made up from the solid obtained from American International Chemical, Inc. (Natick, Mass., United States of America). Alternately, for the introduction of phosphorothioate linkages, Beaucage reagent ($^3$H-1,2-Benzodithiol-3-one 1,1-dioxide 0.05 M in acetonitrile) is used.

Deprotection of the RNA can be performed, for example, using either a two-pot or one-pot protocol. For the two-pot protocol, the polymer-bound trityl-on oligoribonucleotide is transferred to a 4 mL glass screw top vial and suspended in a solution of 40% aqueous methylamine (1 mL) at 65° C. for 10 minutes. After cooling to −20° C., the supernatant is removed from the polymer support. The support is washed three times with 1.0 mL of EtOH:MeCN:H2O (3:1:1), vortexed, and the supernatant is then added to the first supernatant. The combined supernatants, containing the oligoribonucleotide, are dried to a white powder. The base deprotected oligoribonucleotide is resuspended in anhydrous TEA/HF/NMP solution (300 µL of a solution of 1.5 mL N-methylpyrrolidinone, 750 μL TEA and 1 mL TEA.3HF to provide a 1.4 M HF concentration) and heated to 65° C. After 1.5 hours, the oligomer is quenched with 1.5 M NH$_4$HCO$_3$.

Alternatively, for the one-pot protocol, the polymer-bound trityl-on oligoribonucleotide is transferred to a 4 mL glass screw top vial and suspended in a solution of 33% ethanolic methylamine:DMSO (1:1; 0.8 mL) at 65° C. for 15 minutes. The vial is brought to room temperature, TEA.3HF (0.1 mL) is added, and the vial is heated at 65° C. for 15 minutes. The sample is cooled at −20° C., and then quenched with 1.5 M NH$_4$HCO$_3$.

For purification of the trityl-on oligomers, the quenched NH$_4$HCO$_3$ solution is loaded onto a C-18 containing cartridge that had been prewashed with acetonitrile followed by 50 mM TEAA. After washing the loaded cartridge with water, the RNA is detritylated with 0.5% trifluoroacetic acid (TFA) for 13 min. The cartridge is then washed again with water, salt exchanged with 1 M NaCl, and washed with water again. The oligonucleotide is then eluted with 30% acetonitrile.

The average stepwise coupling yields are typically greater than 98% (Wincott et al., 1995). Those of ordinary skill in the art will recognize that the scale of synthesis can be adapted to be larger or smaller than the example described above including but not limited to 96-well format: all that is important is the ratio of chemicals used in the reaction.

Alternatively, the nucleic acid molecules of the presently disclosed subject matter can be synthesized separately and joined together post-synthetically, for example, by ligation (PCT International Publication No. WO 93/23569; Shabarova et al., 1991; Bellon et al., 1997), or by hybridization following synthesis and/or deprotection.

The siRNA molecules of the presently disclosed subject matter can also be synthesized via a tandem synthesis methodology, wherein both siRNA strands are synthesized as a single contiguous oligonucleotide fragment or a strand separated by a linker which, in some embodiments, is subsequently cleaved to provide separate siRNA fragments or strands that hybridize and permit purification of the siRNA duplex. The linker can be a polynucleotide linker or a non-nucleotide linker. The tandem synthesis of siRNA can be readily adapted to both multiwell and multiplate synthesis platforms such as 96 well or similarly larger multi-well platforms. The tandem synthesis of siRNA can also be readily adapted to large-scale synthesis platforms employing batch reactors, synthesis columns and the like.

A siRNA molecule can also be assembled from two distinct nucleic acid strands or fragments wherein one fragment includes the sense region and the second fragment includes the antisense region of the RNA molecule.

In some embodiments, recombinant techniques can be used to synthesize an siRNA, which can thereafter be purified from the source and transferred to a target cell. There are many techniques that are known in the art for the synthesis RNA molecules in recombinant cells, and any such technique can be used in the practice of the presently disclosed subject matter. One such general strategy for synthesizing an RNA molecule includes cloning a DNA sequence downstream of an RNA polymerase promoter and introducing the recombinant molecule into a cell in which the promoter is competent to direct transcription of the cloned sequence. This can be accomplished using a plasmid constructed for this purpose.

Alternatively, the RNA can be synthesized in the target cell using an expression vector, for example an expression plasmid. Such plasmids include, but are not limited to the pSILENCER™ series of plasmids (Ambion, Inc., Austin, Tex., United States of America), and the plasmid disclosed by Miyagishi & Taira, 2002.

The pSILENCER™ series of plasmids contain a cloning site downstream of a mammalian RNA polymerase III promoter. A nucleic acid encoding a hairpin with a 19 base pair duplex region can be cloned into the cloning site of one of these plasmids. When the recombinant plasmid is introduced into a mammalian cell, the RNA polymerase III promoter directs transcription of the hairpin RNA molecule, which thereafter forms the hairpin characterized by the 19 base pair duplex. This hairpin is apparently recognized by the Dicer nuclease, which cleaves the hairpin to form a functional siRNA.

Mivagishi & Taira, 2002 discloses another strategy for producing siRNA molecules. This reference discloses a plasmid that has two RNA polymerase III promoters. To produce an siRNA, the same 19 base pair nucleic acid molecule is cloned downstream of each promoter, but in opposite orientations. Thus, the plasmid produces distinct sense and antisense RNA strands, which then undergo intermolecular hybridization to produce an siRNA. In this case, the promoter is the U6 promoter. An RNA transcribed from a U6 promoter has a stretch of about four uridines at its 3' end. Thus, the use of this plasmid results in the production of two RNA strands, each of which contains a 19 base region that is capable of hybridizing to a 19 base region in the other, with a short 3' overhang.

Chemically synthesizing nucleic acid molecules incorporating various modifications (e.g., to base, sugar, and/or phosphate moieties) can reduce the degradation of the nucleic acid molecules by ribonucleases present in biological fluids, and can thus can increase the potency of therapeutic nucleic acid molecules (see e.g., PCT International Publication Nos. WO 92/07065, WO 93/15187, and WO 91/03162; U.S. Pat. Nos. 5,334,711 and 6,300,074; Perrault et al., 1990; Pieken et al., 1991; Usman & Cedergren, 1992; Limbach et al., 1994; Burgin et al., 1996; Usman et al., 1996; all of which are incorporated by reference herein). Each of the above references describes various chemical modifications that can be made to the base, phosphate, and/or sugar moieties of the nucleic acid molecules described herein. Modifications can be employed to enhance the efficacy of the disclosed nucleic acid molecules in cells. Some of the non-limiting examples of base modifications that can be introduced into nucleic acid molecules include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine), 6-azapyrimidines and 6-alkylpyrimidines (e.g. 6-methyluridine), propyne, and others (Burgin et al., 1996; Uhlman & Peyman, 1990).

There are several examples in the art describing sugar, base, and phosphate modifications that can be introduced into nucleic acid molecules with significant enhancement in their nuclease stability and efficacy. For example, oligonucleotides can be modified to enhance their stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications (reviewed in Usman & Cedergren, 1992; Usman et al., 1994; Burgin et al., 1996). Sugar modification of nucleic acid molecules have been extensively described in the art (see PCT International Publication Nos. WO 92/07065, WO 93/15187, WO 98/13526, and WO 97/26270; U.S. Pat. Nos. 5,334,711; 5,716,824; and 5,627,053; Perrault et al., 1990; Pieken et al., 1991; Usman & Cedergren, 1992; Beigelman et al., 1995; Karpeisky et al., 1998; Earnshaw & Gait, 1998; Verma & Eckstein, 1998; Burlina et al., 1997; all of which are incorporated by reference herein). Such publications describe general methods and strategies to determine the location of incorporation of sugar, base, and/or phosphate modifications and the like into nucleic acid molecules without modulating catalysis. In view of such teachings, similar modifications can be used as described herein to modify the siRNA nucleic acid molecules of the presently disclosed subject matter so long as the ability of the siRNAs to promote RNAi in a cell is not significantly inhibited.

While chemical modification of oligonucleotide internucleotide linkages with phosphorothioate and/or 5'-methylphosphonate linkages improves stability, excessive modifications can cause toxicity or decreased activity. Therefore, when designing nucleic acid molecules, the number of these internucleotide linkages should be minimized. Reducing the concentration of these linkages should lower toxicity, resulting in increased efficacy and higher specificity of these molecules.

The term "universal base" as used herein refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see e.g., Loakes, 2001).

Small interfering RNA (siRNA) molecules having chemical modifications that maintain or enhance activity are provided. Such a nucleic acid is also generally more resistant to nucleases than an unmodified nucleic acid. Accordingly, the in vitro and/or in vivo activity should not be significantly lowered. In cases in which modulation is the goal, nucleic acid molecules delivered exogenously should optimally be stable within cells until translation of the target RNA has been modulated long enough to reduce the levels of the undesirable protein. This period of time varies between hours to days depending upon the disease state. Improvements in the chemical synthesis of RNA (Wincott et al., 1995; Caruthers et al., 1992) have expanded the ability to modify nucleic acid molecules by introducing nucleotide modifications to enhance their nuclease stability, as described above. siRNA constructs can be purified by gel electrophoresis using general methods or can be purified by high pressure liquid chromatography (HPLC; see Wincott et al., 1995) and re-suspended in water.

In some embodiments, the presently disclosed subject matter features conjugates and/or complexes of siRNA molecules. Such conjugates and/or complexes can be used to facilitate delivery of siRNA molecules into a biological system, such as a cell. The conjugates and complexes provided by the presently disclosed subject matter can impart therapeutic activity by transferring therapeutic compounds across cellular membranes, altering the pharmacokinetics of, and/or modulating the localization of nucleic acid molecules of the presently disclosed subject matter. The presently disclosed subject matter encompasses the design and synthesis of novel conjugates and complexes for the delivery of molecules, including, but not limited to, small molecules, lipids, phospholipids, nucleosides, nucleotides, nucleic acids, antibodies, toxins, negatively charged polymers, and other polymers, for example proteins, peptides, hormones, carbohydrates, polyethylene glycols, or polyamines, across cellular membranes. In general, the transporters described are designed to be used either individually or as part of a multi-component system, with or without degradable linkers. These compounds are expected to improve delivery and/or localization of nucleic acid molecules of the presently disclosed subject matter into a number of cell types originating from different tissues, in the presence or absence of serum (see U.S. Pat. No. 5,854,038). Conjugates of the molecules described herein can be attached to biologically active molecules via linkers that are biodegradable, such as biodegradable nucleic acid linker molecules.

The term "biodegradable linker" as used herein, refers to a nucleic acid or non-nucleic acid linker molecule that is designed as a biodegradable linker to connect one molecule to another molecule, for example, a biologically active molecule to a siRNA molecule of the presently disclosed subject matter or the sense and antisense strands of a siRNA molecule of the presently disclosed subject matter. The biodegradable linker is designed such that its stability can be modulated for a particular purpose, such as delivery to a particular tissue or cell type. The stability of a nucleic acid-based biodegradable linker molecule can be modulated by using various chemistries, for example combinations of ribonucleotides, deoxyribonucleotides, and chemically modified nucleotides, such as 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus-based linkage, for example, a phosphoramidate or phosphodiester linkage. The biodegradable nucleic acid linker molecule can also comprise nucleic acid backbone, nucleic acid sugar, or nucleic acid base modifications.

The term "biodegradable" as used herein, refers to degradation in a biological system, for example enzymatic degradation or chemical degradation.

The term "biologically active molecule" as used herein, refers to compounds or molecules that are capable of eliciting or modifying a biological response in a system. Non-limiting examples of biologically active siRNA molecules either alone or in combination with other molecules provided by the presently disclosed subject matter include therapeutically active molecules such as antibodies, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, siRNA, dsRNA, allozymes, aptamers, decoys, and analogs thereof. Biologically active molecules of the presently disclosed subject matter also include molecules capable of modulating the pharmacokinetics and/or pharmacodynamics of other biologically active molecules, for example, lipids and polymers such as polyamines, polyamides, polyethylene glycol, and other polyethers.

The term "phospholipid" as used herein, refers to a hydrophobic molecule comprising at least one phosphorus group. For example, a phospholipid can comprise a phosphorus-containing group and saturated or unsaturated alkyl group, optionally substituted with OH, COOH, oxo, amine, or substituted or unsubstituted aryl groups.

Nucleic acid molecules (e.g., siRNA molecules) delivered exogenously are intended to be stable within cells until the level of the target RNA has been reduced sufficiently. The nucleic acid molecules are resistant to nucleases in order to function as effective intracellular therapeutic agents. Improvements in the chemical synthesis of nucleic acid molecules described in the presently disclosed subject matter and in the art have expanded the ability to modify nucleic acid molecules by introducing nucleotide modifications to enhance their nuclease stability as described above.

In some embodiments, siRNA molecules having chemical modifications that maintain or enhance enzymatic activity of proteins involved in RNAi are provided. Such nucleic acids are also generally more resistant to nucleases than unmodified nucleic acids. Thus, in vitro and/or in vivo activity should not be significantly lowered.

Use of the nucleic acid-based molecules of the presently disclosed subject matter will lead to better treatment of the disease progression by affording the possibility of combination therapies (e.g., multiple siRNA molecules targeted to different genes; nucleic acid molecules coupled with known small molecule modulators; or intermittent treatment with combinations of molecules, including different motifs and/or other chemical or biological molecules). The treatment of subjects with siRNA molecules can also include combinations of different types of nucleic acid molecules, such as enzymatic nucleic acid molecules (ribozymes), allozymes, antisense, 2,5-A oligoadenylate, decoys, aptamers etc.

In another aspect a siRNA molecule of the presently disclosed subject matter comprises one or more 5' and/or 3'-cap structures, for example on only the sense siRNA strand, antisense siRNA strand, or both siRNA strands.

As used herein, the phrase "cap structure" is meant to refer to chemical modifications that have been incorporated at either terminus of the oligonucleotide (see e.g., U.S. Pat. No. 5,998,203, incorporated by reference herein). These terminal modifications protect the nucleic acid molecule from exonuclease degradation, and can help in delivery and/or localization within a cell. The cap can be present at the 5'-terminus (5'-cap) or at the 3'-terminal (3'-cap), or can be present on both termini. In non-limiting examples: the 5'-cap is selected from the group comprising inverted abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threopentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

In some embodiments, the 3'-cap is selected from a group comprising 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threopentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (see generally Beaucage & Iyer, 1993; incorporated by reference herein).

As used herein, the term "non-nucleotide" refers to any group or compound which can be incorporated into a nucleic acid chain in the place of one or more nucleotide units, including either sugar and/or phosphate substitutions, and allows the remaining bases to exhibit their enzymatic activity. The group or compound is typically abasic, in that it does not typically contain a commonly recognized nucleotide base, such as adenine (A), guanine (G), cytosine (C), thymine (T), or uracil (U), and therefore lacks a base at the 1'-position.

As used herein, the term "alkyl" group refers to a saturated aliphatic hydrocarbon, including straight-chain, branched-chain, and cyclic alkyl groups. In some embodiments, the alkyl group has 1 to 12 carbons. In some embodiments, it is a lower alkyl of from 1 to 7 carbons, and in some embodiments it is a lower alkyl of from 1 to 4 carbons. The alkyl group can be substituted or unsubstituted. When substituted the substituted group(s) is in alternative embodiments, hydroxyl, cyano, alkoxy, =O, =S, $NO_2$ or $N(CH_3)_2$, amino, or SH.

The term "alkyl" also includes alkenyl groups that are unsaturated hydrocarbon groups containing at least one carbon-carbon double bond, including straight-chain, branched-chain, and cyclic groups. In some embodiments, the alkenyl group has 1 to 12 carbons. In some embodiments, it is a lower alkenyl of from 1 to 7 carbons, and in some embodiments it is a lower alkenyl of from 1 to 4 carbons. The alkenyl group can be substituted or unsubstituted. When substituted the substituted group(s) is in alternative embodiments, hydroxyl, cyano, alkoxy, =O, =S, $NO_2$, halogen, $N(CH_3)_2$, amino, or SH.

The term "alkyl" also includes alkynyl groups that have an unsaturated hydrocarbon group containing at least one carbon-carbon triple bond, including straight-chain, branched-chain, and cyclic groups. In some embodiments, the alkynyl group has 1 to 12 carbons. In some embodiments, it is a lower alkynyl of from 1 to 7 carbons, and in some embodiments it is a lower alkynyl of from 1 to 4 carbons. The alkynyl group can be substituted or unsubstituted. When substituted the substituted group(s) is in alternative embodiments, hydroxyl, cyano, alkoxy, =O, =S, $NO_2$ or $N(CH_3)_2$, amino or SH.

Such alkyl groups can also include aryl, alkylaryl, carbocyclic aryl, heterocyclic aryl, amide, and ester groups. An "aryl" group refers to an aromatic group that has at least one ring having a conjugated pi electron system and includes carbocyclic aryl, heterocyclic aryl, and biaryl groups, all of which can be optionally substituted. Exemplary substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to a —C(O)—NH—R, where R is either alkyl, aryl, alkylaryl, or hydrogen. An "ester" refers to an C(O)—OR', where R is either alkyl, aryl, alkylaryl, or hydrogen.

The term "nucleotide" is used herein as recognized in the art to include natural bases (standard), and modified bases well known in the art. Such bases are generally located at the 1' position of a nucleotide sugar moiety. Nucleotides generally comprise a base, sugar, and a phosphate group. The nucleotides can be unmodified or modified at the sugar, phosphate, and/or base moiety, (also referred to interchangeably as nucleotide analogs, modified nucleotides, non-natural nucleotides, non-standard nucleotides, and other; see e.g., Usman et al., 1996; PCT International Publication Nos. WO 92/07065 and WO 93/15187, all incorporated by reference herein). There are several examples of modified nucleic acid bases known in the art as summarized by Limbach et al., 1994. Some of the non-limiting examples of base modifications that can be introduced into nucleic acid molecules include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine), 6-azapyrimidines and 6-alkylpyrimidines (e.g., 6-methyluridine), propyne, and others (Burgin et al., 1996; Uhlman & Peyman, 1990). By "modified bases" in this aspect is meant nucleotide bases other than adenine, guanine, cytosine, and uracil at 1' position or their equivalents.

In some embodiments, the presently disclosed subject matter features modified siRNA molecules, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications, see Hunziker & Leumann, 1995 and De Mesmaeker et al., 1994.

As used herein, the term "abasic" refers to sugar moieties lacking a commonly recognized nucleoside base (e.g., A, C, G, T, or U) or having other chemical groups in place of the commonly recognized base at the 1' position. See e.g., U.S. Pat. No. 5,998,203.

As used herein, the phrase "unmodified nucleoside" refers to one of the bases adenine, cytosine, guanine, thymine, or uracil joined to the 1' carbon of β-D-ribo-furanose.

By "modified nucleoside" is meant any nucleotide base which contains a modification in the chemical structure of an unmodified nucleotide base, sugar and/or phosphate.

In connection with 2'-modified nucleotides as described for the presently disclosed subject matter, by "amino" is meant 2'—NH$_2$ or 2'-O—NH$_2$, which can be modified or unmodified. Such modified groups are described, for example, in U.S. Pat. Nos. 5,672,695 and 6,248,878, which are both incorporated by reference in their entireties.

Various modifications to nucleic acid siRNA structure can be made to enhance the utility of these molecules. Such modifications will enhance shelf-life, half-life in vitro, stability, and/or ease of introduction of such oligonucleotides to the target site (for example, to enhance penetration of cellular membranes, and confer the ability to recognize and bind to targeted cells).

IV.E. Sustained Bioavailability

The term "sustained bioavailability" is used herein to describe a composition comprising a Bmx antagonist and a carrier, whereby the bioavailability of a Bmx antagonist at a target site is sufficient to achieve radiosensitization of a target (e.g., a tumor). The term "sustained bioavailability" also refers to a bioavailability sufficient to inhibit blood vessel growth of and/or within the target (e.g., a tumor and/or the vasculature thereof). The term "sustained bioavailability" encompasses factors including but not limited to sustained release of a Bmx antagonist from a carrier, metabolic stability of a Bmx antagonist, systemic transport of a composition comprising a Bmx antagonist, and effective dose of a Bmx antagonist.

As disclosed herein, an immediate response of tumor blood vessels to radiation is a decrease in tumor blood flow. This response can diminish administration of an anti-tumor composition (e.g., a Bmx antagonist). Recognizing this response, the disclosure of the presently claimed subject matter provides that sustained bioavailability of a Bmx antagonist, for example by selection of a carrier and administration regimen that achieve sustained bioavailability, can improve anti-tumor activity. One example of carrier comprises a gene therapy vector encoding a Bmx antagonist (e.g., a neutralizing antibody or fragment or derivative thereof or an siRNA targeted to a Bmx gene product).

A method comprising a carrier or administration approach for sustained bioavailability can also improve therapies directed toward modulation of other components of the Bmx signaling pathway. Thus, the presently claimed subject matter provides in some embodiments an improved method for inhibiting tumor growth, the method comprising administration of a gene therapy vector encoding an inhibitor of Bmx signaling, whereby bioavailability of the inhibitor at a tumor is sustained, and whereby tumor growth delay is improved.

V. Compositions

In accordance with the methods of the presently claimed subject matter, a composition that is administered to increase the radiosensitivity of a target tissue in a subject comprises: (a) a Bmx antagonist; and (b) a pharmaceutically acceptable carrier. Any suitable carrier that facilitates drug preparation and/or administration can be used.

V.A. Carriers

The carrier can be a viral vector or a non-viral vector. Suitable viral vectors include adenoviruses, adeno-associated viruses (AAVs), retroviruses, pseudotyped retroviruses, herpes viruses, vaccinia viruses, Semiliki forest virus, and baculoviruses. In some embodiments of the presently claimed subject matter, the carrier comprises an adenoviral gene therapy construct that encodes a Bmx antagonist.

Suitable non-viral vectors that can be used to deliver a Bmx antagonist include but are not limited to a plasmid, a nanosphere (Manome et al., 1994; Saltzman & Fung, 1997), a peptide (U.S. Pat. Nos. 6,127,339 and 5,574,172), a glycosaminoglycan (U.S. Pat. No. 6,106,866), a fatty acid (U.S. Pat. No. 5,994,392), a fatty emulsion (U.S. Pat. No. 5,651,991), a lipid or lipid derivative (U.S. Pat. No. 5,786,387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman et al., 1997) and U.S. Pat. Nos. 4,551,482, 5,714,166, 5,510,103, 5,490,840, and 5,855,900), and a polysome (U.S. Pat. No. 5,922,545).

Where appropriate, two or more types of carriers can be used together. For example, a plasmid vector can be used in conjunction with liposomes. Currently, some embodiments of the presently claimed subject matter envisions the use of an adenovirus.

In some embodiments, a composition of the presently claimed subject matter comprises a Bmx antagonist and a carrier to effect sustained bioavailability of the Bmx antagonist following administration to a subject. Representative compositions for sustained bioavailability of a Bmx antagonist can include but are not limited to polymer matrices, including swelling and biodegradable polymer matrices, (U.S. Pat. Nos. 6,335,035; 6,312,713; 6,296,842; 6,287,587; 6,267,981; 6,262,127; and 6,221,958), polymer-coated microparticles (U.S. Pat. Nos. 6,120,787 and 6,090,925) a polyol:oil suspension (U.S. Pat. No. 6,245,740), porous particles (U.S. Pat. No. 6,238,705), latex/wax coated granules (U.S. Pat. No. 6,238,704), chitosan microcapsules, and microsphere emulsions (U.S. Pat. No. 6,190,700).

An exemplary embodiment for sustained bioavailability of a Bmx antagonist comprises a gene therapy construct comprising a gene therapy vector, for example a gene therapy vector described herein below.

Viral Gene Therapy Vectors. In some embodiments, viral vectors of the presently claimed subject matter are disabled; e.g., replication-deficient. That is, they lack one or more functional genes required for their replication, which prevents their uncontrolled replication in vivo and avoids undesirable side effects of viral infection. In some embodiments, all of the viral genome is removed except for the minimum genomic elements required to package the viral genome incorporating the therapeutic gene into the viral coat or capsid. For example, it is desirable to delete all the viral genome except: (a) the Long Terminal Repeats (LTRs) or Inverted Terminal Repeats (ITRs); and (b) a packaging signal. In the case of adenoviruses, deletions are typically made in the E1 region and optionally in one or more of the E2, E3, and/or E4 regions. Other viral vectors can be similarly deleted of genes required for replication. Deletion of sequences can be achieved by recombinant approaches, for example, involving digestion with appropriate restriction enzymes, followed by religation. Replication-competent self-limiting or self-destructing viral vectors can also be used.

Nucleic acid constructs of the presently claimed subject matter can be incorporated into viral genomes by any suitable approach known in the art. Typically, such incorporation is performed by ligating the construct into an appropriate restriction site in the genome of the virus. Viral genomes can then be packaged into viral coats or capsids using any suitable procedure. In particular, any suitable packaging cell line can be used to generate viral vectors of the presently claimed subject matter. These packaging lines complement the replication-deficient viral genomes of the presently claimed subject matter, as they include, for example by incorporation into their genomes, the genes that have been deleted from the replication-deficient genome. Thus, the use of packaging lines allows viral vectors of the presently claimed subject matter to be generated in culture.

Suitable packaging lines for retroviruses include derivatives of PA317 cells, ψ-2 cells, CRE cells, CRIP cells, E-86-GP cells, and 293GP cells. Line 293 cells can be used with adenoviruses and adeno-associated viruses.

Plasmid Gene Therapy Vectors. Certain of the Bmx antagonists of the presently disclosed subject matter can also be encoded by a plasmid. Advantages of a plasmid carrier include low toxicity and easy large-scale production. A polymer-coated plasmid can be delivered using electroporation as described by Fewell et al., 2001. Alternatively, a plasmid can be combined with an additional carrier, for example a cationic polyamine, a dendrimer, or a lipid, that facilitates delivery (Baher et al., 1999; Maruyama-Tabata et al., 2000; Tam et al., 2000).

Liposomes. A Bmx antagonist of the presently claimed subject matter can also be delivered using a liposome. For example, a nucleic acid molecule encoding a Bmx antagonist can be encapsulated in a liposome. Liposomes can be prepared by any of a variety of techniques that are known in the art. See e.g., Dracopoli et al., 1997; Lasic & Martin, 1995; Janoff, 1999; Gregoriadis, 1993; Betageri et al., 1993.; and U.S. Pat. Nos. 4,235,871; 4,551,482; 6,197,333; and 6,132,766. Temperature-sensitive liposomes can also be used, for example THERMOSOMES™, as disclosed in U.S. Pat. No. 6,200,598. Entrapment of a Bmx antagonist within liposomes of the presently claimed subject matter can be carried out using any conventional method in the art. In preparing liposome compositions, stabilizers such as antioxidants and other additives can be used.

Other lipid carriers can also be used in accordance with the claimed presently claimed subject matter, such as lipid microparticles, micelles, lipid suspensions, and lipid emulsions. See e.g., Labat-Moleur et al., 1996; and U.S. Pat. Nos. 5,011,634; 6,056,938; 6,217,886; 5,948,767; and 6,210,707.

V.B. Targeting Ligands

As desired, a composition of the presently claimed subject matter can include one or more ligands having affinity for a specific cellular marker to thereby enhance delivery of a Bmx antagonist to a target tissue, such as a tumor, in vivo. Ligands include antibodies, cell surface markers, peptides, and the like, which act to home the Bmx antagonist to a tumor, including the tumor vasculature.

The terms "targeting" and "homing", as used herein to describe the in vivo activity of a ligand following administration to a subject, each refer to the preferential movement and/or accumulation of a ligand in a target tissue (e.g., a tumor) as compared with a control tissue.

The term "control tissue" as used herein refers to a site suspected to substantially lack binding and/or accumulation of an administered ligand. For example, in some embodiments, a non-cancerous tissue can be a control tissue.

The terms "selective targeting" of "selective homing" as used herein each refer to a preferential localization of a ligand that results in some embodiments in an amount of ligand in a target tissue that is about 2-fold greater than an amount of ligand in a control tissue, in another embodiment in an amount that is about 5-fold or greater, and in still another embodiment in an amount that is about 10-fold or greater. The terms "selective targeting" and "selective homing" also refer to binding or accumulation of a ligand in a target tissue concomitant with an absence of targeting to a control tissue, or the absence of targeting to all control tissues.

The terms "targeting ligand" and "targeting molecule" as used herein each refer to a ligand that displays targeting activity. In some embodiments, a targeting ligand displays selective targeting. Representative targeting ligands include peptides and antibodies.

The term "peptide" encompasses any of a variety of forms of peptide derivatives that include amides, conjugates with proteins, cyclized peptides, polymerized peptides, conservatively substituted variants, analogs, fragments, peptoids, chemically modified peptides, and peptide mimetics. Representative peptide ligands that show tumor-binding activity include, for example, those described in U.S. Pat. Nos. 6,180,084 and 6,296,832.

The term "antibody" indicates an immunoglobulin protein, or functional portion thereof, including a polyclonal antibody, a monoclonal antibody, a chimeric antibody, a hybrid antibody, a single chain antibody (e.g., a single chain antibody represented in a phage library), a mutagenized antibody, a humanized antibody, and antibody fragments that comprise an antigen binding site (e.g., Fab and Fv antibody fragments). Representative antibody ligands that can be used in accordance with the methods of the presently claimed subject matter include antibodies that bind the tumor-specific antigens Her2/neu (v-erb-b2 avian erythroblastic leukemia viral oncogene homologue-2; Kirpotin et al., 1997; Becerril et al., 1999) and antibodies that bind to CEA (carcinoembryonic antigen; Ito et al., 1991). See also U.S. Pat. Nos. 5,111,867; 5,632,991; 5,849,877; 5,948,647; 6,054,561 and PCT International Publication No. WO 98/10795.

In an effort to identify ligands that are capable of targeting to multiple tumor types, targeting ligands have been developed that bind to target molecules present on tumor vasculature (Baillie et al., 1995; Pasqualini & Ruoslahti, 1996; Arap et al., 1998; Burg et al., 1999; Ellerby et al., 1999).

A targeting ligand can also comprise a ligand that specifically binds to a radiation induced target molecule. Ionizing radiation induces proteins in tumor vascular endothelium through transcriptional induction and/or posttranslational modification of cell adhesion molecules such as integrins (Hallahan et al., 1995; Hallahan et al., 1996; Hallahan et al., 1998; Hallahan & Virudachalam, 1999). For example, radiation induces activation of the integrin $\alpha_{2b}\beta_3$, also called the fibrinogen receptor, on platelets. The induced molecules can serve as binding sites for targeting ligands. A representative peptide ligand that binds to irradiated tumors comprises Bibapcitide (ACUTECT® available from Diatide, Inc. of Londonberry, N.H., United States of America), which specifically binds to glycoprotein (GP) IIb/IIIa receptors on activated platelets (Hawiger et al., 1989; Hawiger & Timmons, 1992; Hallahan et al., 2001).

Antibodies, peptides, or other ligands can be coupled to drugs (e.g., a Bmx antagonist) or drug carriers using methods known in the art, including but not limited to carbodiimide conjugation, esterification, sodium periodate oxidation followed by reductive alkylation, and glutaraldehyde crosslinking. See e.g., Bauminger & Wilchek, 1980; Dracopoli et al., 1997; Goldman et al., 1997; Kirpotin et al., 1997; Neri et al., 1997; Park et al., 1997; Pasqualini et al., 1997; U.S. Pat. No. 6,071,890; and European Patent No. 0 439 095. Alternatively, pseudotyping of a retrovirus can be used to target a virus towards a particular cell (Marin et al., 1997).

A composition of the presently claimed subject matter comprises in some embodiments a Bmx antagonist and a pharmaceutically acceptable carrier. Suitable formulations include aqueous and non-aqueous sterile injection solutions, which can contain anti-oxidants, buffers, bacteriostats, bactericidal antibiotics, and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Examples of useful ingredients are sodium dodecyl sulfate (SDS), for example in the range of 0.1 to 10 mg/ml, in another example about 2.0 mg/ml; and/or mannitol or another sugar, for example in the range of 10 to 100 mg/ml, in another example about 30 mg/ml; phosphate buffered saline (PBS), and any other formulation agents conventional in the art.

The therapeutic regimens and pharmaceutical compositions of the presently claimed subject matter can be used with additional adjuvants or biological response modifiers including, but not limited to, the cytokines interferon alpha (IFN-α), interferon gamma (IFN-γ), interleukin 2 (IL2), interleukin 4 (IL4), interleukin 6 (IL6), tumor necrosis factor (TNF), or other cytokine affecting immune cells.

VI. Therapeutic Methods

The presently disclosed subject matter also provides therapeutic methods that can be employed for treating and/or otherwise ameliorating one or more symptoms and/or consequences of undesirable underexpression or undesirable overexpression of a Bmx gene product.

In some embodiments, the presently disclosed subject matter provides methods for modulating proliferation of a cell or of a tissue (e.g., a tumor) in a subject, the methods comprising administering to the subject an effective amount of a modulator of a biological activity of a bone marrow X kinase (Bmx) gene product.

In some embodiments, the presently claimed subject matter provides methods for suppressing tumor growth comprising (a) administering a Bmx antagonist to a subject bearing a tumor to increase the radiosensitivity of the tumor; and (b) treating the tumor with ionizing radiation, whereby tumor growth is delayed. Also provided is a method for inhibiting tumor blood vessel growth via administration of a Bmx antagonist.

In some embodiments, the presently disclosed subject matter provides methods for inhibiting tumor blood vessel growth comprising (a) administering a bone marrow X kinase (Bmx) antagonist, a vector encoding a bone marrow X kinase (Bmx) antagonist, or a combination thereof to a subject bearing a tumor to increase the radiosensitivity of tumor blood vessels; and (b) treating the tumor with ionizing radiation, whereby tumor blood vessel growth is inhibited.

While applicants do not intend to be bound by any particular theory of operation, it is believed that the Bmx antagonists disclosed herein effectively suppress proliferation of a cell or of a tissue (e.g., a tumor growth) by blocking perfusion of the tissue (e.g., reperfusion of a tumor subsequent to and/or concurrent with radiation). Specifically, a Bmx antagonist can block processes that require Bmx, including the mediation of growth factor signals that result in endothelial cell infiltration and budding of tumor blood vessels. Similarly, a Bmx antagonist is believed to effectively inhibit the growth of tumor blood vessels by blocking the ability of growth factors to mediate blood vessel growth.

In some embodiments, the presently disclosed subject matter provides methods for inhibiting a condition associated with undesirable angiogenesis in a subject, the method comprising administering to the subject an effective amount of a bone marrow X kinase (Bmx) antagonist. As used herein, the phrase "condition associated with undesirable angiogenesis" refers to any condition at least one symptom of which is caused by the presence in a subject of a vascular network that is abnormal in some clinically relevant manner including, but not limited to the extent to which the vascular network develops and/or the time and/or place at which it develops. In some embodiments, a condition associated with undesirable angiogenesis is macular degeneration or endometriosis.

As would be understood by one of ordinary skill in the art, angiogenesis is the process whereby new blood vessels are formed. Angiogenesis, also called neovascularization, occurs normally during embryogenesis and development, and occurs in fully developed organisms during wound healing and placental development. In addition, angiogenesis occurs in various pathological conditions, including in ocular diseases such as diabetic retinopathy and macular degeneration due to neovascularization, in conditions associated with tissue inflammation such as rheumatoid arthritis and inflammatory bowel disease, in cancer, where blood vessel formation in the growing tumor provides oxygen and nutrients to the tumor cells, as well as providing a route via which tumor cells metastasize throughout the body, and in endometriosis.

Angiogenesis occurs in response to stimulation by one or more known growth factors, and can also involve other as yet unidentified factors. Endothelial cells, which are the cells that line mature blood vessels, normally do not proliferate. However, in response to an appropriate stimulus, the endothelial cells become activated and begin to proliferate and migrate into unvascularized tissue to form new blood vessels. In some cases, precursor cells can be activated to differentiate into endothelial cells, which form new blood vessels.

In pathological conditions such as age-related macular degeneration and diabetic retinopathy, decreasing availability of oxygen to the retina results in a hypoxic condition that stimulates the secretion of angiogenic growth factors such as vascular endothelial growth factors (VEGF), which induce abnormal migration and proliferation of endothelial cells into tissues of the eye. Such vascularization in ocular tissues can induce corneal scarring, retinal detachment, and fluid accumulation in the choroid, each of which can adversely affect vision and lead to blindness.

Angiogenesis also is associated with the progression and exacerbation of inflammatory diseases, including psoriasis, rheumatoid arthritis, osteoarthritis, and inflammatory bowel diseases such as ulcerative colitis and Crohn's disease. In inflammatory arthritic disease, for example, influx of lymphocytes into the region surrounding the joints stimulates angiogenesis in the synovial lining. The increased vasculature provides a means for greater influx of leukocytes, which facilitate the destruction of cartilage and bone in the joint. Angiogenic vascularization that occurs in inflammatory bowel disease results in similar effects in the bowel.

The growth of capillaries into atherosclerotic plaques in the coronary arteries represents another pathological condition associated with growth factor induced angiogenesis. Excessive blood flow into neovascularized plaques can result in rupture and hemorrhage of the blood-filled plaques, releasing blood clots that can result in coronary thrombosis.

The involvement of angiogenesis in such diverse diseases as cancer, ocular disease, and inflammatory diseases has led to an effort to identify methods for specifically inhibiting angiogenesis as a means to treat these diseases. For cancer patients, such methods of treatment can provide a substantial advantage over currently used methods such as chemotherapy, which kill or impair not only the target tumor cells, but also normal cells in the patient, particularly proliferating normal cells such as blood cells, epithelial cells, and cells lining the intestinal lumen. Such non-specific killing by chemotherapeutic agents results in side effects that are, at best, unpleasant, and can often result in unacceptable patient morbidity, or mortality. In fact, the undesirable side effects associated with cancer therapies often limit the treatment a patient can receive.

VI.A. Administration of a Bmx Antagonist

Suitable methods for administration of a composition of the presently claimed subject matter include but are not limited to intravascular, subcutaneous, intramuscular, intraperitoneal, or intratumoral administration. For delivery of compositions to pulmonary pathways, compositions can be administered as an aerosol or coarse spray. A delivery method is selected based on considerations such as the type of Bmx antagonist, the type of carrier or vector, toxicity of the Bmx antagonist, therapeutic efficacy of the Bmx antagonist, and the condition of the tumor to be treated. In some embodiments of the presently claimed subject matter, intravascular administration is employed.

In some embodiments, an effective amount of a composition of the presently claimed subject matter is administered to a subject. An "effective amount" is an amount of a composition comprising a Bmx antagonist sufficient to produce a measurable response, such as but not limited to an anti-tumor response (e.g., increase of radiation sensitivity, an anti-angiogenic response, a cytotoxic response, and/or tumor regression). Actual dosage levels of active ingredients in a therapeutic composition of the presently claimed subject matter can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, tumor size and longevity, and the physical condition and prior medical history of the subject being treated. Determination and adjustment of a therapeutically effective dose, as well as evaluation of when and how to make such adjustments, are known to those of ordinary skill in the art of medicine.

In some embodiments of the presently claimed subject matter, a minimally therapeutic dose of a Bmx antagonist is administered. The term "minimally therapeutic dose" refers to the smallest dose, or smallest range of doses, determined to be a therapeutically effective amount as defined herein above.

VI.B. Radiation Treatment

For treatment of a radiosensitized target tissue, the target tissue is irradiated concurrent with, or subsequent to, administration of a composition comprising a Bmx antagonist. In accordance with the methods of the presently claimed subject matter, the target tissue can be irradiated daily for 2 weeks to 7 weeks (for a total of 10 treatments to 35 treatments). Alternatively, target tissues can be irradiated with brachytherapy utilizing high dose rate or low dose rate brachytherapy internal emitters.

Subtherapeutic or therapeutic doses of radiation can be used for treatment of a radiosensitized target tissue as disclosed herein. In some embodiments, a subtherapeutic or minimally therapeutic dose (when administered alone) of ionizing radiation is used. For example, the dose of radiation can comprise at least about 2 Gy ionizing radiation, in another example about 2 Gy to about 6 Gy ionizing radiation, and in yet another example about 2 Gy to about 3 Gy ionizing radiation. When radiosurgery is used, representative doses of radiation include about 10 Gy to about 20 Gy administered as a single dose during radiosurgery or about 7 Gy administered daily for 3 days (about 21 Gy total). When high dose rate brachytherapy is used, a representative radiation dose comprises about 7 Gy daily for 3 days (about 21 Gy total). For low dose rate brachytherapy, radiation doses typically comprise about 12 Gy administered twice over the course of 1 month. $^{125}$I seeds can be implanted into a target tissue and can be used to deliver very high doses of about 110 Gy to about 140 Gy in a single administration.

Radiation can be localized to a target tissue using conformal irradiation, brachytherapy, stereotactic irradiation, or intensity modulated radiation therapy (IMRT). The threshold dose for treatment can thereby be exceeded in the target tissue but avoided in surrounding normal tissues. For treatment of a subject having two or more target tissues, local irradiation enables differential drug administration and/or radiotherapy at each of the two or more target tissues. Alternatively, whole body irradiation can be used, as permitted by the low doses of radiation required following radiosensitization of the target tissue.

Radiation can also comprise administration of internal emitters, for example $^{131}$I for treatment of thyroid cancer, NETASTRON™ and QUADRAGEN® pharmaceutical compositions (Cytogen Corp. of Princeton, N.J., United States of America) for treatment of bone metastases, and $^{32}$P for treatment of ovarian cancer. Other internal emitters include $^{125}$I, iridium, and cesium. Internal emitters can be encapsulated for administration or can be loaded into a brachytherapy device. Radiotherapy methods suitable for use in the practice of the presently disclosed subject matter can be found in Leibel & Phillips, 2004, among other sources.

EXAMPLES

The following EXAMPLES provide illustrative embodiments. In light of the present disclosure and the general level of skill in the art, those of skill will appreciate that the following EXAMPLES are intended to be exemplary only and that numerous changes, modifications, and alterations can be employed without departing from the scope of the presently disclosed subject matter.

Materials and Methods for the Examples

Cell culture. HUVECs were purchased from Clonetics Corp. (San Diego, Calif., United States of America) and maintained in EBM-2 medium supplemented with EBM-2 singlequots (Cambrex Corp., East Rutherford, N.J., United States of America). HUVECs were limited to passages 3-6. Lewis Lung carcinoma (LLC) cells were purchased from American Type Culture Collection (Manassas, Va., United States of America) and maintained in DMEM supplemented with 10% FBS and 1% penicillin-streptomycin. Cell lines were incubated at 37° C. in a 5% $CO_2$ incubator.

LFM-A13 (30 µM in vitro or 50 mg/kg, intraperitoneal (i.p.) in vivo) and DMSO was obtained from Sigma-Aldrich Co. (St. Louis, Mo., United States of America). Drug was administered to cells 30-60 min prior irradiation. A Mark-1 Irradiator $^{137}$Cs (JL Shepard and Assoc., San Fernando, Calif., United States of America) was used to irradiate HUVEC cultures at a dose rate of 1.897 Gy/min.

Retrovirus production and HUVEC infection. Negative control and Bmx shRNA retroviral constructs were purchased from OriGene Inc (Rockville, Md., United States of America). A total of 5 different constructs (labeled Bmx A-E) were tested for Bmx knockdown in HUVEC. The retroviruses were produced according to manufacturer's protocol with some modifications. LiNX packaging cell line, purchased from Open Biosystems Inc. (Huntsville, Ala., United States of America), was grown on 10 cm tissue culture plates to 30-40% confluency in media containing DMEM with 10% fetal bovine serum (referred to herein as Complete Growth Medium (CGM)) with hygromycin, penicillin, and streptomycin supplementation. These cells were then transfected with retroviral plasmid DNA by incubation with 5 ml transfection mix for 4-6 hours. The transfection mix contained 12 µg of shRNA retroviral vector DNA within 600 µl serum-free DMEM without antibiotics, 240 µl of room temperature Arrest-In transfection reagent (Open Biosystems Inc.) within 4.4 ml serum-free DMEM without antibiotics which was prepared and kept at room temperature for 45 minutes prior to transfection to allow for transfection complexes to be formed. Following initially 4-6 hours transfection, 5 ml of CGM was added and incubated overnight. The media was changed and the cells were incubated for at least an additional 24 hours. Supernatant was collected and filtered through a 45 µm filter to produce the viral stock.

For HUVEC infection, HUVEC were grown on tissue culture plates to 50% confluency. On the day of infection, the HUVEC was incubated in medium containing 5 µg/ml polybrene for 4 hours prior to infection. Medium was removed and 1.5 ml of virus supernatant supplemented with 5 µg/ml polybrene was added directly to the cells and allowed to adsorb for 40-60 minutes. 7 ml of HUVEC media containing 5 µg/ml of polybrene was added and the cells are incubated for 24 hours. The media was changed to regular HUVEC growth media and the cells were incubated for an additional 2 days to allow for Bmx knockdown.

Cell lysis and immunoblot analysis. HUVECs of passage 3-6 were treated with or without Bmx inhibition (LFM-A13 for 60 minutes or shRNA retrovirus infection 48 hours prior) followed by irradiation and then harvested at the indicated times. Cells were processed and immunoblotted as described in Cuneo et al., 2007. Antibodies were the following: PY20HRP (BD Biosciences, San Jose, Calif., United States of America), actin (Sigma-Aldrich Co.), Bmx and PY40 Bmx (Cell Signaling Technology, Danvers, Mass., United States of America), phospho-Akt (S473), Akt (Cell Signaling Technology) as well as HRP labeled mouse anti-rabbit secondary antibodies (Sigma-Aldrich) except for PY20HRP which was pre-labeled. Films were scanned into Adobe Photoshop with subsequent densitometry analysis. Experiments were performed at least three times.

Immunoprecipitation and in vitro kinase assay. HUVECs of passage 3-6 were grown to 70-80% confluency and then serum starved for 5 hours. The cells were then treated with sham or 3 Gy irradiation. After treatment, the cells were incubated at 37° C. with 5% $CO_2$ for the indicated times. For inhibition studies, inhibitor was added at a 1:1000 dilution 60 minutes prior to irradiation. Following incubation, the tissue culture dishes were placed on ice and washed twice with ice cold 1× Phosphate-buffered Saline (PBS) followed by lysis using 400 µM-PER containing protease and phosphatase inhibitors (Sigma-Aldrich Co.) for 5 minutes. The cells were scraped and transferred to Eppendorf tubes, vortexed for 20 seconds, and incubated on ice for 30 minutes. After clearing the lysate by centrifugation at 15,000 g for 15 minutes at 4° C., the supernatant was quantified for protein concentration using the bicinchoninic acid (BCA) method prior to immunoprecipitation. Immunoprecipitation was performed using the CATCH AND RELEASE® v 2.0 system (Upstate Group, LLC, Charlottesville, Va., United States of America) according to manufacturer's protocol with some modification.

Briefly, spin columns containing binding resin were prepared by washing twice with 1× wash buffer (2000 g/30 seconds). After column preparation, 500 µg of cell lysate was combined with 2 µg of anti-Bmx antibody (Santa Cruz Biotechnology, Inc., Santa Cruz, Calif., United States of America), 10 µl of affinity ligand, and enough 1× wash buffer to have a 500 µl final volume. This was added to the capped spin column which was rotated end-over-end overnight at 4° C. The spin column was washed thrice with 1× wash buffer followed by elution using 70 µl of 1× non-denaturing elution (native protein elution) buffer. For in vitro kinase assay, 35 µl of eluate was then combined with 25 µl of kinase buffer containing 25 mM Tris (pH 7.5), 5 mM β-Glycerophosphate, 2 mM DTT, 0.1 mM $Na_3VO_4$, 10 mM $MgCl_2$ with 1 µl of 10 mM ATP and this was incubated for 20 minutes at 37° C. The reaction was stopped by adding 20 µl of 4×SDS sample buffer and boiling for 5 minutes. Samples were then run on SDS-PAGE and anti-PY20HRP (BD Biosciences) Western blotting was performed to identify phosphorylated protein bands at 75-80 kilodaltons (kDa). Blots were then stripped and re-probed for total Bmx.

WST-1 assay. This assay is a modification of an MTT assay and was performed per the manufacturer's protocol (Calbiochem, San Diego, Calif., United States of America). Briefly, HUVEC were infected with shRNA retrovirus and after 48 hours incubation, cells were lifted by trypsinization, counted, and plated at 10,000 cells/well of 96-well microtiter plates in duplicate. These plates were then subjected to 0 or 2 Gy and incubated for 24 hours at 37° C. with 5% $CO_2$. Following incubation, 10 µl of WST-1 labeling mixture was added to each well and mixed gently prior to returning to the incubator for 2 hours. Optical density at 450 nm ($OD_{450}$ nm) was measured on a microplate reader and results were plotted using Microsoft Excel Software (Microsoft Corp., Redmond, Wash., United States of America).

Clonogenic survival. LLC's or passage 3-6 HUVECs were grown to 70-80% confluency. Cells were washed with 1×PBS, trypsin suspended, and were counted and adjusted to specific densities for each condition. The cells were plated on tissue culture plates and allowed to attach for 4 hours. LFM-A13 or DMSO was added at a 1:1000 dilution followed 60 min later by 0, 2, 4 or 6 Gy. Media was changed after irradiation. 10-14 days after irradiation, the plates were fixed with 70% ethanol and stained with 1% methylene blue. Colonies were then counted using a dissection microscopy with positive colonies containing at least 50 cells. Surviving fraction (SF) was calculated by the equation (number of colonies formed/number of cells plated)/(number of colonies for sham irradiated group/number of cells plated). Dose enhancing ratios were calculated by dividing the dose (Gy) for radiation alone by the dose for radiation plus treatment (normalized for plating efficiency of treatment) for which a SF of 0.2 is achieved. These results were then plotted in a semilogarithmic format using Microsoft Excel software (Microsoft Corp.).

Endothelial cell tubule formation assay. HUVEC of passage 3-6 were grown to 70-80% confluency. Cells were then washed with 1×PBS and suspended by trypsinization. Cells were counted and adjusted to $2.5-5\times10^4$ cells/ml in media. 75 µl MATRIGEL™ (BD Biosciences) were plated into each well of a 96 well plate and allowed to polymerize at 37° C. Cell suspensions (200 µl; $8-12\times10^3$ cells) were added to each well. After thirty minutes, DMSO control or LFM-A13 was added. Thirty minutes later, dishes were treated with sham or 3 Gy and were then incubated until tubules had formed in control plates (4-6 hours). Digital photographs were taken of individual wells and tubules were counted by an observer blinded to the treatment conditions. The mean and standard error were calculated (n=3).

Endothelial closure assay. HUVEC of passage 3-6 were grown on glass slides and were subjected to gap formation as described previously (Cuneo et al., 2007). Cells were treated with LFM-A13 or DMSO control prior to 0 or 3 Gy and incubated for the indicated times. Photographs of cell defect and surrounding cells were taken and relative cell density within the defect was calculated as follows: (number of cells/original cell defect area)/(number of cells/surrounding area).

Apoptosis assays. HUVEC were grown to 70-80% confluency prior to treatment with LFM-A13 or DMSO control. Cells were then irradiated with 0 or 3 Gy and harvested 24 hours after irradiation. Annexin V-FITC Apoptosis Detection kit (BD PharMingen, San Diego, Calif., United States of America) was used to stain cells (propidium iodide (50 ng) and annexin V-FITC (5 ng) were added to $10^5$ cells) for flow cytometry according to manufacturer's protocol. For each treatment, the percent of cells undergoing apoptosis (±SE) was calculated. Camptothecin (5 µmol/L) treatment for 6 hours served as positive control HUVEC were also assayed for apoptosis using a 4',6-Diamidino-2-phenylindole (DAPI) staining of the nuclei to identify cells undergoing morphological changes. 70%-80% confluent HUVECs were treated with or without LFM-A13, incubated for 1 hours, and then irradiated at 3 Gy. Cells were returned to the incubator for an additional 24 hr prior to DAPI staining. Multiple high powered fields (at least 7) were examined by an observer who was blinded to the experimental conditions for each of the cultures. The percentage of cells demonstrating apoptotic nuclei were quantified. The mean and standard error were calculated for each treatment group.

Tumor vascular window model. The tumor vascular window model technique is described in Edwards et al., 2002. Briefly, three mice for each group had tumors grown within a vascular window such that tumor vasculature could be visualized within window frames containing a coordinate system for serial photography. Animals were treated with LFM-A13 by i.p. injection 60 minutes prior to 2 Gy irradiation using an 80 kVp superficial X-ray machine (Pantak X-ray Generator; East Haven, Conn., United States of America). Serial color photographs were taken to document blood vessel appearance on days 0-7. Photographs were scanned and processed using ADOBE® PHOTOSHOP® software (Adobe Systems Inc., San Jose, Calif., United States of America) to mark the center of vessels, verified by an observer blinded to treatment groups. Vascular length density (VLD) was quantified for each microscopic field using IMAGE-PRO® Plus v. 5.1 software (Media Cybernetics, Inc. Silver Spring, Md., United States of America). The mean and standard error of VLD in each treatment group were calculated and plotted. All animals used were cared for according to Vanderbilt University's Institutional Animal Care and Use Committees guidelines.

Tumor immunohistochemistry. LLC's were subcutaneously injected into the hind limb of C57BL/6 mice to form xenografts. When tumors grew to 200 mm³, (approximately 7 days) the mice were treated with five consecutive daily treatments of i.p. LFM-A13 followed 45 minutes later by 3 Gy irradiation using an 80 kVp superficial x-ray generator. Twelve hours following the last radiation treatment, mice were sacrificed and tumors were harvested, fixed in paraffin, and sectioned by the Vanderbilt University Immunohistochemistry Core Facility as described previously (see Cuneo et al., 2007). Immunostaining was with goat anti-CD34 (Santa Cruz Biotechnology) and microvascular photos were analyzed using IMAGE-PRO® software with pixel number quantified.

Tumor growth delay. LLC's were subcutaneously injected into the hind limb of C57/BL6 mice to form xenografts. When tumors grew to 200 mm³, (approximately 7 days) the mice were treated with five consecutive daily treatments of i.p. LFM-A13 followed 45 minutes later by 3 Gy irradiation using an 80 kVp superficial x-ray generator. Serial measurements of tumor dimensions were taken by caliper and tumor volume was calculated using the modified ellipsoid formula (length×width×depth)/2. The mean and standard error were plotted using Microsoft Excel software.

Statistical analysis. The mean and standard errors for all assays were calculated using Microsoft Excel software. Student's t test was performed to determine P values between treatment groups. P values less than or equal to 0.05 were considered statistically significant.

Example 1

Bmx is Activated in Endothelium Upon Irradiation

Primary culture vascular endothelial cells (HUVEC) were examined to determine whether Bmx was activated by IR because of its similarities in structure and signaling to the serine/threonine protein kinase Akt/PKB, and also whether it contributed to radiation resistance. FIG. 1A depicts analysis of a time course of Bmx activation upon irradiation with a clinically relevant dose of 2 Gy. Tyrosine 40, present in the PH domain of Bmx, becomes phosphorylated during its activation (Chen et al., 2001). As shown in FIG. 1A, Bmx was phosphorylated at 60 minutes following 2 Gy of irradiation.

Figure 1B:
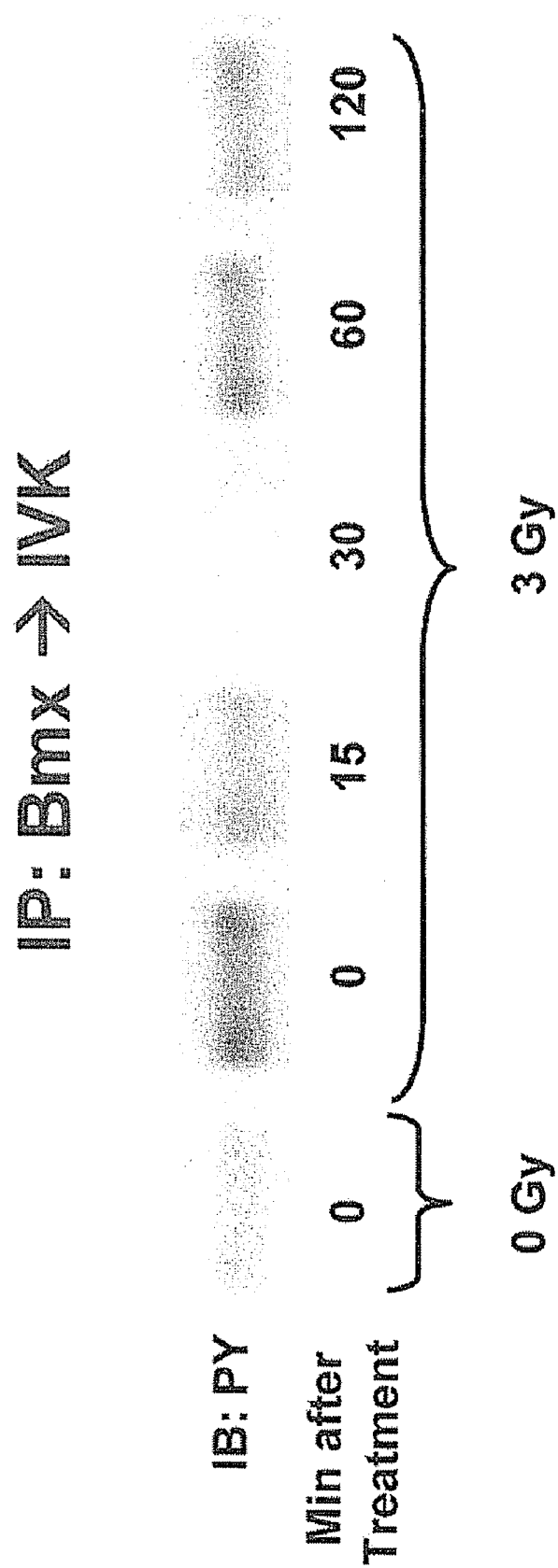

To confirm this result, an in vitro kinase (IVK) assay was employed in which Bmx was immunoprecipitated from irradiated or sham irradiated endothelial cells and then incubated with ATP in a kinase reaction. These samples were run on SDS-PAGE and probed with an anti-phosphotyrosine antibody to analyze autophosphorylation of Bmx. As shown in FIG. 1B, Bmx was activated after irradiation. Interestingly, Bmx showed significant kinase activity immediately following irradiation and then has a second peak of activity at 1 hour.

Example 2

Bmx Knockdown Enhanced Radiation Efficacy in Endothelium

Figure 2A:
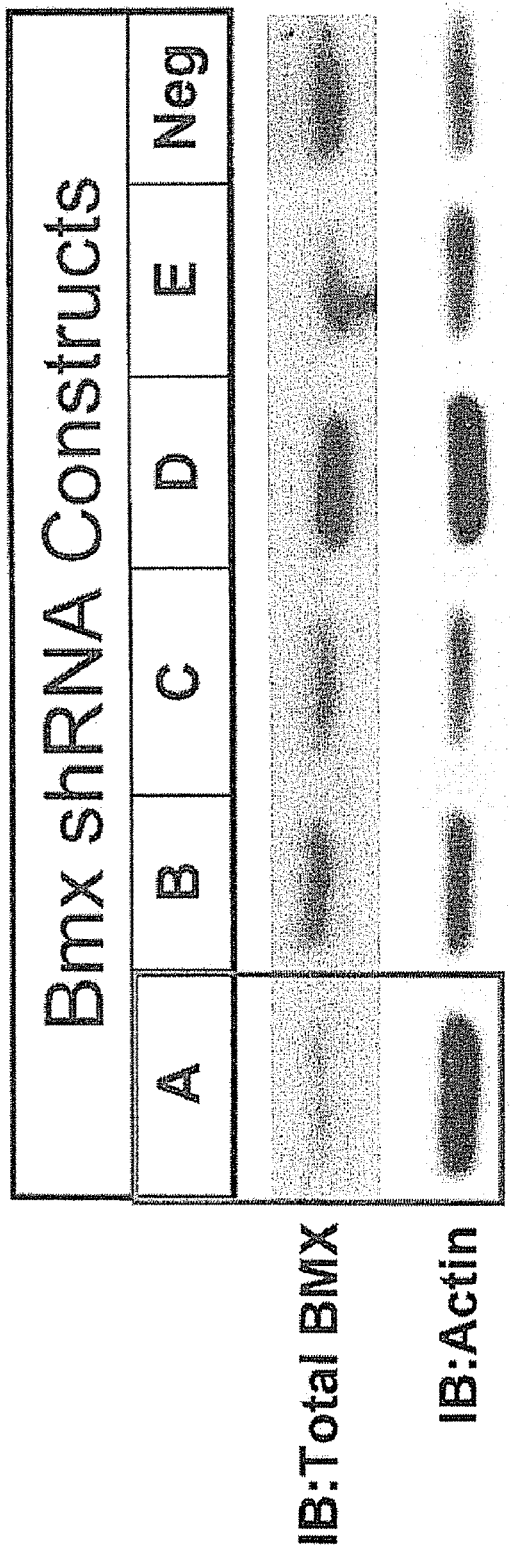
FIGS. 2A and 2B present the results of experiments showing retroviral shRNA knockdown of Bmx in HUVEC. Multiple shRNA retroviral plasmid constructs (Bmx constructs A-E, and negative control construct; Neg) were transfected into LiNX cells to produce retroviral supernatants as described in Materials and Methods for the EXAMPLES hereinbelow. HUVEC were infected with the retroviral supernatants and incubated for 48 hours.

Because a clear activation of Bmx following a clinically relevant dose of IR was observed, whether Bmx activation protected the endothelial cells from cytoxic damage was examined. Since primary culture endothelial cells, such as HUVEC, have low transfection yields, a retroviral shRNA system was employed to knockdown Bmx levels prior to irradiation. FIG. 2A shows five different retroviral constructs (A through E) for Bmx as well as a negative control construct (Neg) that were used to infect HUVEC. After 48 hours, infected cells were harvested and lysates were prepared for total Bmx Western blotting. As can be seen, construct A (shBmxA) provided about a 90% knockdown of Bmx protein levels compared to the negative control shRNA vector. Bmx knockdown experiments were performed with or without irradiation.

Figure 2B:
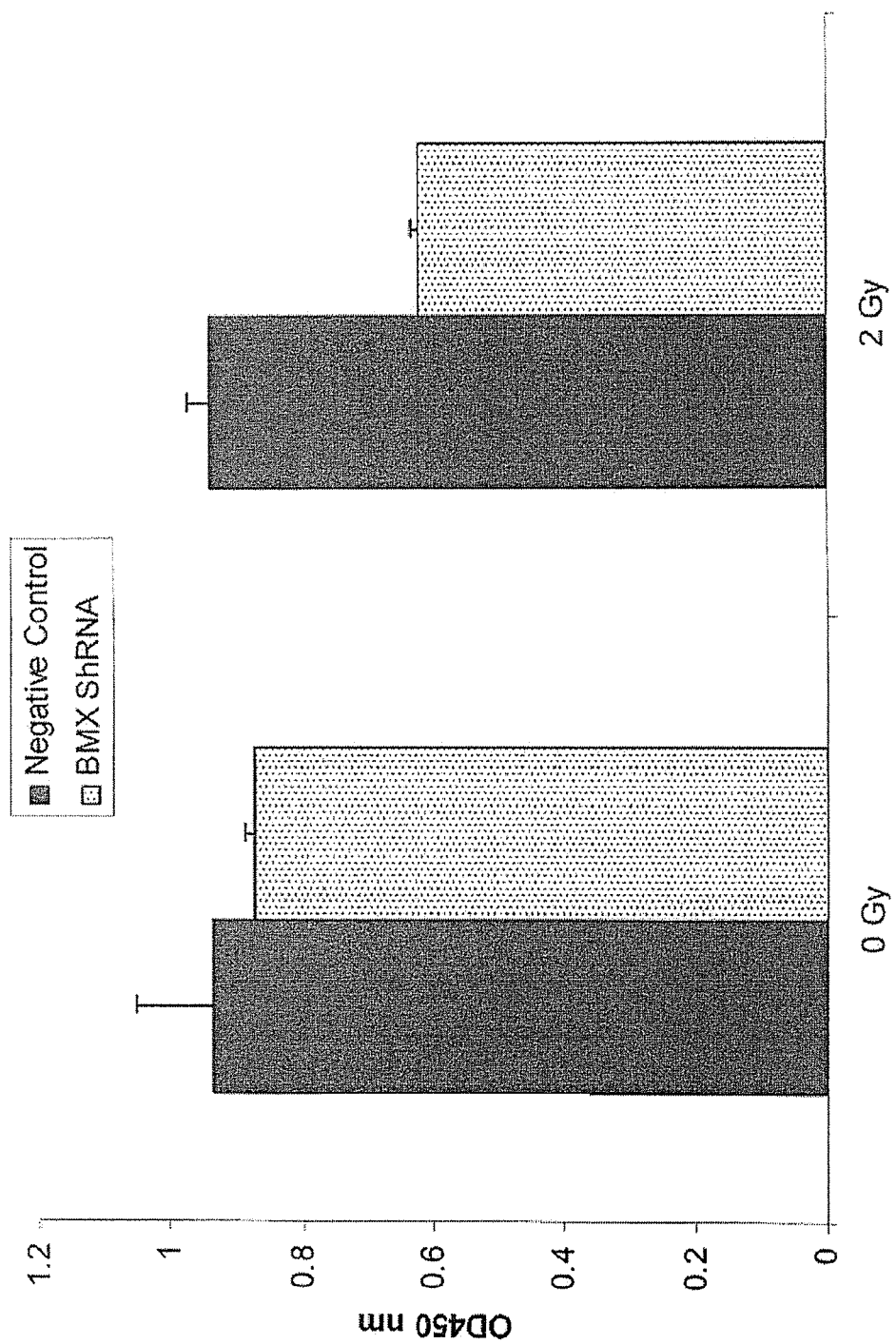

FIG. 2B shows the results of MTT-based (WST-1) survival assays. HUVEC were infected with either shBmxA or negative control vectors. After 48 hours, cells were counted and plated at 10,000 cells/well in duplicate within 96-well dishes. The cells were treated with either sham (0 Gy) or 2 Gy irradiation and incubated for 24 hours. Following this incubation, WST-1 labeling mixture was added to each well and analyzed at to determine mitochondrial viability by optical density at 45 nm ($OD_{450}$). Normalized values for $OD_{450}$ are shown as mean and standard error. Combined Bmx knockdown with irradiation decreased HUVEC survival.

Example 3

Pharmacological Inhibition of Bmx

Figures 3A, 3B:
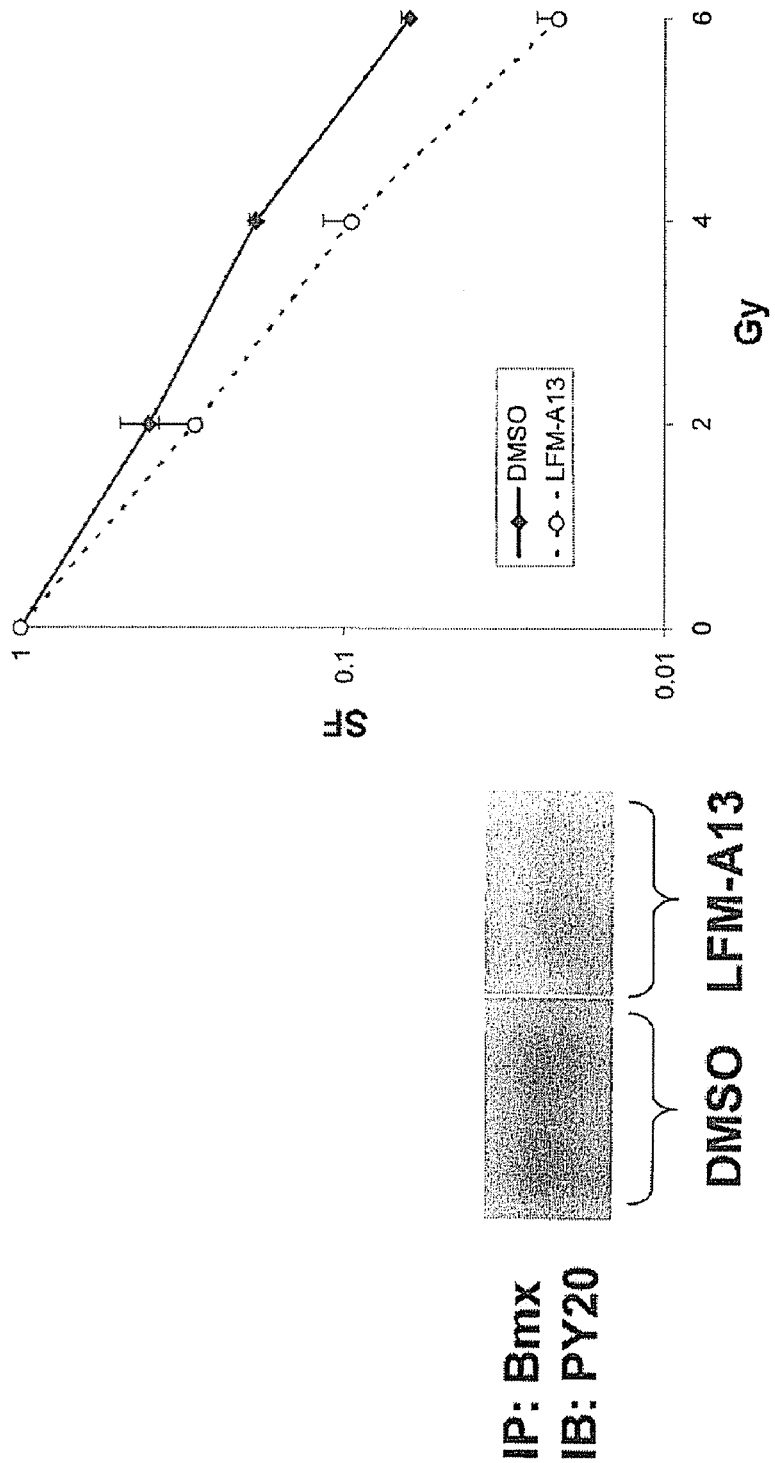
FIGS. 3A-3D depict the results of experiments showing that radiation-induced endothelial cell cytotoxicity is enhanced by Bmx inhibition.

Having established that Bmx knockdown enhanced radiation efficacy in endothelial cells, whether or not pharmacological inhibition of Bmx would show the same effect was examined. Bmx specific inhibitors have been described (see e.g., Kawakami et al., 1999; Mahajan et al., 1999; Uckun et al., 2002; He et al., 2004), particularly LFM-A13, which targets the Tec family. Since Bmx is the only Tec family member expressed in endothelium, this drug was studied in HUVEC. LFM-A13 has been shown to block VEGF induced signaling through Bmx inhibition in HUVEC at a dose of 25 µM. Therefore, 30 µM LFM-A13 was employed for in vitro studies. FIG. 3A shows the use of vehicle control (DMSO) or 30 µM LFM-A13 pre-incubation on radiation-induced Bmx activation in the in vitro kinase assay. As can be seen, LFM-A13 attenuated the activation of Bmx in response to 3 Gy.

Example 4

Bmx Inhibition Attenuated Endothelial Cell Viability

To determine whether LFM-A13 produces a radiosensitization effect in HUVEC, clonogenic survival assays in HUVEC with LFM-A13 pre-incubation was studied (see FIG. 3B). HUVEC were pre-treated with DMSO vehicle control or 30 µM LFM-A13 for 45 minutes prior to irradiation with 0, 2, 4, or 6 Gy. Colonies were allowed to form over 10 days, which were then counted and the surviving fraction was calculated for each radiation dose. These studies indicated that 30 µM LFM-A13 radiosensitized HUVEC compared to the control as evidenced by the downward survival curve shift. The dose enhancing ratio (DER) was 1.47.

Figure 3C:
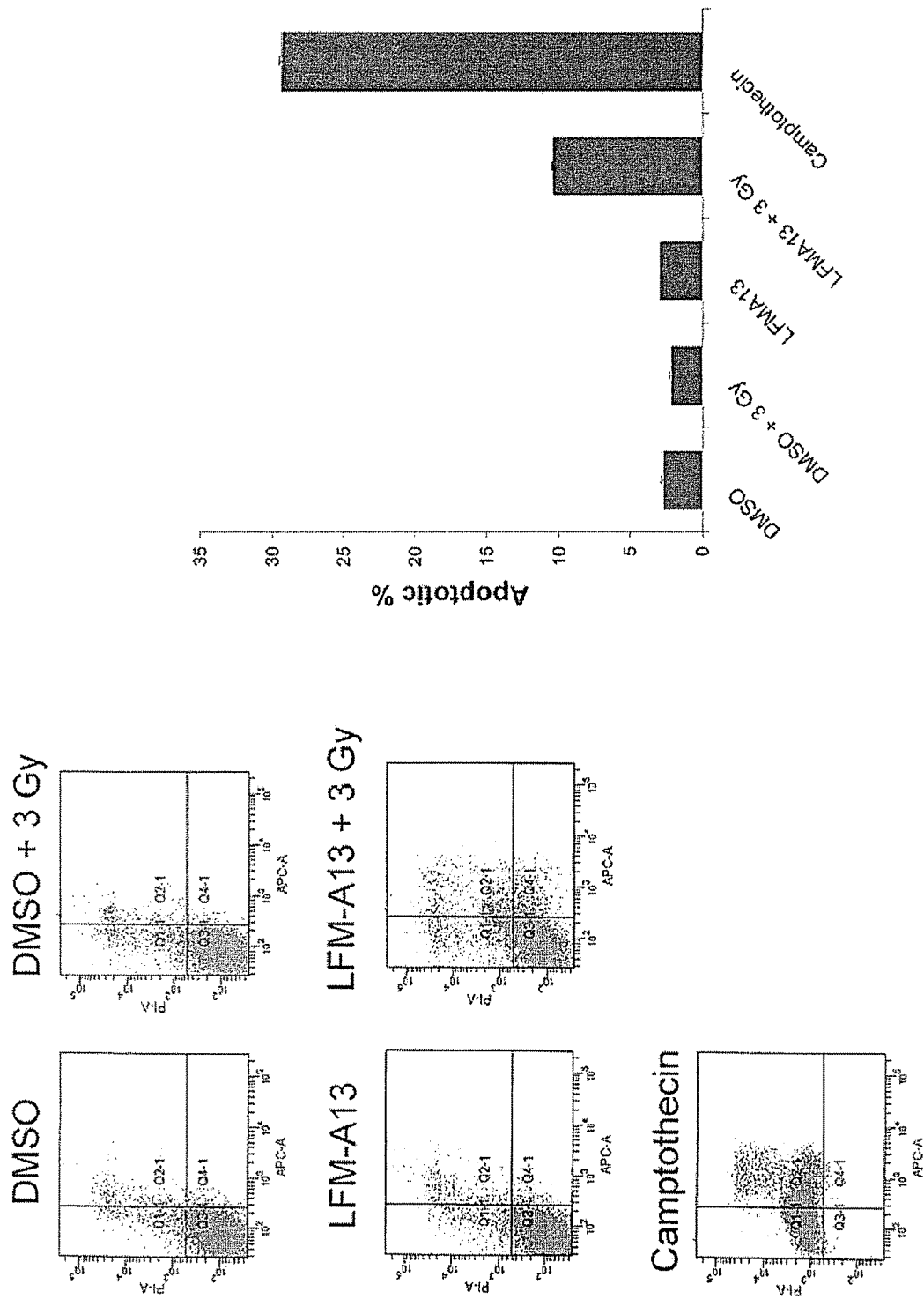
Figure 3D:
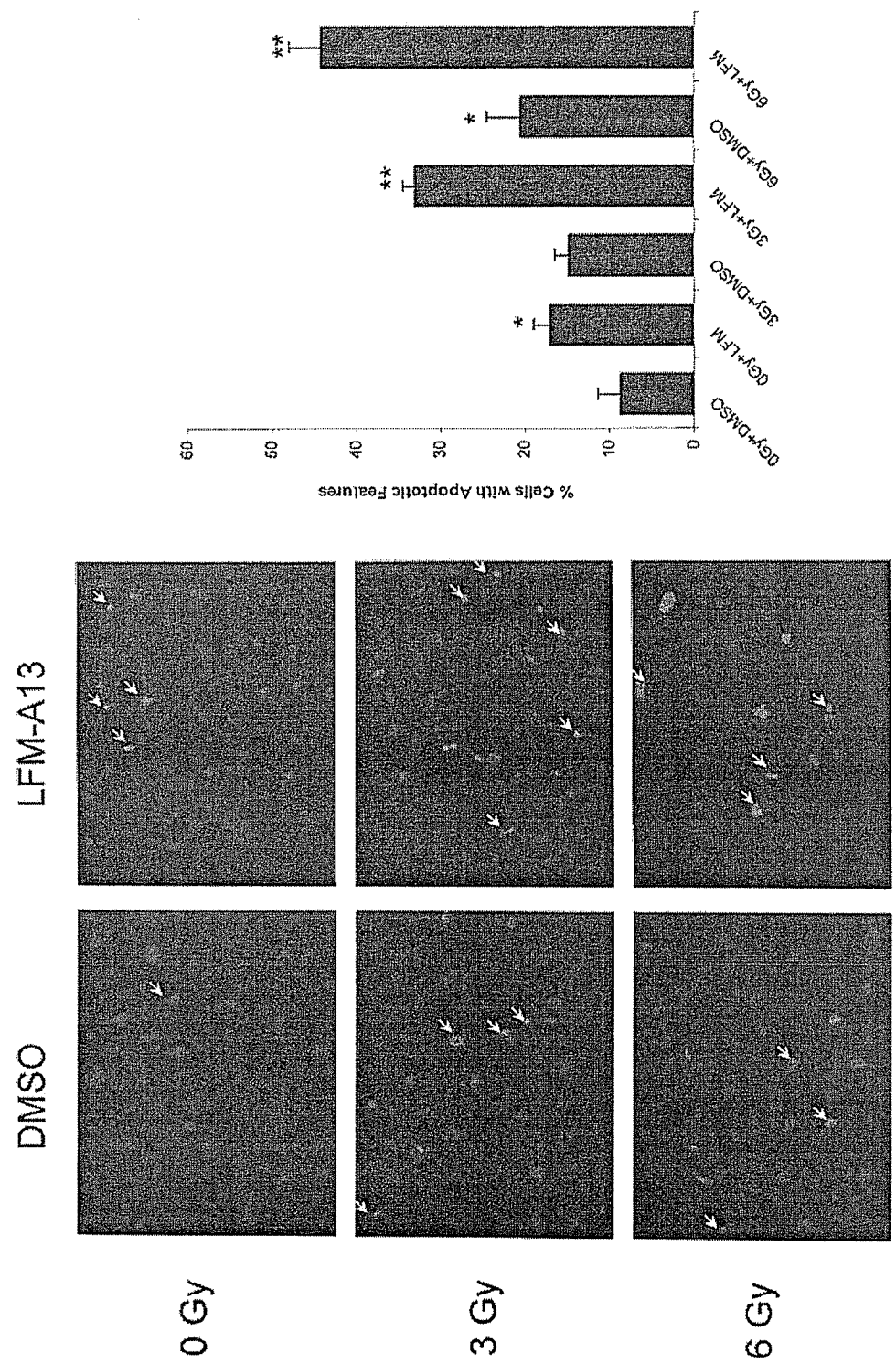

Apoptosis was studied to determine whether this was a mechanism of enhanced cytotoxicity. FIG. 3C illustrates the effect of LFM-A13 on apoptosis within these cells. HUVEC treated with 30 µM LFM-A13 or DMSO control were subjected to sham or 3 Gy irradiation and then incubated for 24 hours prior to trypsinization and flow cytometric analysis. Annexin V-propidium iodide staining revealed that drug or 3 Gy alone was not capable of shifting cells into either early (Q4-1) or late (Q2-1) apoptosis, but that the combination of LFM-A13 and 3 Gy caused a statistically significant ($p<0.001$ vs. LFM-A13 or 3 Gy alone) increase in apoptosis. To confirm these findings, HUVEC were treated with either 30 µM LFM-A13 or DMSO control with or without 3 or 6 Gy irradiation and incubated for 24 hours. The cells were fixed and stained with DAPI and the percent of apoptotic cells was quantified. As shown in FIG. 3D, the combination of LFM-A13 and irradiation resulted in enhancement of apoptosis. In FIG. 3D, * indicates $p<0.05$ vs. DMSO control and ** indicates $p<0.001$ vs. LFM alone.

Example 5

Bmx Inhibition Attenuated Endothelial Cell Function

Figure 4A:
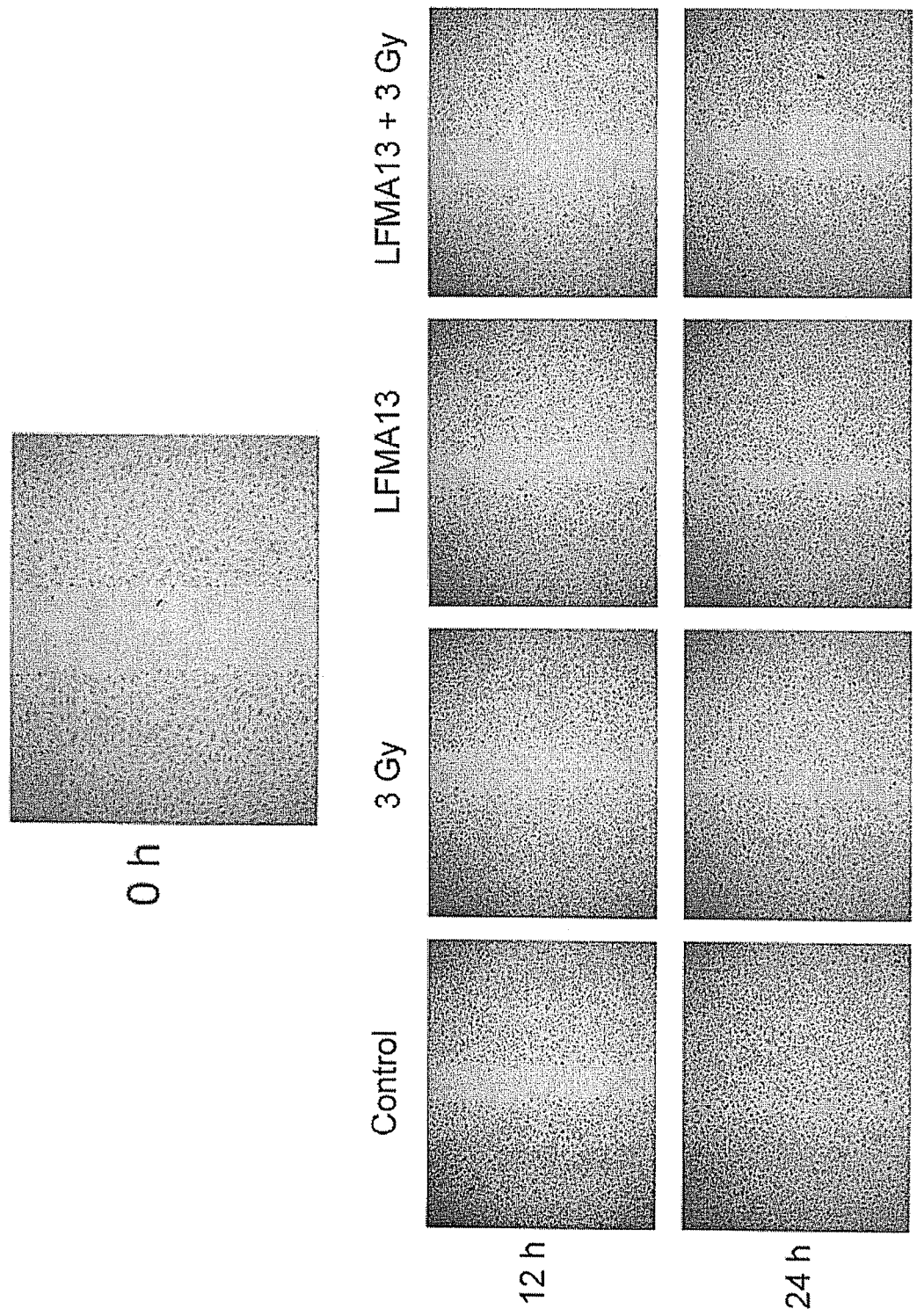
FIGS. 4A-4D depict the results of experiments showing that endothelial cell function is attenuated by Bmx inhibition and radiation.
Figure 4B:
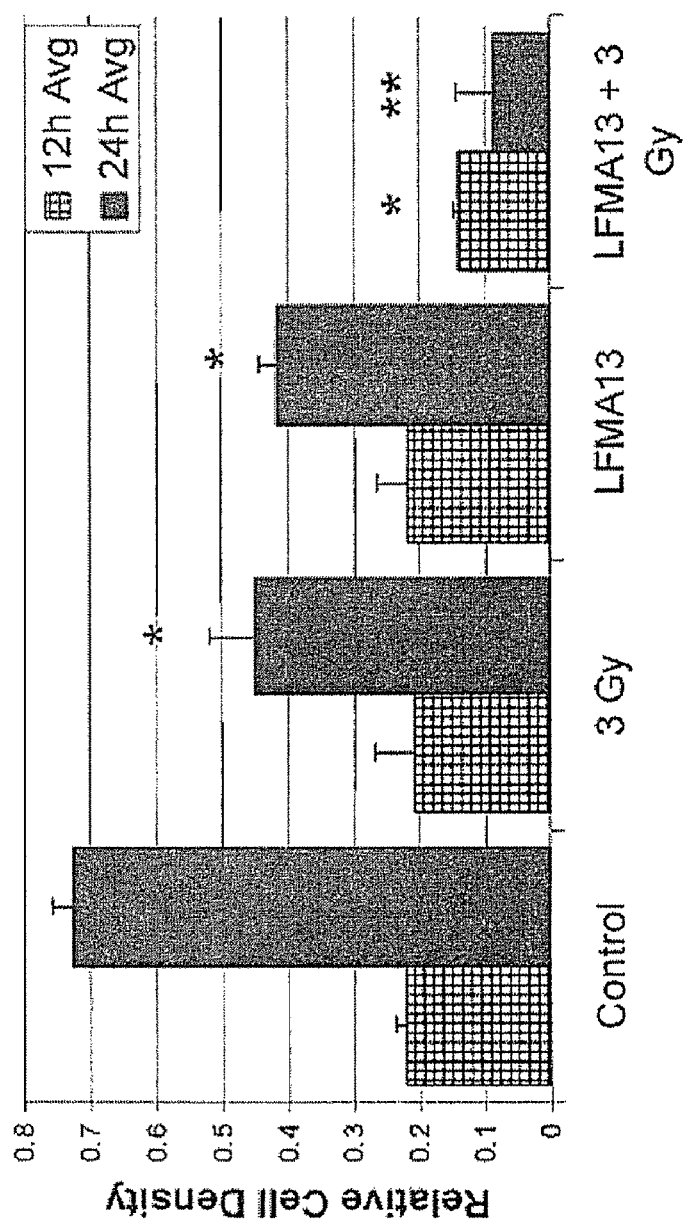

Functional assays of endothelial cells include cell migration and capillary-like tubule formation. FIG. 4A illustrates the effect of LFM-A13 and irradiation on endothelial migration across a gap (endothelial cell closure assay) at 12 and 24 hours. HUVEC were plated on glass slides and grown to 80% confluency. A gap region (i.e., a region on the glass slide that was made free of cells) was then created using a 200 µl pipette tip. The slides were then treated with 30 µM LFM-A13 or DMSO control for 45 minutes prior to either 0 or 3 Gy. Cells were fixed and stained at 12 or 24 hours and photographs were taken of the gap region and the surrounding cells to determine the ability of the HUVEC to migrate across and fill the gap. Relative cell density was calculated for each condition to control for the cytotoxic effects of treatment as shown in FIG. 4B. By 24 hours, control cells effectively migrated across the gap. 30 µM LFM-A13 or 3 Gy alone had minimal effect on attenuating endothelial cell closure at both 12 hours and 24 hours compared to vehicle treated control. However, the combination induced a greater than additive effect which was statistically significant (* indicates $p<0.05$ vs. control, and ** is $p<0.01$ vs. LFM-A13).

Figure 4C:
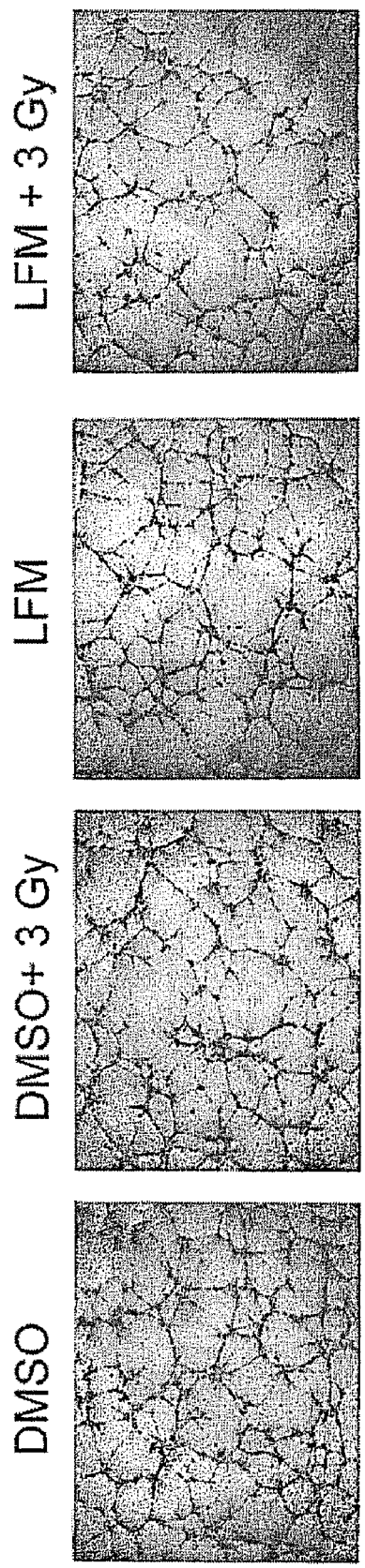
Figure 4D:
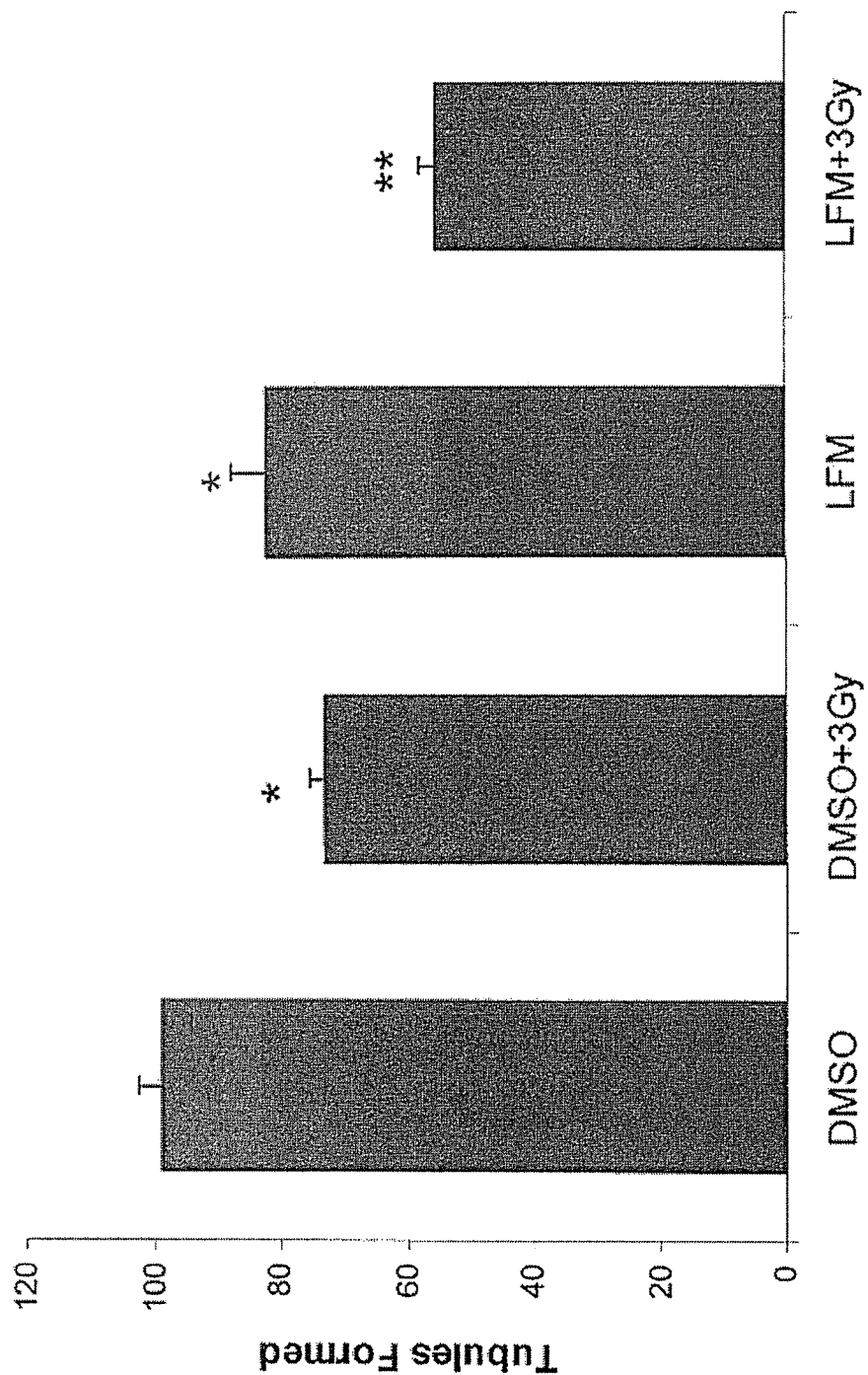

FIGS. 4C and 4D show the results of capillary tubule formation assays. HUVEC plated onto a MATRIGEL™ matrix were treated with 30 µM LFM-A13 or DMSO with or without 3 Gy irradiation and allowed to form tubules. The cells were then fixed and stained. The number of tubules was quantified and plotted. Representative photographs are shown in FIG. 4C and quantified in FIG. 4D. Cells that were treated with both LFM-A13 and 3 Gy showed a significant reduction ($p<0.005$) in tubules formed compared to cells treated with either treatment alone.

Example 6

Bmx Inhibition Attenuated Tumor Vasculature

Figure 5A:
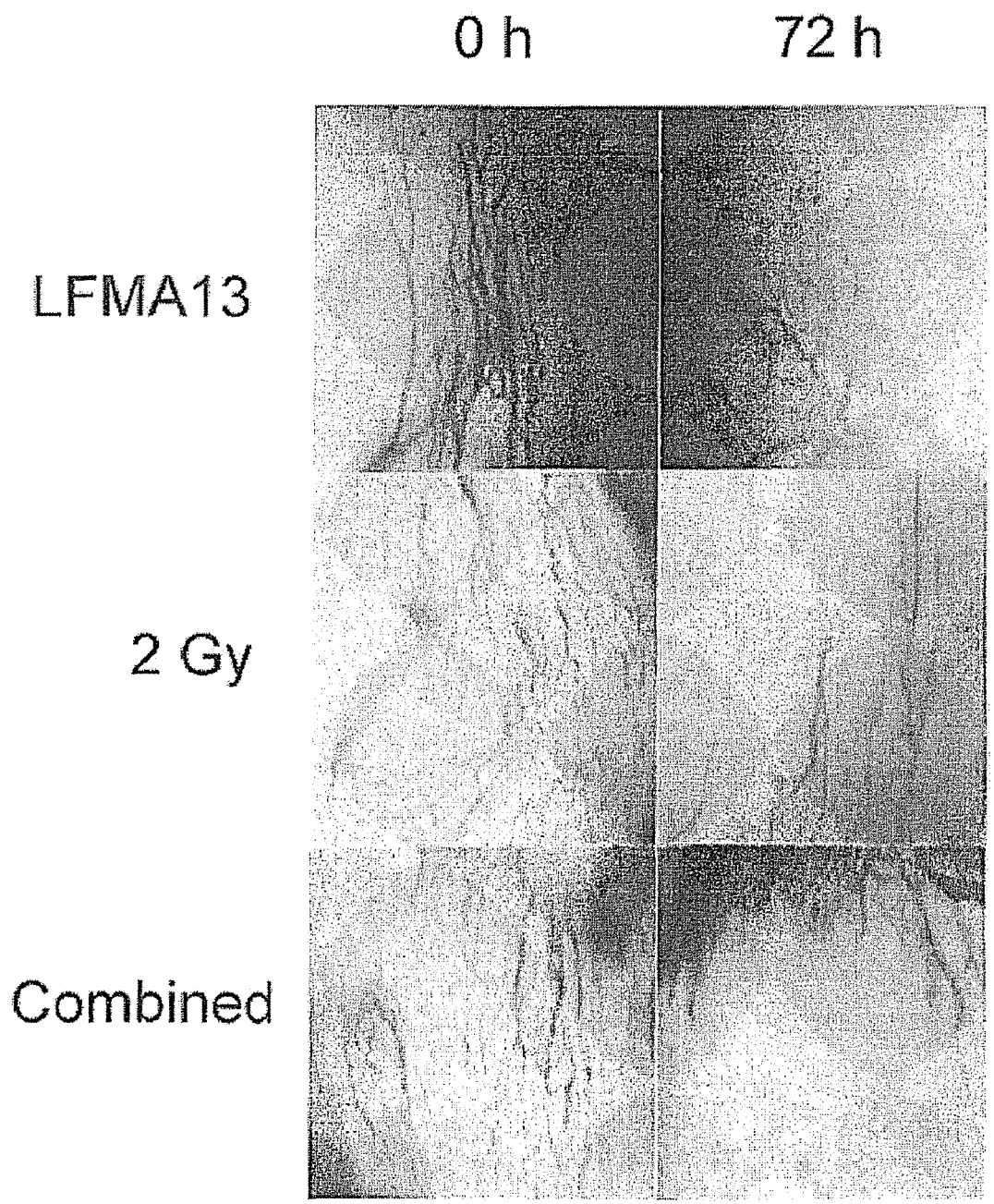
FIGS. 5A-5D depict the results of experiments showing that tumor vascular destruction is enhanced by Bmx inhibition and radiation. In the tumor vascular window model, a transparent window chamber was placed onto the dorsal skin fold of C57BL/6 mice to allow for visualization of blood vessels. LLC cells were injected into the chamber and once vessels formed (6-8 days), the mice were treated with one intraperitoneal dose of 50 mg/kg LFM-A13 or DMSO vehicle control followed one hour followed by 2 Gy. Microscopic photos were taken daily and the density of blood vessels was quantified for each treatment group.
Figure 5B:
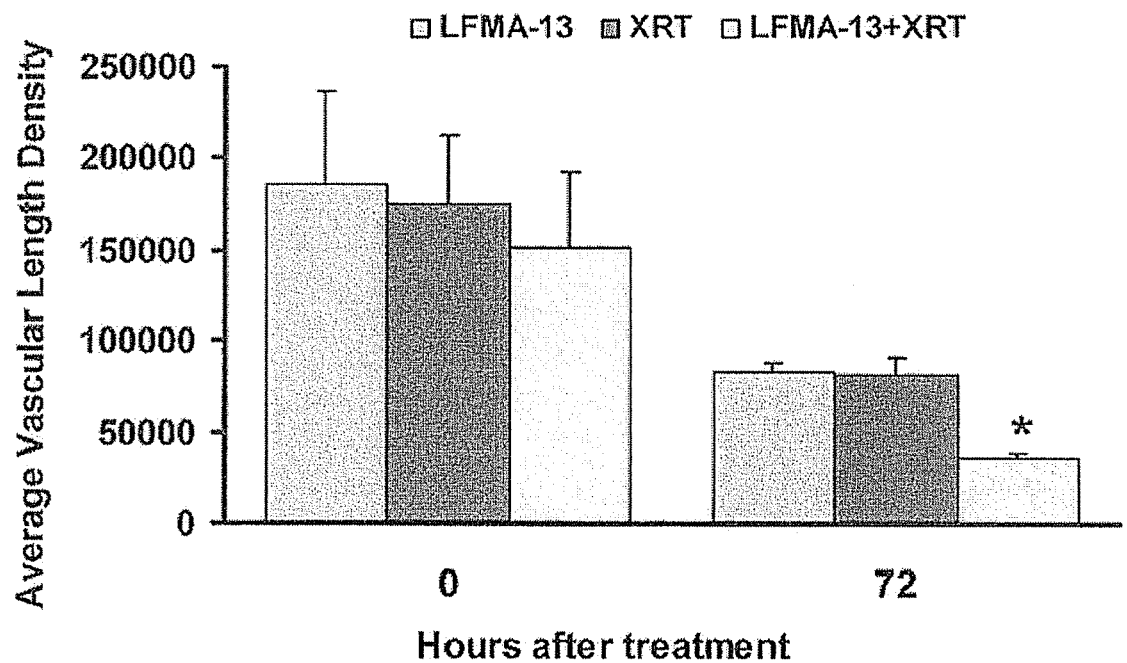

To determine whether Bmx inhibition enhanced radiation-induced destruction of tumor vasculature in vivo, intraperitoneal (i.p.) injection of LFM-A13 was utilized prior to irradiation. A tumor vascular window chamber was placed on the dorsum of C57BL/6 mice and Lewis Lung Carcinoma (LLC) cells were implanted within the dorsal skin fold to allow for visualization of intravital tumor vasculature. Serial photographs were taken of the same region of the tumor allowing for assessment of blood vessel formation and destruction. FIG. 5A shows the effect of a single 50 mg/kg i.p. administration of LFM-A13 prior to 2 Gy irradiation. Representative photographs show that combination treatment resulted in a dramatic reduction in tumor blood vessels. These results were quantified for each treatment condition as mean vascular length density with standard error (see FIG. 5B; p<0.0014 vs. LFM-A13 or 2 Gy alone).

Figure 5C:
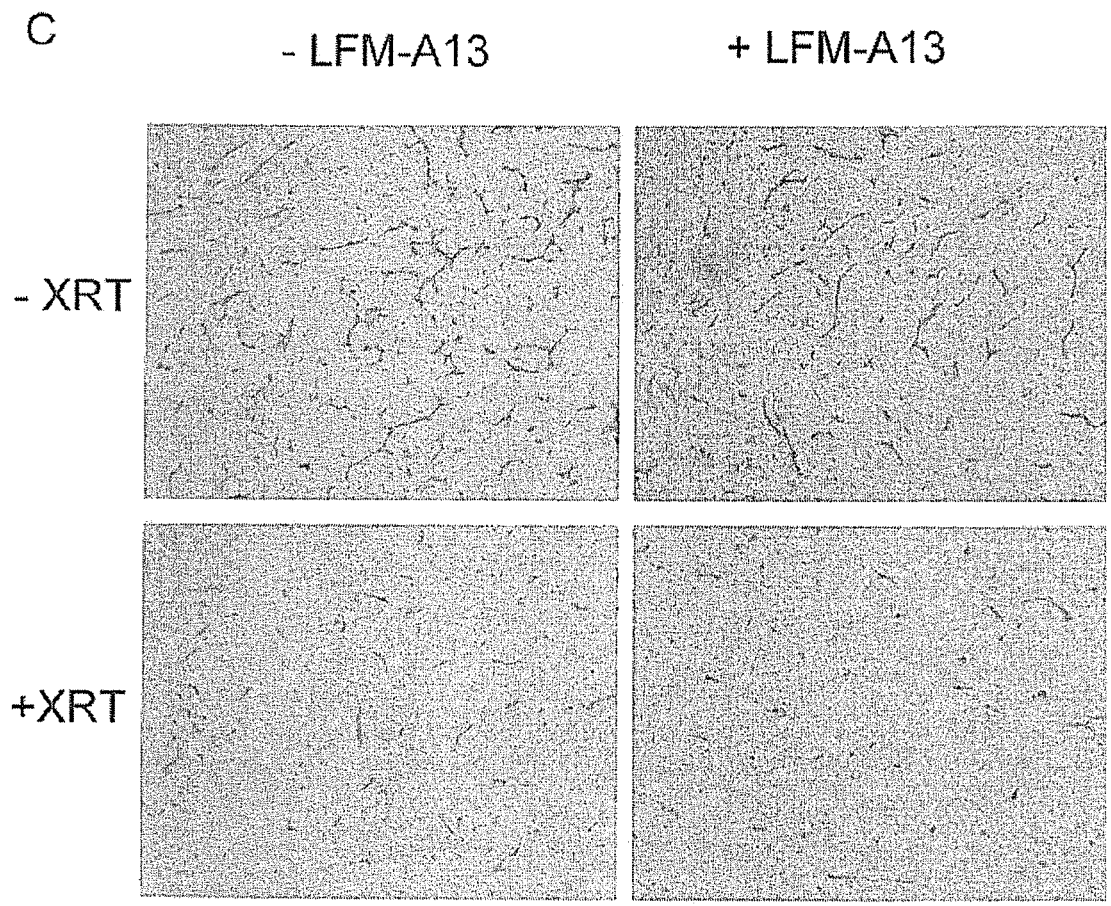
Figure 5D:
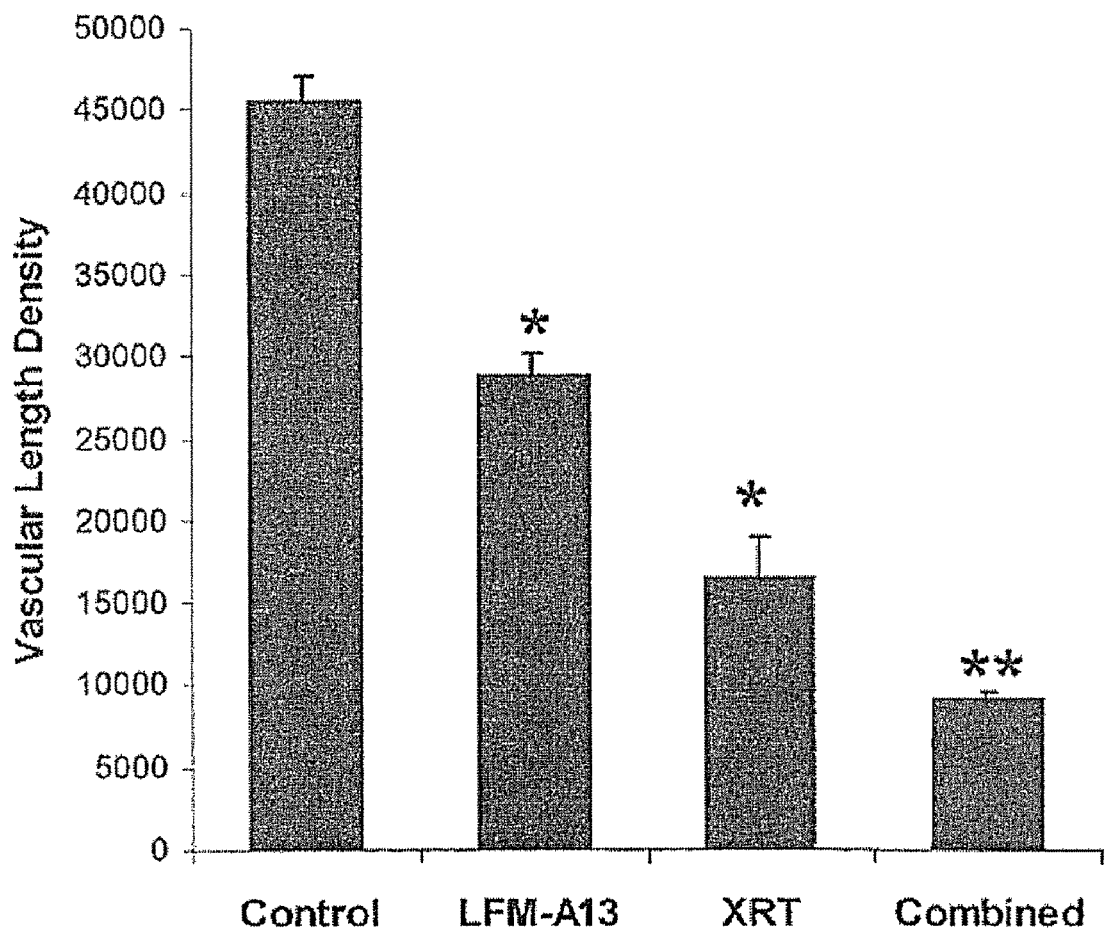

To confirm these results, a hind limb xenograft model was employed for determining vascular density within tumor sections. LLCs were implanted into the hind limbs of C57BL/6 mice. After tumors were formed, they were subjected to either daily LFM-A13 (50 mg/kg i.p. injection) or DMSO followed 45 minutes later by 3 Gy or sham irradiation for a total of five treatments. The tumors were then harvested and prepared for immunohistochemistry analysis. Vessels were stained by anti-CD34 as shown in FIG. 5C and these were quantified as shown in FIG. 5D. As can be seen, combination treatment was most effective at attenuating blood vessel formation (p=0.043 vs. IR; p=0.0001 vs. LFM-A13 or vehicle control).

Example 7

Bmx Inhibition did not Affect Radiation Sensitivity of LLC

Figure 6A:
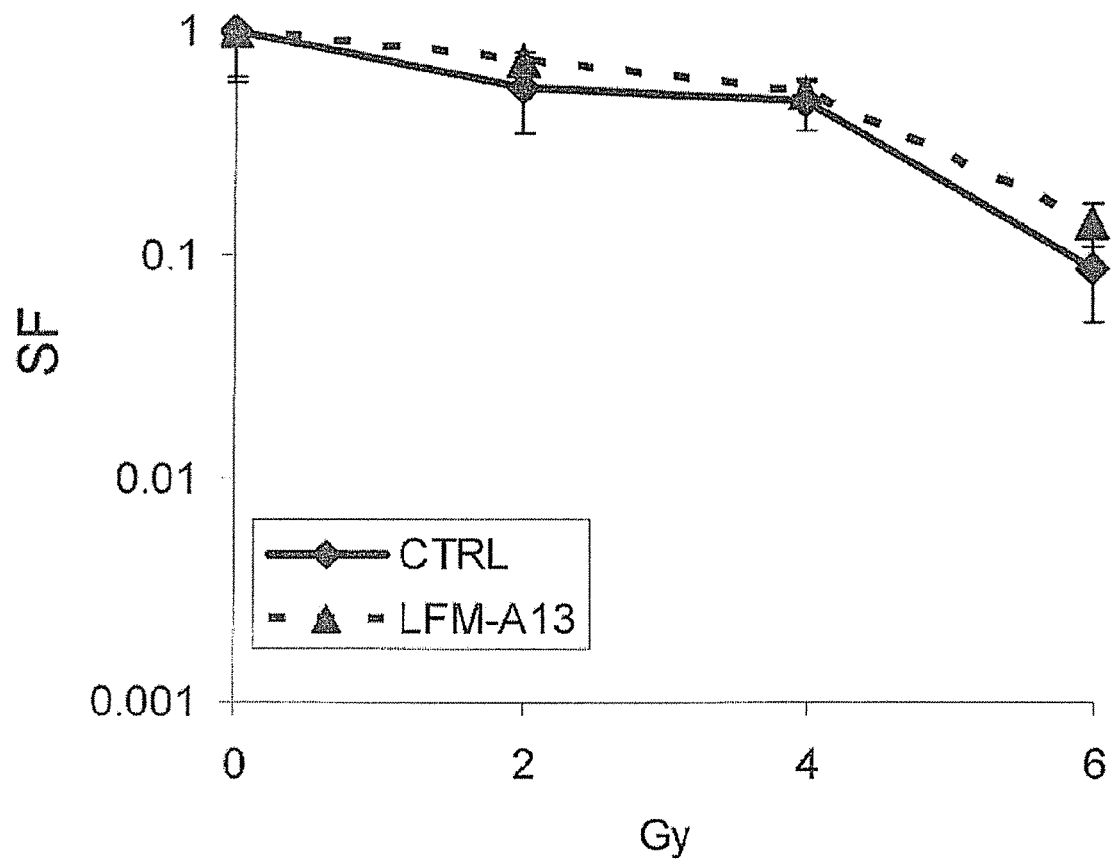
FIGS. 6A and 6B are graphs showing that Bmx inhibition enhances radiation efficacy in a xenograft lung cancer model. For FIG. 6A, LLCs were treated with DMSO or LFM-A13 prior to 0, 2, 4, or 6 Gy irradiation for clonogenic survival assay as performed with HUVEC in FIGS. 2 and 3. Surviving colonies were plotted as a fraction of cells plated that was normalized by the plating efficiency for each condition. SE Bars are shown. For FIG. 6B, LLCs were injected into the hind limb of C57BL/6 mice and tumors were allowed to form. Animals were separated into 4 treatment groups, DMSO vehicle control with sham irradiation (C), LFM-A13 with sham irradiation (L), radiation alone (X), or combined LFM-A13 with radiation (L+X). Treatments were given as i.p. injection of 50 mg/kg LFM-A13 45 min prior to 3 Gy which was given daily for 5 consecutive days. Tumor size was measured and volume was calculated and mean tumor volume and standard error for each group was plotted. Tumor growth delay was determined for 1.5 cm$^3$ volume time point for each group. p=0.027 for combination treatment group.

Whether Bmx inhibition could affect radiation sensitization in the Lewis Lung Carcinoma (LLC) cell line was also tested. As shown in FIG. 6A, LFM-A13 showed no difference in clonogenic survival compared to DMSO control in LLCs, suggesting that LFM-A13 enhancement of radiation pertained to its anti-vascular effect in this tumor model, although it is not desired to be bound by any particular theory of operation.

Example 8

Bmx Inhibition Enhanced Radiation Efficacy in Tumor Growth Delay

Figure 6B:
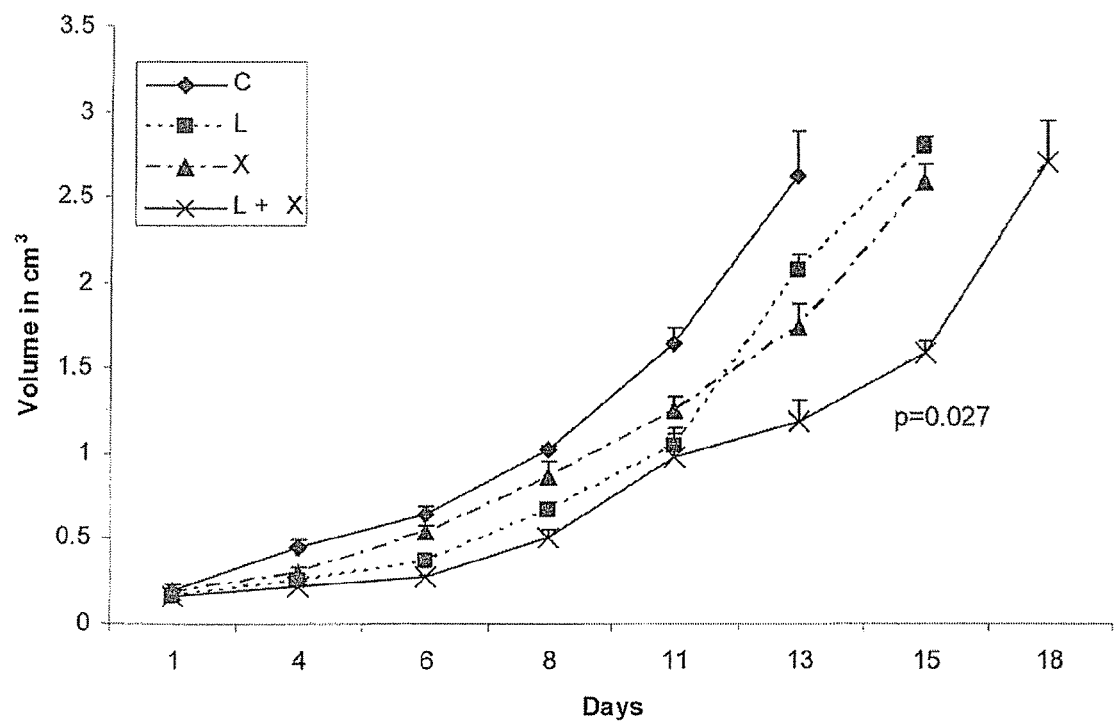

Although LFM-A13 treatment did not affect the radiosensitivity of the LLCs, LFM-A13 could still enhance radiation effects in vivo as an anti-vascular treatment. To determine whether treatment with LFM-A13 could enhance tumor growth delay in irradiated tumors, mice bearing LLC hind limb tumors were treated as in FIG. 5C, with i.p. injection of 50 mg/kg LFM-A13 or DMSO 45 minutes prior to 3 Gy or sham irradiation for 5 consecutive days. The mean tumor volume and standard error are plotted for each treatment group in FIG. 6B. Whereas LFM-A13 or radiation treatment alone resulted in a small growth delay, combination treatment demonstrated a statistically significant enhancement of growth delay (p=0.027), suggesting that LFM-A13 can enhance the efficacy of therapeutic radiation.

Discussion of the Examples

Disclosed herein are investigations into the roles of Bmx in the radiation response of tumor vasculature. Activation of Bmx occurred at clinically relevant doses of radiation: 2-3 Gy. shRNA knockdown of Bmx resulted in radiation sensitization in HUVEC, suggesting that Bmx inhibition is a promising pharmacological target for radiation enhancement.

Although LMF-A13 is clinically used as a Btk inhibitor, many groups have utilized LFM-A13 as a Bmx inhibitor due to the high homology between Bmx and Btk. Since Btk is only found in bone marrow derived cells, it was believed that LFM-A13 could be used effectively for Bmx inhibition in the model systems disclosed herein. As demonstrated in the in vitro kinase assays disclosed herein, LFM-A13 effectively attenuated Bmx activation in response to radiation. This drug not only enhanced the cytotoxic effects of irradiation on HUVEC, but also inhibited the function of these cultured endothelial cells. Apoptosis and clonogenic studies revealed that LFM-A13 was capable of inducing radiosensitization in HUVEC. Moreover, LFM-A13 in combination with radiation resulted in dramatic effects on endothelial cell migration as evidenced by the endothelial closure assay and tubule formation assay.

The vascular effects were more pronounced in the in vivo tumor models. Tumor vascular window blood vessels were minimally inhibited by 2 Gy or LFM-A13 alone. However, in combination, LFM-A13 and 2 Gy substantially disrupted tumor blood vessel formation. This anti-vascular effect was confirmed in hind limb tumor models, which showed that daily LFM-A13 and 3 Gy significantly affected the tumor microvasculature. Tumor growth delay was displayed in the combination arm which was more than additive.

Tec family kinase inhibition has garnered attention, although mainly in relation to anti-inflammation. Interestingly, ImClone Systems Inc. has developed a Bmx single chain intrabody system which can partially attenuate Src transformation potential (Paz et al., 2005). Recently, Pan et al. described a number of selective irreversible Btk inhibitors aimed at treating rheumatoid arthritis (Pan et al., 2007). Moreover, CGI Pharmaceuticals, Inc. has been developing their own novel Btk inhibitors, cgi1316 and cgi1746, for use in inflammatory diseases. However, LFM-A13, a rationally designed inhibitor developed by the Parker Hughes Institute, has been extensively tested in pre-clinical models. The pharmacokinetics and toxicity data have been previously published (Uckun et al., 2002) which provided the basis for the present study. The drug appears to be well-tolerated based on these murine studies. Another commercially available Tec family inhibitor, terreic acid (Kawakami et al., 1999), seemed to be at least as effective as LFM-A13 in the in vitro studies disclosed herein. However, since very little is known about in vivo toxicity and pharmacokinetics for terreic acid, the presently disclosed investigations focused on LFM-A13.

Bmx provides an alternative cell survival pathway to that of PI3K-Akt signal transduction. It is possible that treatments that have targeted PI3K-Akt signaling might be deriving some of their efficacy from concomitant Bmx inhibition. Further studies can determine whether Bmx inhibition in combination with PI3K-Akt blockade provide additional benefit. Nevertheless, Bmx inhibition remains an attractive potential target for radiation enhancement because Bmx activation occurs rapidly and transiently following radiation such that prolonged Bmx inhibition is probably not necessary for radiation sensitization to occur, which is consistent with the cell culture assays disclosed herein in which the drug was removed shortly after irradiation. Therefore, short acting drug formulations together with radiation are candidates for causing less systemic effects than typically occur with long-term administration.

In summary, Bmx is a new molecular target for radiation sensitization based on in vitro and in vivo experimentation in vascular endothelium.

REFERENCES

All references listed in the instant disclosure, including but not limited to all patents, patent applications and publications thereof, scientific journal articles, and database entries (including but not limited to GENBANK® database entries including all annotations available therein) are incorporated herein by reference in their entireties to the extent that they supplement, explain, provide a background for, or teach methodology, techniques, and/or compositions employed herein.

Abassi et al. (2003) *J Biol Chem* 278:35636-35643.
Adelman et al. (1983) *DNA* 2:183-193.
Advani et al. (1998) *Gene Ther* 5:160-165.
Allam et al. (1993) *Intl J Radiat Oncol Biol Phys* 27:303-308.
Antonakopoulos et al. (1994) *Histopathology* 25:447-454.
Arap et al. (1998) *Science* 279:377-380.
Ausubel (ed.) (1995) *Short Protocols in Molecular Biology*, 3rd ed. Wiley, New York, United States of America.
Ausubel et al. (eds.) (1992) *Current Protocols in Molecular Biology*. Wiley, New York, N.Y., United States of America.
Baher et al. (1999) *Anticancer Res* 19:2917-2924.
Baillie et al. (1995) *Br J Cancer* 72:257-267.
Bass (2001) *Nature* 411:428-429.
Batzer et al. (1991) *Nucleic Acids Res* 19:5081.
Baumann et al. (1992) *Intl J Radiat Oncol Biol Phys* 23:803-809.
Bauminger & Wilchek (1980) *Methods Enzymol* 70:151-159.
Beaucage & Iyer (1993) *Tetrahedron* 49:1925-1963.
Becerril et al. (1999) *Biochem Biophys Res Commun* 255:386-393.
Beigelman et al. (1995) *J Biol Chem* 270:25702-25708.
Bellon et al. (1997) *Bioconjugate Chem* 8:204-212.
Betageri et al. (eds.) (1993) *Liposome Drug Delivery Systems*. Technomic Publishing, Lancaster; Pa., United States of America.
Blanchard et al. (1992) *Mol Cell Biol* 12:5373-5385.
Brennan et al. (1998) *Biotechnol Bioeng* 61:33-45.
Brown & Attardi (2005) *Nat Rev Cancer* 5:231-237.
Burg et al. (1999) *Cancer Res* 59:2869-2874.
Burgin et al. (1996) *Biochemistry* 35:14090-14097.
Burlina et al. (1997) *Bioorg Med Chem* 5:1999-2010.
Canadian Patent Application No. 2,359,180
Cantley (2002) *Science* 296:1655-1657.
Caruthers et al. (1992) *Methods Enzymol* 211:3-19.
Chan et al. (1999) *Annu Rev Biochem* 68:965-1014.
Chau et al. (2002) *Oncogene* 21:8817-8829.
Chau et al. (2005) *Am J Physiol Cell Physiol* 289:C444-454.
Chen et al. (2001) *Nat Cell Biol* 3:439-444.
Cote et al. (2005) *Nat Cell Biol* 7:797-807.
Cuneo et al. (2007) *Cancer Res* 67:4886-4893.
Datta et al. (1999) *Genes Dev* 13:2905-2927.
De Mesmaeker et al. (1994) in *Carbohydrate Modifications in Antisense Research*, American Chemical Society, Washington, D.C., Symposium Series No. 580:24-39.
Dent et al. (2003) *Oncogene* 22:5885-5896.
Dracopoli et al. (eds.) (1997) *Current Protocols in Human Genetics on CD-ROM*. John Wiley & Sons, New York, United States of America.
Dudek et al. (1997) *Science* 275:661-665.
Earnshaw & Gait (1998) *Biopolymers* 48:39-55.
Ebert & Bunn (1998) *Mol Cell Biol* 18:4089-4096.
Edwards et al. (2002) *Cancer Res* 62:4671-4677.
Ekman et al. (2000) *Oncogene* 19:4151-4158.
Elbashir et al. (2001a) *Nature* 411:494-498.
Elbashir et al. (2001b) *Genes Dev* 15:188-200.
Elbashir et al. (2001c) *EMBO J* 20:6877-6888.
Ellerby et al. (1999) *Nat Med* 5:1032-1038.
European Patent No. 0 439 095.
Fang et al. (2000) *Biochem J* 352:135-143.
Fewell et al. (2001) *Mol Ther* 3:574-583.
Fire (1999) *Trends Genet* 15:358-363.
Fire et al. (1998) *Nature* 391:806-811.
Firth et al. (1995) *J Biol Chem* 270:21021-21027.
Freier et al. (1986) *Proc Natl Acad Sci U* Glover & Hames, 1995
Garcia-Barros et al. (2003) *Science* 300:1155-1159.
GENBANK® Accession Nos. NM_001109016; NM_001721; NM_009759; NM_203281; NP_001102486; NP_001712; NP_033889; NP_975010; XM_001101166; XM_001101250; XM_001101349; XM_001490091; XM_548870; XM_610012; XP_001101166; XP_001101250; XP_001101349; XP_001490141; XP_548870; XP_610012.
Glover & Hames (1995) *DNA Cloning: A Practical Approach*, 2nd ed. IRL Press at Oxford University Press, Oxford/N.Y., United States of America.
Goldman et al. (1997) *Cancer Res* 57:1447-1451.
Gorski et al. (1999) *Cancer Res* 59:3374-3378.
Greenberg et al. (1994) *Mol Endocrinol* 8:230-239.
Gregoriadis (ed) (1993) *Liposome Technology*, 2nd ed. CRC Press, Boca Raton, Fla., United States of America.
Haimovitz-Friedman et al. (1994) *J Exp Med* 180:525-535.
Hallahan & Virudachalam (1999) *Radiat Res* 152:6-13.
Hallahan et al. (1995) *Nat Med* 1:786-791.
Hallahan et al. (1996) *Cancer Res* 56:5150-5155.
Hallahan et al. (1998) *Cancer Res* 58:5216-5220.
Hallahan et al. (2001) *J Control Release* 74:183-191.
Harlow & Lane (1988) *Antibodies: A Laboratory Manual*. Cold Spring Harbor Laboratory Press, Cold Spring Harbor, N.Y., United States of America.
Hawiger & Timmons (1992) *Methods Enzymol* 215:228-243.
Hawiger et al. (1989) *Biochemistry* 28:2909-2914.
He et al. (2004) *Cancer Biol Ther* 3:96-101.
Hilmas & Gillette (1975) *Radiat Res* 61:128-143.
Hunziker & Leumann (1995) in *Modern Synthetic Methods*, VCH, Basel, Switzerland 331-417.
Ito et al. (1991) *Cancer Res* 51:255-260.
Janoff (ed) (1999) *Liposomes: Rational Design*. M. Dekker, New York, United States of America.
Johnson (1976) *Intl J Radiat Oncol Biol Phys* 1:659-670.
Jui et al. (2000) *J Biol Chem* 275:41124-41132.
Kallman et al. (1972) *Cancer Res* 32:483-49.
Karpeisky et al. (1998) *Tetrahedron Lett* 39:1131-1134.
Katoh et al. (1995) *Cancer Res* 55:5687-5692.
Kauffmann-Zeh et al. (1997) *Nature* 385:544-548.
Kaukonen et al. (1996) *Br J Haematol* 94:455-460.
Kawakami et al. (1999) *Proc Natl Acad Sci USA* 96:2227-2232.
Kelley et al. (1999) *J Biol Chem* 274:26393-26398.
Kim et al. (2002) *J Biol Chem* 277:30066-30071.
Kirpotin et al. (1997) *Biochemistry* 36:66-75.
Kurihara et al. (2000) *J Clin Invest* 106:763-771.
Kyte & Doolittle (1982) *J Mol Biol* 157:105-132.
Labat-Moleur et al. (1996) *Gene Ther* 3:1010-1017.
Lasic & Martin (eds.) (1995) *STEALTH® Liposomes*. CRC Press, Boca Raton, Fla., United States of America.
Lee et al. (2000) *Anticancer Res* 20:417-422.
Lee et al. (2001) *Mol Cell Biol* 21:8385-8397.
Leibel & Phillips (2004) *Textbook of Radiation Oncology*, $2^{nd}$ Edition, W.B. Saunders, Philadelphia, Pa., United States of America.
Li et al. (1994) *Leuk Lymphoma* 13:65-70.
Limbach et al. (1994) *Nucleic Acids Res* 22:2183-2196.
Loakes (2001) *Nucleic Acids Res* 29:2437-2447.
Mahajan et al. (1999) *J Biol Chem* 274:9587-9599.
Mano (1999) *Cytokine Growth Factor Rev* 10:267-280.

Manome et al. (1994) *Cancer Res* 54:5408-5413.
Marin et al. (1997) *Mol Med Today* 3:396-403.
Maruyama-Tabata et al. (2000) *Gene Ther* 7:53-60.
Mesner et al. (1997) *Adv Pharmacol* 41:461-499.
Miyagishi & Taira (2002) *Nat Biotechnol* 20:497-500.
Neri et al. (1997) *Nat Biotechnol* 15:1271-1275.
Nore et al. (2003) *Biochim Biophys Acta* 1645:123-132.
Nykanen et al. (2001) *Cell* 107:309-321.
Ohtsuka et al. (1985) *J Biol Chem* 260:2605-2608.
Packer (1999) *Arch Neurol* 56:421-425.
Pan et al. (2002) *Mol Cell Biol* 22:7512-7523.
Pan et al. (2007) *Chem Med Chem* 2:58-61.
Park et al. (1997) *Cancer Lett* 118:153-160.
Pasqualini & Ruoslahti (1996) *Nature* 380:364-366.
Pasqualini et al. (1997) *Nat Biotechnol* 15:542-546.
Paz et al. (2005) *Mol Cancer Ther* 4:1801-1809.
PCT International Patent Application Publication No. WO 91/03162; WO 92/07065; WO 92/07065; WO 93/15187; WO 93/23569; WO 97/26270; WO 98/10795; WO 98/13526; WO 99/07409; WO 99/32619; WO 99/54459; WO 00/01846; WO 00/44895; WO 00/44914; WO 00/63364; WO 01/04313; WO 01/29058; WO 01/36646; WO 01/68836; WO 01/75164; WO 01/92513; WO 02/044321; WO 02/055692.
Qiu & Kung (2000) *Oncogene* 19:5651-5661.
Perrault et al. (1990) *Nature* 344:565.
Pieken et al. (1991) *Science* 253:314-317.
Qiu et al. (1998) *Proc Natl Acad Sci USA* 95:3644-3649.
Rossolini et al. (1994) *Mol Cell Probes* 8:91-98.
Saltzman & Fung (1997) *Adv Drug Deliv Rev* 26:209-230.
Sambrook & Russell (eds.) (2001) *Molecular Cloning: A Laboratory Manual* (Third Edition), Cold Spring Harbor Laboratory Press, Cold Spring Harbor, N.Y., United States of America.
Scaringe et al. (1990) *Nucleic Acids Res* 18:5433-5441.
Scharfmann et al. (1991) *Proc Natl Acad Sci USA* 88:4626-4630.
Semenza & Wang (1992) *Mol Cell Biol* 12:5447-5454.
Shabarova et al. (1991) *Nature* 359:843-845.
Silhavy et al. (1984) *Experiments with Gene Fusions*. Cold Spring Harbor Laboratory, Cold Spring Harbor, N.Y., United States of America.
Smith et al. (2001) *Bioessays* 23:436-446.
Somervaille et al. (2001) *Blood* 98:1374-1381.
Song et al. (1972) *Radiology* 104:693-697.
Sonveaux et al. (2007) *Int J Radiat Oncol Biol Phys* 67:1155-1162.
Staba et al. (1998) *Gene Ther* 5:293-300.
Taghian et al. (1993) *Intl J Radiat Oncol Biol Phys* 25:243-249.
Tam et al. (2000) *Gene Ther* 7:1867-1874.
Tan & Hallahan (2003) *Cancer Res* 63:7663-7667.
Tan et al. (2006) *Cancer Res* 66:2320-2327.
Ting et al. (1991) *Intl J Radiat Biol* 60:335-339.
Tomlinson et al. (2004) *J Biol Chem* 279:55089-55096.
Turner et al. (1987) *Cold Spring Harb Symp Quant Biol* LII:123-133.
U.S. Patent Application Publication No. 20030175703.
U.S. Pat. Nos. 4,196,265; 4,235,871; 4,551,482; 4,554,101; 4,946,778; 5,011,634; 5,091,513; 5,111,867; 5,132,405; 5,260,203; 5,270,163; 5,334,711; 5,490,840; 5,510,103; 5,567,588; 5,574,172; 5,627,053; 5,632,991; 5,651,991; 5,667,988; 5,672,695; 5,677,427; 5,683,867; 5,688,931; 5,702,892; 5,714,166; 5,716,824; 5,780,225; 5,786,387; 5,840,479; 5,849,877; 5,854,027; 5,854,038; 5,855,900; 5,858,410; 5,892,019; 5,922,254; 5,922,356; 5,922,545; 5,948,647; 5,948,767; 5,985,279; 5,994,392; 5,998,203; 6,001,311; 6,054,561; 6,056,938; 6,057,098; 6,071,890; 6,090,925; 6,106,866; 6,120,787; 6,127,339; 6,132,766; 6,174,708; 6,180,084; 6,190,700; 6,197,333; 6,200,598; 6,210,707; 6,217,886; 6,221,958; 6,238,704; 6,238,705; 6,245,740; 6,248,878; 6,262,127; 6,267,981; 6,287,587; 6,296,832; 6,296,842; 6,300,074; 6,312,713; 6,335,035; 6,506,559; 6,706,482; 6,855,496; 7,067,649; 7,176,295.
Uckun et al. (2002) *Clin Cancer Res* 8:1224-1233.
Uhlman & Peyman (1990) *Chem Rev* 90:543-549.
Usman & Cedergren (1992) *Trends Biochem Sci* 17:334-339.
Usman et al. (1987) *J Am Chem Soc* 109: 7845-7854.
Usman et al. (1994) *Nucleic Acids Symp Ser* 31:163-164.
Usman et al. (1996) *Curr Opin Struct Biol* 6:527-533.
Valerie et al. (2007) *Mol Cancer Ther* 6:789-801.
Vargas et al. (2002) *J Biol Chem* 277:9351-9357.
Verma & Eckstein (1998) *Annu Rev Biochem* 67:99-134.
Walker et al. (1980) *N Engl J Med* 303:1323-1329.
Wallner et al. (1989) *Intl J Radiat Oncol Biol Phys* 16:1405-1409.
Weiner & Chun (1999) *Proc Natl Acad Sci USA* 96:5233-5238.
Wen et al. (1999) *J Biol Chem* 274:38204-38210.
Wianny & Zernicka-Goetz (1999) *Nature Cell Biol* 2:70-75.
Williams et al. (1993) *J Clin Invest* 92:503-508.
Wincott & Usman (1997) *Methods Mol Bio* 74: 59-68.
Wincott et al. (1995) *Nucleic Acids Res* 23:2677-2684.
Wymann & Pirola (1998) *Biochim Biophys Acta* 1436:127-150.
Yacoub et al. (2006) *Endocr Relat Cancer* 13 Suppl 1:S99-S114.
Yamaura et al. (1976) *Intl J Radiat Biol Relat Stud Phys Chem Med* 30:179-187.
Yang et al. (2002) *J Biol Chem* 277:30219-30226.
Yao & Cooper (1995) *Science* 267:2003-2006.
Yu et al. (1999) *Cancer Res* 59:4200-4203.
Zamore et al. (2000) *Cell* 101:25-33.
Zhang et al. (2003) *J Biol Chem* 278:51267-51276.
Zingg et al. (2004) *Cancer Res* 64:5398-5406.

It will be understood that various details of the described subject matter can be changed without departing from the scope of the described subject matter. Furthermore, the foregoing description is for the purpose of illustration only, and not for the purpose of limitation.

What is claimed is:

1. A method for inhibiting proliferation of a tumor in a subject, the method comprising:
   (a) administering to the subject an effective amount of an inhibitor of a biological activity of a bone marrow X kinase (Bmx) gene product; and
   (b) irradiating vasculature supplying blood flow to the tumor, wherein the vasculature supplying blood flow to the tumor expresses the Bmx gene product and whereby proliferation of the tumor in the subject is inhibited.

2. The method of claim 1, wherein the subject is a mammal.

3. The method of claim 2, wherein the Bmx gene product:
   (a) is encoded by a naturally occurring nucleic acid sequence that is at least 95% identical to nucleotides 174-2198 of SEQ ID NO: 1; or
   (b) is encoded by a naturally occurring nucleic acid sequence that is at least 95% identical to nucleotides 112-2136 of SEQ ID NO: 3.

4. The method of claim 1, wherein the inhibitor is selected from the group consisting of (2Z)-2-Cyano-N-(2,5-dibromophenyl)-3-hydroxy-2-butenamide, an antibody that specifically binds to the Bmx gene product to inhibit a biological activity of the Bmx gene product, and a nucleic acid that inhibits a biological activity of the Bmx gene product by RNA interference.

5. The method of claim 4, wherein the nucleic acid that inhibits a biological activity of the Bmx gene product by RNA interference comprises a short interfering RNA (siRNA) or a short hairpin RNA (shRNA) that targets a Bmx gene product encoded by a nucleic acid sequence comprising nucleotides 174-2198 of SEQ ID NO: 1 or nucleotides 112-2136 of SEQ ID NO: 3.

6. The method of claim 5, wherein the siRNA or the shRNA is encoded by a recombinant virus and the administering comprises administering an effective amount of the recombinant virus to the subject to modulate proliferation of a cell or of a tissue in the subject.

7. A method for increasing the radiosensitivity of a tumor, the method comprising:
   (a) contacting a cell of vasculature supplying blood flow to the tumor with an effective amount of an inhibitor of a biological activity of a bone marrow X kinase (Bmx) gene product; and
   (b) irradiating the cell of the vasculature supplying blood flow to the tumor,
   whereby the radiosensitivity of the tumor is increased.

8. The method of claim 7, wherein the inhibitor of a biological activity of a Bmx gene product comprises a bone marrow X kinase (Bmx) antagonist, a vector encoding a bone marrow X kinase (Bmx) antagonist, or a combination thereof.

9. The method of claim 7, wherein the tumor is a radiation resistant tumor.

10. The method of claim 7, wherein the subject is a mammal.

11. The method of claim 7, wherein the tumor is present within a subject and the method comprises administering a bone marrow X kinase (Bmx) antagonist to the subject.

12. The method of claim 11, wherein the administering comprises administering a composition comprising:
(a) a bone marrow X kinase (Bmx) antagonist, a vector encoding a bone marrow X kinase (Bmx) antagonist, or a combination thereof; and
(b) a pharmaceutically acceptable carrier.

13. The method of claim 12, wherein the bone marrow X kinase (Bmx) antagonist is selected from the group consisting of (2Z)-2-Cyano-N-(2,5-dibromophenyl)-3-hydroxy-2-butenamide, an antibody that specifically binds to the Bmx gene product to inhibit a biological activity of the Bmx gene product, and a nucleic acid that inhibits a biological activity of the Bmx gene product by RNA interference.

14. The method of claim 7, wherein the bone marrow X kinase (Bmx) antagonist comprises a small interfering RNA (siRNA) targeted to a Bmx gene product.

15. A method for suppressing tumor growth in a subject, the method comprising:
(a) administering to the subject an effective amount of an inhibitor of a biological activity of a bone marrow X kinase (Bmx) gene product; and
(b) treating vasculature supplying blood flow to the tumor with ionizing radiation,
whereby tumor growth is suppressed.

16. The method of claim 15, wherein the subject is a mammal.

17. The method of claim 15, wherein the administering comprises administering a minimally therapeutic dose of the inhibitor.

18. The method of claim 15, wherein the administering comprises administering a composition comprising:
(a) a bone marrow X kinase (Bmx) antagonist, a vector encoding a bone marrow X kinase (Bmx) antagonist, or a combination thereof; and
(b) a pharmaceutically acceptable carrier.

19. The method of claim 15, wherein the inhibitor is selected from the group consisting of (2Z)-2-Cyano-N-(2,5-dibromophenyl)-3-hydroxy-2-butenamide, an antibody that specifically binds to the Bmx gene product to inhibit a biological activity of the Bmx gene product, and a nucleic acid that inhibits a biological activity of the Bmx gene product by RNA interference.

20. The method of claim 15, wherein the inhibitor comprises a small interfering RNA (siRNA) targeted to a Bmx gene product.

21. The method of claim 15, wherein the tumor is a radiation resistant tumor.

22. The method of claim 15, wherein the treating vasculature supplying blood flow to the tumor with ionizing radiation comprises treating vasculature supplying blood flow to the tumor with a subtherapeutic dose of ionizing radiation.

23. A method for inhibiting tumor blood vessel growth in a subject, the method comprising:
(a) administering to the subject an effective amount of an inhibitor of a biological activity of a bone marrow X kinase (Bmx) gene product; and
(b) treating vasculature supplying blood flow to the tumor with ionizing radiation,
whereby tumor blood vessel growth is inhibited.

24. The method of claim 23, wherein the administering comprises administering a minimally therapeutic dose of the inhibitor.

25. The method of claim 23, wherein the inhibitor comprises a composition comprising:
(a) a bone marrow X kinase (Bmx) antagonist, a vector encoding a bone marrow X kinase (Bmx) antagonist, or a combination thereof; and
(b) a pharmaceutically acceptable carrier.

26. The method of claim 23, wherein the inhibitor is selected from the group consisting of (2Z)-2-Cyano-N-(2,5-dibromophenyl)-3-hydroxy-2-butenamide, an antibody that specifically binds to the Bmx gene product to inhibit a biological activity of the Bmx gene product, and a nucleic acid that inhibits a biological activity of the Bmx gene product by RNA interference.

27. The method of claim 26, wherein the inhibitor comprises a small interfering RNA (siRNA) targeted to a Bmx gene product.

28. The method of claim 23, wherein the subject is a mammal.

29. The method of claim 23, wherein the tumor is a radiation resistant tumor.

30. The method of claim 23, wherein the treating vasculature supplying blood flow to the tumor with ionizing radiation comprises treating vasculature supplying blood flow to the tumor with a subtherapeutic dose of ionizing radiation.

31. The method of claim 23, further comprising reducing the vascular length density of tumor blood vessels present within the vasculature supplying blood flow to the tumor.

32. A method for inhibiting a condition associated with undesirable angiogenesis in a subject, the method comprising:
(a) administering to the subject an effective amount of a bone marrow X kinase (Bmx) antagonist; and
(b) irradiating a site of undesirable angiogenesis in the subject, wherein the site of undesirable angiogenesis comprises vascular endothelium cells that express a Bmx gene product,
whereby a condition associated with undesirable angiogenesis in the subject is inhibited.

33. The method of claim 32, wherein the condition associated with undesirable angiogenesis is selected from the group consisting of a cancer, a tumor, macular degeneration, and endometriosis.

34. The method of claim 32, wherein the Bmx antagonist is selected from the group consisting of (2Z)-2-Cyano-N-(2,5-dibromophenyl)-3-hydroxy-2-butenamide, an antibody that specifically binds to the Bmx gene product to inhibit a biological activity of the Bmx gene product, and a nucleic acid that inhibits a biological activity of the Bmx gene product by RNA interference.

35. The method of claim 34, wherein the nucleic acid that inhibits a biological activity of the Bmx gene product by RNA interference comprises a small interfering RNA (siRNA) targeted to a Bmx gene product.

36. The method of claim 32, wherein the subject is a mammal.

37. The method of claim 11, wherein the administering comprises administering a minimally therapeutic dose of the Bmx antagonist to the subject.

* * * * *

SEQUENCE LISTING

```
<160> NUMBER OF SEQ ID NOS: 20

<210> SEQ ID NO 1
<211> LENGTH: 2592
<212> TYPE: DNA
<213> ORGANISM: Homo sapiens
<220> FEATURE:
```

```
<221> NAME/KEY: CDS
<222> LOCATION: (174)..(2201)

<400> SEQUENCE: 1
aataaacgtg ttgggggcac tgagtaatgt agccatttct gacccggcag ccaggaaaat      60
gtgaaacaat ttgcttctgg aaacaggaca gccggggccg tgttcctgca acagcagacc    120
aagcaccgcg gcggacccag gcaagcacgg aacaagctga gacggatgat aat atg       176
                                                              Met
                                                              1 gat aca aaa tct att cta gaa gaa ctt ctt ctc aaa aga tca cag caa      224
Asp Thr Lys Ser Ile Leu Glu Glu Leu Leu Leu Lys Arg Ser Gln Gln
            5                  10                  15 aag aag aaa atg tca cca aat aat tac aaa gaa cgg ctt ttt gtt ttg      272
Lys Lys Lys Met Ser Pro Asn Asn Tyr Lys Glu Arg Leu Phe Val Leu
 20                  25                  30 acc aaa aca aac ctt tcc tac tat gaa tat gac aaa atg aaa agg ggc      320
Thr Lys Thr Asn Leu Ser Tyr Tyr Glu Tyr Asp Lys Met Lys Arg Gly
 35                  40                  45 agc aga aaa gga tcc att gaa att aag aaa atc aga tgt gtg gag aaa      368
Ser Arg Lys Gly Ser Ile Glu Ile Lys Lys Ile Arg Cys Val Glu Lys
50                  55                  60                  65 gta aat ctc gag gag cag acg cct gta gag aga cag tac cca ttt cag      416
Val Asn Leu Glu Glu Gln Thr Pro Val Glu Arg Gln Tyr Pro Phe Gln
                70                  75                  80 att gtc tat aaa gat ggg ctt ctc tat gtc tat gca tca aat gaa gag      464
Ile Val Tyr Lys Asp Gly Leu Leu Tyr Val Tyr Ala Ser Asn Glu Glu
             85                  90                  95 agc cga agt cag tgg ttg aaa gca tta caa aaa gag ata agg ggt aac      512
Ser Arg Ser Gln Trp Leu Lys Ala Leu Gln Lys Glu Ile Arg Gly Asn
        100                 105                 110 ccc cac ctg ctg gtc aag tac cat agt ggg ttc ttc gtg gac ggg aag      560
Pro His Leu Leu Val Lys Tyr His Ser Gly Phe Phe Val Asp Gly Lys
    115                 120                 125 ttc ctg tgt tgc cag cag agc tgt aaa gca gcc cca gga tgt acc ctc      608
Phe Leu Cys Cys Gln Gln Ser Cys Lys Ala Ala Pro Gly Cys Thr Leu
130                 135                 140                 145 tgg gaa gca tat gct aat ctg cat act gca gtc aat gaa gag aaa cac      656
Trp Glu Ala Tyr Ala Asn Leu His Thr Ala Val Asn Glu Glu Lys His
                150                 155                 160 aga gtt ccc acc ttc cca gac aga gtg ctg aag ata cct cgg gca gtt      704
Arg Val Pro Thr Phe Pro Asp Arg Val Leu Lys Ile Pro Arg Ala Val
            165                 170                 175 cct gtt ctc aaa atg gat gca cca tct tca agt acc act cta gcc caa      752
Pro Val Leu Lys Met Asp Ala Pro Ser Ser Ser Thr Thr Leu Ala Gln
        180                 185                 190 tat gac aac gaa tca aag aaa aac tat ggc tcc cag cca cca tct tca      800
Tyr Asp Asn Glu Ser Lys Lys Asn Tyr Gly Ser Gln Pro Pro Ser Ser
    195                 200                 205 agt acc agt cta gcg caa tat gac agc aac tca aag aaa atc tat ggc      848
Ser Thr Ser Leu Ala Gln Tyr Asp Ser Asn Ser Lys Lys Ile Tyr Gly
210                 215                 220                 225 tcc cag cca aac ttc aac atg cag tat att cca agg gaa gac ttc cct      896
Ser Gln Pro Asn Phe Asn Met Gln Tyr Ile Pro Arg Glu Asp Phe Pro
                230                 235                 240 gac tgg tgg caa gta aga aaa ctg aaa agt agc agc agt gaa gat          944
Asp Trp Trp Gln Val Arg Lys Leu Lys Ser Ser Ser Ser Glu Asp
            245                 250                 255 gtt gca agc agt aac caa aaa gaa aga aat gtg aat cac acc acc tca      992
Val Ala Ser Ser Asn Gln Lys Glu Arg Asn Val Asn His Thr Thr Ser
        260                 265                 270
```

```
aag att tca tgg gaa ttc cct gag tca agt tca tct gaa gaa gag gaa    1040
Lys Ile Ser Trp Glu Phe Pro Glu Ser Ser Ser Ser Glu Glu Glu Glu
275                 280                 285 aac ctg gat gat tat gac tgg ttt gct ggt aac atc tcc aga tca caa    1088
Asn Leu Asp Asp Tyr Asp Trp Phe Ala Gly Asn Ile Ser Arg Ser Gln
290                 295                 300                 305 tct gaa cag tta ctc aga caa aag gga aaa gaa gga gca ttt atg gtt    1136
Ser Glu Gln Leu Leu Arg Gln Lys Gly Lys Glu Gly Ala Phe Met Val
                310                 315                 320 aga aat tcg agc caa gtg gga atg tac aca gtg tcc tta ttt agt aag    1184
Arg Asn Ser Ser Gln Val Gly Met Tyr Thr Val Ser Leu Phe Ser Lys
            325                 330                 335 gct gtg aat gat aaa aaa gga act gtc aaa cat tac cac gtg cat aca    1232
Ala Val Asn Asp Lys Lys Gly Thr Val Lys His Tyr His Val His Thr
        340                 345                 350 aat gct gag aac aaa tta tac ctg gca gaa aac tac tgt ttt gat tcc    1280
Asn Ala Glu Asn Lys Leu Tyr Leu Ala Glu Asn Tyr Cys Phe Asp Ser
355                 360                 365 att cca aag ctt att cat tat cat caa cac aat tca gca ggc atg atc    1328
Ile Pro Lys Leu Ile His Tyr His Gln His Asn Ser Ala Gly Met Ile
370                 375                 380                 385 aca cgg ctc cgc cac cct gtg tca aca aag gcc aac aag gtc ccc gac    1376
Thr Arg Leu Arg His Pro Val Ser Thr Lys Ala Asn Lys Val Pro Asp
                390                 395                 400 tct gtg tcc ctg gga aat gga atc tgg gaa ctg aaa aga gaa gag att    1424
Ser Val Ser Leu Gly Asn Gly Ile Trp Glu Leu Lys Arg Glu Glu Ile
            405                 410                 415 acc ttg ttg aag gag ctg gga agt ggc cag ttt gga gtg gtc cag ctg    1472
Thr Leu Leu Lys Glu Leu Gly Ser Gly Gln Phe Gly Val Val Gln Leu
        420                 425                 430 ggc aag tgg aag ggg cag tat gat gtt gct gtt aag atg atc aag gag    1520
Gly Lys Trp Lys Gly Gln Tyr Asp Val Ala Val Lys Met Ile Lys Glu
435                 440                 445 ggc tcc atg tca gaa gat gaa ttc ttt cag gag gcc cag act atg atg    1568
Gly Ser Met Ser Glu Asp Glu Phe Phe Gln Glu Ala Gln Thr Met Met
450                 455                 460                 465 aaa ctc agc cat ccc aag ctg gtt aaa ttc tat gga gtg tgt tca aag    1616
Lys Leu Ser His Pro Lys Leu Val Lys Phe Tyr Gly Val Cys Ser Lys
                470                 475                 480 gaa tac ccc ata tac ata gtg act gaa tat ata agc aat ggc tgc ttg    1664
Glu Tyr Pro Ile Tyr Ile Val Thr Glu Tyr Ile Ser Asn Gly Cys Leu
            485                 490                 495 ctg aat tac ctg agg agt cac gga aaa gga ctt gaa cct tcc cag ctc    1712
Leu Asn Tyr Leu Arg Ser His Gly Lys Gly Leu Glu Pro Ser Gln Leu
        500                 505                 510 tta gaa atg tgc tac gat gtc tgt gaa ggc atg gcc ttc ttg gag agt    1760
Leu Glu Met Cys Tyr Asp Val Cys Glu Gly Met Ala Phe Leu Glu Ser
515                 520                 525 cac caa ttc ata cac cgg gac ttg gct gct cgt aac tgc ttg gtg gac    1808
His Gln Phe Ile His Arg Asp Leu Ala Ala Arg Asn Cys Leu Val Asp
530                 535                 540                 545 aga gat ctc tgt gtg aaa gta tct gac ttt gga atg aca agg tat gtt    1856
Arg Asp Leu Cys Val Lys Val Ser Asp Phe Gly Met Thr Arg Tyr Val
                550                 555                 560 ctt gat gac cag tat gtc agt tca gtc gga aca aag ttt cca gtc aag    1904
Leu Asp Asp Gln Tyr Val Ser Ser Val Gly Thr Lys Phe Pro Val Lys
            565                 570                 575 tgg tca gct cca gag gtg ttt cat tac ttc aaa tac agc agc aag tca    1952
Trp Ser Ala Pro Glu Val Phe His Tyr Phe Lys Tyr Ser Ser Lys Ser
        580                 585                 590
```

```
gac gta tgg gca ttt ggg atc ctg atg tgg gag gtg ttc agc ctg ggg    2000
Asp Val Trp Ala Phe Gly Ile Leu Met Trp Glu Val Phe Ser Leu Gly
    595                 600                 605 aag cag ccc tat gac ttg tat gac aac tcc cag gtg gtt ctg aag gtc    2048
Lys Gln Pro Tyr Asp Leu Tyr Asp Asn Ser Gln Val Val Leu Lys Val
610                 615                 620                 625 tcc cag ggc cac agg ctt tac cgg ccc cac ctg gca tcg gac acc atc    2096
Ser Gln Gly His Arg Leu Tyr Arg Pro His Leu Ala Ser Asp Thr Ile
                630                 635                 640 tac cag atc atg tac agc tgc tgg cac gag ctt cca gaa aag cgt ccc    2144
Tyr Gln Ile Met Tyr Ser Cys Trp His Glu Leu Pro Glu Lys Arg Pro
            645                 650                 655 aca ttt cag caa ctc ctg tct tcc att gaa cca ctt cgg gaa aaa gac    2192
Thr Phe Gln Gln Leu Leu Ser Ser Ile Glu Pro Leu Arg Glu Lys Asp
        660                 665                 670 aag cat tga agaagaaatt aggagtgctg ataagaatga atatagatgc            2241
Lys His
    675 tggccagcat ttcattcat tttaaggaaa gtagcaaggc ataatgtaat ttagctagtt    2301 tttaatagtg ttctctgtat tgtctattat ttagaaatga acaaggcagg aaacaaaaga    2361 ttcccttgaa atttagatca aattagtaat tttgtttatg ctgctcctga tataacactt    2421 tccagcctat agcagaagca catttcaga ctgcaatata gagactgtgt tcatgtgtaa    2481 agactgagca gaactgaaaa attacttatt ggatattcat tcttttcttt atattgtcat    2541 tgtcacaaca attaaatata ctaccaagta cagaaatgtg gaaaaaaaaa a            2592

<210> SEQ ID NO 2
<211> LENGTH: 675
<212> TYPE: PRT
<213> ORGANISM: Homo sapiens

<400> SEQUENCE: 2

Met Asp Thr Lys Ser Ile Leu Glu Glu Leu Leu Leu Lys Arg Ser Gln
1               5                   10                  15

Gln Lys Lys Lys Met Ser Pro Asn Asn Tyr Lys Glu Arg Leu Phe Val
            20                  25                  30

Leu Thr Lys Thr Asn Leu Ser Tyr Tyr Glu Tyr Asp Lys Met Lys Arg
        35                  40                  45

Gly Ser Arg Lys Gly Ser Ile Glu Ile Lys Lys Ile Arg Cys Val Glu
    50                  55                  60

Lys Val Asn Leu Glu Glu Gln Thr Pro Val Glu Arg Gln Tyr Pro Phe
65                  70                  75                  80

Gln Ile Val Tyr Lys Asp Gly Leu Leu Tyr Val Tyr Ala Ser Asn Glu
                85                  90                  95

Glu Ser Arg Ser Gln Trp Leu Lys Ala Leu Gln Lys Glu Ile Arg Gly
            100                 105                 110

Asn Pro His Leu Leu Val Lys Tyr His Ser Gly Phe Val Asp Gly
        115                 120                 125

Lys Phe Leu Cys Cys Gln Gln Ser Cys Lys Ala Ala Pro Gly Cys Thr
    130                 135                 140

Leu Trp Glu Ala Tyr Ala Asn Leu His Thr Ala Val Asn Glu Glu Lys
145                 150                 155                 160

His Arg Val Pro Thr Phe Pro Asp Arg Val Leu Lys Ile Pro Arg Ala
                165                 170                 175

Val Pro Val Leu Lys Met Asp Ala Pro Ser Ser Ser Thr Thr Leu Ala
            180                 185                 190
```

```
Gln Tyr Asp Asn Glu Ser Lys Lys Asn Tyr Gly Ser Gln Pro Pro Ser
        195                 200                 205

Ser Ser Thr Ser Leu Ala Gln Tyr Asp Ser Asn Ser Lys Lys Ile Tyr
    210                 215                 220

Gly Ser Gln Pro Asn Phe Asn Met Gln Tyr Ile Pro Arg Glu Asp Phe
225                 230                 235                 240

Pro Asp Trp Trp Gln Val Arg Lys Leu Lys Ser Ser Ser Ser Ser Glu
                245                 250                 255

Asp Val Ala Ser Ser Asn Gln Lys Glu Arg Asn Val Asn His Thr Thr
            260                 265                 270

Ser Lys Ile Ser Trp Glu Phe Pro Glu Ser Ser Ser Glu Glu Glu
        275                 280                 285

Glu Asn Leu Asp Asp Tyr Asp Trp Phe Ala Gly Asn Ile Ser Arg Ser
290                 295                 300

Gln Ser Glu Gln Leu Leu Arg Gln Lys Gly Lys Glu Gly Ala Phe Met
305                 310                 315                 320

Val Arg Asn Ser Ser Gln Val Gly Met Tyr Thr Val Ser Leu Phe Ser
                325                 330                 335

Lys Ala Val Asn Asp Lys Lys Gly Thr Val Lys His Tyr His Val His
            340                 345                 350

Thr Asn Ala Glu Asn Lys Leu Tyr Leu Ala Glu Asn Tyr Cys Phe Asp
        355                 360                 365

Ser Ile Pro Lys Leu Ile His Tyr His Gln His Asn Ser Ala Gly Met
370                 375                 380

Ile Thr Arg Leu Arg His Pro Val Ser Thr Lys Ala Asn Lys Val Pro
385                 390                 395                 400

Asp Ser Val Ser Leu Gly Asn Gly Ile Trp Glu Leu Lys Arg Glu Glu
                405                 410                 415

Ile Thr Leu Leu Lys Glu Leu Gly Ser Gly Gln Phe Gly Val Val Gln
            420                 425                 430

Leu Gly Lys Trp Lys Gly Gln Tyr Asp Val Ala Val Lys Met Ile Lys
        435                 440                 445

Glu Gly Ser Met Ser Glu Asp Glu Phe Phe Gln Glu Ala Gln Thr Met
450                 455                 460

Met Lys Leu Ser His Pro Lys Leu Val Lys Phe Tyr Gly Val Cys Ser
465                 470                 475                 480

Lys Glu Tyr Pro Ile Tyr Ile Val Thr Glu Tyr Ile Ser Asn Gly Cys
                485                 490                 495

Leu Leu Asn Tyr Leu Arg Ser His Gly Lys Gly Leu Glu Pro Ser Gln
            500                 505                 510

Leu Leu Glu Met Cys Tyr Asp Val Cys Glu Gly Met Ala Phe Leu Glu
        515                 520                 525

Ser His Gln Phe Ile His Arg Asp Leu Ala Ala Arg Asn Cys Leu Val
530                 535                 540

Asp Arg Asp Leu Cys Val Lys Val Ser Asp Phe Gly Met Thr Arg Tyr
545                 550                 555                 560

Val Leu Asp Asp Gln Tyr Val Ser Ser Val Gly Thr Lys Phe Pro Val
                565                 570                 575

Lys Trp Ser Ala Pro Glu Val Phe His Tyr Phe Lys Tyr Ser Ser Lys
            580                 585                 590

Ser Asp Val Trp Ala Phe Gly Ile Leu Met Trp Glu Val Phe Ser Leu
        595                 600                 605

Gly Lys Gln Pro Tyr Asp Leu Tyr Asp Asn Ser Gln Val Val Leu Lys
```

```
            610                 615                 620
Val Ser Gln Gly His Arg Leu Tyr Arg Pro His Leu Ala Ser Asp Thr
625                 630                 635                 640

Ile Tyr Gln Ile Met Tyr Ser Cys Trp His Glu Leu Pro Glu Lys Arg
                645                 650                 655

Pro Thr Phe Gln Gln Leu Leu Ser Ser Ile Glu Pro Leu Arg Glu Lys
            660                 665                 670

Asp Lys His
        675

<210> SEQ ID NO 3
<211> LENGTH: 2530
<212> TYPE: DNA
<213> ORGANISM: Homo sapiens
<220> FEATURE:
<221> NAME/KEY: CDS
<222> LOCATION: (112)..(2139)

<400> SEQUENCE: 3
gggaatatga gtgatggtgc ctcaaagcag taacttttg cttagagctt gagagtcaaa      60
gttaaggacc cacatgtata cttcggctct agcgagtcta aggatgataa t atg gat     117
                                                          Met Asp
                                                            1 aca aaa tct att cta gaa gaa ctt ctt ctc aaa aga tca cag caa aag      165
Thr Lys Ser Ile Leu Glu Glu Leu Leu Leu Lys Arg Ser Gln Gln Lys
        5                  10                  15 aag aaa atg tca cca aat aat tac aaa gaa cgg ctt ttt gtt ttg acc      213
Lys Lys Met Ser Pro Asn Asn Tyr Lys Glu Arg Leu Phe Val Leu Thr
 20                  25                  30 aaa aca aac ctt tcc tac tat gaa tat gac aaa atg aaa agg ggc agc      261
Lys Thr Asn Leu Ser Tyr Tyr Glu Tyr Asp Lys Met Lys Arg Gly Ser
 35                  40                  45                  50 aga aaa gga tcc att gaa att aag aaa atc aga tgt gtg gag aaa gta      309
Arg Lys Gly Ser Ile Glu Ile Lys Lys Ile Arg Cys Val Glu Lys Val
                 55                  60                  65 aat ctc gag gag cag acg cct gta gag aga cag tac cca ttt cag att      357
Asn Leu Glu Glu Gln Thr Pro Val Glu Arg Gln Tyr Pro Phe Gln Ile
         70                  75                  80 gtc tat aaa gat ggg ctt ctc tat gtc tat gca tca aat gaa gag agc      405
Val Tyr Lys Asp Gly Leu Leu Tyr Val Tyr Ala Ser Asn Glu Glu Ser
     85                  90                  95 cga agt cag tgg ttg aaa gca tta caa aaa gag ata agg ggt aac ccc      453
Arg Ser Gln Trp Leu Lys Ala Leu Gln Lys Glu Ile Arg Gly Asn Pro
100                 105                 110 cac ctg ctg gtc aag tac cat agt ggg ttc ttc gtg gac ggg aag ttc      501
His Leu Leu Val Lys Tyr His Ser Gly Phe Phe Val Asp Gly Lys Phe
115                 120                 125                 130 ctg tgt tgc cag cag agc tgt aaa gca gcc cca gga tgt acc ctc tgg      549
Leu Cys Cys Gln Gln Ser Cys Lys Ala Ala Pro Gly Cys Thr Leu Trp
                135                 140                 145 gaa gca tat gct aat ctg cat act gca gtc aat gaa gag aaa cac aga      597
Glu Ala Tyr Ala Asn Leu His Thr Ala Val Asn Glu Glu Lys His Arg
            150                 155                 160 gtt ccc acc ttc cca gac aga gtg ctg aag ata cct cgg gca gtt cct      645
Val Pro Thr Phe Pro Asp Arg Val Leu Lys Ile Pro Arg Ala Val Pro
        165                 170                 175 gtt ctc aaa atg gat gca cca tct tca agt acc act cta gcc caa tat      693
Val Leu Lys Met Asp Ala Pro Ser Ser Ser Thr Thr Leu Ala Gln Tyr
    180                 185                 190 gac aac gaa tca aag aaa aac tat ggc tcc cag cca cca tct tca agt      741
```

-continued

```
Asp Asn Glu Ser Lys Lys Asn Tyr Gly Ser Gln Pro Ser Ser
195             200                 205             210 acc agt cta gcg caa tat gac agc aac tca aag aaa atc tat ggc tcc    789
Thr Ser Leu Ala Gln Tyr Asp Ser Asn Ser Lys Lys Ile Tyr Gly Ser
            215                 220                 225 cag cca aac ttc aac atg cag tat att cca agg gaa gac ttc cct gac    837
Gln Pro Asn Phe Asn Met Gln Tyr Ile Pro Arg Glu Asp Phe Pro Asp
        230                 235                 240 tgg tgg caa gta aga aaa ctg aaa agt agc agc agt gaa gat gtt        885
Trp Trp Gln Val Arg Lys Leu Lys Ser Ser Ser Ser Glu Asp Val
            245                 250                 255 gca agc agt aac caa aaa gaa aga aat gtg aat cac acc acc tca aag    933
Ala Ser Ser Asn Gln Lys Glu Arg Asn Val Asn His Thr Thr Ser Lys
        260                 265                 270 att tca tgg gaa ttc cct gag tca agt tca tct gaa gaa gag gaa aac    981
Ile Ser Trp Glu Phe Pro Glu Ser Ser Ser Glu Glu Glu Glu Asn
275                 280                 285                 290 ctg gat gat tat gac tgg ttt gct ggt aac atc tcc aga tca caa tct   1029
Leu Asp Asp Tyr Asp Trp Phe Ala Gly Asn Ile Ser Arg Ser Gln Ser
                295                 300                 305 gaa cag tta ctc aga caa aag gga aaa gaa gga gca ttt atg gtt aga   1077
Glu Gln Leu Leu Arg Gln Lys Gly Lys Glu Gly Ala Phe Met Val Arg
            310                 315                 320 aat tcg agc caa gtg gga atg tac aca gtg tcc tta ttt agt aag gct   1125
Asn Ser Ser Gln Val Gly Met Tyr Thr Val Ser Leu Phe Ser Lys Ala
        325                 330                 335 gtg aat gat aaa aaa gga act gtc aaa cat tac cac gtg cat aca aat   1173
Val Asn Asp Lys Lys Gly Thr Val Lys His Tyr His Val His Thr Asn
340                 345                 350 gct gag aac aaa tta tac ctg gca gaa aac tac tgt ttt gat tcc att   1221
Ala Glu Asn Lys Leu Tyr Leu Ala Glu Asn Tyr Cys Phe Asp Ser Ile
355                 360                 365                 370 cca aag ctt att cat tat cat caa cac aat tca gca ggc atg atc aca   1269
Pro Lys Leu Ile His Tyr His Gln His Asn Ser Ala Gly Met Ile Thr
            375                 380                 385 cgg ctc cgc cac cct gtg tca aca aag gcc aac aag gtc ccc gac tct   1317
Arg Leu Arg His Pro Val Ser Thr Lys Ala Asn Lys Val Pro Asp Ser
        390                 395                 400 gtg tcc ctg gga aat gga atc tgg gaa ctg aaa aga gaa gag att acc   1365
Val Ser Leu Gly Asn Gly Ile Trp Glu Leu Lys Arg Glu Glu Ile Thr
        405                 410                 415 ttg ttg aag gag ctg gga agt ggc cag ttt gga gtg gtc cag ctg ggc   1413
Leu Leu Lys Glu Leu Gly Ser Gly Gln Phe Gly Val Val Gln Leu Gly
        420                 425                 430 aag tgg aag ggg cag tat gat gtt gct gtt aag atg atc aag gag ggc   1461
Lys Trp Lys Gly Gln Tyr Asp Val Ala Val Lys Met Ile Lys Glu Gly
435                 440                 445                 450 tcc atg tca gaa gat gaa ttc ttt cag gag gcc cag act atg atg aaa   1509
Ser Met Ser Glu Asp Glu Phe Phe Gln Glu Ala Gln Thr Met Met Lys
            455                 460                 465 ctc agc cat ccc aag ctg gtt aaa ttc tat gga gtg tgt tca aag gaa   1557
Leu Ser His Pro Lys Leu Val Lys Phe Tyr Gly Val Cys Ser Lys Glu
        470                 475                 480 tac ccc ata tac ata gtg act gaa tat ata agc aat ggc tgc ttg ctg   1605
Tyr Pro Ile Tyr Ile Val Thr Glu Tyr Ile Ser Asn Gly Cys Leu Leu
        485                 490                 495 aat tac ctg agg agt cac gga aaa gga ctt gaa cct tcc cag ctc tta   1653
Asn Tyr Leu Arg Ser His Gly Lys Gly Leu Glu Pro Ser Gln Leu Leu
500                 505                 510 gaa atg tgc tac gat gtc tgt gaa ggc atg gcc ttc ttg gag agt cac   1701
```

```

Glu Met Cys Tyr Asp Val Cys Glu Gly Met Ala Phe Leu Glu Ser His
515                 520                 525                 530 caa ttc ata cac cgg gac ttg gct gct cgt aac tgc ttg gtg gac aga    1749
Gln Phe Ile His Arg Asp Leu Ala Ala Arg Asn Cys Leu Val Asp Arg
                535                 540                 545 gat ctc tgt gtg aaa gta tct gac ttt gga atg aca agg tat gtt ctt    1797
Asp Leu Cys Val Lys Val Ser Asp Phe Gly Met Thr Arg Tyr Val Leu
            550                 555                 560 gat gac cag tat gtc agt tca gtc gga aca aag ttt cca gtc aag tgg    1845
Asp Asp Gln Tyr Val Ser Ser Val Gly Thr Lys Phe Pro Val Lys Trp
        565                 570                 575 tca gct cca gag gtg ttt cat tac ttc aaa tac agc agc aag tca gac    1893
Ser Ala Pro Glu Val Phe His Tyr Phe Lys Tyr Ser Ser Lys Ser Asp
    580                 585                 590 gta tgg gca ttt ggg atc ctg atg tgg gag gtg ttc agc ctg ggg aag    1941
Val Trp Ala Phe Gly Ile Leu Met Trp Glu Val Phe Ser Leu Gly Lys
595                 600                 605                 610 cag ccc tat gac ttg tat gac aac tcc cag gtg gtt ctg aag gtc tcc    1989
Gln Pro Tyr Asp Leu Tyr Asp Asn Ser Gln Val Val Leu Lys Val Ser
                615                 620                 625 cag ggc cac agg ctt tac cgg ccc cac ctg gca tcg gac acc atc tac    2037
Gln Gly His Arg Leu Tyr Arg Pro His Leu Ala Ser Asp Thr Ile Tyr
            630                 635                 640 cag atc atg tac agc tgc tgg cac gag ctt cca gaa aag cgt ccc aca    2085
Gln Ile Met Tyr Ser Cys Trp His Glu Leu Pro Glu Lys Arg Pro Thr
        645                 650                 655 ttt cag caa ctc ctg tct tcc att gaa cca ctt cgg gaa aaa gac aag    2133
Phe Gln Gln Leu Leu Ser Ser Ile Glu Pro Leu Arg Glu Lys Asp Lys
    660                 665                 670 cat tga agaagaaatt aggagtgctg ataagaatga atatagatgc tggccagcat    2189
His
675 tttcattcat ttaaggaaa gtagcaaggc ataatgtaat ttagctagtt tttaatagtg    2249 ttctctgtat tgtctattat ttagaaatga acaaggcagg aaacaaaaga ttcccttgaa    2309 atttagatca aattagtaat tttgtttatg ctgctcctga tataacactt tccagcctat    2369 agcagaagca cattttcaga ctgcaatata gagactgtgt tcatgtgtaa agactgagca    2429 gaactgaaaa attacttatt ggatattcat tcttttcttt atattgtcat tgtcacaaca    2489 attaaatata ctaccaagta cagaaatgtg gaaaaaaaaa a                        2530

<210> SEQ ID NO 4
<211> LENGTH: 675
<212> TYPE: PRT
<213> ORGANISM: Homo sapiens

<400> SEQUENCE: 4

Met Asp Thr Lys Ser Ile Leu Glu Glu Leu Leu Leu Lys Arg Ser Gln
1               5                   10                  15

Gln Lys Lys Lys Met Ser Pro Asn Asn Tyr Lys Glu Arg Leu Phe Val
                20                  25                  30

Leu Thr Lys Thr Asn Leu Ser Tyr Tyr Glu Tyr Asp Lys Met Lys Arg
            35                  40                  45

Gly Ser Arg Lys Gly Ser Ile Glu Ile Lys Ile Arg Cys Val Glu
        50                  55                  60

Lys Val Asn Leu Glu Glu Gln Thr Pro Val Glu Arg Gln Tyr Pro Phe
65                  70                  75                  80

Gln Ile Val Tyr Lys Asp Gly Leu Leu Tyr Val Tyr Ala Ser Asn Glu
                85                  90                  95
```

```
Glu Ser Arg Ser Gln Trp Leu Lys Ala Leu Gln Lys Glu Ile Arg Gly
            100                 105                 110

Asn Pro His Leu Leu Val Lys Tyr His Ser Gly Phe Phe Val Asp Gly
            115                 120                 125

Lys Phe Leu Cys Cys Gln Gln Ser Cys Lys Ala Ala Pro Gly Cys Thr
            130                 135                 140

Leu Trp Glu Ala Tyr Ala Asn Leu His Thr Ala Val Asn Glu Glu Lys
145                 150                 155                 160

His Arg Val Pro Thr Phe Pro Asp Arg Val Leu Lys Ile Pro Arg Ala
                165                 170                 175

Val Pro Val Leu Lys Met Asp Ala Pro Ser Ser Ser Thr Thr Leu Ala
                180                 185                 190

Gln Tyr Asp Asn Glu Ser Lys Lys Asn Tyr Gly Ser Gln Pro Pro Ser
            195                 200                 205

Ser Ser Thr Ser Leu Ala Gln Tyr Asp Ser Asn Ser Lys Lys Ile Tyr
            210                 215                 220

Gly Ser Gln Pro Asn Phe Asn Met Gln Tyr Ile Pro Arg Glu Asp Phe
225                 230                 235                 240

Pro Asp Trp Trp Gln Val Arg Lys Leu Lys Ser Ser Ser Ser Ser Glu
                245                 250                 255

Asp Val Ala Ser Ser Asn Gln Lys Glu Arg Asn Val Asn His Thr Thr
                260                 265                 270

Ser Lys Ile Ser Trp Glu Phe Pro Glu Ser Ser Ser Glu Glu Glu
            275                 280                 285

Glu Asn Leu Asp Asp Tyr Asp Trp Phe Ala Gly Asn Ile Ser Arg Ser
            290                 295                 300

Gln Ser Glu Gln Leu Leu Arg Gln Lys Gly Lys Glu Gly Ala Phe Met
305                 310                 315                 320

Val Arg Asn Ser Ser Gln Val Gly Met Tyr Thr Val Ser Leu Phe Ser
                325                 330                 335

Lys Ala Val Asn Asp Lys Lys Gly Thr Val Lys His Tyr His Val His
                340                 345                 350

Thr Asn Ala Glu Asn Lys Leu Tyr Leu Ala Glu Asn Tyr Cys Phe Asp
            355                 360                 365

Ser Ile Pro Lys Leu Ile His Tyr His Gln His Asn Ser Ala Gly Met
370                 375                 380

Ile Thr Arg Leu Arg His Pro Val Ser Thr Lys Ala Asn Lys Val Pro
385                 390                 395                 400

Asp Ser Val Ser Leu Gly Asn Gly Ile Trp Glu Leu Lys Arg Glu Glu
                405                 410                 415

Ile Thr Leu Leu Lys Glu Leu Gly Ser Gly Gln Phe Gly Val Val Gln
                420                 425                 430

Leu Gly Lys Trp Lys Gly Gln Tyr Asp Val Ala Val Lys Met Ile Lys
            435                 440                 445

Glu Gly Ser Met Ser Glu Asp Glu Phe Phe Gln Glu Ala Gln Thr Met
450                 455                 460

Met Lys Leu Ser His Pro Lys Leu Val Lys Phe Tyr Gly Val Cys Ser
465                 470                 475                 480

Lys Glu Tyr Pro Ile Tyr Ile Val Thr Glu Tyr Ile Ser Asn Gly Cys
                485                 490                 495

Leu Leu Asn Tyr Leu Arg Ser His Gly Lys Gly Leu Glu Pro Ser Gln
            500                 505                 510

Leu Leu Glu Met Cys Tyr Asp Val Cys Glu Gly Met Ala Phe Leu Glu
```

-continued

```
                515                 520                 525
Ser His Gln Phe Ile His Arg Asp Leu Ala Ala Arg Asn Cys Leu Val
    530                 535                 540

Asp Arg Asp Leu Cys Val Lys Val Ser Asp Phe Gly Met Thr Arg Tyr
545                 550                 555                 560

Val Leu Asp Asp Gln Tyr Val Ser Ser Val Gly Thr Lys Phe Pro Val
                565                 570                 575

Lys Trp Ser Ala Pro Glu Val Phe His Tyr Phe Lys Tyr Ser Ser Lys
                    580                 585                 590

Ser Asp Val Trp Ala Phe Gly Ile Leu Met Trp Glu Val Phe Ser Leu
                595                 600                 605

Gly Lys Gln Pro Tyr Asp Leu Tyr Asp Asn Ser Gln Val Val Leu Lys
    610                 615                 620

Val Ser Gln Gly His Arg Leu Tyr Arg Pro His Leu Ala Ser Asp Thr
625                 630                 635                 640

Ile Tyr Gln Ile Met Tyr Ser Cys Trp His Glu Leu Pro Glu Lys Arg
                645                 650                 655

Pro Thr Phe Gln Gln Leu Leu Ser Ser Ile Glu Pro Leu Arg Glu Lys
                    660                 665                 670

Asp Lys His
    675

<210> SEQ ID NO 5
<211> LENGTH: 2583
<212> TYPE: DNA
<213> ORGANISM: Macaca mulatta
<220> FEATURE:
<221> NAME/KEY: CDS
<222> LOCATION: (162)..(2201)

<400> SEQUENCE: 5
aataaatgtg ttgggggcac tgagtaatgt agccatttct gacccggcag ccaggaaaat    60
gtgaaacaat ttgcttctgg aaacaggaca gctggagctg tgttcctgca agagcagacc   120
aaccaccacg gcggacccag gcaagcacgg aacaagccga g atg gat gat aat atg   176
                                              Met Asp Asp Asn Met
                                                1               5 gat aca aaa tct att cta gaa gaa ctt ctt ctc aaa agg tca cag caa      224
Asp Thr Lys Ser Ile Leu Glu Glu Leu Leu Leu Lys Arg Ser Gln Gln
            10                  15                  20 aag aag aaa atg tca cca aat aat tac aaa gaa cgg ctt ttt gtt ttg      272
Lys Lys Lys Met Ser Pro Asn Asn Tyr Lys Glu Arg Leu Phe Val Leu
        25                  30                  35 acc aaa aca aac ctt tcc tac tat gaa tat gac aaa atg aaa agg ggc      320
Thr Lys Thr Asn Leu Ser Tyr Tyr Glu Tyr Asp Lys Met Lys Arg Gly
    40                  45                  50 agc aga aaa gga tcc atc gaa att aag aaa atc aga tgt gtg gag aaa      368
Ser Arg Lys Gly Ser Ile Glu Ile Lys Lys Ile Arg Cys Val Glu Lys
55                  60                  65 gta aat ctc gag gag cag acg cct gtg gag aga cag tac cca ttt cag      416
Val Asn Leu Glu Glu Gln Thr Pro Val Glu Arg Gln Tyr Pro Phe Gln
70                  75                  80                  85 att gtc tat aaa gat ggg ctt ctc tat gtc tat gca tca aat gaa gag      464
Ile Val Tyr Lys Asp Gly Leu Leu Tyr Val Tyr Ala Ser Asn Glu Glu
                90                  95                  100 agc cga agt cag tgg ttg aaa gca tta caa aaa gag ata agg ggt aac      512
Ser Arg Ser Gln Trp Leu Lys Ala Leu Gln Lys Glu Ile Arg Gly Asn
            105                 110                 115 ccc cat ctg ctg atc aag tac cat agt ggg ttc ttc gtg gac ggg aag      560
```

-continued

```
            Pro His Leu Leu Ile Lys Tyr His Ser Gly Phe Phe Val Asp Gly Lys
                    120                 125                 130 ttc ctg tgt tgc cag cag agt tgt aaa gca gcc cca gga tgt acc ctc           608
Phe Leu Cys Cys Gln Gln Ser Cys Lys Ala Ala Pro Gly Cys Thr Leu
        135                 140                 145 tgg gaa gca tat gct aat ctg cat att gca gtc aat gaa gag aaa tac           656
Trp Glu Ala Tyr Ala Asn Leu His Ile Ala Val Asn Glu Glu Lys Tyr
150                 155                 160                 165 aga gtt cct acc ttc cca gac aga gtg ctg aag ata cct cgg gca gtt           704
Arg Val Pro Thr Phe Pro Asp Arg Val Leu Lys Ile Pro Arg Ala Val
                170                 175                 180 cct gtt ctc aaa atg gat gca cca tct tca agt acc act cta gcc caa           752
Pro Val Leu Lys Met Asp Ala Pro Ser Ser Ser Thr Thr Leu Ala Gln
            185                 190                 195 tac gac aac gaa tca atg aaa aac tat ggc ttc cag cca cca tct tca           800
Tyr Asp Asn Glu Ser Met Lys Asn Tyr Gly Phe Gln Pro Pro Ser Ser
        200                 205                 210 agt acc act gta gcc caa tat gac agc aac tca aag aaa atc tat ggc           848
Ser Thr Thr Val Ala Gln Tyr Asp Ser Asn Ser Lys Lys Ile Tyr Gly
    215                 220                 225 tcc cag cca aac ttc aac atg cag tat att cca aaa gaa gac tac cct           896
Ser Gln Pro Asn Phe Asn Met Gln Tyr Ile Pro Lys Glu Asp Tyr Pro
230                 235                 240                 245 gac tgg ggg caa gaa aga aaa ctg aaa agt agc agc agc agt gaa gat           944
Asp Trp Gly Gln Glu Arg Lys Leu Lys Ser Ser Ser Ser Ser Glu Asp
                250                 255                 260 gtt gca agt agt aac caa aaa gaa aga aat gta aat cac acc acc aca           992
Val Ala Ser Ser Asn Gln Lys Glu Arg Asn Val Asn His Thr Thr Thr
            265                 270                 275 aag att tca tgg gga ttc cct gag tca agt tca tct gaa gaa gag gca          1040
Lys Ile Ser Trp Gly Phe Pro Glu Ser Ser Ser Ser Glu Glu Glu Ala
        280                 285                 290 aac ctg gat gat tat gac tgg ttt gct ggt aac atc tcc aga tca caa          1088
Asn Leu Asp Asp Tyr Asp Trp Phe Ala Gly Asn Ile Ser Arg Ser Gln
    295                 300                 305 tct gaa cag tta ctc aga caa aag gga aaa gaa gga gca ttt atg gtt          1136
Ser Glu Gln Leu Leu Arg Gln Lys Gly Lys Glu Gly Ala Phe Met Val
310                 315                 320                 325 aga aat tcg agc caa gtg gga atg tac aca gtg tcc tta ttt agt aag          1184
Arg Asn Ser Ser Gln Val Gly Met Tyr Thr Val Ser Leu Phe Ser Lys
                330                 335                 340 gct gtg aat gat aaa aaa gga act gtc aaa cat tac cat gtg cat aca          1232
Ala Val Asn Asp Lys Lys Gly Thr Val Lys His Tyr His Val His Thr
            345                 350                 355 aat gct gag aac aag tta tac ctg gca gaa aac tac tgt ttt gat tcc          1280
Asn Ala Glu Asn Lys Leu Tyr Leu Ala Glu Asn Tyr Cys Phe Asp Ser
        360                 365                 370 att cca aag ctt att cat tat cac caa cac aat tca gca ggc atg atc          1328
Ile Pro Lys Leu Ile His Tyr His Gln His Asn Ser Ala Gly Met Ile
    375                 380                 385 aca cgg ctc cgc cac cct gtg tca aaa aag gcc aac aag gtc cca gac          1376
Thr Arg Leu Arg His Pro Val Ser Lys Lys Ala Asn Lys Val Pro Asp
390                 395                 400                 405 tct gtg tcc ctg gga aat gga atc tgg gaa ctg aaa aga gaa gag att          1424
Ser Val Ser Leu Gly Asn Gly Ile Trp Glu Leu Lys Arg Glu Glu Ile
                410                 415                 420 acc ttg ttg aag gag ctg gga agt ggc cag ttt gga gtg gtc cag ctg          1472
Thr Leu Leu Lys Glu Leu Gly Ser Gly Gln Phe Gly Val Val Gln Leu
            425                 430                 435 ggc aag tgg aag ggg cag tat gat gtt gct gtt aag atg atc aag gag          1520
```

| | | | | | | | | | | | | | |
|---|---|---|---|---|---|---|---|---|---|---|---|---|---|
|Gly|Lys|Trp|Lys|Gly|Gln|Tyr|Asp|Val|Ala|Val|Lys|Met|Ile|Lys|Glu|
| | |440| | | |445| | | |450| | | | | |

```
ggc tcc atg tca gaa gat gaa ttc ttt cag gag gcc cag act atg aca       1568
Gly Ser Met Ser Glu Asp Glu Phe Phe Gln Glu Ala Gln Thr Met Thr
    455                 460                 465 aaa ctc agc cat ccc aag ctg gtt aaa ttc tat gga gtg tgt tca aag       1616
Lys Leu Ser His Pro Lys Leu Val Lys Phe Tyr Gly Val Cys Ser Lys
470                 475                 480                 485 gaa tac ccc ata tac ata gtg act gaa tat ata agc aat ggc tgc ttg       1664
Glu Tyr Pro Ile Tyr Ile Val Thr Glu Tyr Ile Ser Asn Gly Cys Leu
                490                 495                 500 ctg aat tac ctg agg agt cat gga aaa gga ctt gaa cct tcc cag ctc       1712
Leu Asn Tyr Leu Arg Ser His Gly Lys Gly Leu Glu Pro Ser Gln Leu
            505                 510                 515 tta gaa atg tgc tac gat gtc tgt gaa ggc atg gcc ttc ttg gag agc       1760
Leu Glu Met Cys Tyr Asp Val Cys Glu Gly Met Ala Phe Leu Glu Ser
        520                 525                 530 cac caa ttc ata cac cgg gac ttg gct gcc cgt aac tgc ttg gtg gac       1808
His Gln Phe Ile His Arg Asp Leu Ala Ala Arg Asn Cys Leu Val Asp
535                 540                 545 agc gat ctc tgt gtg aaa gta tct gac ttt gga atg aca agg tat gtt       1856
Ser Asp Leu Cys Val Lys Val Ser Asp Phe Gly Met Thr Arg Tyr Val
550                 555                 560                 565 ctt gat gac cag tat gtc agt tca gtt gga aca aag ttt cca gtc aag       1904
Leu Asp Asp Gln Tyr Val Ser Ser Val Gly Thr Lys Phe Pro Val Lys
                570                 575                 580 tgg tca gct cca gag gtg ttt cat tac ttc aaa tac agc agc aag tca       1952
Trp Ser Ala Pro Glu Val Phe His Tyr Phe Lys Tyr Ser Ser Lys Ser
            585                 590                 595 gac gta tgg gca ttt ggg atc ctg atg tgg gag gtg ttc agc ctg ggg       2000
Asp Val Trp Ala Phe Gly Ile Leu Met Trp Glu Val Phe Ser Leu Gly
        600                 605                 610 aag cag ccc tat gac tta tat gac aac tcc cag gtg gtt ctg aag gtc       2048
Lys Gln Pro Tyr Asp Leu Tyr Asp Asn Ser Gln Val Val Leu Lys Val
    615                 620                 625 tcc cag ggc cac agg ctc tac cgg ccc cac ctg gca tcg gac acc atc       2096
Ser Gln Gly His Arg Leu Tyr Arg Pro His Leu Ala Ser Asp Thr Ile
630                 635                 640                 645 tac cag atc atg tac agc tgc tgg cac gag ctt cca gaa aag cgt ccc       2144
Tyr Gln Ile Met Tyr Ser Cys Trp His Glu Leu Pro Glu Lys Arg Pro
                650                 655                 660 aca ttt cag caa ctc ctg tct tcc att gaa cca ctt cgg gaa aaa gac       2192
Thr Phe Gln Gln Leu Leu Ser Ser Ile Glu Pro Leu Arg Glu Lys Asp
            665                 670                 675 aag cct tga agaagaaact aggagtgctg ataagaatga atatagatgt               2241
Lys Pro tggccagcat tttcattcat tttaaggaaa gtagcaaggc ataatgtaat ttagctagtt     2301
tttaatagtg ttctctgtat tgtatattat ttagaaatga acaaggcagg aaacaaaga      2361 tttccttgaa atttagatca aatcagtaat tttgtttatg ctgctcctga tataacactt     2421
tccagcctat agcagaagca cattttcaga ttgcaatata gagactgcgt tcatgtgtaa     2481
agactgggca gaattgaaaa attacttatt ggatagtcat tcttttcttt atattgtcac     2541
tgtcacaaca attaaatata ctaccaagta cagaaatgtg ga                       2583

<210> SEQ ID NO 6
<211> LENGTH: 679
<212> TYPE: PRT
<213> ORGANISM: Macaca mulatta
```

-continued

<400> SEQUENCE: 6

```
Met Asp Asp Asn Met Asp Thr Lys Ser Ile Leu Glu Glu Leu Leu Leu
1               5                   10                  15

Lys Arg Ser Gln Gln Lys Lys Met Ser Pro Asn Asn Tyr Lys Glu
            20                  25                  30

Arg Leu Phe Val Leu Thr Lys Thr Asn Leu Ser Tyr Tyr Glu Tyr Asp
                35                  40                  45

Lys Met Lys Arg Gly Ser Arg Lys Gly Ser Ile Glu Ile Lys Lys Ile
50                  55                  60

Arg Cys Val Glu Lys Val Asn Leu Glu Glu Gln Thr Pro Val Glu Arg
65                  70                  75                  80

Gln Tyr Pro Phe Gln Ile Val Tyr Lys Asp Gly Leu Leu Tyr Val Tyr
                85                  90                  95

Ala Ser Asn Glu Glu Ser Arg Ser Gln Trp Leu Lys Ala Leu Gln Lys
                100                 105                 110

Glu Ile Arg Gly Asn Pro His Leu Leu Ile Lys Tyr His Ser Gly Phe
            115                 120                 125

Phe Val Asp Gly Lys Phe Leu Cys Cys Gln Gln Ser Cys Lys Ala Ala
130                 135                 140

Pro Gly Cys Thr Leu Trp Glu Ala Tyr Ala Asn Leu His Ile Ala Val
145                 150                 155                 160

Asn Glu Glu Lys Tyr Arg Val Pro Thr Phe Pro Asp Arg Val Leu Lys
                165                 170                 175

Ile Pro Arg Ala Val Pro Val Leu Lys Met Asp Ala Pro Ser Ser Ser
            180                 185                 190

Thr Thr Leu Ala Gln Tyr Asp Asn Glu Ser Met Lys Asn Tyr Gly Phe
            195                 200                 205

Gln Pro Pro Ser Ser Ser Thr Thr Val Ala Gln Tyr Asp Ser Asn Ser
210                 215                 220

Lys Lys Ile Tyr Gly Ser Gln Pro Asn Phe Asn Met Gln Tyr Ile Pro
225                 230                 235                 240

Lys Glu Asp Tyr Pro Asp Trp Gly Gln Glu Arg Lys Leu Lys Ser Ser
                245                 250                 255

Ser Ser Ser Glu Asp Val Ala Ser Ser Asn Gln Lys Glu Arg Asn Val
            260                 265                 270

Asn His Thr Thr Thr Lys Ile Ser Trp Gly Phe Pro Glu Ser Ser Ser
            275                 280                 285

Ser Glu Glu Glu Ala Asn Leu Asp Asp Tyr Asp Trp Phe Ala Gly Asn
            290                 295                 300

Ile Ser Arg Ser Gln Ser Glu Gln Leu Leu Arg Gln Lys Gly Lys Glu
305                 310                 315                 320

Gly Ala Phe Met Val Arg Asn Ser Ser Gln Val Gly Met Tyr Thr Val
                325                 330                 335

Ser Leu Phe Ser Lys Ala Val Asn Asp Lys Lys Gly Thr Val Lys His
            340                 345                 350

Tyr His Val His Thr Asn Ala Glu Asn Lys Leu Tyr Leu Ala Glu Asn
            355                 360                 365

Tyr Cys Phe Asp Ser Ile Pro Lys Leu Ile His Tyr His Gln His Asn
370                 375                 380

Ser Ala Gly Met Ile Thr Arg Leu Arg His Pro Val Ser Lys Lys Ala
385                 390                 395                 400

Asn Lys Val Pro Asp Ser Val Ser Leu Gly Asn Gly Ile Trp Glu Leu
                405                 410                 415
```

```
Lys Arg Glu Glu Ile Thr Leu Leu Lys Glu Leu Gly Ser Gly Gln Phe
            420                 425                 430

Gly Val Val Gln Leu Gly Lys Trp Lys Gly Gln Tyr Asp Val Ala Val
            435                 440                 445

Lys Met Ile Lys Glu Gly Ser Met Ser Glu Asp Glu Phe Phe Gln Glu
        450                 455                 460

Ala Gln Thr Met Thr Lys Leu Ser His Pro Lys Leu Val Lys Phe Tyr
465                 470                 475                 480

Gly Val Cys Ser Lys Glu Tyr Pro Ile Tyr Ile Val Thr Glu Tyr Ile
                485                 490                 495

Ser Asn Gly Cys Leu Leu Asn Tyr Leu Arg Ser His Gly Lys Gly Leu
            500                 505                 510

Glu Pro Ser Gln Leu Leu Glu Met Cys Tyr Asp Val Cys Glu Gly Met
        515                 520                 525

Ala Phe Leu Glu Ser His Gln Phe Ile His Arg Asp Leu Ala Ala Arg
530                 535                 540

Asn Cys Leu Val Asp Ser Asp Leu Cys Val Lys Val Ser Asp Phe Gly
545                 550                 555                 560

Met Thr Arg Tyr Val Leu Asp Asp Gln Tyr Val Ser Ser Val Gly Thr
                565                 570                 575

Lys Phe Pro Val Lys Trp Ser Ala Pro Glu Val Phe His Tyr Phe Lys
            580                 585                 590

Tyr Ser Ser Lys Ser Asp Val Trp Ala Phe Gly Ile Leu Met Trp Glu
        595                 600                 605

Val Phe Ser Leu Gly Lys Gln Pro Tyr Asp Leu Tyr Asp Asn Ser Gln
610                 615                 620

Val Val Leu Lys Val Ser Gln Gly His Arg Leu Tyr Arg Pro His Leu
625                 630                 635                 640

Ala Ser Asp Thr Ile Tyr Gln Ile Met Tyr Ser Cys Trp His Glu Leu
                645                 650                 655

Pro Glu Lys Arg Pro Thr Phe Gln Gln Leu Leu Ser Ser Ile Glu Pro
            660                 665                 670

Leu Arg Glu Lys Asp Lys Pro
        675

<210> SEQ ID NO 7
<211> LENGTH: 2611
<212> TYPE: DNA
<213> ORGANISM: Macaca mulatta
<220> FEATURE:
<221> NAME/KEY: CDS
<222> LOCATION: (187)..(2229)

<400> SEQUENCE: 7
tggaggtgcc tggatgaaca tacatcacag tgtgaacagt ggtcatctcc agatagtaga      60
atttcagata tgtttctttc cattttctg atagcttgaa ttttctgtaa taattaattg     120
gcttttatac aatgaaagca acattttat tttggaaaaa acaaagatgc tgccactaat     180 cagtgg atg aaa gat gat aat atg gat aca aaa tct att cta gaa gaa       228
       Met Lys Asp Asp Asn Met Asp Thr Lys Ser Ile Leu Glu Glu
           1               5                  10 ctt ctt ctc aaa agg tca cag caa aag aag aaa atg tca cca aat aat      276
Leu Leu Leu Lys Arg Ser Gln Gln Lys Lys Lys Met Ser Pro Asn Asn
15                  20                  25                  30 tac aaa gaa cgg ctt ttt gtt ttg acc aaa aca aac ctt tcc tac tat      324
Tyr Lys Glu Arg Leu Phe Val Leu Thr Lys Thr Asn Leu Ser Tyr Tyr
                35                  40                  45
```

-continued

| | |
|---|---|
| gaa tat gac aaa atg aaa agg ggc agc aga aaa gga tcc atc gaa att<br>Glu Tyr Asp Lys Met Lys Arg Gly Ser Arg Lys Gly Ser Ile Glu Ile<br>      50                  55                  60 | 372 |
| aag aaa atc aga tgt gtg gag aaa gta aat ctc gag gag cag acg cct<br>Lys Lys Ile Arg Cys Val Glu Lys Val Asn Leu Glu Glu Gln Thr Pro<br>65                  70                  75 | 420 |
| gtg gag aga cag tac cca ttt cag att gtc tat aaa gat ggg ctt ctc<br>Val Glu Arg Gln Tyr Pro Phe Gln Ile Val Tyr Lys Asp Gly Leu Leu<br>    80                  85                  90 | 468 |
| tat gtc tat gca tca aat gaa gag agc cga agt cag tgg ttg aaa gca<br>Tyr Val Tyr Ala Ser Asn Glu Glu Ser Arg Ser Gln Trp Leu Lys Ala<br>95                 100                 105                 110 | 516 |
| tta caa aaa gag ata agg ggt aac ccc cat ctg ctg atc aag tac cat<br>Leu Gln Lys Glu Ile Arg Gly Asn Pro His Leu Leu Ile Lys Tyr His<br>            115                 120                 125 | 564 |
| agt ggg ttc ttc gtg gac ggg aag ttc ctg tgt tgc cag cag agt tgt<br>Ser Gly Phe Phe Val Asp Gly Lys Phe Leu Cys Cys Gln Gln Ser Cys<br>        130                 135                 140 | 612 |
| aaa gca gcc cca gga tgt acc ctc tgg gaa gca tat gct aat ctg cat<br>Lys Ala Ala Pro Gly Cys Thr Leu Trp Glu Ala Tyr Ala Asn Leu His<br>    145                 150                 155 | 660 |
| att gca gtc aat gaa gag aaa tac aga gtt cct acc ttc cca gac aga<br>Ile Ala Val Asn Glu Glu Lys Tyr Arg Val Pro Thr Phe Pro Asp Arg<br>160                 165                 170 | 708 |
| gtg ctg aag ata cct cgg gca gtt cct gtt ctc aaa atg gat gca cca<br>Val Leu Lys Ile Pro Arg Ala Val Pro Val Leu Lys Met Asp Ala Pro<br>175                 180                 185                 190 | 756 |
| tct tca agt acc act cta gcc caa tac gac aac gaa tca atg aaa aac<br>Ser Ser Ser Thr Thr Leu Ala Gln Tyr Asp Asn Glu Ser Met Lys Asn<br>            195                 200                 205 | 804 |
| tat ggc ttc cag cca cca tct tca agt acc act gta gcc caa tat gac<br>Tyr Gly Phe Gln Pro Pro Ser Ser Ser Thr Thr Val Ala Gln Tyr Asp<br>        210                 215                 220 | 852 |
| agc aac tca aag aaa atc tat ggc tcc cag cca aac ttc aac atg cag<br>Ser Asn Ser Lys Lys Ile Tyr Gly Ser Gln Pro Asn Phe Asn Met Gln<br>    225                 230                 235 | 900 |
| tat att cca aaa gaa gac tac cct gac tgg ggg caa gaa aga aaa ctg<br>Tyr Ile Pro Lys Glu Asp Tyr Pro Asp Trp Gly Gln Glu Arg Lys Leu<br>240                 245                 250 | 948 |
| aaa agt agc agc agc agt gaa gat gtt gca agt agt aac caa aaa gaa<br>Lys Ser Ser Ser Ser Ser Glu Asp Val Ala Ser Ser Asn Gln Lys Glu<br>255                 260                 265                 270 | 996 |
| aga aat gta aat cac acc acc aca aag att tca tgg gga ttc cct gag<br>Arg Asn Val Asn His Thr Thr Thr Lys Ile Ser Trp Gly Phe Pro Glu<br>            275                 280                 285 | 1044 |
| tca agt tca tct gaa gaa gag gca aac ctg gat gat tat gac tgg ttt<br>Ser Ser Ser Ser Glu Glu Glu Ala Asn Leu Asp Asp Tyr Asp Trp Phe<br>        290                 295                 300 | 1092 |
| gct ggt aac atc tcc aga tca caa tct gaa cag tta ctc aga caa aag<br>Ala Gly Asn Ile Ser Arg Ser Gln Ser Glu Gln Leu Leu Arg Gln Lys<br>    305                 310                 315 | 1140 |
| gga aaa gaa gga gca ttt atg gtt aga aat tcg agc caa gtg gga atg<br>Gly Lys Glu Gly Ala Phe Met Val Arg Asn Ser Ser Gln Val Gly Met<br>320                 325                 330 | 1188 |
| tac aca gtg tcc tta ttt agt aag gct gtg aat gat aaa aaa gga act<br>Tyr Thr Val Ser Leu Phe Ser Lys Ala Val Asn Asp Lys Lys Gly Thr<br>335                 340                 345                 350 | 1236 |
| gtc aaa cat tac cat gtg cat aca aat gct gag aac aag tta tac ctg<br>Val Lys His Tyr His Val His Thr Asn Ala Glu Asn Lys Leu Tyr Leu<br>            355                 360                 365 | 1284 |

```
gca gaa aac tac tgt ttt gat tcc att cca aag ctt att cat tat cac      1332
Ala Glu Asn Tyr Cys Phe Asp Ser Ile Pro Lys Leu Ile His Tyr His
        370                 375                 380 caa cac aat tca gca ggc atg atc aca cgg ctc cgc cct gtg tca          1380
Gln His Asn Ser Ala Gly Met Ile Thr Arg Leu Arg His Pro Val Ser
    385                 390                 395 aaa aag gcc aac aag gtc cca gac tct gtg tcc ctg gga aat gga atc      1428
Lys Lys Ala Asn Lys Val Pro Asp Ser Val Ser Leu Gly Asn Gly Ile
        400                 405                 410 tgg gaa ctg aaa aga gaa gag att acc ttg ttg aag gag ctg gga agt      1476
Trp Glu Leu Lys Arg Glu Glu Ile Thr Leu Leu Lys Glu Leu Gly Ser
415                 420                 425                 430 ggc cag ttt gga gtg gtc cag ctg ggc aag tgg aag ggg cag tat gat      1524
Gly Gln Phe Gly Val Val Gln Leu Gly Lys Trp Lys Gly Gln Tyr Asp
                435                 440                 445 gtt gct gtt aag atg atc aag gag ggc tcc atg tca gaa gat gaa ttc      1572
Val Ala Val Lys Met Ile Lys Glu Gly Ser Met Ser Glu Asp Glu Phe
            450                 455                 460 ttt cag gag gcc cag act atg aca aaa ctc agc cat ccc aag ctg gtt      1620
Phe Gln Glu Ala Gln Thr Met Thr Lys Leu Ser His Pro Lys Leu Val
        465                 470                 475 aaa ttc tat gga gtg tgt tca aag gaa tac ccc ata tac ata gtg act      1668
Lys Phe Tyr Gly Val Cys Ser Lys Glu Tyr Pro Ile Tyr Ile Val Thr
    480                 485                 490 gaa tat ata agc aat ggc tgc ttg ctg aat tac ctg agg agt cat gga      1716
Glu Tyr Ile Ser Asn Gly Cys Leu Leu Asn Tyr Leu Arg Ser His Gly
495                 500                 505                 510 aaa gga ctt gaa cct tcc cag ctc tta gaa atg tgc tac gat gtc tgt      1764
Lys Gly Leu Glu Pro Ser Gln Leu Leu Glu Met Cys Tyr Asp Val Cys
                515                 520                 525 gaa ggc atg gcc ttc ttg gag agc cac caa ttc ata cac cgg gac ttg      1812
Glu Gly Met Ala Phe Leu Glu Ser His Gln Phe Ile His Arg Asp Leu
            530                 535                 540 gct gcc cgt aac tgc ttg gtg gac agc gat ctc tgt gtg aaa gta tct      1860
Ala Ala Arg Asn Cys Leu Val Asp Ser Asp Leu Cys Val Lys Val Ser
        545                 550                 555 gac ttt gga atg aca agg tat gtt ctt gat gac cag tat gtc agt tca      1908
Asp Phe Gly Met Thr Arg Tyr Val Leu Asp Asp Gln Tyr Val Ser Ser
    560                 565                 570 gtt gga aca aag ttt cca gtc aag tgg tca gct cca gag gtg ttt cat      1956
Val Gly Thr Lys Phe Pro Val Lys Trp Ser Ala Pro Glu Val Phe His
575                 580                 585                 590 tac ttc aaa tac agc agc aag tca gac gta tgg gca ttt ggg atc ctg      2004
Tyr Phe Lys Tyr Ser Ser Lys Ser Asp Val Trp Ala Phe Gly Ile Leu
                595                 600                 605 atg tgg gag gtg ttc agc ctg ggg aag cag ccc tat gac tta tat gac      2052
Met Trp Glu Val Phe Ser Leu Gly Lys Gln Pro Tyr Asp Leu Tyr Asp
            610                 615                 620 aac tcc cag gtg gtt ctg aag gtc tcc cag ggc cac agg ctc tac cgg      2100
Asn Ser Gln Val Val Leu Lys Val Ser Gln Gly His Arg Leu Tyr Arg
        625                 630                 635 ccc cac ctg gca tcg gac acc atc tac cag atc atg tac agc tgc tgg      2148
Pro His Leu Ala Ser Asp Thr Ile Tyr Gln Ile Met Tyr Ser Cys Trp
    640                 645                 650 cac gag ctt cca gaa aag cgt ccc aca ttt cag caa ctc ctg tct tcc      2196
His Glu Leu Pro Glu Lys Arg Pro Thr Phe Gln Gln Leu Leu Ser Ser
655                 660                 665                 670 att gaa cca ctt cgg gaa aaa gac aag cct tga agaagaaact aggagtgctg    2249
Ile Glu Pro Leu Arg Glu Lys Asp Lys Pro
                675                 680
```

```
ataagaatga atatagatgt tggccagcat tttcattcat tttaaggaaa gtagcaaggc   2309
ataatgtaat ttagctagtt tttaatagtg ttctctgtat tgtatattat ttagaaatga   2369
acaaggcagg aaacaaaaga tttccttgaa atttagatca aatcagtaat tttgtttatg   2429
ctgctcctga tataacactt tccagcctat agcagaagca cattttcaga ttgcaatata   2489
gagactgcgt tcatgtgtaa agactgggca gaattgaaaa attacttatt ggatagtcat   2549
tcttttcttt atattgtcac tgtcacaaca attaaatata ctaccaagta cagaaatgtg   2609
ga                                                                 2611

<210> SEQ ID NO 8
<211> LENGTH: 680
<212> TYPE: PRT
<213> ORGANISM: Macaca mulatta

<400> SEQUENCE: 8
```

Met Lys Asp Asp Asn Met Asp Thr Lys Ser Ile Leu Glu Glu Leu Leu
1               5                   10                  15

Leu Lys Arg Ser Gln Gln Lys Lys Met Ser Pro Asn Asn Tyr Lys
            20                  25                  30

Glu Arg Leu Phe Val Leu Thr Lys Thr Asn Leu Ser Tyr Tyr Glu Tyr
        35                  40                  45

Asp Lys Met Lys Arg Gly Ser Arg Lys Gly Ser Ile Glu Ile Lys Lys
    50                  55                  60

Ile Arg Cys Val Glu Lys Val Asn Leu Glu Glu Gln Thr Pro Val Glu
65                  70                  75                  80

Arg Gln Tyr Pro Phe Gln Ile Val Tyr Lys Asp Gly Leu Leu Tyr Val
                85                  90                  95

Tyr Ala Ser Asn Glu Glu Ser Arg Ser Gln Trp Leu Lys Ala Leu Gln
            100                 105                 110

Lys Glu Ile Arg Gly Asn Pro His Leu Leu Ile Lys Tyr His Ser Gly
        115                 120                 125

Phe Phe Val Asp Gly Lys Phe Leu Cys Cys Gln Gln Ser Cys Lys Ala
    130                 135                 140

Ala Pro Gly Cys Thr Leu Trp Glu Ala Tyr Ala Asn Leu His Ile Ala
145                 150                 155                 160

Val Asn Glu Glu Lys Tyr Arg Val Pro Thr Phe Pro Asp Arg Val Leu
                165                 170                 175

Lys Ile Pro Arg Ala Val Pro Val Leu Lys Met Asp Ala Pro Ser Ser
            180                 185                 190

Ser Thr Thr Leu Ala Gln Tyr Asp Asn Glu Ser Met Lys Asn Tyr Gly
        195                 200                 205

Phe Gln Pro Pro Ser Ser Thr Thr Val Ala Gln Tyr Asp Ser Asn
    210                 215                 220

Ser Lys Lys Ile Tyr Gly Ser Gln Pro Asn Phe Asn Met Gln Tyr Ile
225                 230                 235                 240

Pro Lys Glu Asp Tyr Pro Asp Trp Gly Gln Glu Arg Lys Leu Lys Ser
                245                 250                 255

Ser Ser Ser Ser Glu Asp Val Ala Ser Ser Asn Gln Lys Glu Arg Asn
            260                 265                 270

Val Asn His Thr Thr Thr Lys Ile Ser Trp Gly Phe Pro Glu Ser Ser
        275                 280                 285

Ser Ser Glu Glu Glu Ala Asn Leu Asp Asp Tyr Asp Trp Phe Ala Gly
    290                 295                 300

Asn Ile Ser Arg Ser Gln Ser Glu Gln Leu Leu Arg Gln Lys Gly Lys

```
                305                 310                 315                 320

Glu Gly Ala Phe Met Val Arg Asn Ser Ser Gln Val Gly Met Tyr Thr
                    325                 330                 335

Val Ser Leu Phe Ser Lys Ala Val Asn Asp Lys Lys Gly Thr Val Lys
                340                 345                 350

His Tyr His Val His Thr Asn Ala Glu Asn Lys Leu Tyr Leu Ala Glu
            355                 360                 365

Asn Tyr Cys Phe Asp Ser Ile Pro Lys Leu Ile His Tyr His Gln His
370                 375                 380

Asn Ser Ala Gly Met Ile Thr Arg Leu Arg His Pro Val Ser Lys Lys
385                 390                 395                 400

Ala Asn Lys Val Pro Asp Ser Val Ser Leu Gly Asn Gly Ile Trp Glu
                405                 410                 415

Leu Lys Arg Glu Glu Ile Thr Leu Leu Lys Glu Leu Gly Ser Gly Gln
                420                 425                 430

Phe Gly Val Val Gln Leu Gly Lys Trp Lys Gly Gln Tyr Asp Val Ala
            435                 440                 445

Val Lys Met Ile Lys Glu Gly Ser Met Ser Glu Asp Glu Phe Phe Gln
450                 455                 460

Glu Ala Gln Thr Met Thr Lys Leu Ser His Pro Lys Leu Val Lys Phe
465                 470                 475                 480

Tyr Gly Val Cys Ser Lys Glu Tyr Pro Ile Tyr Ile Val Thr Glu Tyr
                485                 490                 495

Ile Ser Asn Gly Cys Leu Leu Asn Tyr Leu Arg Ser His Gly Lys Gly
                500                 505                 510

Leu Glu Pro Ser Gln Leu Leu Glu Met Cys Tyr Asp Val Cys Glu Gly
            515                 520                 525

Met Ala Phe Leu Glu Ser His Gln Phe Ile His Arg Asp Leu Ala Ala
530                 535                 540

Arg Asn Cys Leu Val Asp Ser Asp Leu Cys Val Lys Val Ser Asp Phe
545                 550                 555                 560

Gly Met Thr Arg Tyr Val Leu Asp Asp Gln Tyr Val Ser Ser Val Gly
                565                 570                 575

Thr Lys Phe Pro Val Lys Trp Ser Ala Pro Glu Val Phe His Tyr Phe
                580                 585                 590

Lys Tyr Ser Ser Lys Ser Asp Val Trp Ala Phe Gly Ile Leu Met Trp
            595                 600                 605

Glu Val Phe Ser Leu Gly Lys Gln Pro Tyr Asp Leu Tyr Asp Asn Ser
        610                 615                 620

Gln Val Val Leu Lys Val Ser Gln Gly His Arg Leu Tyr Arg Pro His
625                 630                 635                 640

Leu Ala Ser Asp Thr Ile Tyr Gln Ile Met Tyr Ser Cys Trp His Glu
                645                 650                 655

Leu Pro Glu Lys Arg Pro Thr Phe Gln Gln Leu Leu Ser Ser Ile Glu
                660                 665                 670

Pro Leu Arg Glu Lys Asp Lys Pro
            675                 680

<210> SEQ ID NO 9
<211> LENGTH: 2552
<212> TYPE: DNA
<213> ORGANISM: Macaca mulatta
<220> FEATURE:
<221> NAME/KEY: CDS
<222> LOCATION: (143)..(2170)
```

```
<400> SEQUENCE: 9
tcttttgaat gcatgaccct ggcatagcca gagggaatat gagtgatggt gcctcaaagc      60 agtaacttc  tgcttagagc ttgagagtta aaggtaagga ccacacgtat actttggctc     120
tagcgagtct aaggatgata at atg gat aca aaa tct att cta gaa gaa ctt      172
                         Met Asp Thr Lys Ser Ile Leu Glu Glu Leu
                          1               5                    10 ctt ctc aaa agg tca cag caa aag aag aaa atg tca cca aat aat tac      220
Leu Leu Lys Arg Ser Gln Gln Lys Lys Lys Met Ser Pro Asn Asn Tyr
             15                  20                  25 aaa gaa cgg ctt ttt gtt ttg acc aaa aca aac ctt tcc tac tat gaa      268
Lys Glu Arg Leu Phe Val Leu Thr Lys Thr Asn Leu Ser Tyr Tyr Glu
         30                  35                  40 tat gac aaa atg aaa agg ggc agc aga aaa gga tcc atc gaa att aag      316
Tyr Asp Lys Met Lys Arg Gly Ser Arg Lys Gly Ser Ile Glu Ile Lys
     45                  50                  55 aaa atc aga tgt gtg gag aaa gta aat ctc gag gag cag acg cct gtg      364
Lys Ile Arg Cys Val Glu Lys Val Asn Leu Glu Glu Gln Thr Pro Val
 60                  65                  70 gag aga cag tac cca ttt cag att gtc tat aaa gat ggg ctt ctc tat      412
Glu Arg Gln Tyr Pro Phe Gln Ile Val Tyr Lys Asp Gly Leu Leu Tyr
 75                  80                  85                  90 gtc tat gca tca aat gaa gag agc cga agt cag tgg ttg aaa gca tta      460
Val Tyr Ala Ser Asn Glu Glu Ser Arg Ser Gln Trp Leu Lys Ala Leu
                 95                 100                 105 caa aaa gag ata agg ggt aac ccc cat ctg ctg atc aag tac cat agt      508
Gln Lys Glu Ile Arg Gly Asn Pro His Leu Leu Ile Lys Tyr His Ser
         110                 115                 120 ggg ttc ttc gtg gac ggg aag ttc ctg tgt tgc cag cag agt tgt aaa      556
Gly Phe Phe Val Asp Gly Lys Phe Leu Cys Cys Gln Gln Ser Cys Lys
     125                 130                 135 gca gcc cca gga tgt acc ctc tgg gaa gca tat gct aat ctg cat att      604
Ala Ala Pro Gly Cys Thr Leu Trp Glu Ala Tyr Ala Asn Leu His Ile
 140                 145                 150 gca gtc aat gaa gag aaa tac aga gtt cct acc ttc cca gac aga gtg      652
Ala Val Asn Glu Glu Lys Tyr Arg Val Pro Thr Phe Pro Asp Arg Val
155                 160                 165                 170 ctg aag ata cct cgg gca gtt cct gtt ctc aaa atg gat gca cca tct      700
Leu Lys Ile Pro Arg Ala Val Pro Val Leu Lys Met Asp Ala Pro Ser
                 175                 180                 185 tca agt acc act cta gcc caa tac gac aac gaa tca atg aaa aac tat      748
Ser Ser Thr Thr Leu Ala Gln Tyr Asp Asn Glu Ser Met Lys Asn Tyr
         190                 195                 200 ggc ttc cag cca cca tct tca agt acc act gta gcc caa tat gac agc      796
Gly Phe Gln Pro Pro Ser Ser Ser Thr Thr Val Ala Gln Tyr Asp Ser
     205                 210                 215 aac tca aag aaa atc tat ggc tcc cag cca aac ttc aac atg cag tat      844
Asn Ser Lys Lys Ile Tyr Gly Ser Gln Pro Asn Phe Asn Met Gln Tyr
 220                 225                 230 att cca aaa gaa gac tac cct gac tgg ggg caa gaa aga aaa ctg aaa      892
Ile Pro Lys Glu Asp Tyr Pro Asp Trp Gly Gln Glu Arg Lys Leu Lys
235                 240                 245                 250 agt agc agc agc agt gaa gat gtt gca agt agt aac caa aaa gaa aga      940
Ser Ser Ser Ser Ser Glu Asp Val Ala Ser Ser Asn Gln Lys Glu Arg
                 255                 260                 265 aat gta aat cac acc acc aca aag att tca tgg gga ttc cct gag tca      988
Asn Val Asn His Thr Thr Thr Lys Ile Ser Trp Gly Phe Pro Glu Ser
         270                 275                 280 agt tca tct gaa gaa gag gca aac ctg gat gat tat gac tgg ttt gct     1036
Ser Ser Ser Glu Glu Glu Ala Asn Leu Asp Asp Tyr Asp Trp Phe Ala
```

```
            285                 290                 295
ggt aac atc tcc aga tca caa tct gaa cag tta ctc aga caa aag gga      1084
Gly Asn Ile Ser Arg Ser Gln Ser Glu Gln Leu Leu Arg Gln Lys Gly
300                 305                 310 aaa gaa gga gca ttt atg gtt aga aat tcg agc caa gtg gga atg tac      1132
Lys Glu Gly Ala Phe Met Val Arg Asn Ser Ser Gln Val Gly Met Tyr
315                 320                 325                 330 aca gtg tcc tta ttt agt aag gct gtg aat gat aaa aaa gga act gtc      1180
Thr Val Ser Leu Phe Ser Lys Ala Val Asn Asp Lys Lys Gly Thr Val
                335                 340                 345 aaa cat tac cat gtg cat aca aat gct gag aac aag tta tac ctg gca      1228
Lys His Tyr His Val His Thr Asn Ala Glu Asn Lys Leu Tyr Leu Ala
350                 355                 360 gaa aac tac tgt ttt gat tcc att cca aag ctt att cat tat cac caa      1276
Glu Asn Tyr Cys Phe Asp Ser Ile Pro Lys Leu Ile His Tyr His Gln
    365                 370                 375 cac aat tca gca ggc atg atc aca cgg ctc cgc cac cct gtg tca aaa      1324
His Asn Ser Ala Gly Met Ile Thr Arg Leu Arg His Pro Val Ser Lys
380                 385                 390 aag gcc aac aag gtc cca gac tct gtg tcc ctg gga aat gga atc tgg      1372
Lys Ala Asn Lys Val Pro Asp Ser Val Ser Leu Gly Asn Gly Ile Trp
395                 400                 405                 410 gaa ctg aaa aga gaa gag att acc ttg ttg aag gag ctg gga agt ggc      1420
Glu Leu Lys Arg Glu Glu Ile Thr Leu Leu Lys Glu Leu Gly Ser Gly
                415                 420                 425 cag ttt gga gtg gtc cag ctg ggc aag tgg aag ggg cag tat gat gtt      1468
Gln Phe Gly Val Val Gln Leu Gly Lys Trp Lys Gly Gln Tyr Asp Val
            430                 435                 440 gct gtt aag atg atc aag gag ggc tcc atg tca gaa gat gaa ttc ttt      1516
Ala Val Lys Met Ile Lys Glu Gly Ser Met Ser Glu Asp Glu Phe Phe
445                 450                 455 cag gag gcc cag act atg aca aaa ctc agc cat ccc aag ctg gtt aaa      1564
Gln Glu Ala Gln Thr Met Thr Lys Leu Ser His Pro Lys Leu Val Lys
460                 465                 470 ttc tat gga gtg tgt tca aag gaa tac ccc ata tac ata gtg act gaa      1612
Phe Tyr Gly Val Cys Ser Lys Glu Tyr Pro Ile Tyr Ile Val Thr Glu
475                 480                 485                 490 tat ata agc aat ggc tgc ttg ctg aat tac ctg agg agt cat gga aaa      1660
Tyr Ile Ser Asn Gly Cys Leu Leu Asn Tyr Leu Arg Ser His Gly Lys
                495                 500                 505 gga ctt gaa cct tcc cag ctc tta gaa atg tgc tac gat gtc tgt gaa      1708
Gly Leu Glu Pro Ser Gln Leu Leu Glu Met Cys Tyr Asp Val Cys Glu
            510                 515                 520 ggc atg gcc ttc ttg gag agc cac caa ttc ata cac cgg gac ttg gct      1756
Gly Met Ala Phe Leu Glu Ser His Gln Phe Ile His Arg Asp Leu Ala
                525                 530                 535 gcc cgt aac tgc ttg gtg gac agc gat ctc tgt gtg aaa gta tct gac      1804
Ala Arg Asn Cys Leu Val Asp Ser Asp Leu Cys Val Lys Val Ser Asp
540                 545                 550 ttt gga atg aca agg tat gtt ctt gat gac cag tat gtc agt tca gtt      1852
Phe Gly Met Thr Arg Tyr Val Leu Asp Asp Gln Tyr Val Ser Ser Val
555                 560                 565                 570 gga aca aag ttt cca gtc aag tgg tca gct cca gag gtg ttt cat tac      1900
Gly Thr Lys Phe Pro Val Lys Trp Ser Ala Pro Glu Val Phe His Tyr
                575                 580                 585 ttc aaa tac agc agc aag tca gac gta tgg gca ttt ggg atc ctg atg      1948
Phe Lys Tyr Ser Ser Lys Ser Asp Val Trp Ala Phe Gly Ile Leu Met
            590                 595                 600 tgg gag gtg ttc agc ctg ggg aag cag ccc tat gac tta tat gac aac      1996
Trp Glu Val Phe Ser Leu Gly Lys Gln Pro Tyr Asp Leu Tyr Asp Asn
```

```
                    605                 610                 615
tcc cag gtg gtt ctg aag gtc tcc cag ggc cac agg ctc tac cgg ccc    2044
Ser Gln Val Val Leu Lys Val Ser Gln Gly His Arg Leu Tyr Arg Pro
    620                 625                 630 cac ctg gca tcg gac acc atc tac cag atc atg tac agc tgc tgg cac    2092
His Leu Ala Ser Asp Thr Ile Tyr Gln Ile Met Tyr Ser Cys Trp His
635                 640                 645                 650 gag ctt cca gaa aag cgt ccc aca ttt cag caa ctc ctg tct tcc att    2140
Glu Leu Pro Glu Lys Arg Pro Thr Phe Gln Gln Leu Leu Ser Ser Ile
                655                 660                 665 gaa cca ctt cgg gaa aaa gac aag cct tga agaagaaact aggagtgctg      2190
Glu Pro Leu Arg Glu Lys Asp Lys Pro
            670                 675 ataagaatga atatagatgt tggccagcat tttcattcat tttaaggaaa gtagcaaggc  2250
ataatgtaat ttagctagtt tttaatagtg ttctctgtat tgtatattat ttagaaatga  2310
acaaggcagg aaacaaaaga tttccttgaa atttagatca aatcagtaat tttgtttatg  2370
ctgctcctga tataacactt tccagcctat agcagaagca cattttcaga ttgcaatata  2430
gagactgcgt tcatgtgtaa agactgggca gaattgaaaa attacttatt ggatagtcat  2490
tcttttcttt atattgtcac tgtcacaaca attaaatata ctaccaagta cagaaatgtg  2550
ga                                                                 2552

<210> SEQ ID NO 10
<211> LENGTH: 675
<212> TYPE: PRT
<213> ORGANISM: Macaca mulatta

<400> SEQUENCE: 10

Met Asp Thr Lys Ser Ile Leu Glu Glu Leu Leu Leu Lys Arg Ser Gln
1               5                   10                  15

Gln Lys Lys Lys Met Ser Pro Asn Asn Tyr Lys Glu Arg Leu Phe Val
            20                  25                  30

Leu Thr Lys Thr Asn Leu Ser Tyr Tyr Glu Tyr Asp Lys Met Lys Arg
        35                  40                  45

Gly Ser Arg Lys Gly Ser Ile Glu Ile Lys Lys Ile Arg Cys Val Glu
    50                  55                  60

Lys Val Asn Leu Glu Glu Gln Thr Pro Val Glu Arg Gln Tyr Pro Phe
65                  70                  75                  80

Gln Ile Val Tyr Lys Asp Gly Leu Leu Tyr Val Tyr Ala Ser Asn Glu
                85                  90                  95

Glu Ser Arg Ser Gln Trp Leu Lys Ala Leu Gln Lys Glu Ile Arg Gly
            100                 105                 110

Asn Pro His Leu Leu Ile Lys Tyr His Ser Gly Phe Phe Val Asp Gly
        115                 120                 125

Lys Phe Leu Cys Cys Gln Gln Ser Cys Lys Ala Ala Pro Gly Cys Thr
    130                 135                 140

Leu Trp Glu Ala Tyr Ala Asn Leu His Ile Ala Val Asn Glu Glu Lys
145                 150                 155                 160

Tyr Arg Val Pro Thr Phe Pro Asp Arg Val Leu Lys Ile Pro Arg Ala
                165                 170                 175

Val Pro Val Leu Lys Met Asp Ala Pro Ser Ser Ser Thr Thr Leu Ala
            180                 185                 190

Gln Tyr Asp Asn Glu Ser Met Lys Asn Tyr Gly Phe Gln Pro Pro Ser
        195                 200                 205

Ser Ser Thr Thr Val Ala Gln Tyr Asp Ser Asn Ser Lys Lys Ile Tyr
```

```
              210                 215                 220
Gly Ser Gln Pro Asn Phe Asn Met Gln Tyr Ile Pro Lys Glu Asp Tyr
225                 230                 235                 240

Pro Asp Trp Gly Gln Glu Arg Lys Leu Lys Ser Ser Ser Ser Ser Glu
                245                 250                 255

Asp Val Ala Ser Ser Asn Gln Lys Glu Arg Asn Val Asn His Thr Thr
                260                 265                 270

Thr Lys Ile Ser Trp Gly Phe Pro Glu Ser Ser Ser Glu Glu Glu
                275                 280                 285

Ala Asn Leu Asp Asp Tyr Asp Trp Phe Ala Gly Asn Ile Ser Arg Ser
290                 295                 300

Gln Ser Glu Gln Leu Leu Arg Gln Lys Gly Lys Glu Gly Ala Phe Met
305                 310                 315                 320

Val Arg Asn Ser Ser Gln Val Gly Met Tyr Thr Val Ser Leu Phe Ser
                325                 330                 335

Lys Ala Val Asn Asp Lys Lys Gly Thr Val Lys His Tyr His Val His
                340                 345                 350

Thr Asn Ala Glu Asn Lys Leu Tyr Leu Ala Glu Asn Tyr Cys Phe Asp
                355                 360                 365

Ser Ile Pro Lys Leu Ile His Tyr His Gln His Asn Ser Ala Gly Met
370                 375                 380

Ile Thr Arg Leu Arg His Pro Val Ser Lys Ala Asn Lys Val Pro
385                 390                 395                 400

Asp Ser Val Ser Leu Gly Asn Gly Ile Trp Glu Leu Lys Arg Glu Glu
                405                 410                 415

Ile Thr Leu Leu Lys Glu Leu Gly Ser Gly Gln Phe Gly Val Val Gln
                420                 425                 430

Leu Gly Lys Trp Lys Gly Gln Tyr Asp Val Ala Val Lys Met Ile Lys
                435                 440                 445

Glu Gly Ser Met Ser Glu Asp Glu Phe Phe Gln Glu Ala Gln Thr Met
450                 455                 460

Thr Lys Leu Ser His Pro Lys Leu Val Lys Phe Tyr Gly Val Cys Ser
465                 470                 475                 480

Lys Glu Tyr Pro Ile Tyr Ile Val Thr Glu Tyr Ile Ser Asn Gly Cys
                485                 490                 495

Leu Leu Asn Tyr Leu Arg Ser His Gly Lys Gly Leu Glu Pro Ser Gln
                500                 505                 510

Leu Leu Glu Met Cys Tyr Asp Val Cys Glu Gly Met Ala Phe Leu Glu
                515                 520                 525

Ser His Gln Phe Ile His Arg Asp Leu Ala Ala Arg Asn Cys Leu Val
530                 535                 540

Asp Ser Asp Leu Cys Val Lys Val Ser Asp Phe Gly Met Thr Arg Tyr
545                 550                 555                 560

Val Leu Asp Asp Gln Tyr Val Ser Val Gly Thr Lys Phe Pro Val
                565                 570                 575

Lys Trp Ser Ala Pro Glu Val Phe His Tyr Phe Lys Tyr Ser Ser Lys
                580                 585                 590

Ser Asp Val Trp Ala Phe Gly Ile Leu Met Trp Glu Val Phe Ser Leu
                595                 600                 605

Gly Lys Gln Pro Tyr Asp Leu Tyr Asp Asn Ser Gln Val Val Leu Lys
                610                 615                 620

Val Ser Gln Gly His Arg Leu Tyr Arg Pro His Leu Ala Ser Asp Thr
625                 630                 635                 640
```

```
Ile Tyr Gln Ile Met Tyr Ser Cys Trp His Glu Leu Pro Glu Lys Arg
                645                 650                 655

Pro Thr Phe Gln Gln Leu Leu Ser Ser Ile Glu Pro Leu Arg Glu Lys
            660                 665                 670

Asp Lys Pro
        675

<210> SEQ ID NO 11
<211> LENGTH: 2985
<212> TYPE: DNA
<213> ORGANISM: Mus musculus
<220> FEATURE:
<221> NAME/KEY: CDS
<222> LOCATION: (156)..(2111)

<400> SEQUENCE: 11
agccatttct gacccaacag ccaggggaaa aaaaaatgtg atacaattca ctgctgctgg      60
agagaggaca gcccgaggtt gcgttcttgc aggagcagct tcgcttcacc gtggtggacc     120
ccagggagac agaaggagcc caaatggacg acaat atg gag agt aaa tcc att        173
                                      Met Glu Ser Lys Ser Ile
                                        1               5 ctg gaa gaa ctg ctt ctc aaa aag tca cag caa aag aag aaa atg tca       221
Leu Glu Glu Leu Leu Leu Lys Lys Ser Gln Gln Lys Lys Lys Met Ser
         10                  15                  20 cca aat aat tac aag gag cgg ctt ttt gtt cta acc aaa aca agc ctt       269
Pro Asn Asn Tyr Lys Glu Arg Leu Phe Val Leu Thr Lys Thr Ser Leu
     25                  30                  35 tcc tac tat gaa tac gac aaa atg aaa aga gga agc aga aaa gga tca       317
Ser Tyr Tyr Glu Tyr Asp Lys Met Lys Arg Gly Ser Arg Lys Gly Ser
 40                  45                  50 ata gaa att aag aaa atc aga tgt gtg gaa aaa gtc aac ctt gag gag       365
Ile Glu Ile Lys Lys Ile Arg Cys Val Glu Lys Val Asn Leu Glu Glu
55                  60                  65                  70 cag aca ccg gtg gag aga cag tac cca ttt cag att gtg tat aaa gat       413
Gln Thr Pro Val Glu Arg Gln Tyr Pro Phe Gln Ile Val Tyr Lys Asp
                 75                  80                  85 ggg ctt ctt tat gtc tat gca tcg aat gaa gag agc cga tgt cag tgg       461
Gly Leu Leu Tyr Val Tyr Ala Ser Asn Glu Glu Ser Arg Cys Gln Trp
             90                  95                 100 tta aaa gcg ctg caa aaa gag ata cgg ggc aac cct cac ctg ttg atc       509
Leu Lys Ala Leu Gln Lys Glu Ile Arg Gly Asn Pro His Leu Leu Ile
         105                 110                 115 aag tat cac agt ggc ttc ttt gtg gat gga aag ttc ctg tgt tgc cag       557
Lys Tyr His Ser Gly Phe Phe Val Asp Gly Lys Phe Leu Cys Cys Gln
     120                 125                 130 cag agc tgc aaa gca gcc cca gga tgc act ctc tgg gaa gca tat gct       605
Gln Ser Cys Lys Ala Ala Pro Gly Cys Thr Leu Trp Glu Ala Tyr Ala
135                 140                 145                 150 gat ctg cac atc gca atc agt gat gag aaa cac aga gct ccc act ttc       653
Asp Leu His Ile Ala Ile Ser Asp Glu Lys His Arg Ala Pro Thr Phe
                155                 160                 165 cca gag agg cta ctg aag att cca agg gca gtt ccc gtt ctc aaa atg       701
Pro Glu Arg Leu Leu Lys Ile Pro Arg Ala Val Pro Val Leu Lys Met
            170                 175                 180 gat gca tca tct tca ggt gcc att cta ccc caa tat gac agc tat tca       749
Asp Ala Ser Ser Ser Gly Ala Ile Leu Pro Gln Tyr Asp Ser Tyr Ser
        185                 190                 195 aag aaa agt tgt ggt tcc cag cca acc agc aac ata cgc tat att cca       797
Lys Lys Ser Cys Gly Ser Gln Pro Thr Ser Asn Ile Arg Tyr Ile Pro
    200                 205                 210
```

```
agg gaa gac tgc cct gac tgg tgg caa gta aga aaa ctg aaa agc gag      845
Arg Glu Asp Cys Pro Asp Trp Trp Gln Val Arg Lys Leu Lys Ser Glu
215                 220                 225                 230 gaa gac att gca tgc agt aac caa ctg gaa aga aat atc gcc tct cac      893
Glu Asp Ile Ala Cys Ser Asn Gln Leu Glu Arg Asn Ile Ala Ser His
                235                 240                 245 agc acc tca aag atg tca tgg gga ttc cct gag tca agt tca tca gaa      941
Ser Thr Ser Lys Met Ser Trp Gly Phe Pro Glu Ser Ser Ser Ser Glu
            250                 255                 260 gaa gag gaa aat ctg cat gct tat gac tgg ttt gct ggg aat atc tcc      989
Glu Glu Glu Asn Leu His Ala Tyr Asp Trp Phe Ala Gly Asn Ile Ser
        265                 270                 275 agg tca caa tct gag cag tta ctg aga caa aag gga aaa gaa gga gca     1037
Arg Ser Gln Ser Glu Gln Leu Leu Arg Gln Lys Gly Lys Glu Gly Ala
    280                 285                 290 ttt atg gtt cgg aat tcc agc cag atg gga atg tac act gtg tcc tta     1085
Phe Met Val Arg Asn Ser Ser Gln Met Gly Met Tyr Thr Val Ser Leu
295                 300                 305                 310 ttt agt aag gct gta aat gat aaa aaa gga act gtc aag cat tac cac     1133
Phe Ser Lys Ala Val Asn Asp Lys Lys Gly Thr Val Lys His Tyr His
                315                 320                 325 gtg cat act aat gct gaa aat aaa tta tac ctg gct gaa aac tac tgc     1181
Val His Thr Asn Ala Glu Asn Lys Leu Tyr Leu Ala Glu Asn Tyr Cys
            330                 335                 340 ttt gat tcc att cca aag ctc att cac tat cac caa cat aat tca gca     1229
Phe Asp Ser Ile Pro Lys Leu Ile His Tyr His Gln His Asn Ser Ala
        345                 350                 355 ggc atg atc aca cgg ctc cgc cac cca gtg tca acc aag gcc aac aag     1277
Gly Met Ile Thr Arg Leu Arg His Pro Val Ser Thr Lys Ala Asn Lys
    360                 365                 370 gtc ccg gtg tct gtg gct ctg gga agt gga att tgg gaa ctg aaa aga     1325
Val Pro Val Ser Val Ala Leu Gly Ser Gly Ile Trp Glu Leu Lys Arg
375                 380                 385                 390 gaa gag att acc ttg ctg aag gag ctg ggc aat ggc cag ttt gga gtg     1373
Glu Glu Ile Thr Leu Leu Lys Glu Leu Gly Asn Gly Gln Phe Gly Val
                395                 400                 405 gtc cag ctg ggc cag tgg aag ggg caa tat gat gtg gct gta aag atg     1421
Val Gln Leu Gly Gln Trp Lys Gly Gln Tyr Asp Val Ala Val Lys Met
            410                 415                 420 atc aag gag ggt gcc atg tca gaa gat gaa ttc ttt cag gag gcc cag     1469
Ile Lys Glu Gly Ala Met Ser Glu Asp Glu Phe Phe Gln Glu Ala Gln
        425                 430                 435 acc atg atg aaa ctc agc cat ccc aag ctg gtg aag ttc tac gga gta     1517
Thr Met Met Lys Leu Ser His Pro Lys Leu Val Lys Phe Tyr Gly Val
    440                 445                 450 tgc tca aag aaa tac ccc atc tat ata gta act gag tat ata aca aat     1565
Cys Ser Lys Lys Tyr Pro Ile Tyr Ile Val Thr Glu Tyr Ile Thr Asn
455                 460                 465                 470 ggt tgc ttg ctt aat tac ctg aag agt cat ggg aaa gga cta gaa agt     1613
Gly Cys Leu Leu Asn Tyr Leu Lys Ser His Gly Lys Gly Leu Glu Ser
                475                 480                 485 tgc cag ctc tta gaa atg tgt tat gat gtc tgt gaa ggc atg gcc ttc     1661
Cys Gln Leu Leu Glu Met Cys Tyr Asp Val Cys Glu Gly Met Ala Phe
            490                 495                 500 ttg gag agc cat cag ttc ata cat cga gat ttg gct gct cgg aac tgt     1709
Leu Glu Ser His Gln Phe Ile His Arg Asp Leu Ala Ala Arg Asn Cys
        505                 510                 515 ttg gtg gac agt gat ctc tct gtg aaa gtc tca gac ttt gga atg acg     1757
Leu Val Asp Ser Asp Leu Ser Val Lys Val Ser Asp Phe Gly Met Thr
    520                 525                 530
```

```
aga tat gtc ctt gat gat cag tat gtc agc tca gta gga acc aag ttt      1805
Arg Tyr Val Leu Asp Asp Gln Tyr Val Ser Ser Val Gly Thr Lys Phe
535                 540                 545                 550 cca gtc aag tgg tca gct cca gag gtg ttt cac tac ttc aaa tac agc      1853
Pro Val Lys Trp Ser Ala Pro Glu Val Phe His Tyr Phe Lys Tyr Ser
                555                 560                 565 agc aag tcg gat gta tgg gca ttt ggg atc ctg atg tgg gag gtg ttt      1901
Ser Lys Ser Asp Val Trp Ala Phe Gly Ile Leu Met Trp Glu Val Phe
            570                 575                 580 agt cta ggg aag cag ccc tat gac tta tat gat aac tcc gag gtg gtt      1949
Ser Leu Gly Lys Gln Pro Tyr Asp Leu Tyr Asp Asn Ser Glu Val Val
        585                 590                 595 gtg aag gtc tcc cag ggc cac aga ctc tac cgg ccc caa ctg gca tca      1997
Val Lys Val Ser Gln Gly His Arg Leu Tyr Arg Pro Gln Leu Ala Ser
    600                 605                 610 gac acc atc tac cag atc atg tac agc tgc tgg cat gag ctt cca gaa      2045
Asp Thr Ile Tyr Gln Ile Met Tyr Ser Cys Trp His Glu Leu Pro Glu
615                 620                 625                 630 aag cgc ccc aca ttt cag caa ctc ctg tct gcc ata gaa cca ctt cgg      2093
Lys Arg Pro Thr Phe Gln Gln Leu Leu Ser Ala Ile Glu Pro Leu Arg
                635                 640                 645 gaa caa gat aaa cca tga agagaaattt cagagtggtg atgagaacaa             2141
Glu Gln Asp Lys Pro
                650 atgtcaatat taactaacac tctcattgtt tgtaagggaa gtagaaagac tcaatgcaat    2201 gtagctcgtt cttaacaatg gtctatgtgc tgtttatctg ttatattatc taccaaaaaa    2261 agcaaggtag gaaacaagat agttctttga aatttaggtc aaattggtaa ttttgtttgt    2321 gctgctttta aggtatactt ccaagactat ggtagaagtt catttttaga ttgcaattta    2381 caaattgtac tgtgtataaa ggtagagcag aattgaaaag gtgatttgtt gggaactccc    2441 ttttttttaaa aaaaaattgg cactagtgtg ataattaaat atcttttcaa gaacggaaat   2501 gtatatgttt gcttctgtat gagaaatgtc tcaggcattt gaatatttgt tctctgtggc    2561 actgtttggg ggaggtttag gaggtatggg cttgatggag gaatgatgtc aatggagcgg    2621 gctgtgagag cctaaggctt caccctacta tctctgcttc ttgcttacaa ttcaagatgt    2681 gagctctcag aagctgaaaa ggtggcttgg tgcttaagaa caccggctgt tcttctagag    2741 gacccagact caattcctag cacccacaca gtggtttaca acttgtctat gaatccagtt    2801 ctaaggtatc tgatgacgtc ttttggcctt catggacacc atggacacgt gtggtacact    2861 gacatgtata caggcaaaga agaaaaataa aggatgagag ctctcagcat cctgctctat    2921 ctgcctgttt gcaagttgcc tttgccctgc cattttgaac tctaactttc tggaactata    2981 agcc                                                                  2985

<210> SEQ ID NO 12
<211> LENGTH: 651
<212> TYPE: PRT
<213> ORGANISM: Mus musculus

<400> SEQUENCE: 12

Met Glu Ser Lys Ser Ile Leu Glu Glu Leu Leu Leu Lys Lys Ser Gln
1               5                   10                  15

Gln Lys Lys Lys Met Ser Pro Asn Asn Tyr Lys Glu Arg Leu Phe Val
                20                  25                  30

Leu Thr Lys Thr Ser Leu Ser Tyr Tyr Glu Tyr Asp Lys Met Lys Arg
            35                  40                  45

Gly Ser Arg Lys Gly Ser Ile Glu Ile Lys Lys Ile Arg Cys Val Glu
```

```
            50                  55                  60
Lys Val Asn Leu Glu Glu Gln Thr Pro Val Glu Arg Gln Tyr Pro Phe
 65                  70                  75                  80

Gln Ile Val Tyr Lys Asp Gly Leu Leu Tyr Val Tyr Ala Ser Asn Glu
                 85                  90                  95

Glu Ser Arg Cys Gln Trp Leu Lys Ala Leu Gln Lys Glu Ile Arg Gly
            100                 105                 110

Asn Pro His Leu Leu Ile Lys Tyr His Ser Gly Phe Phe Val Asp Gly
            115                 120                 125

Lys Phe Leu Cys Cys Gln Gln Ser Cys Lys Ala Ala Pro Gly Cys Thr
            130                 135                 140

Leu Trp Glu Ala Tyr Ala Asp Leu His Ile Ala Ile Ser Asp Glu Lys
145                 150                 155                 160

His Arg Ala Pro Thr Phe Pro Glu Arg Leu Leu Lys Ile Pro Arg Ala
                165                 170                 175

Val Pro Val Leu Lys Met Asp Ala Ser Ser Gly Ala Ile Leu Pro
            180                 185                 190

Gln Tyr Asp Ser Tyr Ser Lys Lys Ser Cys Gly Ser Gln Pro Thr Ser
            195                 200                 205

Asn Ile Arg Tyr Ile Pro Arg Glu Asp Cys Pro Asp Trp Trp Gln Val
210                 215                 220

Arg Lys Leu Lys Ser Glu Asp Ile Ala Cys Ser Asn Gln Leu Glu
225                 230                 235                 240

Arg Asn Ile Ala Ser His Ser Thr Ser Lys Met Ser Trp Gly Phe Pro
                245                 250                 255

Glu Ser Ser Ser Ser Glu Glu Glu Asn Leu His Ala Tyr Asp Trp
            260                 265                 270

Phe Ala Gly Asn Ile Ser Arg Ser Gln Ser Glu Gln Leu Leu Arg Gln
            275                 280                 285

Lys Gly Lys Glu Gly Ala Phe Met Val Arg Asn Ser Ser Gln Met Gly
            290                 295                 300

Met Tyr Thr Val Ser Leu Phe Ser Lys Ala Val Asn Asp Lys Lys Gly
305                 310                 315                 320

Thr Val Lys His Tyr His Val His Thr Asn Ala Glu Asn Lys Leu Tyr
                325                 330                 335

Leu Ala Glu Asn Tyr Cys Phe Asp Ser Ile Pro Lys Leu Ile His Tyr
            340                 345                 350

His Gln His Asn Ser Ala Gly Met Ile Thr Arg Leu Arg His Pro Val
            355                 360                 365

Ser Thr Lys Ala Asn Lys Val Pro Val Ser Val Ala Leu Gly Ser Gly
370                 375                 380

Ile Trp Glu Leu Lys Arg Glu Glu Ile Thr Leu Leu Lys Glu Leu Gly
385                 390                 395                 400

Asn Gly Gln Phe Gly Val Val Gln Leu Gly Gln Trp Lys Gly Gln Tyr
                405                 410                 415

Asp Val Ala Val Lys Met Ile Lys Glu Gly Ala Met Ser Glu Asp Glu
            420                 425                 430

Phe Phe Gln Glu Ala Gln Thr Met Met Lys Leu Ser His Pro Lys Leu
            435                 440                 445

Val Lys Phe Tyr Gly Val Cys Ser Lys Tyr Pro Ile Tyr Ile Val
            450                 455                 460

Thr Glu Tyr Ile Thr Asn Gly Cys Leu Leu Asn Tyr Leu Lys Ser His
465                 470                 475                 480
```

```
Gly Lys Gly Leu Glu Ser Cys Gln Leu Leu Glu Met Cys Tyr Asp Val
                485                 490                 495

Cys Glu Gly Met Ala Phe Leu Glu Ser His Gln Phe Ile His Arg Asp
            500                 505                 510

Leu Ala Ala Arg Asn Cys Leu Val Asp Ser Asp Leu Ser Val Lys Val
        515                 520                 525

Ser Asp Phe Gly Met Thr Arg Tyr Val Leu Asp Gln Tyr Val Ser
    530                 535                 540

Ser Val Gly Thr Lys Phe Pro Val Lys Trp Ser Ala Pro Glu Val Phe
545                 550                 555                 560

His Tyr Phe Lys Tyr Ser Ser Lys Ser Asp Val Trp Ala Phe Gly Ile
                565                 570                 575

Leu Met Trp Glu Val Phe Ser Leu Gly Lys Gln Pro Tyr Asp Leu Tyr
            580                 585                 590

Asp Asn Ser Glu Val Val Val Lys Val Ser Gln Gly His Arg Leu Tyr
        595                 600                 605

Arg Pro Gln Leu Ala Ser Asp Thr Ile Tyr Gln Ile Met Tyr Ser Cys
    610                 615                 620

Trp His Glu Leu Pro Glu Lys Arg Pro Thr Phe Gln Gln Leu Leu Ser
625                 630                 635                 640

Ala Ile Glu Pro Leu Arg Glu Gln Asp Lys Pro
                645                 650

<210> SEQ ID NO 13
<211> LENGTH: 2984
<212> TYPE: DNA
<213> ORGANISM: Rattus norvegicus
<220> FEATURE:
<221> NAME/KEY: CDS
<222> LOCATION: (139)..(2106)

<400> SEQUENCE: 13
cagccatttc tgacccaaca gccagaaaaa atgtgacaca attcactgct gctggagaga      60
agacagcccg aagttgagtt cttgcaggag cagcttcgct tcaccgtggt gaaccccagg     120
gaggcagaag aagcctaa atg gac aac aat atg gat agt aaa tcc att ttg      171
                    Met Asp Asn Asn Met Asp Ser Lys Ser Ile Leu
                     1               5                   10 gaa gaa ctg ctt ctc aaa aag tca cag caa aag aag aaa atg tca cct      219
Glu Glu Leu Leu Leu Lys Lys Ser Gln Gln Lys Lys Lys Met Ser Pro
             15                  20                  25 att aat tac aag gag cgg ctt ttt gtt cta acc aaa aca agc ctt tcc      267
Ile Asn Tyr Lys Glu Arg Leu Phe Val Leu Thr Lys Thr Ser Leu Ser
         30                  35                  40 tac tat gaa tat gac aaa atg aaa cga gga agc aga aaa gga tcg ata      315
Tyr Tyr Glu Tyr Asp Lys Met Lys Arg Gly Ser Arg Lys Gly Ser Ile
     45                  50                  55 gaa gtt aag aaa atc cga tgt gtg gaa aaa gtc aac ctt gag gag cag      363
Glu Val Lys Lys Ile Arg Cys Val Glu Lys Val Asn Leu Glu Glu Gln
60                  65                  70                  75 aca ccc gtg gag aga cag tat cca ttt cag att gtg tac aaa gat ggg      411
Thr Pro Val Glu Arg Gln Tyr Pro Phe Gln Ile Val Tyr Lys Asp Gly
                 80                  85                  90 ctt ctt tat gtc tat gcg tcg aat gaa gag agc cga tgt cag tgg ttg      459
Leu Leu Tyr Val Tyr Ala Ser Asn Glu Glu Ser Arg Cys Gln Trp Leu
             95                 100                 105 aaa gcg ctg caa aaa gag ata cgg ggc aac ccc cac ctg ttg atc aag      507
Lys Ala Leu Gln Lys Glu Ile Arg Gly Asn Pro His Leu Leu Ile Lys
        110                 115                 120
```

```
tat cac agt ggc ttc ttt gtg gat ggg aag ttc ctg tgt tgc cag cag        555
Tyr His Ser Gly Phe Phe Val Asp Gly Lys Phe Leu Cys Cys Gln Gln
    125                 130                 135 agc tgc aaa gca gcc cca gga tgc act ctc tgg gaa gca tat gct gat        603
Ser Cys Lys Ala Ala Pro Gly Cys Thr Leu Trp Glu Ala Tyr Ala Asp
140                 145                 150                 155 ctg cac att gca atc agt gat gag aaa cac aga gcc ccc act ttt cca        651
Leu His Ile Ala Ile Ser Asp Glu Lys His Arg Ala Pro Thr Phe Pro
                160                 165                 170 gag agg ata ctg aag atc cca agg gca gtt ccc att ctc aaa atg gat        699
Glu Arg Ile Leu Lys Ile Pro Arg Ala Val Pro Ile Leu Lys Met Asp
            175                 180                 185 gca tca tcc tca agt gcc att cca ccc caa tat gac agc cac tta aag        747
Ala Ser Ser Ser Ser Ala Ile Pro Pro Gln Tyr Asp Ser His Leu Lys
190                 195                 200 aaa agt tat gac tcc cag cca acc gtc aac ata cgc tat att cca agg        795
Lys Ser Tyr Asp Ser Gln Pro Thr Val Asn Ile Arg Tyr Ile Pro Arg
    205                 210                 215 gaa gac tgc cct gac tgg tgg caa ata agg aaa ccg aaa agt gag gaa        843
Glu Asp Cys Pro Asp Trp Trp Gln Ile Arg Lys Pro Lys Ser Glu Glu
220                 225                 230                 235 gac att gcc cgc agt aac caa ttg gaa aga aat att gta tct cac agc        891
Asp Ile Ala Arg Ser Asn Gln Leu Glu Arg Asn Ile Val Ser His Ser
                240                 245                 250 ccc tca aag atg tca tgg gga ttc cct gag tca agt tca tct gaa gaa        939
Pro Ser Lys Met Ser Trp Gly Phe Pro Glu Ser Ser Ser Ser Glu Glu
            255                 260                 265 gag gaa aat ctg gat gct tat gac tgg ttt gct ggg aat atc tcc agg        987
Glu Glu Asn Leu Asp Ala Tyr Asp Trp Phe Ala Gly Asn Ile Ser Arg
270                 275                 280 tca caa tct gag cag tta ctg aga caa aag gga aaa gaa ggc gca ttc       1035
Ser Gln Ser Glu Gln Leu Leu Arg Gln Lys Gly Lys Glu Gly Ala Phe
    285                 290                 295 atg gtg agg aat tcc agc cag atg ggg atg tac acc gtg tcc tta ttc       1083
Met Val Arg Asn Ser Ser Gln Met Gly Met Tyr Thr Val Ser Leu Phe
300                 305                 310                 315 agc aag gct gta aat gac aaa aaa gga act gtc aaa cat tat cac gtg       1131
Ser Lys Ala Val Asn Asp Lys Lys Gly Thr Val Lys His Tyr His Val
                320                 325                 330 cat acc aat gct gaa aat aaa tta tac ttg gct gaa aac tac tgc ttt       1179
His Thr Asn Ala Glu Asn Lys Leu Tyr Leu Ala Glu Asn Tyr Cys Phe
            335                 340                 345 gat tct att cca aag ctc att cac tat cac caa cat aat tca gca ggc       1227
Asp Ser Ile Pro Lys Leu Ile His Tyr His Gln His Asn Ser Ala Gly
350                 355                 360 atg atc aca agg ctc cgc cac cca gtg tca acc aag gcc aac aag gtc       1275
Met Ile Thr Arg Leu Arg His Pro Val Ser Thr Lys Ala Asn Lys Val
    365                 370                 375 ccg gtg tct gtg gct ctg gga agt gga att tgg gaa ctg aaa aga gaa       1323
Pro Val Ser Val Ala Leu Gly Ser Gly Ile Trp Glu Leu Lys Arg Glu
380                 385                 390                 395 gag atc gcc ttg ttg aag gag ctg ggc agt ggc cag ttt gga gtg gtc       1371
Glu Ile Ala Leu Leu Lys Glu Leu Gly Ser Gly Gln Phe Gly Val Val
                400                 405                 410 cag ctg ggc aag tgg aag ggg cag tat tct gtg gct gta aag atg atc       1419
Gln Leu Gly Lys Trp Lys Gly Gln Tyr Ser Val Ala Val Lys Met Ile
            415                 420                 425 aag gag ggc gcc atg tca gaa gat gaa ttc ttt cag gag gcc cag acc       1467
Lys Glu Gly Ala Met Ser Glu Asp Glu Phe Phe Gln Glu Ala Gln Thr
430                 435                 440
```

-continued

| | |
|---|---|
| atg atg aaa ctc agc cat ccc aag ctg gtg aaa ttc tat ggc gta tgc<br>Met Met Lys Leu Ser His Pro Lys Leu Val Lys Phe Tyr Gly Val Cys<br>445         450                 455 | 1515 |
| tca aag aaa tac ccc atc tat ata gta aca gag tat ata acg aat ggt<br>Ser Lys Lys Tyr Pro Ile Tyr Ile Val Thr Glu Tyr Ile Thr Asn Gly<br>460             465                 470                 475 | 1563 |
| tgc ttg ctt aat tac ctg aag aat cat ggg aaa gga cta gaa agc tcc<br>Cys Leu Leu Asn Tyr Leu Lys Asn His Gly Lys Gly Leu Glu Ser Ser<br>                480                 485                 490 | 1611 |
| cag ctc tta gaa atg tgc tat gat gtc tgt gaa ggc atg gcc ttc ttg<br>Gln Leu Leu Glu Met Cys Tyr Asp Val Cys Glu Gly Met Ala Phe Leu<br>            495                 500                 505 | 1659 |
| gag agc cat cag ttc ata cat cgg gat ttg gct gct cgg aac tgt ttg<br>Glu Ser His Gln Phe Ile His Arg Asp Leu Ala Ala Arg Asn Cys Leu<br>        510                 515                 520 | 1707 |
| gtg gac agt gat ctc tcc gtg aaa gtc tca gac ttt gga atg acg aga<br>Val Asp Ser Asp Leu Ser Val Lys Val Ser Asp Phe Gly Met Thr Arg<br>525                 530                 535 | 1755 |
| tat gtc ctt gat gac cag tat gtc agt tca gta gga acc aag ttt cca<br>Tyr Val Leu Asp Asp Gln Tyr Val Ser Ser Val Gly Thr Lys Phe Pro<br>540                 545                 550                 555 | 1803 |
| gtc aag tgg tcg gcc cca gag gtg ttt cac tat ttc aaa tac agc agc<br>Val Lys Trp Ser Ala Pro Glu Val Phe His Tyr Phe Lys Tyr Ser Ser<br>                560                 565                 570 | 1851 |
| aag tcg gac gta tgg gcg ttt ggg atc ctg atg tgg gag gtg ttt agc<br>Lys Ser Asp Val Trp Ala Phe Gly Ile Leu Met Trp Glu Val Phe Ser<br>            575                 580                 585 | 1899 |
| cta ggc aag cag ccc tat gac tta tat gat aac tct gaa gtg gtt gtg<br>Leu Gly Lys Gln Pro Tyr Asp Leu Tyr Asp Asn Ser Glu Val Val Val<br>        590                 595                 600 | 1947 |
| aag gtc tcc cag ggc cac aga ctc tac cgg ccc caa cta gca tca gac<br>Lys Val Ser Gln Gly His Arg Leu Tyr Arg Pro Gln Leu Ala Ser Asp<br>    605                 610                 615 | 1995 |
| act atc tac cag ata atg tac agc tgc tgg cat gag ctt cca gaa aag<br>Thr Ile Tyr Gln Ile Met Tyr Ser Cys Trp His Glu Leu Pro Glu Lys<br>620                 625                 630                 635 | 2043 |
| cgc ccc aca ttt cag caa ctc cta tct gcc ata gaa cca ctc cgg gaa<br>Arg Pro Thr Phe Gln Gln Leu Leu Ser Ala Ile Glu Pro Leu Arg Glu<br>                640                 645                 650 | 2091 |
| caa gat aag cca tga agagaaattt cagaatggtg atgaaatga atataaacat<br>Gln Asp Lys Pro<br>            655 | 2146 |
| tgaccaacac tctcattgtt tgtaagggga gtagaaagac gccatgtatt atagctagtt | 2206 |
| cttaataatg gtctgtgtat tgtttaactg ttatattacc taccaagaaa agcaaggtag | 2266 |
| gaaacaaggt atttctttga aatttagctt aaattggtca tttttgtttg tgctgctttt | 2326 |
| aatgtactac ttcccagact atggtagaag ttcatttta gattacactt tccaagggt | 2386 |
| gtgtactgtg tataagggga gagcgggatt gaaaaggtaa tttgttggga gttcagtttt | 2446 |
| tttctattgg cacttgtgtg gtaattaaat atcttttcaa gaacagaaat gtgtatgttt | 2506 |
| gcttctgtat gagaaatgtc tcaggcattt gaatatttgt tctccagttt gtggcactgt | 2566 |
| ttgtagaggt ttaggaagaa tggcctcgat ggaggaatta tgtcaatagg gcaggctttg | 2626 |
| agagcttaag gcttcaccct acctgtagtt tacttcttgc atgcagttca agatgtgagc | 2686 |
| tctcagaagc tgaagaagtg gcttagtggt taagaacact ggctgttcct ccagaggaca | 2746 |
| caggttcaat tcccagaact gcacagtggc ttacaacttg tctatgaatc cagttctaaa | 2806 |
| gaatattatg gcttcttcta gccttcacgc gtacctagta cacatgtggt acaccaacat | 2866 |

```
atatacaagc aaagaagaaa actaaagggt gggagctctc agcatcctgc tctgtctgcc  2926
atgtctgcaa gtagcctttg acctgccatt ttgaactctc tctctggaac tataagca    2984
```

<210> SEQ ID NO 14
<211> LENGTH: 655
<212> TYPE: PRT
<213> ORGANISM: Rattus norvegicus

<400> SEQUENCE: 14

```
Met Asp Asn Asn Met Asp Ser Lys Ser Ile Leu Glu Glu Leu Leu Leu
1               5                   10                  15

Lys Lys Ser Gln Gln Lys Lys Met Ser Pro Ile Asn Tyr Lys Glu
            20                  25                  30

Arg Leu Phe Val Leu Thr Lys Thr Ser Leu Ser Tyr Tyr Glu Tyr Asp
        35                  40                  45

Lys Met Lys Arg Gly Ser Arg Lys Gly Ser Ile Glu Val Lys Lys Ile
    50                  55                  60

Arg Cys Val Glu Lys Val Asn Leu Glu Glu Gln Thr Pro Val Glu Arg
65                  70                  75                  80

Gln Tyr Pro Phe Gln Ile Val Tyr Lys Asp Gly Leu Leu Tyr Val Tyr
                85                  90                  95

Ala Ser Asn Glu Glu Ser Arg Cys Gln Trp Leu Lys Ala Leu Gln Lys
            100                 105                 110

Glu Ile Arg Gly Asn Pro His Leu Leu Ile Lys Tyr His Ser Gly Phe
        115                 120                 125

Phe Val Asp Gly Lys Phe Leu Cys Cys Gln Gln Ser Cys Lys Ala Ala
    130                 135                 140

Pro Gly Cys Thr Leu Trp Glu Ala Tyr Ala Asp Leu His Ile Ala Ile
145                 150                 155                 160

Ser Asp Glu Lys His Arg Ala Pro Thr Phe Pro Glu Arg Ile Leu Lys
                165                 170                 175

Ile Pro Arg Ala Val Pro Ile Leu Lys Met Asp Ala Ser Ser Ser Ser
            180                 185                 190

Ala Ile Pro Pro Gln Tyr Asp Ser His Leu Lys Lys Ser Tyr Asp Ser
        195                 200                 205

Gln Pro Thr Val Asn Ile Arg Tyr Ile Pro Arg Glu Asp Cys Pro Asp
    210                 215                 220

Trp Trp Gln Ile Arg Lys Pro Lys Ser Glu Glu Asp Ile Ala Arg Ser
225                 230                 235                 240

Asn Gln Leu Glu Arg Asn Ile Val Ser His Ser Pro Ser Lys Met Ser
                245                 250                 255

Trp Gly Phe Pro Glu Ser Ser Ser Glu Glu Glu Asn Leu Asp
            260                 265                 270

Ala Tyr Asp Trp Phe Ala Gly Asn Ile Ser Arg Ser Gln Ser Glu Gln
        275                 280                 285

Leu Leu Arg Gln Lys Gly Lys Glu Gly Ala Phe Met Val Arg Asn Ser
    290                 295                 300

Ser Gln Met Gly Met Tyr Thr Val Ser Leu Phe Ser Lys Ala Val Asn
305                 310                 315                 320

Asp Lys Lys Gly Thr Val Lys His Tyr His Val His Thr Asn Ala Glu
                325                 330                 335

Asn Lys Leu Tyr Leu Ala Glu Asn Tyr Cys Phe Asp Ser Ile Pro Lys
            340                 345                 350

Leu Ile His Tyr His Gln His Asn Ser Ala Gly Met Ile Thr Arg Leu
        355                 360                 365
```

```
Arg His Pro Val Ser Thr Lys Ala Asn Lys Val Pro Val Ser Val Ala
    370                 375                 380

Leu Gly Ser Gly Ile Trp Glu Leu Lys Arg Glu Ile Ala Leu Leu
385                 390                 395                 400

Lys Glu Leu Gly Ser Gly Gln Phe Gly Val Val Gln Leu Gly Lys Trp
                405                 410                 415

Lys Gly Gln Tyr Ser Val Ala Val Lys Met Ile Lys Glu Gly Ala Met
                420                 425                 430

Ser Glu Asp Glu Phe Phe Gln Glu Ala Gln Thr Met Met Lys Leu Ser
                435                 440                 445

His Pro Lys Leu Val Lys Phe Tyr Gly Val Cys Ser Lys Tyr Pro
    450                 455                 460

Ile Tyr Ile Val Thr Glu Tyr Ile Thr Asn Gly Cys Leu Leu Asn Tyr
465                 470                 475                 480

Leu Lys Asn His Gly Lys Gly Leu Glu Ser Ser Gln Leu Leu Glu Met
                485                 490                 495

Cys Tyr Asp Val Cys Glu Gly Met Ala Phe Leu Glu Ser His Gln Phe
                500                 505                 510

Ile His Arg Asp Leu Ala Ala Arg Asn Cys Leu Val Asp Ser Asp Leu
    515                 520                 525

Ser Val Lys Val Ser Asp Phe Gly Met Thr Arg Tyr Val Leu Asp Asp
    530                 535                 540

Gln Tyr Val Ser Ser Val Gly Thr Lys Phe Pro Val Lys Trp Ser Ala
545                 550                 555                 560

Pro Glu Val Phe His Tyr Phe Lys Tyr Ser Ser Lys Ser Asp Val Trp
                565                 570                 575

Ala Phe Gly Ile Leu Met Trp Glu Val Phe Ser Leu Gly Lys Gln Pro
                580                 585                 590

Tyr Asp Leu Tyr Asp Asn Ser Glu Val Val Lys Val Ser Gln Gly
    595                 600                 605

His Arg Leu Tyr Arg Pro Gln Leu Ala Ser Asp Thr Ile Tyr Gln Ile
    610                 615                 620

Met Tyr Ser Cys Trp His Glu Leu Pro Glu Lys Arg Pro Thr Phe Gln
625                 630                 635                 640

Gln Leu Leu Ser Ala Ile Glu Pro Leu Arg Glu Gln Asp Lys Pro
                645                 650                 655

<210> SEQ ID NO 15
<211> LENGTH: 1965
<212> TYPE: DNA
<213> ORGANISM: Bos taurus
<220> FEATURE:
<221> NAME/KEY: CDS
<222> LOCATION: (1)..(1965)

<400> SEQUENCE: 15 atg gac aca aaa tcc att cta gaa gaa ctt ctt ctc aaa agg tca cag    48
Met Asp Thr Lys Ser Ile Leu Glu Glu Leu Leu Leu Lys Arg Ser Gln
1               5                   10                  15 caa aag aag aaa atg tca ccc aat aat tac aag gag cgg ctt ttt gtt    96
Gln Lys Lys Lys Met Ser Pro Asn Asn Tyr Lys Glu Arg Leu Phe Val
            20                  25                  30 tta acc aaa aca aac ctc tcc tac tat gaa tat gac aaa atg aaa aga   144
Leu Thr Lys Thr Asn Leu Ser Tyr Tyr Glu Tyr Asp Lys Met Lys Arg
        35                  40                  45 ggc agc aga aaa gga tcg att gag att aag aaa atc aga tgt gtg gag   192
Gly Ser Arg Lys Gly Ser Ile Glu Ile Lys Lys Ile Arg Cys Val Glu
```

```
            50                  55                  60
aaa gtt aat ctt gag gag cag acc cct gtg gag aga cag tac cca ttt       240
Lys Val Asn Leu Glu Glu Gln Thr Pro Val Glu Arg Gln Tyr Pro Phe
 65                  70                  75                  80 cag att gtc tat aaa gat ggg ctt ctc tat gtg tat gca tca aat gaa       288
Gln Ile Val Tyr Lys Asp Gly Leu Leu Tyr Val Tyr Ala Ser Asn Glu
                     85                  90                  95 gag agc cga agt cag tgg ctg aaa gca tta caa aaa gag ata agg ggc       336
Glu Ser Arg Ser Gln Trp Leu Lys Ala Leu Gln Lys Glu Ile Arg Gly
                100                 105                 110 aac ccc cac ctg ctg atc aag tac cac agt ggg ttc ttc gtg gac ggg       384
Asn Pro His Leu Leu Ile Lys Tyr His Ser Gly Phe Phe Val Asp Gly
            115                 120                 125 aag ttc ctg tgc tgc cag cag agt tgc aaa gcg gcc cca gga tgt act       432
Lys Phe Leu Cys Cys Gln Gln Ser Cys Lys Ala Ala Pro Gly Cys Thr
        130                 135                 140 ctc tgg gaa gca tat gct gat ctg cac act gcc ccc aaa gaa gaa aaa       480
Leu Trp Glu Ala Tyr Ala Asp Leu His Thr Ala Pro Lys Glu Glu Lys
145                 150                 155                 160 cac ggg gtt ccc atc ttc cca gac aga gtg ctg aag att cct aga gca       528
His Gly Val Pro Ile Phe Pro Asp Arg Val Leu Lys Ile Pro Arg Ala
                165                 170                 175 gtt cct att ctc aaa gta gat gaa cca tct tca agt acc act cta gcc       576
Val Pro Ile Leu Lys Val Asp Glu Pro Ser Ser Ser Thr Thr Leu Ala
                180                 185                 190 cag tat gac agt gat tcc aag aaa aac tat ggc tcc cag tca aac atc       624
Gln Tyr Asp Ser Asp Ser Lys Lys Asn Tyr Gly Ser Gln Ser Asn Ile
            195                 200                 205 aac atg aag tat att tca aaa gaa gac ttc cct gac tgg tgg caa gta       672
Asn Met Lys Tyr Ile Ser Lys Glu Asp Phe Pro Asp Trp Trp Gln Val
        210                 215                 220 aga aaa ctg aga agc gcg tca agt agt gaa gat ttg gca tgc agt aat       720
Arg Lys Leu Arg Ser Ala Ser Ser Ser Glu Asp Leu Ala Cys Ser Asn
225                 230                 235                 240 caa agg gaa aga aat gtt gta aat cac aac acc tca aag atg tca tgg       768
Gln Arg Glu Arg Asn Val Val Asn His Asn Thr Ser Lys Met Ser Trp
                245                 250                 255 ggc tcc cct gaa tca agt tca tct gaa gaa gag gaa aac ctt gat gat       816
Gly Ser Pro Glu Ser Ser Ser Ser Glu Glu Glu Glu Asn Leu Asp Asp
                260                 265                 270 tat gac tgg ttt gca ggt aac atc tcc agg tca caa tct gag cag tta       864
Tyr Asp Trp Phe Ala Gly Asn Ile Ser Arg Ser Gln Ser Glu Gln Leu
            275                 280                 285 ctg aga caa aag ggg aaa gaa gga gca ttt atg gtt aga aac tcc agc       912
Leu Arg Gln Lys Gly Lys Glu Gly Ala Phe Met Val Arg Asn Ser Ser
        290                 295                 300 cag gcg gga atg tac aca gtg tcc ttg ttt agt aag gct atg aat gat       960
Gln Ala Gly Met Tyr Thr Val Ser Leu Phe Ser Lys Ala Met Asn Asp
305                 310                 315                 320 aaa aaa gga act gtc aaa cat tac cat gtg cat aca aat gct gag aac      1008
Lys Lys Gly Thr Val Lys His Tyr His Val His Thr Asn Ala Glu Asn
                325                 330                 335 aaa ttg tac ctg gca gaa aac tac tgt ttt gat tcc att cca aag ctt      1056
Lys Leu Tyr Leu Ala Glu Asn Tyr Cys Phe Asp Ser Ile Pro Lys Leu
                340                 345                 350 att cac tat cat caa cac aat tca gca ggc atg atc aca cga ctc cgc      1104
Ile His Tyr His Gln His Asn Ser Ala Gly Met Ile Thr Arg Leu Arg
            355                 360                 365 cac cct gtg tcg acc aag gcc aat aag gtt ccc atc tct gtg tcc ttg      1152
His Pro Val Ser Thr Lys Ala Asn Lys Val Pro Ile Ser Val Ser Leu
```

```
                     370                 375                 380
gga agc gga atc tgg gaa ctg aaa cgt gaa gag att acc ctg ttg aag      1200
Gly Ser Gly Ile Trp Glu Leu Lys Arg Glu Glu Ile Thr Leu Leu Lys
385                 390                 395                 400 gag ctg gga agt ggc cag ttt gga gtg gtc cat ctg ggc aag tgg aag      1248
Glu Leu Gly Ser Gly Gln Phe Gly Val Val His Leu Gly Lys Trp Lys
                405                 410                 415 ggg aag tat gat gtt gct gtt aag atg atc aag gag ggc tcc atg tca      1296
Gly Lys Tyr Asp Val Ala Val Lys Met Ile Lys Glu Gly Ser Met Ser
            420                 425                 430 gaa gat gaa ttc ttc cag gag gcc cag acc atg acg aaa ctc aac cat      1344
Glu Asp Glu Phe Phe Gln Glu Ala Gln Thr Met Thr Lys Leu Asn His
        435                 440                 445 ccc aag ctg gtg aaa ttc tac gga gtg tgt tca aag aga tac cct ata      1392
Pro Lys Leu Val Lys Phe Tyr Gly Val Cys Ser Lys Arg Tyr Pro Ile
    450                 455                 460 tac ata gtg act gaa tat ata acc aat ggc tgc tta ctg agt tac ctg      1440
Tyr Ile Val Thr Glu Tyr Ile Thr Asn Gly Cys Leu Leu Ser Tyr Leu
465                 470                 475                 480 aag agt cat gga aaa aga ctt gaa ccc tcc cag ctc tta gaa atg tgc      1488
Lys Ser His Gly Lys Arg Leu Glu Pro Ser Gln Leu Leu Glu Met Cys
                485                 490                 495 tat gat gtt tgt gaa ggc atg gcc ttc ttg gag agc cac caa ttc ata      1536
Tyr Asp Val Cys Glu Gly Met Ala Phe Leu Glu Ser His Gln Phe Ile
            500                 505                 510 cat cgg gac ttg gct gct cgg aac tgc ttg gta gac agt gat ctc tct      1584
His Arg Asp Leu Ala Ala Arg Asn Cys Leu Val Asp Ser Asp Leu Ser
        515                 520                 525 gtg aag gtt tct gac ttt ggg atg acg agg tat gtt ctt gat gac caa      1632
Val Lys Val Ser Asp Phe Gly Met Thr Arg Tyr Val Leu Asp Asp Gln
    530                 535                 540 tat gtc agt tcc gta gga aca aag ttt cca gtc aag tgg tca gcc cca      1680
Tyr Val Ser Ser Val Gly Thr Lys Phe Pro Val Lys Trp Ser Ala Pro
545                 550                 555                 560 gag gtg ttt cac tac ttc aaa tac agc agc aag tca gac gta tgg gcg      1728
Glu Val Phe His Tyr Phe Lys Tyr Ser Ser Lys Ser Asp Val Trp Ala
                565                 570                 575 ttc ggg atc ctg atg tgg gaa gtg ttc agc ctg ggg aag cag ccc tac      1776
Phe Gly Ile Leu Met Trp Glu Val Phe Ser Leu Gly Lys Gln Pro Tyr
            580                 585                 590 gac ttg tac gac aac tcg cag gtg gtc gtg aag gtc tcc cag ggc cac      1824
Asp Leu Tyr Asp Asn Ser Gln Val Val Val Lys Val Ser Gln Gly His
        595                 600                 605 cgg ctc tac cgg ccc cag ctg gcg tcg gac acc gtc tac cac atc atg      1872
Arg Leu Tyr Arg Pro Gln Leu Ala Ser Asp Thr Val Tyr His Ile Met
    610                 615                 620 tac agc tgc tgg cac gag ctt cca gaa aag cgt ccc aca ttt cag cag      1920
Tyr Ser Cys Trp His Glu Leu Pro Glu Lys Arg Pro Thr Phe Gln Gln
625                 630                 635                 640 ctc cta tca tcc att gaa cca ctt cgg gaa aaa gac aag cct tga          1965
Leu Leu Ser Ser Ile Glu Pro Leu Arg Glu Lys Asp Lys Pro
                645                 650

<210> SEQ ID NO 16
<211> LENGTH: 654
<212> TYPE: PRT
<213> ORGANISM: Bos taurus

<400> SEQUENCE: 16

Met Asp Thr Lys Ser Ile Leu Glu Glu Leu Leu Leu Lys Arg Ser Gln
1               5                   10                  15
```

```
Gln Lys Lys Lys Met Ser Pro Asn Asn Tyr Lys Glu Arg Leu Phe Val
             20                  25                  30
Leu Thr Lys Thr Asn Leu Ser Tyr Tyr Glu Tyr Asp Lys Met Lys Arg
         35                  40                  45
Gly Ser Arg Lys Gly Ser Ile Glu Ile Lys Lys Ile Arg Cys Val Glu
     50                  55                  60
Lys Val Asn Leu Glu Glu Gln Thr Pro Val Glu Arg Gln Tyr Pro Phe
65                  70                  75                  80
Gln Ile Val Tyr Lys Asp Gly Leu Leu Tyr Val Tyr Ala Ser Asn Glu
                 85                  90                  95
Glu Ser Arg Ser Gln Trp Leu Lys Ala Leu Gln Lys Glu Ile Arg Gly
            100                 105                 110
Asn Pro His Leu Leu Ile Lys Tyr His Ser Gly Phe Phe Val Asp Gly
            115                 120                 125
Lys Phe Leu Cys Cys Gln Gln Ser Cys Lys Ala Ala Pro Gly Cys Thr
            130                 135                 140
Leu Trp Glu Ala Tyr Ala Asp Leu His Thr Ala Pro Lys Glu Glu Lys
145                 150                 155                 160
His Gly Val Pro Ile Phe Pro Asp Arg Val Leu Lys Ile Pro Arg Ala
                165                 170                 175
Val Pro Ile Leu Lys Val Asp Glu Pro Ser Ser Ser Thr Thr Leu Ala
            180                 185                 190
Gln Tyr Asp Ser Asp Ser Lys Lys Asn Tyr Gly Ser Gln Ser Asn Ile
            195                 200                 205
Asn Met Lys Tyr Ile Ser Lys Glu Asp Phe Pro Asp Trp Trp Gln Val
            210                 215                 220
Arg Lys Leu Arg Ser Ala Ser Ser Ser Glu Asp Leu Ala Cys Ser Asn
225                 230                 235                 240
Gln Arg Glu Arg Asn Val Val Asn His Asn Thr Ser Lys Met Ser Trp
                245                 250                 255
Gly Ser Pro Glu Ser Ser Ser Glu Glu Glu Asn Leu Asp Asp
            260                 265                 270
Tyr Asp Trp Phe Ala Gly Asn Ile Ser Arg Ser Gln Ser Glu Gln Leu
            275                 280                 285
Leu Arg Gln Lys Gly Lys Glu Gly Ala Phe Met Val Arg Asn Ser Ser
290                 295                 300
Gln Ala Gly Met Tyr Thr Val Ser Leu Phe Ser Lys Ala Met Asn Asp
305                 310                 315                 320
Lys Lys Gly Thr Val Lys His Tyr His Val His Thr Asn Ala Glu Asn
                325                 330                 335
Lys Leu Tyr Leu Ala Glu Asn Tyr Cys Phe Asp Ser Ile Pro Lys Leu
            340                 345                 350
Ile His Tyr His Gln His Asn Ser Ala Gly Met Ile Thr Arg Leu Arg
            355                 360                 365
His Pro Val Ser Thr Lys Ala Asn Lys Val Pro Ile Ser Val Ser Leu
            370                 375                 380
Gly Ser Gly Ile Trp Glu Leu Lys Arg Glu Glu Ile Thr Leu Leu Lys
385                 390                 395                 400
Glu Leu Gly Ser Gly Gln Phe Gly Val Val His Leu Gly Lys Trp Lys
                405                 410                 415
Gly Lys Tyr Asp Val Ala Val Lys Met Ile Lys Glu Gly Ser Met Ser
            420                 425                 430
Glu Asp Glu Phe Phe Gln Glu Ala Gln Thr Met Thr Lys Leu Asn His
```

```
              435                 440                 445
Pro Lys Leu Val Lys Phe Tyr Gly Val Cys Ser Lys Arg Tyr Pro Ile
    450                 455                 460

Tyr Ile Val Thr Glu Tyr Ile Thr Asn Gly Cys Leu Leu Ser Tyr Leu
465                 470                 475                 480

Lys Ser His Gly Lys Arg Leu Glu Pro Ser Gln Leu Leu Glu Met Cys
                485                 490                 495

Tyr Asp Val Cys Glu Gly Met Ala Phe Leu Glu Ser His Gln Phe Ile
            500                 505                 510

His Arg Asp Leu Ala Ala Arg Asn Cys Leu Val Asp Ser Asp Leu Ser
        515                 520                 525

Val Lys Val Ser Asp Phe Gly Met Thr Arg Tyr Val Leu Asp Asp Gln
    530                 535                 540

Tyr Val Ser Ser Val Gly Thr Lys Phe Pro Val Lys Trp Ser Ala Pro
545                 550                 555                 560

Glu Val Phe His Tyr Phe Lys Tyr Ser Ser Lys Ser Asp Val Trp Ala
                565                 570                 575

Phe Gly Ile Leu Met Trp Glu Val Phe Ser Leu Gly Lys Gln Pro Tyr
            580                 585                 590

Asp Leu Tyr Asp Asn Ser Gln Val Val Lys Val Ser Gln Gly His
        595                 600                 605

Arg Leu Tyr Arg Pro Gln Leu Ala Ser Asp Thr Val Tyr His Ile Met
    610                 615                 620

Tyr Ser Cys Trp His Glu Leu Pro Glu Lys Arg Pro Thr Phe Gln Gln
625                 630                 635                 640

Leu Leu Ser Ser Ile Glu Pro Leu Arg Glu Lys Asp Lys Pro
                645                 650

<210> SEQ ID NO 17
<211> LENGTH: 3005
<212> TYPE: DNA
<213> ORGANISM: Canis familiaris
<220> FEATURE:
<221> NAME/KEY: CDS
<222> LOCATION: (1)..(2628)

<400> SEQUENCE: 17 atg tta gag acc gca ctc cgg gac cag aaa agg ggg gac caa tgg aga       48
Met Leu Glu Thr Ala Leu Arg Asp Gln Lys Arg Gly Asp Gln Trp Arg
1               5                   10                  15 gtt cag act ggg cga gtg gca gga ttc gag tcg ctt gtg aaa gaa tcg       96
Val Gln Thr Gly Arg Val Ala Gly Phe Glu Ser Leu Val Lys Glu Ser
                20                  25                  30 ctc tgg cta gcc agt gga gaa cag acc tcc agg agc aag agc cga agc      144
Leu Trp Leu Ala Ser Gly Glu Gln Thr Ser Arg Ser Lys Ser Arg Ser
            35                  40                  45 agg gat agc agc cag gag gca ggg gcg aca ttg cag ggt gta agc tcc      192
Arg Asp Ser Ser Gln Glu Ala Gly Ala Thr Leu Gln Gly Val Ser Ser
        50                  55                  60 cct ctt gcg aat tct tcc gaa ggg ctc ttt gcc cct tcc cga acc acg      240
Pro Leu Ala Asn Ser Ser Glu Gly Leu Phe Ala Pro Ser Arg Thr Thr
65                  70                  75                  80 cgg gtt tca agc aga aac gtc aac agc gcc tcg gcc aag ctg ttt tcc      288
Arg Val Ser Ser Arg Asn Val Asn Ser Ala Ser Ala Lys Leu Phe Ser
                85                  90                  95 acg cgc tct act cag cta gac ctt ccc ttg ggg ttc tct gcc tgc agc      336
Thr Arg Ser Thr Gln Leu Asp Leu Pro Leu Gly Phe Ser Ala Cys Ser
            100                 105                 110
```

```
                                                            -continued cga cag aag gcc ctg gaa ggt gcg ggc tgc ccc tgc ccg gcc tac tac    384
Arg Gln Lys Ala Leu Glu Gly Ala Gly Cys Pro Cys Pro Ala Tyr Tyr
            115                 120                 125 ggt ctg cag ccc ctc acg gag ccc ttg gca cat gga agg agg gca gcc    432
Gly Leu Gln Pro Leu Thr Glu Pro Leu Ala His Gly Arg Arg Ala Ala
        130                 135                 140 gcg cct gtg tgc gtg caa gag cag act gac ccc tcg gcg gtg gac ccc    480
Ala Pro Val Cys Val Gln Glu Gln Thr Asp Pro Ser Ala Val Asp Pro
145                 150                 155                 160 cgg cgg ccg atc gag agc cac aat ggt gcg ttg cag cgg cag gtg gcc    528
Arg Arg Pro Ile Glu Ser His Asn Gly Ala Leu Gln Arg Gln Val Ala
                165                 170                 175 aca cga ggt cat agc cga cag gct gac agg ttc aga gtg atg cat atg    576
Thr Arg Gly His Ser Arg Gln Ala Asp Arg Phe Arg Val Met His Met
            180                 185                 190 acg ttg ctg ggg ctc ctc cgg gga ctt tgg atg aga ccg ttt tca tgt    624
Thr Leu Leu Gly Leu Leu Arg Gly Leu Trp Met Arg Pro Phe Ser Cys
        195                 200                 205 gct tat gga aat ggg cag ccc gcc tat ttg gac gac aat atg gac aca    672
Ala Tyr Gly Asn Gly Gln Pro Ala Tyr Leu Asp Asp Asn Met Asp Thr
210                 215                 220 aaa tcc att cta gaa gaa ctt ctt ctc aaa agg tca cag caa aaa aag    720
Lys Ser Ile Leu Glu Glu Leu Leu Leu Lys Arg Ser Gln Gln Lys Lys
225                 230                 235                 240 aaa atg tcg cca agc aat tac aaa gag agg ctt ttt gtt tta acc aaa    768
Lys Met Ser Pro Ser Asn Tyr Lys Glu Arg Leu Phe Val Leu Thr Lys
                245                 250                 255 aca aat ctc tcc tac tat gaa tat gac aaa atg aaa aga ggc agc aaa    816
Thr Asn Leu Ser Tyr Tyr Glu Tyr Asp Lys Met Lys Arg Gly Ser Lys
            260                 265                 270 aaa gga tca att gag att aag aaa atc aga tgt gtg gag aaa gta aat    864
Lys Gly Ser Ile Glu Ile Lys Lys Ile Arg Cys Val Glu Lys Val Asn
        275                 280                 285 ctc gag gag cag acc cct gtg gag aga cag tac cca ttt cag att gtc    912
Leu Glu Glu Gln Thr Pro Val Glu Arg Gln Tyr Pro Phe Gln Ile Val
290                 295                 300 tat aaa gat ggg ctt ctc tat gtc tat gca tca aac gaa gag agc cga    960
Tyr Lys Asp Gly Leu Leu Tyr Val Tyr Ala Ser Asn Glu Glu Ser Arg
305                 310                 315                 320 agc cag tgg ttg aaa gca tta cag aaa gag ata agg ggt aac ccc cac   1008
Ser Gln Trp Leu Lys Ala Leu Gln Lys Glu Ile Arg Gly Asn Pro His
                325                 330                 335 ctg ctg atc aag tac cac agt ggg ttc ttc gtg gat gga aag ttc ctg   1056
Leu Leu Ile Lys Tyr His Ser Gly Phe Phe Val Asp Gly Lys Phe Leu
            340                 345                 350 tgc tgc cag cag agt tgc aaa gcg gcc cca gga tgt act ctc tgg gaa   1104
Cys Cys Gln Gln Ser Cys Lys Ala Ala Pro Gly Cys Thr Leu Trp Glu
        355                 360                 365 gca tac gct gat ctg cac att aca act cac gaa gag aaa cac aga gtt   1152
Ala Tyr Ala Asp Leu His Ile Thr Thr His Glu Glu Lys His Arg Val
370                 375                 380 ccc atc ttc cca gac aga gtg ctg aag att cct cga gca gtt cct att   1200
Pro Ile Phe Pro Asp Arg Val Leu Lys Ile Pro Arg Ala Val Pro Ile
385                 390                 395                 400 ttc aaa atg aat gaa cca tct tcg agc acc act gtg gcc ccg tat gac   1248
Phe Lys Met Asn Glu Pro Ser Ser Ser Thr Thr Val Ala Pro Tyr Asp
                405                 410                 415 agc gac tca aag aaa aac tac ggc tcc cag cta aat gcc aac atg cag   1296
Ser Asp Ser Lys Lys Asn Tyr Gly Ser Gln Leu Asn Ala Asn Met Gln
            420                 425                 430
```

```
                                                      -continued
cat ttt cca aga gaa gac tgc cct gac tgg tgg caa ctt aca aaa tgt      1344
His Phe Pro Arg Glu Asp Cys Pro Asp Trp Trp Gln Leu Thr Lys Cys
        435                 440                 445 gtc ttt tgt cgt agc agt gac gat ttc gcg ggc agt aac cag agg gaa      1392
Val Phe Cys Arg Ser Ser Asp Asp Phe Ala Gly Ser Asn Gln Arg Glu
450                 455                 460 agg act ggt gtc aat cac agc acc tca aag atg tca tgg gga ttt cct      1440
Arg Thr Gly Val Asn His Ser Thr Ser Lys Met Ser Trp Gly Phe Pro
465                 470                 475                 480 gag tcc agt tca tct gaa gaa gag gaa aac ctg gaa gac tat gac tgg      1488
Glu Ser Ser Ser Ser Glu Glu Glu Glu Asn Leu Glu Asp Tyr Asp Trp
                485                 490                 495 ttt gca ggt aac atc tcc agg tca cag tct gag cag tta ctg aga caa      1536
Phe Ala Gly Asn Ile Ser Arg Ser Gln Ser Glu Gln Leu Leu Arg Gln
        500                 505                 510 aag gga aaa gaa ggt gcg ttt atg gtc cga aat tcc cgc cag gtg gga      1584
Lys Gly Lys Glu Gly Ala Phe Met Val Arg Asn Ser Arg Gln Val Gly
        515                 520                 525 atg tat aca gtg tct tta ttt agc aag gct atg aat gat aaa aaa gga      1632
Met Tyr Thr Val Ser Leu Phe Ser Lys Ala Met Asn Asp Lys Lys Gly
530                 535                 540 act gtc aag cat tac cat gtg cat aca aat gcc gag aac aaa ttg tac      1680
Thr Val Lys His Tyr His Val His Thr Asn Ala Glu Asn Lys Leu Tyr
545                 550                 555                 560 ctg gcg gaa aac tac tgt ttt gat tct att ccc aag ctt att cac tac      1728
Leu Ala Glu Asn Tyr Cys Phe Asp Ser Ile Pro Lys Leu Ile His Tyr
                565                 570                 575 cat caa cac aat tca gca ggc atg atc acg cga ctc cgc cac cct gtg      1776
His Gln His Asn Ser Ala Gly Met Ile Thr Arg Leu Arg His Pro Val
        580                 585                 590 tcg acc aag gcc aac aag gtt ccc acc tcc gtg tcc ttg gga agt gga      1824
Ser Thr Lys Ala Asn Lys Val Pro Thr Ser Val Ser Leu Gly Ser Gly
        595                 600                 605 ata tgg gaa ctg aag aga gaa gag att acc ctc ctg aag gag ctg ggg      1872
Ile Trp Glu Leu Lys Arg Glu Glu Ile Thr Leu Leu Lys Glu Leu Gly
        610                 615                 620 agt ggt cag ttt gga gta gtc cat ctg ggc aag tgg aag ggc cag tat      1920
Ser Gly Gln Phe Gly Val Val His Leu Gly Lys Trp Lys Gly Gln Tyr
625                 630                 635                 640 gat gtt gcc att aag atg atc aag gag ggc tcc atg tcc gaa gat gaa      1968
Asp Val Ala Ile Lys Met Ile Lys Glu Gly Ser Met Ser Glu Asp Glu
                645                 650                 655 ttc ttc cag gag gct cag acc atg atg aaa ctc agc cat ccg aag ctg      2016
Phe Phe Gln Glu Ala Gln Thr Met Met Lys Leu Ser His Pro Lys Leu
        660                 665                 670 gtg aaa ttc tat ggg gtg tgc tcc aag aga tac ccc ata tac ata gtg      2064
Val Lys Phe Tyr Gly Val Cys Ser Lys Arg Tyr Pro Ile Tyr Ile Val
        675                 680                 685 acc gag tat atc acc aat ggc tgc ttg ctg aat tac ctg aag agt cac      2112
Thr Glu Tyr Ile Thr Asn Gly Cys Leu Leu Asn Tyr Leu Lys Ser His
        690                 695                 700 ggg aag gga ctg gag gcg tcg cag ctc ttg gag atg tgc tac gac gtg      2160
Gly Lys Gly Leu Glu Ala Ser Gln Leu Leu Glu Met Cys Tyr Asp Val
705                 710                 715                 720 tgt gaa ggc atg gcc ttc ttg gag agc cac cag ttc ata cac agg gac      2208
Cys Glu Gly Met Ala Phe Leu Glu Ser His Gln Phe Ile His Arg Asp
                725                 730                 735 ctg gcg gct cgg aac tgc ttg gta gac agc gac ctc tcg gtg aaa gtg      2256
Leu Ala Ala Arg Asn Cys Leu Val Asp Ser Asp Leu Ser Val Lys Val
        740                 745                 750
```

```
tcg gac ttc gga atg acc agg tat gtt ctc gat gac cag tac gtc agc    2304
Ser Asp Phe Gly Met Thr Arg Tyr Val Leu Asp Asp Gln Tyr Val Ser
    755                 760                 765 tca gta gga aca aag ttc ccg gtc aag tgg tca gcc cca gag gtg ttc    2352
Ser Val Gly Thr Lys Phe Pro Val Lys Trp Ser Ala Pro Glu Val Phe
770                 775                 780 cac tac ttc aaa tac agc agc aag tcg gac gtt tgg gca ttc ggg atc    2400
His Tyr Phe Lys Tyr Ser Ser Lys Ser Asp Val Trp Ala Phe Gly Ile
785                 790                 795                 800 ctg atg tgg gaa gtg ttc agc ctg ggg aag cag ccc tac gac ctg tac    2448
Leu Met Trp Glu Val Phe Ser Leu Gly Lys Gln Pro Tyr Asp Leu Tyr
                805                 810                 815 gac aac tcg cag gtg gtt gtg aag gtc tcc cag ggc cac cgg ctc tac    2496
Asp Asn Ser Gln Val Val Val Lys Val Ser Gln Gly His Arg Leu Tyr
            820                 825                 830 cgg ccc caa ctg gcg tcg gac acc gtc tac cag atc atg tac ggc tgc    2544
Arg Pro Gln Leu Ala Ser Asp Thr Val Tyr Gln Ile Met Tyr Gly Cys
        835                 840                 845 tgg cac gag ctt cca gaa aag cgt ccc aca ttt cag caa ctc cta tct    2592
Trp His Glu Leu Pro Glu Lys Arg Pro Thr Phe Gln Gln Leu Leu Ser
850                 855                 860 tcc att gaa cca ctt cgg gaa aaa gac aag cct tga agaagaaatg         2638
Ser Ile Glu Pro Leu Arg Glu Lys Asp Lys Pro
865                 870                 875 aggagatctg atgagaagga ccgtcaatgc tggccaacat tttcattcct tttaaggaaa  2698
gtagcaaggc gcaaaccatg taatttagct aatcgcattc tgtgtactgt ttgcctcttg  2758
tattatctca aaatgaacaa ggtaagaaac aaaagatttc cttgacattt aagtcaaatt  2818
agtagttttg tgtatgctgc tctttatatt attatacttc ccagcctaca gcagaagcac  2878 atttctgat tgtggtagac agagtgtgta ccatgtgtaa agattgaaca gaattgaaaa   2938
attctttgtt ggatatttgt tcttttcctt atatcatcac tatcacgata attaaatatg  2998
ttgttaa                                                             3005

<210> SEQ ID NO 18
<211> LENGTH: 875
<212> TYPE: PRT
<213> ORGANISM: Canis familiaris

<400> SEQUENCE: 18

Met Leu Glu Thr Ala Leu Arg Asp Gln Lys Arg Gly Asp Gln Trp Arg
1               5                   10                  15

Val Gln Thr Gly Arg Val Ala Gly Phe Glu Ser Leu Val Lys Glu Ser
            20                  25                  30

Leu Trp Leu Ala Ser Gly Glu Gln Thr Ser Arg Ser Lys Ser Arg Ser
        35                  40                  45

Arg Asp Ser Ser Gln Glu Ala Gly Ala Thr Leu Gln Gly Val Ser Ser
    50                  55                  60

Pro Leu Ala Asn Ser Ser Glu Gly Leu Phe Ala Pro Ser Arg Thr Thr
65                  70                  75                  80

Arg Val Ser Ser Arg Asn Val Asn Ser Ala Ser Lys Leu Phe Ser
            85                  90                  95

Thr Arg Ser Thr Gln Leu Asp Leu Pro Leu Gly Phe Ser Ala Cys Ser
            100                 105                 110

Arg Gln Lys Ala Leu Glu Gly Ala Gly Cys Pro Cys Pro Ala Tyr Tyr
        115                 120                 125

Gly Leu Gln Pro Leu Thr Glu Pro Leu Ala His Gly Arg Arg Ala Ala
    130                 135                 140
```

```
Ala Pro Val Cys Val Gln Glu Gln Thr Asp Pro Ser Ala Val Asp Pro
145                 150                 155                 160

Arg Arg Pro Ile Glu Ser His Asn Gly Ala Leu Gln Arg Gln Val Ala
            165                 170                 175

Thr Arg Gly His Ser Arg Gln Ala Asp Arg Phe Arg Val Met His Met
        180                 185                 190

Thr Leu Leu Gly Leu Leu Arg Gly Leu Trp Met Arg Pro Phe Ser Cys
    195                 200                 205

Ala Tyr Gly Asn Gly Gln Pro Ala Tyr Leu Asp Asp Asn Met Asp Thr
210                 215                 220

Lys Ser Ile Leu Glu Glu Leu Leu Lys Arg Ser Gln Gln Lys Lys
225                 230                 235                 240

Lys Met Ser Pro Ser Asn Tyr Lys Glu Arg Leu Phe Val Leu Thr Lys
                245                 250                 255

Thr Asn Leu Ser Tyr Tyr Glu Tyr Asp Lys Met Lys Arg Gly Ser Lys
            260                 265                 270

Lys Gly Ser Ile Glu Ile Lys Lys Ile Arg Cys Val Glu Lys Val Asn
        275                 280                 285

Leu Glu Glu Gln Thr Pro Val Glu Arg Gln Tyr Pro Phe Gln Ile Val
    290                 295                 300

Tyr Lys Asp Gly Leu Leu Tyr Val Tyr Ala Ser Asn Glu Glu Ser Arg
305                 310                 315                 320

Ser Gln Trp Leu Lys Ala Leu Gln Lys Glu Ile Arg Gly Asn Pro His
                325                 330                 335

Leu Leu Ile Lys Tyr His Ser Gly Phe Phe Val Asp Gly Lys Phe Leu
            340                 345                 350

Cys Cys Gln Gln Ser Cys Lys Ala Ala Pro Gly Cys Thr Leu Trp Glu
        355                 360                 365

Ala Tyr Ala Asp Leu His Ile Thr Thr His Glu Glu Lys His Arg Val
370                 375                 380

Pro Ile Phe Pro Asp Arg Val Leu Lys Ile Pro Arg Ala Val Pro Ile
385                 390                 395                 400

Phe Lys Met Asn Glu Pro Ser Ser Ser Thr Val Ala Pro Tyr Asp
                405                 410                 415

Ser Asp Ser Lys Lys Asn Tyr Gly Ser Gln Leu Asn Ala Asn Met Gln
            420                 425                 430

His Phe Pro Arg Glu Asp Cys Pro Asp Trp Trp Gln Leu Thr Lys Cys
        435                 440                 445

Val Phe Cys Arg Ser Ser Asp Asp Phe Ala Gly Ser Asn Gln Arg Glu
    450                 455                 460

Arg Thr Gly Val Asn His Ser Thr Ser Lys Met Ser Trp Gly Phe Pro
465                 470                 475                 480

Glu Ser Ser Ser Ser Glu Glu Glu Asn Leu Glu Asp Tyr Asp Trp
                485                 490                 495

Phe Ala Gly Asn Ile Ser Arg Ser Gln Ser Glu Gln Leu Leu Arg Gln
            500                 505                 510

Lys Gly Lys Glu Gly Ala Phe Met Val Arg Asn Ser Arg Gln Val Gly
        515                 520                 525

Met Tyr Thr Val Ser Leu Phe Ser Lys Ala Met Asn Asp Lys Lys Gly
    530                 535                 540

Thr Val Lys His Tyr His Val His Thr Asn Ala Glu Asn Lys Leu Tyr
545                 550                 555                 560

Leu Ala Glu Asn Tyr Cys Phe Asp Ser Ile Pro Lys Leu Ile His Tyr
```

```
                565                 570                 575
His Gln His Asn Ser Ala Gly Met Ile Thr Arg Leu Arg His Pro Val
            580                 585                 590

Ser Thr Lys Ala Asn Lys Val Pro Thr Ser Val Ser Leu Gly Ser Gly
        595                 600                 605

Ile Trp Glu Leu Lys Arg Glu Glu Ile Thr Leu Leu Lys Glu Leu Gly
    610                 615                 620

Ser Gly Gln Phe Gly Val Val His Leu Gly Lys Trp Lys Gly Gln Tyr
625                 630                 635                 640

Asp Val Ala Ile Lys Met Ile Lys Glu Gly Ser Met Ser Glu Asp Glu
                645                 650                 655

Phe Phe Gln Glu Ala Gln Thr Met Met Lys Leu Ser His Pro Lys Leu
            660                 665                 670

Val Lys Phe Tyr Gly Val Cys Ser Lys Arg Tyr Pro Ile Tyr Ile Val
        675                 680                 685

Thr Glu Tyr Ile Thr Asn Gly Cys Leu Leu Asn Tyr Leu Lys Ser His
    690                 695                 700

Gly Lys Gly Leu Glu Ala Ser Gln Leu Leu Glu Met Cys Tyr Asp Val
705                 710                 715                 720

Cys Glu Gly Met Ala Phe Leu Glu Ser His Gln Phe Ile His Arg Asp
                725                 730                 735

Leu Ala Ala Arg Asn Cys Leu Val Asp Ser Asp Leu Ser Val Lys Val
            740                 745                 750

Ser Asp Phe Gly Met Thr Arg Tyr Val Leu Asp Asp Gln Tyr Val Ser
        755                 760                 765

Ser Val Gly Thr Lys Phe Pro Val Lys Trp Ser Ala Pro Glu Val Phe
    770                 775                 780

His Tyr Phe Lys Tyr Ser Ser Lys Ser Asp Val Trp Ala Phe Gly Ile
785                 790                 795                 800

Leu Met Trp Glu Val Phe Ser Leu Gly Lys Gln Pro Tyr Asp Leu Tyr
                805                 810                 815

Asp Asn Ser Gln Val Val Val Lys Val Ser Gln Gly His Arg Leu Tyr
            820                 825                 830

Arg Pro Gln Leu Ala Ser Asp Thr Val Tyr Gln Ile Met Tyr Gly Cys
        835                 840                 845

Trp His Glu Leu Pro Glu Lys Arg Pro Thr Phe Gln Gln Leu Leu Ser
    850                 855                 860

Ser Ile Glu Pro Leu Arg Glu Lys Asp Lys Pro
865                 870                 875

<210> SEQ ID NO 19
<211> LENGTH: 1965
<212> TYPE: DNA
<213> ORGANISM: Equus caballus
<220> FEATURE:
<221> NAME/KEY: CDS
<222> LOCATION: (1)..(1965)

<400> SEQUENCE: 19 atg gat aca aaa tcc atc cta gaa gaa ctt ctt ctc aaa agg tca cag     48
Met Asp Thr Lys Ser Ile Leu Glu Glu Leu Leu Leu Lys Arg Ser Gln
1               5                   10                  15 caa aag aag aaa atg tca cca aat aac tac aaa gag cgg ctt ttt gtt     96
Gln Lys Lys Lys Met Ser Pro Asn Asn Tyr Lys Glu Arg Leu Phe Val
            20                  25                  30 ttg acc aaa aca aac ctc tcc tac tat gaa tat gac aaa atg aaa aga    144
Leu Thr Lys Thr Asn Leu Ser Tyr Tyr Glu Tyr Asp Lys Met Lys Arg
```

```
                35                  40                  45
ggc agc aga aaa gga tca atc gag att aag aag atc aga tgc gtg gag      192
Gly Ser Arg Lys Gly Ser Ile Glu Ile Lys Lys Ile Arg Cys Val Glu
     50                  55                  60 aaa gta aat gtt gag gag cag acc cct gcg gag agg cag tac cca ttt      240
Lys Val Asn Val Glu Glu Gln Thr Pro Ala Glu Arg Gln Tyr Pro Phe
 65                  70                  75                  80 cag att gtc tat aaa gat ggg ctt ctc tat gtc tat gca tca aat gaa      288
Gln Ile Val Tyr Lys Asp Gly Leu Leu Tyr Val Tyr Ala Ser Asn Glu
                 85                  90                  95 aag agc cga agt cag tgg ttg aaa gca tta caa aaa gag ata agg ggc      336
Lys Ser Arg Ser Gln Trp Leu Lys Ala Leu Gln Lys Glu Ile Arg Gly
            100                 105                 110 aac ccc cac ctg ctg atc aag tac cat agt ggg ttc ttc gtg gac ggg      384
Asn Pro His Leu Leu Ile Lys Tyr His Ser Gly Phe Phe Val Asp Gly
        115                 120                 125 aag ttc ctg tgc tgc caa cag agt tgc aaa gcg gcc ccg gga tgt aca      432
Lys Phe Leu Cys Cys Gln Gln Ser Cys Lys Ala Ala Pro Gly Cys Thr
    130                 135                 140 ctc tgg gaa gca tat gct gat ctg cac att gca acc aat gaa gag aaa      480
Leu Trp Glu Ala Tyr Ala Asp Leu His Ile Ala Thr Asn Glu Glu Lys
145                 150                 155                 160 cac aga gct ccc acc ttc cca gac aga gtg ctg aag att cct cga gca      528
His Arg Ala Pro Thr Phe Pro Asp Arg Val Leu Lys Ile Pro Arg Ala
                165                 170                 175 gtt cct gtt ttc aaa atg gat gaa cca tct tca agt acc act cta gct      576
Val Pro Val Phe Lys Met Asp Glu Pro Ser Ser Ser Thr Thr Leu Ala
            180                 185                 190 cag tat gac agt gac tca aag aaa gac tat ggc tcc cag tca aac gtc      624
Gln Tyr Asp Ser Asp Ser Lys Lys Asp Tyr Gly Ser Gln Ser Asn Val
        195                 200                 205 aag atg cgg tat att ccg aaa gaa gac ttc cct gac tgg tgg caa gtc      672
Lys Met Arg Tyr Ile Pro Lys Glu Asp Phe Pro Asp Trp Trp Gln Val
    210                 215                 220 aga aaa ctg aaa agt agt gtc aac agt gaa gat ttt gcg tgc agt aac      720
Arg Lys Leu Lys Ser Ser Val Asn Ser Glu Asp Phe Ala Cys Ser Asn
225                 230                 235                 240 caa agg gaa aga gat gtt gta aat cac agc acc tca aag atg tca tgg      768
Gln Arg Glu Arg Asp Val Val Asn His Ser Thr Ser Lys Met Ser Trp
                245                 250                 255 gga ttc cct gag tca agt tca tct gaa gaa gag gaa aac ctg gat gac      816
Gly Phe Pro Glu Ser Ser Ser Ser Glu Glu Glu Glu Asn Leu Asp Asp
            260                 265                 270 tat gac tgg ttt gca ggt gac atc tcc agg tca caa tct gag cag tta      864
Tyr Asp Trp Phe Ala Gly Asp Ile Ser Arg Ser Gln Ser Glu Gln Leu
        275                 280                 285 ctg aga caa aag gga aaa gaa gga gcg ttt atg gtt aga aat tcc agc      912
Leu Arg Gln Lys Gly Lys Glu Gly Ala Phe Met Val Arg Asn Ser Ser
    290                 295                 300 cag gcg gga atg tac aca gtg tcc tta ttt agt aag gct gtg aat gat      960
Gln Ala Gly Met Tyr Thr Val Ser Leu Phe Ser Lys Ala Val Asn Asp
305                 310                 315                 320 aag aaa gga acc gtc aaa cat tac cat gtg cat aca aat gct gag aac     1008
Lys Lys Gly Thr Val Lys His Tyr His Val His Thr Asn Ala Glu Asn
                325                 330                 335 aaa ttg tac ctg gca gaa aac tac tgt ttt gat tcc att cca aag ctt     1056
Lys Leu Tyr Leu Ala Glu Asn Tyr Cys Phe Asp Ser Ile Pro Lys Leu
            340                 345                 350 att cac tat cat caa cac aat tca gca ggc atg atc aca cga ctc cgc     1104
Ile His Tyr His Gln His Asn Ser Ala Gly Met Ile Thr Arg Leu Arg
```

```
                  355                   360                   365
cac cct gtg tcg acc aag gcc aac aag gtt ccc atc tcc gtg tcc ttg        1152
His Pro Val Ser Thr Lys Ala Asn Lys Val Pro Ile Ser Val Ser Leu
            370                 375                 380 gga agt gga ctc tgg gaa ctg aaa aga gaa gag att acc ctg ctg aag        1200
Gly Ser Gly Leu Trp Glu Leu Lys Arg Glu Glu Ile Thr Leu Leu Lys
385                 390                 395                 400 gag ctg gga agt ggc cag ttt gga gtg gtc cat ctg ggc aag tgg aag        1248
Glu Leu Gly Ser Gly Gln Phe Gly Val Val His Leu Gly Lys Trp Lys
                405                 410                 415 ggg gag tat gat gtt gct gtt aag atg atc aag gag ggt tcc atg tca        1296
Gly Glu Tyr Asp Val Ala Val Lys Met Ile Lys Glu Gly Ser Met Ser
            420                 425                 430 gag gat gaa ttc ttc cag gag gcc cag acc atg atg aaa ctc agc cat        1344
Glu Asp Glu Phe Phe Gln Glu Ala Gln Thr Met Met Lys Leu Ser His
                435                 440                 445 ccc aag ctg gtg aaa ttc tac gga gtg tgt tca aag aaa tac cct ata        1392
Pro Lys Leu Val Lys Phe Tyr Gly Val Cys Ser Lys Lys Tyr Pro Ile
450                 455                 460 tac ata gtg act gaa tat ata acc aat ggc tgc ttg ctt aat tac ctg        1440
Tyr Ile Val Thr Glu Tyr Ile Thr Asn Gly Cys Leu Leu Asn Tyr Leu
465                 470                 475                 480 aag agt cat ggt aaa gga ctt gaa ccc tcc cag ctc ttg gaa atg tgc        1488
Lys Ser His Gly Lys Gly Leu Glu Pro Ser Gln Leu Leu Glu Met Cys
                485                 490                 495 tat gac gtt tgt gaa ggc atg gcc ttc ttg gag agg cac cag ttc ata        1536
Tyr Asp Val Cys Glu Gly Met Ala Phe Leu Glu Arg His Gln Phe Ile
            500                 505                 510 cat cgg gac ttg gcg gct cgg aac tgc ttg gtg gac agt gat ctc tct        1584
His Arg Asp Leu Ala Ala Arg Asn Cys Leu Val Asp Ser Asp Leu Ser
                515                 520                 525 gtg aaa gta tct gac ttt gga atg acg agg tat gtt ctt gat gac cag        1632
Val Lys Val Ser Asp Phe Gly Met Thr Arg Tyr Val Leu Asp Asp Gln
530                 535                 540 tat gtc agt tca gta gga aca aag ttt cca gtc aag tgg tca gcc cca        1680
Tyr Val Ser Ser Val Gly Thr Lys Phe Pro Val Lys Trp Ser Ala Pro
545                 550                 555                 560 gag gtg ttt cac tac ttc aaa tac agc agc aag tca gac gta tgg gca        1728
Glu Val Phe His Tyr Phe Lys Tyr Ser Ser Lys Ser Asp Val Trp Ala
                565                 570                 575 ttt ggg atc ctg atg tgg gaa gta ttc agc ctg ggg aag cag ccc tac        1776
Phe Gly Ile Leu Met Trp Glu Val Phe Ser Leu Gly Lys Gln Pro Tyr
            580                 585                 590 gac ttg tat gac aac tcc cag gtg gtt gtg aag gtc tcc cag ggc cac        1824
Asp Leu Tyr Asp Asn Ser Gln Val Val Val Lys Val Ser Gln Gly His
                595                 600                 605 agg ctc tat cgg ccc caa ctg gca tca gac acc atc tac cag atc atg        1872
Arg Leu Tyr Arg Pro Gln Leu Ala Ser Asp Thr Ile Tyr Gln Ile Met
610                 615                 620 tac agc tgc tgg cac gag ctt cca gaa aag cgt ccc aca ttt cag caa        1920
Tyr Ser Cys Trp His Glu Leu Pro Glu Lys Arg Pro Thr Phe Gln Gln
625                 630                 635                 640 ctc cta tct tct atg gaa cca ctt cgg gaa aaa gac aag cct tga           1965
Leu Leu Ser Ser Met Glu Pro Leu Arg Glu Lys Asp Lys Pro
                645                 650

<210> SEQ ID NO 20
<211> LENGTH: 654
<212> TYPE: PRT
<213> ORGANISM: Equus caballus
```

-continued

<400> SEQUENCE: 20

Met Asp Thr Lys Ser Ile Leu Glu Glu Leu Leu Lys Arg Ser Gln
1               5                   10                  15

Gln Lys Lys Lys Met Ser Pro Asn Asn Tyr Lys Glu Arg Leu Phe Val
            20                  25                  30

Leu Thr Lys Thr Asn Leu Ser Tyr Tyr Glu Tyr Asp Lys Met Lys Arg
        35                  40                  45

Gly Ser Arg Lys Gly Ser Ile Glu Ile Lys Ile Arg Cys Val Glu
50                  55                  60

Lys Val Asn Val Glu Glu Gln Thr Pro Ala Glu Arg Gln Tyr Pro Phe
65                  70                  75                  80

Gln Ile Val Tyr Lys Asp Gly Leu Leu Tyr Val Tyr Ala Ser Asn Glu
                85                  90                  95

Lys Ser Arg Ser Gln Trp Leu Lys Ala Leu Gln Lys Glu Ile Arg Gly
            100                 105                 110

Asn Pro His Leu Leu Ile Lys Tyr His Ser Gly Phe Phe Val Asp Gly
        115                 120                 125

Lys Phe Leu Cys Cys Gln Gln Ser Cys Lys Ala Ala Pro Gly Cys Thr
130                 135                 140

Leu Trp Glu Ala Tyr Ala Asp Leu His Ile Ala Thr Asn Glu Glu Lys
145                 150                 155                 160

His Arg Ala Pro Thr Phe Pro Asp Arg Val Leu Lys Ile Pro Arg Ala
                165                 170                 175

Val Pro Val Phe Lys Met Asp Glu Pro Ser Ser Ser Thr Thr Leu Ala
            180                 185                 190

Gln Tyr Asp Ser Asp Ser Lys Lys Asp Tyr Gly Ser Gln Ser Asn Val
        195                 200                 205

Lys Met Arg Tyr Ile Pro Lys Glu Asp Phe Pro Asp Trp Trp Gln Val
210                 215                 220

Arg Lys Leu Lys Ser Ser Val Asn Ser Glu Asp Phe Ala Cys Ser Asn
225                 230                 235                 240

Gln Arg Glu Arg Asp Val Val Asn His Ser Thr Ser Lys Met Ser Trp
                245                 250                 255

Gly Phe Pro Glu Ser Ser Ser Glu Glu Glu Asn Leu Asp Asp
            260                 265                 270

Tyr Asp Trp Phe Ala Gly Asp Ile Ser Arg Ser Gln Ser Glu Gln Leu
        275                 280                 285

Leu Arg Gln Lys Gly Lys Glu Gly Ala Phe Met Val Arg Asn Ser Ser
290                 295                 300

Gln Ala Gly Met Tyr Thr Val Ser Leu Phe Ser Lys Ala Val Asn Asp
305                 310                 315                 320

Lys Lys Gly Thr Val Lys His Tyr His Val His Thr Asn Ala Glu Asn
                325                 330                 335

Lys Leu Tyr Leu Ala Glu Asn Tyr Cys Phe Asp Ser Ile Pro Lys Leu
            340                 345                 350

Ile His Tyr His Gln His Asn Ser Ala Gly Met Ile Thr Arg Leu Arg
        355                 360                 365

His Pro Val Ser Thr Lys Ala Asn Lys Val Pro Ile Ser Val Ser Leu
370                 375                 380

Gly Ser Gly Leu Trp Glu Leu Lys Arg Glu Glu Ile Thr Leu Leu Lys
385                 390                 395                 400

Glu Leu Gly Ser Gly Gln Phe Gly Val Val His Leu Gly Lys Trp Lys
                405                 410                 415

```
Gly Glu Tyr Asp Val Ala Val Lys Met Ile Lys Glu Gly Ser Met Ser
            420                 425                 430

Glu Asp Glu Phe Phe Gln Glu Ala Gln Thr Met Met Lys Leu Ser His
        435                 440                 445

Pro Lys Leu Val Lys Phe Tyr Gly Val Cys Ser Lys Lys Tyr Pro Ile
    450                 455                 460

Tyr Ile Val Thr Glu Tyr Ile Thr Asn Gly Cys Leu Leu Asn Tyr Leu
465                 470                 475                 480

Lys Ser His Gly Lys Gly Leu Glu Pro Ser Gln Leu Leu Glu Met Cys
                485                 490                 495

Tyr Asp Val Cys Glu Gly Met Ala Phe Leu Glu Arg His Gln Phe Ile
            500                 505                 510

His Arg Asp Leu Ala Ala Arg Asn Cys Leu Val Asp Ser Asp Leu Ser
        515                 520                 525

Val Lys Val Ser Asp Phe Gly Met Thr Arg Tyr Val Leu Asp Asp Gln
    530                 535                 540

Tyr Val Ser Ser Val Gly Thr Lys Phe Pro Val Lys Trp Ser Ala Pro
545                 550                 555                 560

Glu Val Phe His Tyr Phe Lys Tyr Ser Ser Lys Ser Asp Val Trp Ala
                565                 570                 575

Phe Gly Ile Leu Met Trp Glu Val Phe Ser Leu Gly Lys Gln Pro Tyr
            580                 585                 590

Asp Leu Tyr Asp Asn Ser Gln Val Val Val Lys Val Ser Gln Gly His
        595                 600                 605

Arg Leu Tyr Arg Pro Gln Leu Ala Ser Asp Thr Ile Tyr Gln Ile Met
    610                 615                 620

Tyr Ser Cys Trp His Glu Leu Pro Glu Lys Arg Pro Thr Phe Gln Gln
625                 630                 635                 640

Leu Leu Ser Ser Met Glu Pro Leu Arg Glu Lys Asp Lys Pro
                645                 650
```